(12) United States Patent
Jung et al.

(10) Patent No.: US 12,240,844 B2
(45) Date of Patent: Mar. 4, 2025

(54) PYRROLOPYRIDINE DERIVATIVE AND USE THEREOF IN PREVENTION AND TREATMENT OF PROTEIN KINASE-RELATED DISEASE

(71) Applicant: Voronoi, Inc., Incheon (KR)

(72) Inventors: Myungho Jung, Hwaseong-si (KR); Jungyeon Yun, Goyang-si (KR); Dahoon Ma, Incheon (KR); Sohyun Chung, Incheon (KR); Hyeonho Jeon, Incheon (KR); Heesun Ryu, Incheon (KR); Hyunkyung Kim, Incheon (KR); Hwan Kim, Seoul (KR); Jungbeom Son, Incheon (KR); Namdoo Kim, Incheon (KR); Jieun Choi, Seoul (KR); Daekwon Kim, Daegu (KR)

(73) Assignee: Voronoi, Inc., Incheon (KR)

( * ) Notice: Subject to any disclaimer, the term of this patent is extended or adjusted under 35 U.S.C. 154(b) by 791 days.

(21) Appl. No.: 17/423,186

(22) PCT Filed: Jan. 20, 2020

(86) PCT No.: PCT/KR2020/000944
§ 371 (c)(1),
(2) Date: Jul. 15, 2021

(87) PCT Pub. No.: WO2020/149715
PCT Pub. Date: Jul. 23, 2020

(65) Prior Publication Data
US 2022/0064161 A1 Mar. 3, 2022

(30) Foreign Application Priority Data
Jan. 18, 2019 (KR) ........................ 10-2019-0006930

(51) Int. Cl.
*C07D 471/04* (2006.01)
*C07D 519/00* (2006.01)
*C07F 9/6561* (2006.01)

(52) U.S. Cl.
CPC ......... *C07D 471/04* (2013.01); *C07D 519/00* (2013.01); *C07F 9/6561* (2013.01)

(58) Field of Classification Search
CPC ............................ C07D 471/04; C07D 519/00
USPC ...................................................... 514/300
See application file for complete search history.

(56) References Cited

U.S. PATENT DOCUMENTS

| | | | |
|---|---|---|---|
| 9,012,462 | B2 | 4/2015 | Wang et al. |
| 11,117,892 | B2 * | 9/2021 | Choi ............... A23L 33/10 |
| 2012/0202776 | A1 | 8/2012 | Wang et al. |
| 2014/0066406 | A1 | 3/2014 | Wang et al. |
| 2015/0225436 | A1 | 8/2015 | Wang et al. |
| 2017/0218000 | A1 | 8/2017 | Wang et al. |
| 2020/0048288 | A1 | 2/2020 | Wang et al. |
| 2020/0207756 | A1 | 7/2020 | Choi et al. |
| 2020/0317705 | A1 | 10/2020 | Wang et al. |

FOREIGN PATENT DOCUMENTS

| | | | |
|---|---|---|---|
| CN | 102105150 A | 6/2011 | |
| CN | 105940004 A | 9/2016 | |
| CN | 105980388 A | 9/2016 | |
| CN | 107801397 A | 3/2018 | |
| JP | 2011518219 A | 6/2011 | |
| KR | 10-2013-0121122 A | 11/2013 | |
| KR | 10-2014-0040715 A | 4/2014 | |
| KR | 20160106623 A | 9/2016 | |
| KR | 10-2017-0058465 A | 5/2017 | |
| KR | 10-2017-0106452 A | 9/2017 | |
| KR | 10-2018-0015142 A | 2/2018 | |
| KR | 10-2018-0097162 A | 8/2018 | |
| KR | 101896568 B1 * | 9/2018 | ........... C07D 471/04 |
| KR | 10-2018-0132882 A | 12/2018 | |
| RU | 2434013 C2 | 11/2011 | |
| WO | WO-2006127587 A1 | 11/2006 | |
| WO | WO-2008129152 A1 | 10/2008 | |
| WO | WO-2009032694 A1 | 3/2009 | |
| WO | WO-2009032703 A1 | 3/2009 | |
| WO | WO-2009131687 A2 | 10/2009 | |
| WO | WO-2009143389 A1 | 11/2009 | |
| WO | WO-2011090738 A2 | 7/2011 | |
| WO | WO-2012135631 A1 | 10/2012 | |

(Continued)

OTHER PUBLICATIONS

Cohen et al. Published Dec. 3, 20121, ACS Chemical Biology, vol. 8, pp. 96-104 (Year: 2012).*
Purlyte et al., Published Dec. 6, 2017, The EMBO Journal, vol. 37, pp. 1-18 (Year: 2017).*
Mosse et al., Published Sep. 15, 2009, Clinical Cancer Research, vol. 15, pp. 5609-5614 (Year: 2009).*
KR-101896568-B1, Published Sep. 10, 2018, English Machine Translation (Year: 2018).*
Guo et al., Published Dec. 2018, Tissue and Cell, vol. 55, pp. 63-70 (Year: 2018).*
English translation of International Search Report corresponding to International Patent Application No. PCT/KR2020/000944 (3 pages) (mailed May 6, 2020).
Mojzych et al. "Synthesis and kinase inhibitory activity of new sulfonamide derivatives of pyrazolo[4,3-e][1,2,4] triazines" European Journal of Medicinal Chemistry, 78:217-224 (2014).

(Continued)

*Primary Examiner* — Bahar Craigo
*Assistant Examiner* — Jaret J Crews
(74) *Attorney, Agent, or Firm* — Seed IP Law Group LLP

(57) ABSTRACT

[Summary]
The present invention relates to a pyrrolopyridine derivative and a pharmaceutical composition comprising the same as an active ingredient for prevention or treatment of a protein kinase-related disease. The pyrrolopyridine derivative has excellent inhibitory activity against various protein kinases including LRRK2, DYRK1, and CLK1 and exhibits an excellent suppressive effect on the growth of triple-negative breast cancer cells. A pharmaceutical composition comprising the same as an active ingredient can be advantageously used for treating or preventing protein kinase-related diseases, inter alia, cancers, degenerative brain diseases, and inflammatory diseases, and specifically for treating triple-negative breast cancer.

15 Claims, 1 Drawing Sheet

(56) References Cited

FOREIGN PATENT DOCUMENTS

| WO | WO-2014170248 A1 | 10/2014 |
| WO | WO-2015113451 A1 | 8/2015 |
| WO | WO-2015113452 A1 | 8/2015 |
| WO | 2016130920 A2 | 8/2016 |
| WO | WO-2016195776 A1 | 12/2016 |
| WO | WO-2018155916 A2 | 8/2018 |
| WO | WO-2018174650 A1 | 9/2018 |
| WO | WO-2020149715 A1 | 7/2020 |
| WO | WO-2020149723 A1 | 7/2020 |
| WO | WO-2020232332 A1 | 11/2020 |
| WO | WO-2020235973 A1 | 11/2020 |
| WO | WO-2022123311 A1 | 6/2022 |

OTHER PUBLICATIONS

Kwiatkowski et al., "Small Molecule Kinase Inhibitors Provide Insight into Mps1 Cell Cycle Function", Nat Chem Biol. 2010; 6(5):359-68.

Michellys et al., Design and synthesis of novel selective anaplastic lymphoma kinase inhibitors, Bioorganic & Medicinal Chemistry Letters 26 (2016) 1090-1096.

International Search Report of PCT/KR2018/003459 dated Mar. 23, 2018.

Williamson et al., "Design of Leucine-Rich Repeat Kinase 2 (LRRK2) Inhibitors Using a Crystallographic Surrogate Derived from Checkpoint Kinase 1 (CHK1)." J Med Chem. 2017;60(21):8945-8962.

Ding et al., "Discovery of 4-ethoxy-7H-pyrrolo[2,3-d]pyrimidin-2-amines as potent, selective and orally bioavailable LRRK2 inhibitors." Bioorg Med Chem Lett. 2018;28(9):1615-1620.

Hatcher et al., "Discovery of a Pyrrolopyrimidine (JH-II-127), a Highly Potent, Selective, and Brain Penetrant LRRK2 Inhibitor", ACS Med Chem Lett. Apr. 7, 2015;6(5):584-9.

PCT International Search Report and Written Opinion from PCT/IB2021/000857, dated Apr. 11, 2022.

PCT International Search Report and Written Opinion from PCT/KR2020/000944, dated May 6, 2020.

PCT International Search Report and Written Opinion from PCT/KR2020/000960, dated May 1, 2020.

PCT International Search Report and Written Opinion from PCT/KR2020/006730, dated Sep. 4, 2020.

PCT International Preliminary Report on Patentability from PCT/IB2021/000857, Jun. 13, 2023.

Seo et al., "P001 The novel DYRK1a inhibitor VRN024219 alleviates disease severity on the IBD mouse models by modulating T-cell differentiation," J Crohns Colitis. 2020; 14(suppl 1):S129.

\* cited by examiner

[Figure 1]
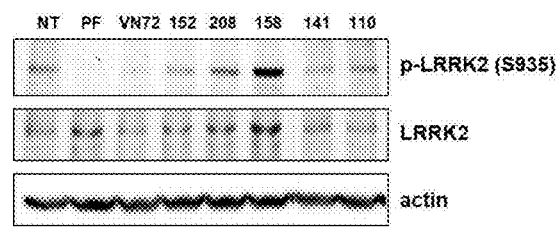
[Figure 2]
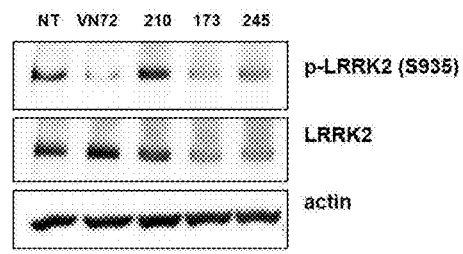

PYRROLOPYRIDINE DERIVATIVE AND USE THEREOF IN PREVENTION AND TREATMENT OF PROTEIN KINASE-RELATED DISEASE

TECHNICAL FIELD

It relates to a pyrrolopyridine derivative and a use thereof for preventing or treating protein kinase related diseases.

BACKGROUND ART

A protein kinase is an enzyme to catalyze a reaction for transferring the terminal phosphate group of adenosine triphosphate (ATP) to specific residues (tyrosine, serine, threonine) of a protein, which is involved in signals that regulate cell activity, growth and differentiation against changes in extracellular mediators and environments.

Inappropriately high protein kinase activity is directly or indirectly associated with a number of diseases resulting from abnormal cellular action. Diseases can be caused by, for example, failure of appropriate regulatory mechanisms of the kinase involved in mutation, over-expression or inadequate enzymatic activity, or excess or deficient generation of factors that participate in signaling upstream or downstream of cytokines or kinases. Therefore, selective inhibition of kinase activity can be a beneficial target to develop new drugs for disease treatment.

Brain cancer is a generic term for primary brain cancer that occurs in the brain tissues and the meninges surrounding the brain, and secondary brain cancer metastasized from cancer that occurs in the cranial bones or other parts of the body. In many ways, such brain cancer is distinguished from cancers that occur in other organs. First of all, cancers that occur in the lung, stomach, breast or the like are limited to one or two types for each organ, and their properties are the same or similar. However, there are many different types of cancers in the brain. For example, these are diverse, such as glioblastoma multiforme, malignant glioma, lymphadenoma, germinoma, metastatic tumor, and the like.

Parkinson's disease is the result of chronic progressive degeneration of neurons, but the cause has been still not fully determined. Although the main cause is unknown, Parkinson's disease is characterized by the degeneration of dopaminergic neurons in the substantia nigra (SN). The substantia nigra is a part or brainstem of the lower brain that helps control unconscious movements. It is known that the loss of such neurons causes symptoms in which the dopamine deficiency in the brain is observable. Clinically, Parkinson's disease manifests in the form of main symptoms of resting tremor, rigidity, bradykinesia and postural instability. An MAO-B inhibitor, selegiline, and a COMT inhibitor, entacapone, as well as levodopa, dopamine agonists (e.g., rotigotine, pramipexole, bromocriptine, ropinirole, cabergoline, pergolide, apomorphine and lisuride), anticholinergics, NMDA antagonists and β-blockers are used as drugs for relieving motor symptoms. Most of these agents are involved in transmission of dopamine and/or choline signaling, thereby affecting typical dyskinesia symptoms of Parkinson's disease.

LRRK2 (leucin-rich repeat kinase-2) is a protein belonging to a leucine-rich repeat kinase family, consists of 2527 amino acid sequences with high similarity between species, and has both GTP hydrolase (GTPase) and serine-threonine kinase activities in a single protein characteristically. It is known that the expressed LRRK2 is observed in various organs and tissues, including the brain, and exists, at the cellular level, in the cytoplasm or the cell membrane and the outer mitochondrial membrane. Currently, researches on the exact in vivo function of LRRK2 have been actively conducted, where it has five functionally important domains, so that self-activity regulatory action by autophosphorylation, and cell function regulatory action through protein interaction and enzymatic action are expected, and it is known that particularly, chaperone machinery, cytoskeleton arrangement, protein translational machinery, synaptic vesicle endocytosis, mitogen-activated protein kinase signaling cascades, and ubiquitin/autophageprotein degradation pathways are regulated by LRRK2.

Parkinson's disease occurs almost sporadically, but 5 to 10% of patients have a family history, where from studies of the samples of these patients, the gene loci of PARK 1-16 have been determined to date and genes causing Parkinson's disease by mutation at some gene loci thereof have been identified. As Parkinson's disease causative genes causing Parkinson's disease by mutation, parkin, PINK1, DJ-1, α-synuclein, LRRK2 (leucine-rich repeat kinase 2), and the like are known. Among them, the LRRK2 gene was first reported in 2004 as a dominant gene of a homologous chromosome like α-synuclein. Parkinson's disease patients caused by LRRK2 mutation have symptoms very similar to those of sporadic Parkinson's disease patients, unlike other Parkinson's disease causative genes. The LRRK2 mutation is found in 1-2% of sporadic Parkinson's disease patients as well as Parkinson's disease patients with a family history, so that it will be of great help in understanding the pathogenesis of Parkinson's disease and developing therapeutics to reveal the pathogenesis of Parkinson's disease caused by mutations in this gene.

In addition, the LRRK2 is known to be involved in the transmission of mild cognitive impairment associated with Alzheimer's disease, L-Dopa induced dyskinesia, CNS disorders associated with neuronal progenitor differentiation, cancers, such as brain cancer, kidney cancer, breast cancer, prostate cancer, blood cancer and lung cancer, and acute myeloid leukemia, papillary renal and thyroid carcinoma, multiple myeloma, amyotrophic lateral sclerosis, rheumatoid arthritis and ankylosing spondylitis, whereby compounds and compositions effective in modulating LRRK2 activity can provide therapeutic effects for neurodegenerative diseases, CNS disorders, cancers, acute myeloid leukemia and multiple myeloma, and inflammatory diseases, and the like.

A DYRK (dual specificity tyrosine-phosphorylation-regulated kinase) is a serine/threonine kinase, which has evolutionally higher maintainability and plays a variety of roles in central nervous system development and function. Humans have five isoforms of DYRK1A, DYRK1B, DYRK2, DYRK3 and DYRK4, from which DYRK1A has received the most attention and has been widely studied in relation to Down syndrome and degenerative brain diseases. The gene of DYRK1A is located in the human chromosome 21 Down syndrome critical region (DSCR) and has attracted more attention as it has been identified as a decisive factor in cognitive impairment which is typical in Down syndrome patients. In the case of Down syndrome patients, from the age of 35 to 40, they experience cognitive impairment and memory impairment, which are mainly seen in Alzheimer's disease. Interestingly, the expression and activity increase of DYRK1A are known to appear not only in Down syndrome, but also in patients with degenerative brain diseases such as Alzheimer's disease, Parkinson's disease, Huntington's disease and Pick's disease (Kimura et al., Hum. Mol. Genet., 2007, 16 (1), 15-23, and Wegiel et al., FEBS J., 2011, 278(2), 236-45 for review).

In addition, according to recent research results, the DYRK1A is also of interest as a target for developing a therapeutic agent for type 1 diabetes. The DYRK1A is involved in regulating the proliferation of beta cells, which are insulin-producing cells of the pancreas, through NFAT signaling, where it has been identified by several studies that inhibition of the DYRK1A activates the proliferation of beta cells. After all, an effective inhibitory drug of DYRK1A activates the proliferation of pancreatic beta-cells to promote insulin production and secretion, whereby a therapeutic effect can be expected in patients with type 1 diabetes (Diabetes. 2016 June; 65(6):1660-71. doi: 10.2337/db15-1127).

Furthermore, the DYRK1A shows high expression in carcinoma, where especially brain tumors and blood cancers are representative examples. It has been reported that the DYRK1A is involved in the generation and progression of cancers through phosphorylation of various intracellular factors (p27, cyclin D1, DREAM, c-myc, Sprouty), and the like. In particular, in the case of Sprouty, it is an important factor regulating the recycling of EGFR, which is important for maintaining the stemness of cancer stem cells, where by inhibiting the DYRK1A, an anticancer effect can be consequently expected in a manner to suppress the stemness of cancer stem cells (J Cell Mol Med. 2019 November; 23(11): 7427-7437). Accordingly, compounds and compositions effective for inhibiting DYRK1A activity can provide therapeutic effects for Down syndrome, central nervous system-related diseases, degenerative brain diseases, cancers, and diabetes, and the like.

PRIOR ART DOCUMENTS

Non-Patent Document

Kimura et al., Hum. Mol. Genet., 2007, 16(1), 15-23
Wegiel et al., FEBS J., 2011, 278(2), 236-45
Diabetes. 2016 June; 65(6):1660-71
J Cell Mol Med. 2019 November; 23(11):7427-7437

DISCLOSURE

Technical Problem

It is one object of the present invention to provide a pyrrolopyridine derivative.

It is another object of the present invention to provide a use of the pyrrolopyridine derivative for prevention or treatment of protein kinase-related diseases.

Technical Solution

In order to achieve the above object,
according to one aspect of the present invention,
a compound of Formula 1 below, an isomer thereof, a solvate thereof, a hydrate thereof or a pharmaceutically acceptable salt thereof is provided:

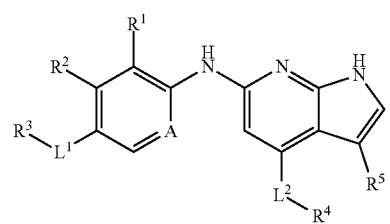

[Formula 1]

In Formula 1 above,
A represents a carbon atom or a nitrogen atom,
$R^1$ is straight or branched C1-6 alkoxy, $R^2$ is hydrogen, or $R^1$ and $R^2$ form an 8 to 10 membered bicyclic ring containing one or more heteroatoms selected from the group consisting of N, O and S, together with the benzene ring including the carbon atoms to which they are attached,
$L^1$ is sulfonyl, carbonyl or absent;
when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl,
when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl,
$L^2$ is —NH—, —O— or absent;
when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl,
when $L^2$ is absent, $R^4$ is C3-9 cycloalkyl or amino, where $R^4$ is unsubstituted or further substituted with one or more of C1-6 alkyl; and
$R^5$ is hydrogen, cyano, C1-6 haloalkyl or halogen.

According to another aspect of the present invention, a pharmaceutical composition for preventing or treating a protein kinase-related disease containing the compound of Formula 1 above, an isomer thereof, a solvate thereof, a hydrate thereof or a pharmaceutically acceptable salt thereof as an active ingredient is provided.

According to another aspect of the present invention, a method for preventing or treating a protein kinase-related disease comprising administering to a subject in need thereof a pharmaceutical composition containing the compound of Formula 1 above or a pharmaceutically acceptable salt thereof as an active ingredient is provided.

According to another aspect of the present invention, a use of a pharmaceutical composition containing the compound of Formula 1 above or a pharmaceutically acceptable salt thereof in prevention or treatment of a protein kinase-related disease is provided.

Advantageous Effects

The pyrrolopyridine derivative according to the present invention has excellent inhibitory activity against various protein kinases including LRRK2, DYRK1 and CLK1, and has an excellent effect of inhibiting proliferation of triple-negative breast cancer cells, so that the pharmaceutical composition comprising the same as an active ingredient may be usefully used for the treatment or prevention of protein kinase-related diseases, particularly cancers, degenerative brain disease and inflammatory diseases, and specifically, may be usefully used for the treatment of triple-negative breast cancer.

DESCRIPTION OF DRAWINGS

FIGS. 1 and 2 are photographs showing the results of the LRRK2 phosphorylation inhibition experiment of the compounds according to the present invention.

MODE FOR INVENTION

Hereinafter, the present invention will be described in detail.

In this specification, "halogen" may be F, Cl, Br, or I.

In this specification, "haloalkyl" may mean straight or branched chain alkyl (hydrocarbon) having a carbon atom substituted with one or more halogen atoms as defined herein. An example of the haloalkyl includes methyl, ethyl, propyl, isopropyl, isobutyl and N-butyl independently substituted with one or more halogen atoms, such as F, Cl, Br and I, but is not limited thereto.

In this specification, "alkyl" may mean a straight or branched acyclic saturated hydrocarbon consisting of carbon atoms. Representative —(C1-8 alkyl) may include -methyl, -ethyl, —N-propyl, —N-butyl, —N-pentyl and —N-hexyl, —N-heptyl and —N-octyl; the branched saturated alkyl may include -isopropyl, -sec-butyl, -isobutyl, -tert-butyl, -isopentyl, 2-methylpentyl, 3-methylpentyl, 4-methylpentyl, 2,3-dimethylbutyl, and the like. The —(C1~8 alkyl) may be substituted or may not be substituted. For example, a C1~8 alkyl group may be substituted with phenyl to form a benzyl group.

In this specification, "cycloalkyl" may mean a saturated or unsaturated carbon ring that is non-aromatic. Representative cycloalkyl includes cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl and cyclooctadienyl, but is not limited thereto. The cycloalkyl group may be substituted or may not be substituted. In one embodiment, the cycloalkyl group may be a C3~8 cycloalkyl group.

In this specification, "heterocycloalkyl" may mean a saturated or partially unsaturated cyclic substituent having a total number of ring atoms from 3 to 10 and containing 1 to 5 heteroatoms selected from N, O and S. Unless otherwise stated, a heterocycloalkyl group may be a monocyclic, bicyclic, spirocyclic or polycyclic ring shape. In addition, the heterocycloalkyl may include a ring shape bridged by one or more elements. The heterocycloalkyl may be attached to the remainder of the molecule through one or more ring carbons or heteroatoms. An example of the heterocycloalkyl includes pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo [3.2.1]octane, (1s,4s)-2-azabicyclo[2.2.2]octane, (1R,4R)-2-oxa-5-azabicyclo[2.2.2]octane, and the like, but is not limited thereto.

In this specification, "aryl" may mean any functional group or substituent derived by removing one hydrogen from an aromatic hydrocarbon ring. The aryl group may be a monocyclic aryl group or a polycyclic aryl group. The number of ring-forming carbon atoms in the aryl group may be 5 or more and 30 or less, 5 or more and 20 or less, or 5 or more and 15 or less. An example of the aryl group can be exemplified by a phenyl group, a naphthyl group, a fluorenyl group, an anthracenyl group, a phenanthryl group, a biphenyl group, a terphenyl group, a quarterphenyl group, a quinquephenyl group, a sexiphenyl group, a triphenylene group, a pyrenyl group, a benzofluoranthenyl group, a chrysenyl group, and the like, without being limited thereto.

In this specification, "heteroaryl" may be an aryl ring group including one or more of O, N, P, Si and S as a heterogeneous element. The number of ring-forming carbon atoms in the heteroaryl group may be 2 or more and 30 or less, or 2 or more and 20 or less. The heteroaryl may be monocyclic heteroaryl or polycyclic heteroaryl. The polycyclic heteroaryl may have, for example, a bicyclic or tricyclic structure. An example of the heteroaryl includes thienyl, thiophene, furyl, pyrrolyl, pyrazolyl, imidazolyl, thiazolyl, oxazolyl, isothiazolyl, oxadiazolyl, triazolyl, pyridinyl, bipyridyl, pyrimidyl, triazinyl, triazolyl, an acridyl group, a pyridazinyl group, pyrazinyl, quinolinyl, quinazoline, quinoxalinyl, phenoxazil, phthalazinyl, pyrimidinyl, pyridopyrimidinyl, pyridopyrazinyl, pyrazinopyrazinyl, isoquinoline, indole, carbazole, imidazopyridazinyl, imidazopyridinyl, imidazopyrimidinyl, pyrazolopyrimidinyl, imidazopyrazinyl or pyrazolopyridinyl, N-arylcarbazole, N-heteroarylcarbazole, an N-alkylcarbazole group, benzoxazole, benzoimidazole, benzothiazole, benzocarbazole, benzothiophene, dibenzothiophenyl, thienothiophene, benzofuranyl, phenanthroline, isoxazolyl, oxadiazolyl, thiadiazolyl, benzothiazolyl, tetrazolyl, phenothiazinyl, dibenzosilol and dibenzofuranyl, and the like, but is not limited thereto. In one embodiment of the present invention, the heteroaryl may also include bicyclic heterocyclo-aryl, including an aryl ring fused to a heterocycloalkyl ring or heteroaryl fused to a cycloalkyl ring.

The present invention provides
a compound of Formula 1 below, an isomer thereof, a solvate thereof, a hydrate thereof or a pharmaceutically acceptable salt thereof.

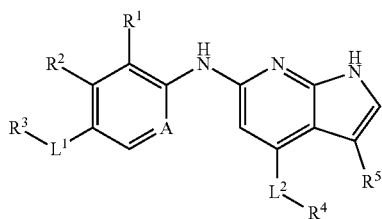

[Formula 1]

In Formula 1 above,

A represents a carbon atom or a nitrogen atom, $R^1$ is straight or branched C1-6 alkoxy, $R^2$ is hydrogen, or $R^1$ and $R^2$ form an 8 to 10 membered bicyclic ring containing one or more heteroatoms selected from the group consisting of N, O and S, together with the benzene ring including the carbon atoms to which they are attached, $L^1$ is sulfonyl, carbonyl or absent;

when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen.

In one embodiment of the present invention, a compound of Formula 1, an isomer thereof, a solvate thereof, a hydrate thereof, or a pharmaceutically acceptable salt thereof, wherein A represents a carbon atom or a nitrogen atom, $R^1$ is straight or branched C1-6 alkoxy, $R^2$ is hydrogen, $L^1$ is sulfonyl, carbonyl or absent;

when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen, is provided.

In another embodiment of the present invention, a compound of Formula 1, an isomer thereof, a solvate thereof, a hydrate thereof, or a pharmaceutically acceptable salt thereof, wherein A represents a carbon atom, $R^1$ and $R^2$ form an 8 to 10 membered bicyclic ring containing one or more heteroatoms selected from the group consisting of N, O and S, together with the benzene ring including the carbon atoms to which they are attached, $L^1$ is sulfonyl, carbonyl or absent;

when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when L² is —NH— or —O—, R⁴ is selected from the group consisting of C3-9 cycloalkyl, straight or branched C1-6 alkylamino and allyl, where R⁴ is unsubstituted or further substituted with one or more non-hydrogen substituents selected from the group consisting of C1-6 alkylsulfonyl, C1-6 alkoxy and C1-6 alkyl, when L² is absent, R⁴ is C3-9 cycloalkyl or amino, where R⁴ is unsubstituted or further substituted with one or more of C1-6 alkyl; and R⁵ is hydrogen, cyano, C1-6 haloalkyl or halogen, is provided.

In another embodiment of the present invention,

R¹ and R² form an 8 to 10 membered bicyclic ring containing one or more heteroatoms selected from the group consisting of N, O and S, together with the benzene ring including the carbon atoms to which they are attached, where the 8 to 10 membered bicyclic ring may be dihydrobenzodioxine, dihydrobenzofuran or benzodioxole.

In another embodiment of the present invention, a compound of Formula 1, an isomer thereof, a solvate thereof, a hydrate thereof or a pharmaceutically acceptable salt thereof, wherein A represents a carbon atom, R¹ is straight or branched C1-6 alkoxy, R² is hydrogen, L¹ is sulfonyl, R³ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where R³ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of R³ is unsubstituted or further substituted with a substituent selected from the group consisting of halogen, hydroxy, C3-9 cycloalkyl and straight or branched C1-6 alkyl, L² is —NH—, —O— or absent;

when L² is —NH— or —O—, R⁴ is selected from the group consisting of C3-9 cycloalkyl, straight or branched C1-6 alkylamino and allyl, where R⁴ is unsubstituted or further substituted with one or more non-hydrogen substituents selected from the group consisting of C1-6 alkylsulfonyl, C1-6 alkoxy and C1-6 alkyl, when L² is absent, R⁴ is C3-9 cycloalkyl or amino, where R⁴ is unsubstituted or further substituted with one or more of C1-6 alkyl and R⁵ is hydrogen, cyano, C1-6 haloalkyl or halogen, is provided.

In another embodiment of the present invention, a compound of Formula 1, wherein A represents a carbon atom, R¹ is straight or branched C1-6 alkoxy, R² is hydrogen, L¹ is absent, R³ is selected from phosphinic acid, azaphosphinane oxide, C1-6 alkylsulfonimidoyl and phosphine oxide, where R3 is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of R³ is unsubstituted or further substituted with C1-6 alkoxy or C1-6 alkyl, L² is —NH—, —O— or absent;

when L² is —NH— or —O—, R⁴ is selected from the group consisting of C3-9 cycloalkyl, straight or branched C1-6 alkylamino and allyl, where R⁴ is unsubstituted or further substituted with one or more non-hydrogen substituents selected from the group consisting of C1-6 alkylsulfonyl, C1-6 alkoxy and C1-6 alkyl, when L² is absent, R⁴ is C3-9 cycloalkyl or amino, where R⁴ is unsubstituted or further substituted with one or more of C1-6 alkyl and R⁵ is hydrogen, cyano, C1-6 haloalkyl or halogen, an isomer thereof, a solvate thereof, a hydrate thereof or a pharmaceutically acceptable salt thereof is provided.

In another embodiment of the present invention, a compound of Formula 1, an isomer thereof, a solvate thereof, a hydrate thereof or a pharmaceutically acceptable salt thereof, wherein A represents a carbon atom, R¹ and R² form an 8 to 10 membered bicyclic ring containing one or more heteroatoms selected from the group consisting of N, O and S, together with the benzene ring including the carbon atoms to which they are attached, L¹ is sulfonyl or carbonyl, R³ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where R³ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of R³ is unsubstituted or further substituted with a substituent selected from the group consisting of halogen, hydroxy, C3-9 cycloalkyl and straight or branched C1-6 alkyl, L² is —NH—, —O— or absent;

when L² is —NH— or —O—, R⁴ is selected from the group consisting of C3-9 cycloalkyl, straight or branched C1-6 alkylamino and allyl, where R⁴ is unsubstituted or further substituted with one or more non-hydrogen substituents selected from the group consisting of C1-6 alkylsulfonyl, C1-6 alkoxy and C1-6 alkyl, when L² is absent, R⁴ is C3-9 cycloalkyl or amino, where R⁴ is unsubstituted or further substituted with one or more of C1-6 alkyl and R⁵ is hydrogen, cyano, C1-6 haloalkyl or halogen, is provided.

In another embodiment of the present invention, a compound of Formula 1, an isomer thereof, a solvate thereof, a hydrate thereof or a pharmaceutically acceptable salt thereof, wherein A represents a carbon atom, R¹ and R² form an 8 to 10 membered bicyclic ring containing one or more heteroatoms selected from the group consisting of N, O and S, together with the benzene ring including the carbon atoms to which they are attached, where the 8 to 10 membered bicyclic ring may be dihydrobenzodioxine, dihydrobenzofuran or benzodioxole, L¹ is sulfonyl or carbonyl, R³ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstitued or further substituted with a substituent selected from the group consisting of halogen, hydroxy, C3-9 cycloalkyl and straight or branched C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl and $R^5$ is hydrogen, cyano, C1-6 haloalkyl or halogen, is provided.

An example of the compound of Formula 1 above according to the present invention may include Compounds 1 to 267 listed in [Table 1] of the following examples, or pharmaceutically acceptable salts thereof, or free bases (when shown as pharmaceutically acceptable salts in Table 1), isomers thereof, solvates thereof or pharmaceutically acceptable salts thereof.

The compound of Formula 1 above of the present invention may be used in the form of a pharmaceutically acceptable salt, and as the salt, an acid addition salt formed by a pharmaceutically acceptable free acid is useful. Acid addition salts are obtained from inorganic acids such as hydrochloric acid, nitric acid, phosphoric acid, sulfuric acid, hydrobromic acid, hydroiodic acid, nitrous acid and phosphorous acid, non-toxic organic acids such as aliphatic mono and dicarboxylates, phenyl-substituted alkanoates, hydroxy alkanoates and alkanedioates, aromatic acids, and aliphatic and aromatic sulfonic acids, and organic acids such as trifluoroacetic acid, acetate, benzoic acid, citric acid, lactic acid, maleic acid, gluconic acid, methanesulfonic acid, 4-toluenesulfonic acid, tartaric acid and fumaric acid. Types of such pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, subelate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, O-hydroxybutyrate, glycolate, malate, tartrate, methanesulfonate, propanesulfonate, naphthalene-1-sulfonate, naphthalene-2-sulfonate, mandelate, and the like.

The acid addition salt according to the present invention can be prepared by a conventional method, and for example, can be prepared by dissolving a derivative of Formula 1 in an organic solvent such as methanol, ethanol, acetone, methylene chloride and acetonitrile, adding an organic acid or an inorganic acid thereto, and filtering and drying the resulting precipitate, or by distilling the solvent and excess acid under reduced pressure, followed by drying and crystallization in an organic solvent.

In addition, bases can be used to prepare pharmaceutically acceptable metal salts. The alkali metal or alkaline earth metal salt is obtained, for example, by dissolving the compound in an excess alkali metal hydroxide or alkaline earth metal hydroxide solution, filtering the undissolved compound salt, and evaporating and drying the filtrate. At this time, it is pharmaceutically suitable to prepare a sodium, potassium or calcium salt as the metal salt. The corresponding salt is also obtained by reacting an alkali metal or alkaline earth metal salt with a suitable negative salt (e.g., silver nitrate).

Furthermore, the present invention includes not only the compound of Formula 1 above and pharmaceutically acceptable salts thereof, but also solvates, optical isomers, hydrates, and the like, which may be prepared therefrom.

"hydrate" may refer to a compound of the present disclosure or salt thereof containing a stoichiometric or non-stoichiometric amount of water bonded by a non-covalent intermolecular force. A hydrate of the compound represented by Formula 1 may contain a stoichiometric or non-stoichiometric amount of water bonded by a non-covalent intermolecular force. The hydrate may contain 1 equivalent or more, preferably, about 1 equivalent to about 5 equivalents of water. Such a hydrate may be prepared by crystallizing the compound represented by Formula 1 of the present disclosure, an isomer thereof, or a pharmaceutically acceptable salt thereof from water or a solvent containing water.

"solvate" may refer to a compound of the present disclosure or salt thereof containing a stoichiometric or non-stoichiometric amount of a solvent bonded by a non-covalent intermolecular force. Suitable solvents therefor include volatile solvents, non-toxic solvents, and/or solvents suitable for administration to humans.

"isomer" may refer to a compound of the present disclosure or salt thereof having the same chemical formula or molecular formula, but being structurally or sterically different. Such isomers include structural isomers such as a tautomer, R or S isomers having an asymmetric carbon center, stereoisomers such as a geometric isomer (trans or cis), and optical isomers (enantiomers). All these isomers and mixtures thereof also fall within the scope of the present disclosure.

As shown in Scheme A below, another aspect of the present invention provides a method for preparing the compound of Formula 1 above comprising: reacting a compound represented by Formula 3 with a compound represented by Formula 4 to prepare a compound represented by Formula 2 (step 1); and reacting the compound represented by Formula 2 to prepare the compound of Formula 1 above (step 2).

[Scheme A]

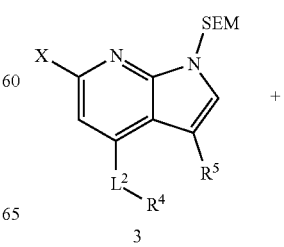

3

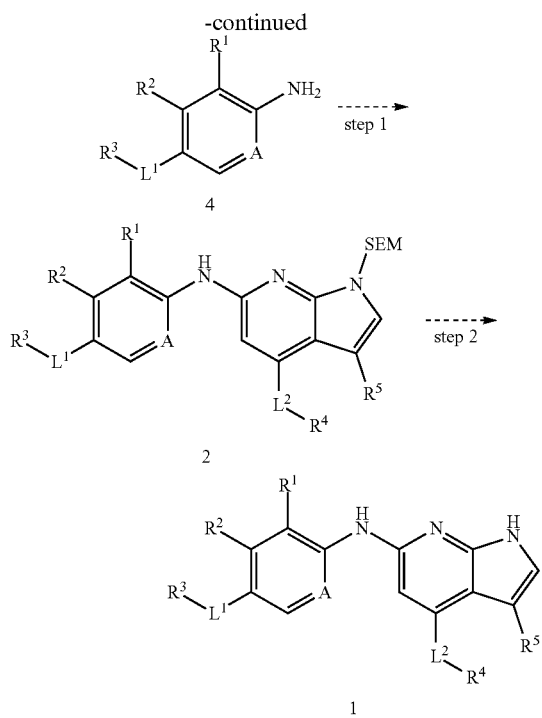

In Scheme A above,

R$^1$, R$^2$, R$^3$, R$^4$, R$^5$, L$^1$ and L$^2$ are as defined in Formula 1 above;

X is halogen and SEM represents a protecting group.

In the preparation method of Scheme A,

Step 1 is a step of preparing a compound represented by Formula 2, in which an amine bond is formed, by reacting a halogen of a compound represented by Formula 3 with a primary amine of a compound represented by Formula 4, which is not limited as long as it is performed under the condition that reacts a halogen with an amine to make an amine bond, and methods well known to those skilled in the art can be used. In the present invention, the reaction was performed under the same conditions as in Example 1, but this is only one example and is not limited thereto.

Step 2 is a step of preparing the compound of Formula 1 by deprotecting the amine-protecting group of the compound represented by Formula 2, which is not limited as long as it is performed under the condition capable of removing the amine-protecting group, and methods well known to those skilled in the art can be used. In the present invention, the reaction was performed under the same conditions as in Example 1, but this is only one example and is not limited thereto. An example of the protecting group may include a 2-(trimethylsilyl)ethoxymethyl group, a trimethylsilyl group (TMS), a benzyl group, or an acetyl group, and the like.

As confirmed through the following examples, the present invention provides a use of a pharmaceutical composition comprising the compound of Formula 1 above or a pharmaceutically acceptable salt thereof in prevention or treatment of a disease related to a protein kinase selected from the group consisting of ALK, ALK (C1156Y), ALK (L1196M), CLK1, CLK2, CLK3, CLK4, DYRK1A, DYRK1B, DYRK2, GAK, LRRK2, LRRK2 (G2019S), MYLK, and TTK.

In addition, the present invention provides a method for preventing or treating a disease related to a protein kinase selected from the group consisting of ALK, ALK (C1156Y), ALK (L1196M), CLK1, CLK2, CLK3, CLK4, DYRK1A, DYRK1B, DYRK2, GAK, LRRK2, LRRK2 (G2019S), MYLK, and TTK, comprising administering to a subject in need thereof a pharmaceutical composition comprising the compound of Formula 1 or a pharmaceutically acceptable salt thereof as an active ingredient.

In another aspect of the present invention, a pharmaceutical composition for preventing or treating a disease related to a protein kinase selected from the group consisting of ALK, ALK (C1156Y), ALK (L1196M), CLK1, CLK2, CLK3, CLK4, DYRK1A, DYRK1B, DYRK2, GAK, LRRK2, LRRK2 (G2019S), MYLK, and TTK, and preferably selected from the group consisting of LRRK2, LRRK2 (G2019S), DYRK1, CLK1 and TTK, comprising the compound of Formula 1, or an isomer thereof, a solvate thereof, a hydrate thereof or a pharmaceutically acceptable salt thereof as an active ingredient is provided.

The protein kinase-related disease may be one or more selected from the group consisting of cancers, degenerative brain diseases and inflammatory diseases.

The degenerative brain diseases may be one or more selected from the group consisting of Alzheimer's disease, Parkinson's disease, Lou Gehrig's disease, dementia, Huntington's disease, multiple sclerosis, amyotrophic lateral sclerosis, stroke, apoplexia cerebri and mild cognitive impairment.

The inflammatory diseases may be one or more selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, urethritis, cystitis, periodontitis and gingivitis.

The cancers may be one or more selected from the group consisting of triple-negative breast cancer, brain cancer, brain tumor, benign astrocytoma, malignant astrocytoma, pituitary adenoma, meningioma, brain lymphoma, oligodendroglioma, intracranial tumor, ependymoma, brain stem tumor, head and neck tumor, laryngeal cancer, oropharyngeal cancer, nasal/sinus cancer, nasopharyngeal cancer, salivary gland cancer, hypopharyngeal cancer, thyroid cancer, oral cancer, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cancer, female urethral cancer and skin cancer.

The compound may exhibit inhibitory activity against one or more protein kinases selected from the group consisting of LRRK2, LRRK2 (G2019S), DYRK1, CLK1 and TTK.

In particular, the compound of Formula 1 according to the present invention inhibits the proliferation of triple-negative breast cancer cells, and thus can be usefully used in the treatment of triple-negative breast cancer.

In addition, the compound of Formula 1 according to the present invention effectively inhibits DYRK1 phosphorylation in cancer-causing cells, and thus can be usefully used as a pharmaceutical composition for treating or preventing DYRK1-related diseases.

The compound of Formula 1 or a pharmaceutically acceptable salt thereof may be administered in various oral and parenteral formulations during clinical administration. In the case of formulation, it is prepared using diluents or excipients, such as fillers, extenders, binders, wetting agents, disintegrants and surfactants, which are commonly used. Solid preparations for oral administration include tablets, pills, powders, granules, capsules, and the like, and such a solid preparation is prepared by mixing at least one excipient, such as for example, starch, calcium carbonate, sucrose or lactose, and gelatin, in one or more compounds. In addition to simple excipients, lubricants such as magnesium stearate and talc are also used. Liquid preparations for oral administration include suspensions, internal solutions, emulsions, syrups, and the like, where various excipients, such as wetting agents, sweeteners, fragrances and preservatives, may be included, in addition to commonly used simple diluents such as water and liquid paraffin. Preparations for parenteral administration include sterile aqueous solutions, non-aqueous solutions, suspensions, and emulsions. As non-aqueous solvents and suspension solvents, propylene glycol, polyethylene glycol, vegetable oils such as olive oil, injectable esters such as ethyl oleate, and the like may be used.

A pharmaceutical composition comprising the compound of Formula 1 above or a pharmaceutically acceptable salt thereof as an active ingredient may be administered parenterally, where the parenteral administration is performed by a method of injecting subcutaneous injection, intravenous injection, intramuscular injection or intrathoracic injection.

At this time, in order to formulate a formulation for parenteral administration, the compound of Formula 1 or a pharmaceutically acceptable salt thereof is mixed in water together with a stabilizer or buffer to prepare a solution or suspension, which may be prepared in an ampoule or vial unit dosage form. The composition may be sterilized and/or contain adjuvants such as preservatives, stabilizing agents, wetting agents or emulsification accelerators, salts and/or buffers for regulating osmotic pressure, and other therapeutically useful substances, and may be formulated according to mixing, granulating or coating methods, which are usual methods.

Formulations for oral administration include, for example, tablets, pills, hard/soft capsules, solutions, suspensions, emulsifiers, syrups, granules, elixirs, troches, and the like, and these formulations contain diluents (e.g., lactose, dextrose, sucrose, mannitol, sorbitol, cellulose and/or glycine), lubricants (e.g., silica, talc, stearic acid and its magnesium or calcium salt and/or polyethylene glycol) in addition to the active ingredient. The tablets may contain binders such as magnesium aluminum silicate, starch paste, gelatin, methylcellulose, sodium carboxymethylcellulose and/or polyvinylpyrrolidine, and may optionally contain disintegrants such as starch, agar, alginic acid or its sodium salt, or boiling mixtures and/or absorbents, colorants, flavoring agents, and sweetening agents.

Hereinafter, the present invention will be described in detail by way of Examples and Experimental Examples. However, the following Examples and Experimental Examples are merely illustrative of the present invention, and the content of the present invention is not limited to the following Examples and Experimental Examples.

<Analysis and Purification Conditions>

The compounds synthesized in Examples of the present invention were purified by the following method or subjected to structural analysis.

1. Medium Pressure Liquid Chromatography (MPLC) for Purification

Medium pressure liquid chromatography was performed using TELEEDYNE ISCO's CombiFlash Rf+UV.

2. Analytical HPLC Conditions (ACQUITY UPLC H-Class Core System)

An equipment equipped with a mass QDA Detector manufactured by Waters was used in the UPLC system (ACQUITY UPLC PDA Detector) manufactured by Waters. The used column was Waters' ACQUITY UPLC®BEH C18 (1.7 µm, 2.1×50 mm), and it was performed such that the column temperature was at 30° C.

As Mobile phase A, water containing 0.1% formic acid was used, and as Mobile phase B, acetonitrile containing 0.1% formic acid was used.

Gradient condition (10-100% B for 3 minutes, movement speed=0.6 ml/min)

3. Prep-LCMS (Preparative-Liquid Chromatography Mass Spectrometry) for Purification An equipment equipped with a mass QDA Detector manufactured by Waters was used in the Autopurification HPLC system (2767 sample manager, 2545 binary gradient module, 2998 Photodiode Array Detector) manufactured by Waters. The used column was Waters' SunFire®Prep C18 OBD™ (5 µm, 19×50 mm), and it was performed such that the column temperature was at room temperature.

As Mobile phase A, water containing 0.035% trifluoroacetic acid was used, and as Mobile phase B, methanol containing 0.035% trifluoroacetic acid was used.

Gradient condition (15-100% B for 10 minutes, movement speed=25 ml/min)

4. Preparative-Liquid Chromatography UV Spectrometry (Prep-150 LC System) for Purification A Prep 150 LC system manufactured by Waters (2545 Quaternary gradient module, 2998 Photodiode Array Detector, Fraction collector III) was used. The column used was XTERRA®Prep RP18 OBD™ available from Waters (10 µm, 30×300 mm), and the column temperature was room temperature.

5. NMR Analysis

NMR analysis was performed using AVANCE II or AVANCE III 400 HD manufactured by Bruker, and data was expressed in parts per million (ppm) (6).

The used commercially available reagents were used without further purification. In the present invention, the room temperature refers to a temperature of 20 to 25° C. or so. For concentration under reduced pressure or solvent distillation removal, a rotary evaporator was used.

<Preparation Example 1-1> Preparation of 6-chloro-N-cyclopropyl-1-((2-(trimethylsilyl)ethoxy)methyl)-1H-pyrrolo[2,3-b]pyridin-4-amine The title compound was prepared through the method shown in Scheme 1 below.

[Scheme 1]

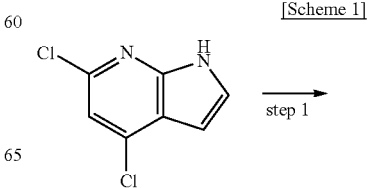

-continued

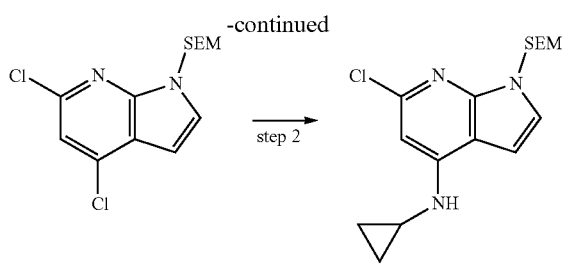

Step 1: 4,6-dichloro-1H-pyrrolo[2,3-b]pyridine (1.0 eq) was dissolved in DMF (0.7 M) under nitrogen, and then NaH (1.5 eq) was slowly added at 0° C. The reaction mixture was reacted at 0° C. for 30 minutes and stirred at 25° C. for 2 hours after further adding (2-(chloromethoxy)ethyl)trimethylsilane (1.2 eq). Distilled water was added to the reactant, and then an organic material was extracted with ethyl acetate (x3). The collected organic layers were washed with brine, and then concentrated under reduced pressure while the remaining water was removed using $Na_2SO_4$. The concentrated mixture was purified through MPLC (EtOAc:Hex) to obtain the target compound as a white solid. (Yield: 88%)

Step 2: 4,6-dichloro-1-((2-(trimethylsilyl)ethoxy)methyl)-1H-pyrrolo[2,3-b]pyridine (1.0 eq) was dissolved in NMP (1.0 M) under nitrogen, and then cyclopropylamine (2.0 eq) was slowly added thereto. The reaction mixture was stirred at 100° C. for 16 hours. Distilled water was added to the reactant, and then an organic material was extracted with EtOAc (x3). The collected organic layers were washed with brine, and then concentrated under reduced pressure while the remaining water was removed using $Na_2SO_4$. The concentrated mixture was purified through MPLC (EtOAc:Hex) to obtain the target compound as a white solid. (Yield: 17%)

<Preparation Example 1-2> Preparation of 6-chloro-N-methyl-1-((2-(trimethylsilyl)ethoxy)methyl)-1H-pyrrolo[2,3-b]pyridin-4-amine The title compound was prepared in a manner similar to Preparation Example 1-1. (Yield: 79%)

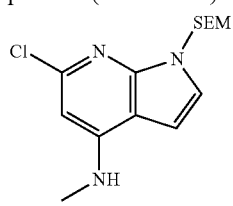

<Preparation Example 1-3> Preparation of 6-chloro-N-ethyl-1-((2-(trimethylsilyl)ethoxy)methyl)-1H-pyrrolo[2,3-b]pyridin-4-amine The title compound was prepared in a manner similar to Preparation Example 1-1. (Yield: 95%)

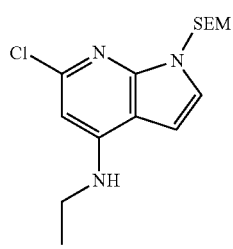 [SMILES: CCNc1cc(Cl)nc2c1ccn2COCC[Si](C)(C)C]

<Preparation Example 1-4> Preparation of 6-chloro-N-propyl-1-((2-(trimethylsilyl)ethoxy)methyl)-1H-pyrrolo[2,3-b]pyridin-4-amine The title compound was prepared in a manner similar to Preparation Example 1-1. (Yield: 50.6%)

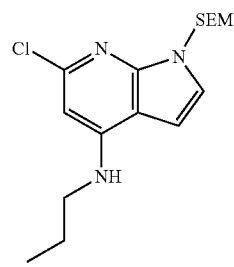 [SMILES: CCCNc1cc(Cl)nc2c1ccn2COCC[Si](C)(C)C]

<Preparation Example 1-5> Preparation of 6-chloro-N-isopropyl-1-((2-(trimethylsilyl)ethoxy)methyl)-1H-pyrrolo[2,3-b]pyridin-4-amine The title compound was prepared in a manner similar to Preparation Example 1-1. (Yield: 37.3%)

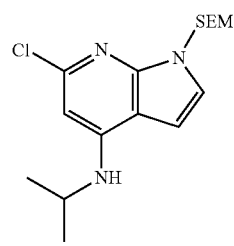 [SMILES: CC(C)Nc1cc(Cl)nc2c1ccn2COCC[Si](C)(C)C]

<Preparation Example 1-6> Preparation of 6-chloro-N-isobutyl-1-((2-(trimethylsilyl)ethoxy)methyl)-1H-pyrrolo[2,3-b]pyridin-4-amine The title compound was prepared in a manner similar to Preparation Example 1-1. (Yield: 37.6%)

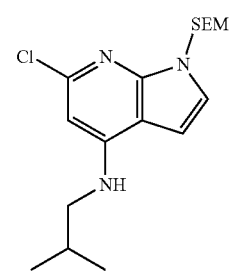 [SMILES: CC(C)CNc1cc(Cl)nc2c1ccn2COCC[Si](C)(C)C]

<Preparation Example 1-7> Preparation of 6-chloro-N-cyclobutyl-1-((2-(trimethylsilyl)ethoxy)methyl)-1H-pyrrolo[2,3-b]pyridin-4-amine The title compound was prepared in a manner similar to Preparation Example 1-1. (Yield: 78%)

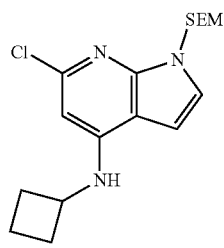 [SMILES: C[Si](C)(C)CCOCn1ccc2c(NC3CCC3)cc(Cl)nc21]

<Preparation Example 1-8> Preparation of 6-chloro-N-cyclopentyl-1-((2-(trimethylsilyl)ethoxy)methyl)-1H-pyrrolo[2,3-b]pyridin-4-amine The title compound was prepared in a manner similar to Preparation Example 1-1. (Yield: 53.8%)

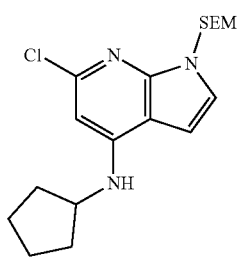 [SMILES: C[Si](C)(C)CCOCn1ccc2c(NC3CCCC3)cc(Cl)nc21]

<Preparation Example 1-9> Preparation of 6-chloro-N-cyclohexyl-1-((2-(trimethylsilyl)ethoxy)methyl)-1H-pyrrolo[2,3-b]pyridin-4-amine The title compound was prepared in a manner similar to Preparation Example 1-1. (Yield: 58.4%)

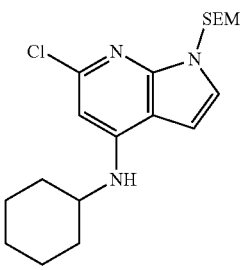 [SMILES: C[Si](C)(C)CCOCn1ccc2c(NC3CCCCC3)cc(Cl)nc21]

<Preparation Example 1-10> Preparation of 6-chloro-N-(2-(methylsulfonyl)ethyl)-1-((2-(trimethylsilyl)ethoxy)methyl)-1H-pyrrolo[2,3-b]pyridin-4-amine The title compound was prepared in a manner similar to Preparation Example 1-1. (Yield: 70.8%)

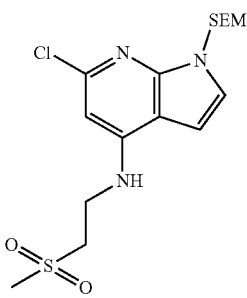 [SMILES: C[Si](C)(C)CCOCn1ccc2c(NCCS(C)(=O)=O)cc(Cl)nc21]

<Preparation Example 1-11> Preparation of 6-chloro-N-(cyclopropylmethyl)-1-((2-(trimethylsilyl)ethoxy)methyl)-1H-pyrrolo[2,3-b]pyridine-4-amine The title compound was prepared in a manner similar to Preparation Example 1-1. (Yield: 60.1%)

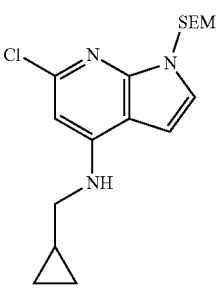 [SMILES: C[Si](C)(C)CCOCn1ccc2c(NCC3CC3)cc(Cl)nc21]

<Preparation Example 1-12> Preparation of 6-chloro-N-(2-methoxyethyl)-1-((2-(trimethylsilyl)ethoxy)methyl)-1H-pyrrolo[2,3-b]pyridine-4-amine The title compound was prepared in a manner similar to Preparation Example 1-1. (Yield: 63.6%)

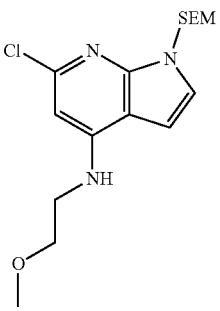 [SMILES: COCCNc1cc(Cl)nc2c1ccn2COCC[Si](C)(C)C]

<Preparation Example 1-13> Preparation of (R)-6-chloro-N-(1-methoxypropan-2-yl)-1-((2-(trimethylsilyl)ethoxy)methyl)-1H-pyrrolo[2,3-b]pyridin-4-amine The title compound was prepared in a manner similar to Preparation Example 1-1. (Yield: 30%)

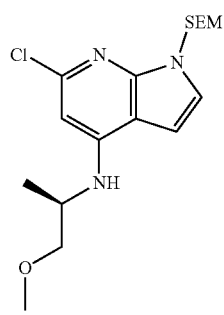 [SMILES: COC[C@@H](C)Nc1cc(Cl)nc2c1ccn2COCC[Si](C)(C)C]

<Preparation Example 1-14> Preparation of 6-chloro-N-(tetrahydro-2H-pyran-4-yl)-1-((2-(trimethylsilyl)ethoxy)methyl)-1H-pyrrolo[2,3-b]pyridin-4-amine The title compound was prepared in a manner similar to Preparation Example 1-1. (Yield: 45.7%)

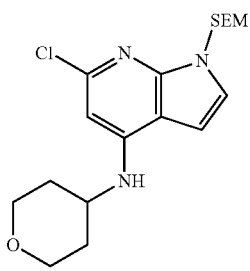 [SMILES: C[Si](C)(C)CCOCn1ccc2c(NC3CCOCC3)cc(Cl)nc21]

<Preparation Example 2-1> Preparation of 3,6-dichloro-N-cyclobutyl-1-((2-(trimethylsilyl)ethoxy)methyl)-1H-pyrrolo[2,3-b]pyridin-4-amine The title compound was prepared through the method shown in Scheme 2 below.

[Scheme 2]

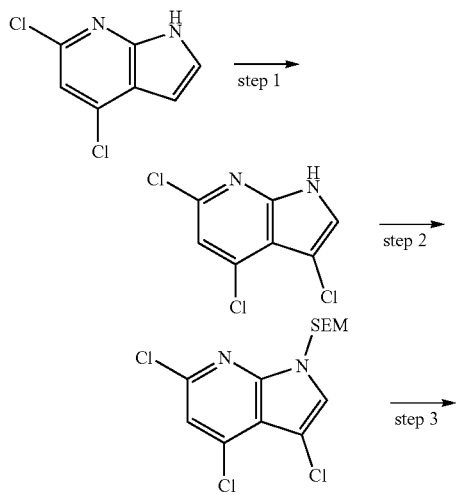

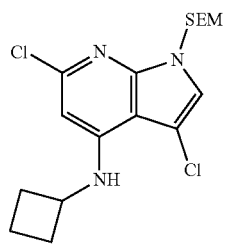

Step 1: 4,6-dichloro-1H-pyrrolo[2,3-b]pyridine (1.0 eq) was dissolved in DMF (0.5 M) under nitrogen, and then NCS (1.1 eq) was slowly added at 0° C. The reaction mixture was reacted at 0° C. for 10 minutes and stirred at room temperature for 4 hours. After adding ice water to the reactant, the resulting solid target compound was filtered. (Yield: 63%)

Step 2: 3,4,6-trichloro-1H-pyrrolo[2,3-b]pyridine (1.0 eq) was dissolved in DMF (1.1 M) under nitrogen, and then NaH (1.5 eq) was slowly added thereto at 0° C. The reaction mixture was reacted at 0° C. for 30 minutes, and stirred at 20° C. for 4 hours after further adding (2-(chloromethoxy)ethyl)trimethylsilane (1.2 eq). Distilled water was added to the reactant, and then an organic material was extracted with ethyl acetate (x3). The collected organic layers were washed with brine, and then concentrated under reduced pressure while the remaining water was removed using $Na_2SO_4$. The concentrated mixture was purified through MPLC (EtOAc:Hex) to obtain the target compound as a white solid. (Yield: 59%)

Step 3: 3,4,6-trichloro-1-((2-(trimethylsilyl)ethoxy)methyl)-1H-pyrrolo[2,3-b]pyridine (1.0 eq) was dissolved in NMP (1.0 M) under nitrogen, and then cyclobutylamine (5.0 eq) was slowly added thereto. The reaction mixture was stirred at 100° C. for 16 hours. Distilled water was added to the reactant, and then an organic material was extracted with EtOAc (x3). The collected organic layers were washed with brine, and then concentrated under reduced pressure while the remaining water was removed using $Na_2SO_4$. The concentrated mixture was purified through MPLC (EtOAc:Hex) to obtain the target compound as a white solid. (Yield: 98%)

<Preparation Example 2-2> Preparation of 3,6-dichloro-N-methyl-1-((2-(trimethylsilyl)ethoxy)methyl)-1H-pyrrolo[2,3-b]pyridin-4-amine The title compound was prepared in a manner similar to Preparation Example 2-1. (Yield: 86%)

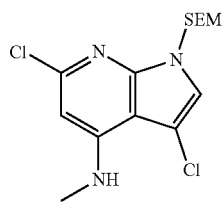

<Preparation Example 2-3> Preparation of 3,6-dichloro-N-ethyl-1-((2-(trimethylsilyl)ethoxy)methyl)-1H-pyrrolo[2,3-b]pyridin-4-amine The title compound was prepared in a manner similar to Preparation Example 2-1. (Yield: 62%)

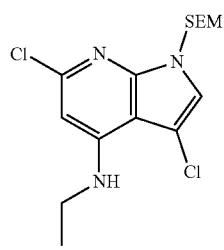

<Preparation Example 2-4> Preparation of 3,6-dichloro-N-propyl-1-((2-(trimethylsilyl)ethoxy)methyl)-1H-pyrrolo[2,3-b]pyridin-4-amine The title compound was prepared in a manner similar to Preparation Example 2-1. (Yield: 93%)

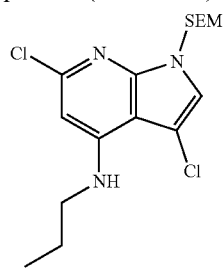

<Preparation Example 2-5> Preparation of 3,6-dichloro-N-isopropyl-1-((2-(trimethylsilyl)ethoxy)methyl)-1H-pyrrolo[2,3-b]pyridin-4-amine The title compound was prepared in a manner similar to Preparation Example 2-1. (Yield: 38%)

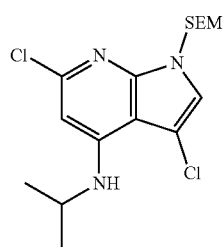 [SMILES: CC(C)Nc1cc(Cl)nc2c1c(Cl)cn2COCC[Si](C)(C)C]

<Preparation Example 2-6> Preparation of 3,6-dichloro-N-isobutyl-1-((2-(trimethylsilyl)ethoxy)methyl)-1H-pyrrolo[2,3-b]pyridin-4-amine The title compound was prepared in a manner similar to Preparation Example 2-1. (Yield: 84%)

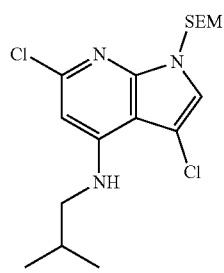 [SMILES: CC(C)CNc1cc(Cl)nc2c1c(Cl)cn2COCC[Si](C)(C)C]

<Preparation Example 2-7> Preparation of 3,6-dichloro-N-cyclopropyl-1-((2-(trimethylsilyl)ethoxy)methyl)-1H-pyrrolo[2,3-b]pyridin-4-amine The title compound was prepared in a manner similar to Preparation Example 2-1. (Yield: 79%)

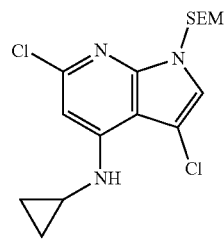

<Preparation Example 2-8> Preparation of 3,6-dichloro-N-cyclopentyl-1-((2-(trimethylsilyl)ethoxy)methyl)-1H-pyrrolo[2,3-b]pyridin-4-amine The title compound was prepared in a manner similar to Preparation Example 2-1. (Yield: 84%)

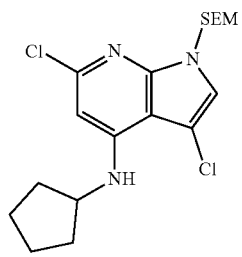 [SMILES: C[Si](C)(C)CCOCn1cc(Cl)c2c(NC3CCCC3)cc(Cl)nc21]

<Preparation Example 2-9> Preparation of 3,6-dichloro-N-cyclohexyl-1-((2-(trimethylsilyl)ethoxy)methyl)-1H-pyrrolo[2,3-b]pyridin-4-amine The title compound was prepared in a manner similar to Preparation Example 2-1. (Yield: 53%)

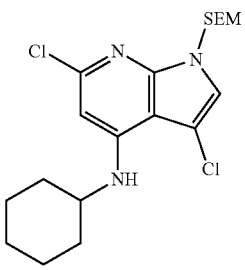 [SMILES: C[Si](C)(C)CCOCn1cc(Cl)c2c(NC3CCCCC3)cc(Cl)nc21]

<Preparation Example 2-10> Preparation of 3,6-dichloro-N-(2-(methylsulfonyl)ethyl)-1-((2-(trimethylsilyl)ethoxy)methyl)-1H-pyrrolo[2,3-b]pyridin-4-amine The title compound was prepared in a manner similar to Preparation Example 2-1. (Yield: 46%)

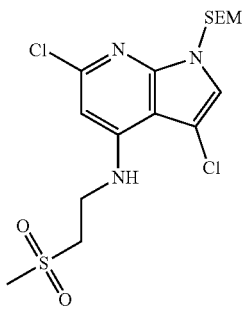 [SMILES: C[Si](C)(C)CCOCn1cc(Cl)c2c(NCCS(C)(=O)=O)cc(Cl)nc21]

<Preparation Example 2-11> Preparation of 3,6-dichloro-N-(2-methoxyethyl)-1-((2-(trimethylsilyl)ethoxy)methyl)-1H-pyrrolo[2,3-b]pyridin-4-amine The title compound was prepared in a manner similar to Preparation Example 2-1. (Yield: 79%)

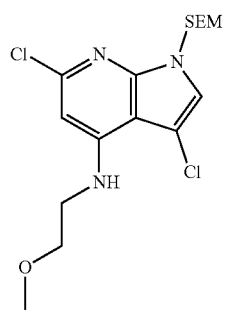 [SMILES: COCCNc1cc(Cl)nc2c1c(Cl)cn2COCC[Si](C)(C)C]

<Preparation Example 2-12> Preparation of 3,6-dichloro-N-(cyclopropylmethyl)-1-((2-(trimethylsilyl)ethoxy)methyl)-1H-pyrrolo[2,3-b]pyridine-4-amine The title compound was prepared in a manner similar to Preparation Example 2-1. (Yield: 83%)

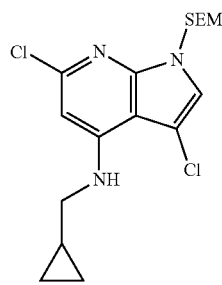 [SMILES: C[Si](C)(C)CCOCn1cc(Cl)c2c(NCC3CC3)cc(Cl)nc21]

<Preparation Example 3-1> Preparation of 6-dichloro-4-(ethylamino)-1-((2-(trimethylsilyl)ethoxy)methyl)-1H-pyrrolo[2,3-b]pyridine-3-carbonitrile The title compound was prepared through the method shown in Scheme 3 below.

[Scheme 3]

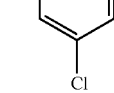

Step 1: 4,6-dichloro-1H-pyrrolo[2,3-b]pyridine (1.0 eq) was dissolved in DCM (0.3 M) under nitrogen, and then NIS (1.5 eq) was slowly added thereto at 0° C. The reaction mixture was reacted at 0° C. for 10 minutes and stirred at room temperature for 4 hours. After adding ice water to the reactant, the resulting solid target compound was filtered. The filtered target compound was washed with n-Hexane to obtain the target compound as a light brown solid. (Yield: 91%)

Step 2: 4,6-dichloro-3-iodo-1H-pyrrolo[2,3-b]pyridine (1.0 eq) was dissolved in DMF (0.5 M) under nitrogen, and then NaH (1.5 eq) was slowly added thereto at 0° C. The reaction mixture was reacted at 0° C. for 30 minutes, and then stirred at 20° C. for 4 hours after further adding (2-(chloromethoxy)ethyl)trimethylsilane (1.2 eq). Distilled water was added to the reactant, and then an organic material was extracted with ether (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 65%)

Step 3: 4,6-dichloro-3-iodo-1-((2-(trimethylsilyl)ethoxy)methyl)-1H-pyrrolo[2,3-b]pyridine (1.0 eq) was dissolved in EtOH (2.0 M), and then ethyl amine (5.0 eq) was slowly added thereto. The reaction mixture was stirred at 100° C.

for 16 hours. Distilled water was added to the reactant, and then an organic material was extracted with ether (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 44%)

Step 4: 6-chloro-N-ethyl-3-iodo-1-((2-(trimethylsilyl)ethoxy)methyl)-1H-pyrrolo[2,3-b]pyridin-4-amine (1.0 eq) was dissolved in DMF (0.25 M), and then CuI (0.7 eq) and CuCN (2.0 eq) were slowly added thereto. Pd(PPh$_3$)$_4$ (0.5 eq) was added thereto at 50° C. under nitrogen and the mixture was stirred at 80° C. for 16 hours. Distilled water was added to the reactant, and then an organic material was extracted with EtOAc (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 45%)

<Preparation Example 3-2> Preparation of 6-chloro-4-(methylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 78%)

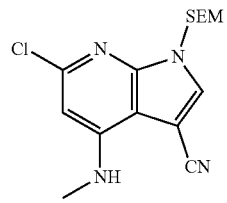 [SMILES: CNc1cc(Cl)nc2c1c(C#N)cn2COCC[Si](C)(C)C]

<Preparation Example 3-3> Preparation of 6-chloro-4-(propylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 66%)

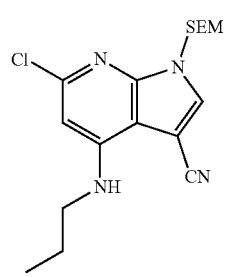 [SMILES: CCCNc1cc(Cl)nc2c1c(C#N)cn2COCC[Si](C)(C)C]

<Preparation Example 3-4> Preparation of 6-chloro-4-(cyclopentylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 70%)

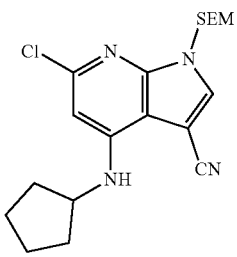 [SMILES: C[Si](C)(C)CCOCn1cc(C#N)c2c(NC3CCCC3)cc(Cl)nc21]

<Preparation Example 3-5> Preparation of 6-chloro-4-(cyclohexylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 74%)

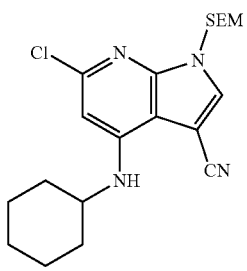 [SMILES: C[Si](C)(C)CCOCn1cc(C#N)c2c(NC3CCCCC3)cc(Cl)nc21]

<Preparation Example 3-6> Preparation of 6-chloro-4-((2-(methylsulfonyl)ethyl)amino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 52%)

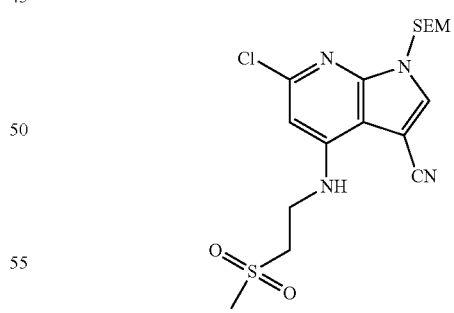

<Preparation Example 3-7> Preparation of 6-chloro-4-(cyclopropylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 67%)

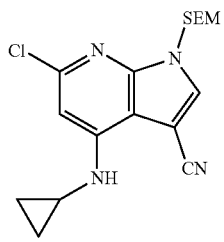 [SMILES: C[Si](C)(C)CCOCn1cc(C#N)c2c(NC3CC3)cc(Cl)nc21]

<Preparation Example 3-8> Preparation of 6-chloro-4-(cyclobutylamino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 97%)

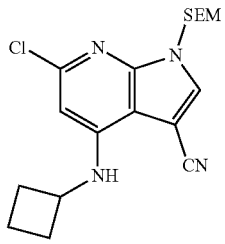 [SMILES: C[Si](C)(C)CCOCn1cc(C#N)c2c(NC3CCC3)cc(Cl)nc21]

<Preparation Example 3-9> Preparation of 6-chloro-4-((2-methoxyethyl)amino)-1-((2-(trimethylsilyl)ethoxy)methyl)-1H-pyrrolo[2,3-b]pyridine-3-carbonitrile The title compound was prepared in a manner similar to Preparation Example 3-1. (Yield: 73%)

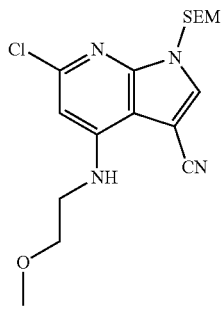 [SMILES: COCCNc1cc(Cl)nc2c1c(C#N)cn2COCC[Si](C)(C)C]

<Preparation Example 4-1> Preparation of 6-chloro-N-methyl-3-(trifluoromethyl)-1-((2-(trimethylsilyl)ethoxy)methyl)-1H-pyrrolo[2,3-b]pyridine-4-amino The title compound was prepared by the method shown in Scheme 4 below.

[Scheme 4]

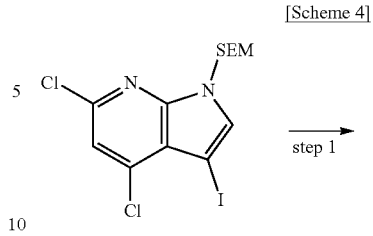

Step 1: CuI (5.0 eq) and KF (5.0 eq) were maintained at a temperature of 200° C. under reduced pressure near vacuum for 2 hours to remove moisture. After the reactant was cooled to room temperature, TMS-CF$_3$ (5.0 eq) was dissolved in DMF and NMP (1:1 ratio, total 0.2 M) under nitrogen, and then slowly added thereto through a syringe. The reaction mixture was reacted for 1 hour at room temperature, and 4-dichloro-3-iodo-1-((2-(trimethylsilyl)ethoxy)methyl)-1H-pyrrolo[2,3-b]pyridine (1.0 eq) was further dissolved in DMF and NMP (1:1 ratio, total 0.2 M), and then slowly added thereto through a syringe. The reaction mixture was stirred at 50° C. for 16 hours. Distilled water was added to the reactant, and then an organic material was extracted with ether (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 74%)

Step 2: 4,6-dichloro-3-(trifluoromethyl)-1-((2-(trimethylsilyl)ethoxy)methyl)-1H-pyrrolo[2,3-b]pyridine (1.0 eq) was dissolved in DMSO (1.0 M) under nitrogen, and then K$_2$CO$_3$ (3.0 eq) and 33% methyl amine in ethanol (5.0 eq) were slowly added thereto. The reaction mixture was stirred at 100° C. for 16 hours. Distilled water was added to the reactant, and then an organic material was extracted with EtOAc (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 52%)

<Preparation Example 4-2> Preparation of 6-chloro-N-ethyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 88%)

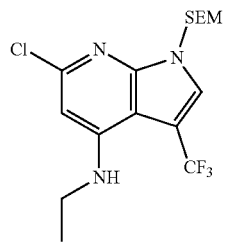 [SMILES: CCNc1cc(Cl)nc2c1c(C(F)(F)F)cn2COCC[Si](C)(C)C]

<Preparation Example 4-3> Preparation of 6-chloro-N-propyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 61%)

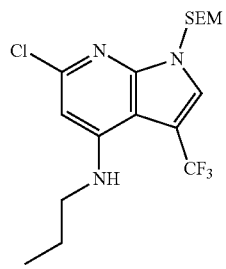 [SMILES: CCCNc1cc(Cl)nc2c1c(C(F)(F)F)cn2COCC[Si](C)(C)C]

<Preparation Example 4-4> Preparation of N-butyl-6-chloro-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 50.2%)

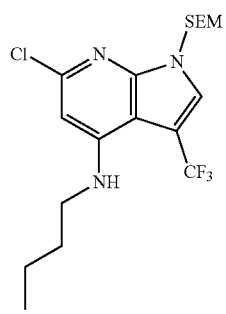

<Preparation Example 4-5> Preparation of 6-chloro-N-isopropyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 57%)

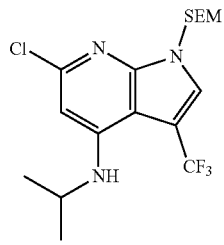 [SMILES: CC(C)Nc1cc(Cl)nc2c1c(C(F)(F)F)cn2COCC[Si](C)(C)C]

<Preparation Example 4-6> Preparation of 6-chloro-N-isobutyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 69%)

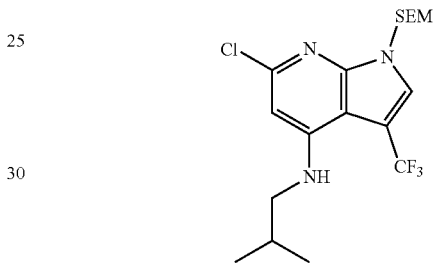

<Preparation Example 4-7> Preparation of 6-chloro-N-(2-(methylsulfonyl)ethyl)-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 20%)

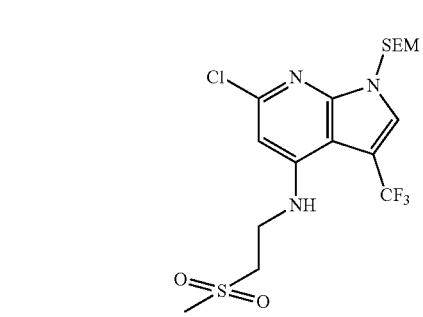 [SMILES: C[Si](C)(C)CCOCn1cc(C(F)(F)F)c2c(NCCS(C)(=O)=O)cc(Cl)nc21]

<Preparation Example 4-8> Preparation of 6-chloro-N-(2-methoxyethyl)-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 68%)

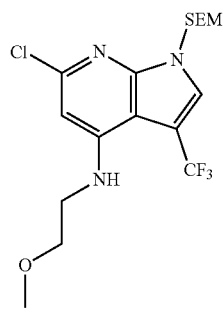

<Preparation Example 4-9> Preparation of 6-chloro-N-(2-ethoxyethyl)-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 88%)

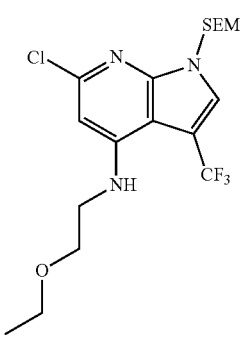 [SMILES: CCOCCNc1cc(Cl)nc2c1c(C(F)(F)F)cn2COCC[Si](C)(C)C]

<Preparation Example 4-10> Preparation of 6-chloro-N-cyclopropyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 62%)

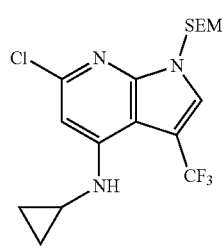

<Preparation Example 4-11> Preparation of 6-chloro-N-cyclobutyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 45.9%)

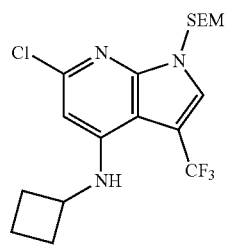 [SMILES: C[Si](C)(C)CCOCn1cc(C(F)(F)F)c2c(NC3CCC3)cc(Cl)nc21]

<Preparation Example 4-12> Preparation of 6-chloro-N-cyclopentyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 62%)

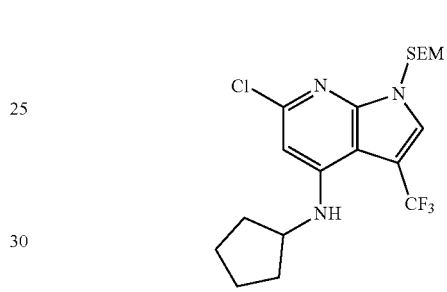

<Preparation Example 4-13> Preparation of 6-chloro-N-cyclohexyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 58%)

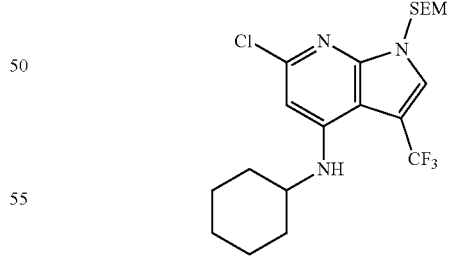

<Preparation Example 4-14> Preparation of (R)-6-chloro-N-(1-methoxypropan-2-yl)-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 49%)

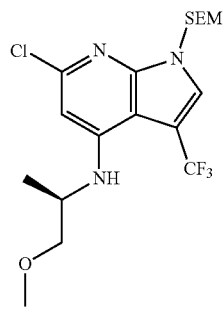 [SMILES: COC[C@@H](C)Nc1cc(Cl)nc2c1c(C(F)(F)F)cn2COCC[Si](C)(C)C]

<Preparation Example 4-15> Preparation of 6-chloro-N-(oxetan-3-yl)-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 21%)

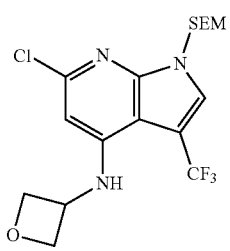 [SMILES: C[Si](C)(C)CCOCn1cc(C(F)(F)F)c2c(NC3COC3)cc(Cl)nc21]

<Preparation Example 4-16> Preparation of $N^1$-(6-chloro-3-(trifluoromethyl)-1-((2-(trimethylsilyl)ethoxy)methyl)-1H-pyrrolo[2,3-b]pyridin-4-yl)-$N^2$,$N^2$-dimethylethane-1,2-diamine The title compound was prepared in a manner similar to Preparation Example 4-1. (Yield: 14.7%)

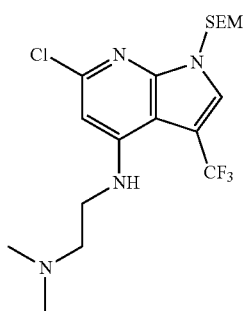 [SMILES: CN(C)CCNc1cc(Cl)nc2c1c(C(F)(F)F)cn2COCC[Si](C)(C)C]

<Preparation Example 4-17> Preparation of 6-chloro-N-(2-(isopropylsulfonyl)ethyl-3-(trifluoromethyl)-1-((2-(trimethylsilyl)ethoxy)methyl)-1H-pyrrolo[2,3-b]pyridin-4-amine The title compound was prepared in a manner similar to Preparation Example 4-1. (Yield: 10%)

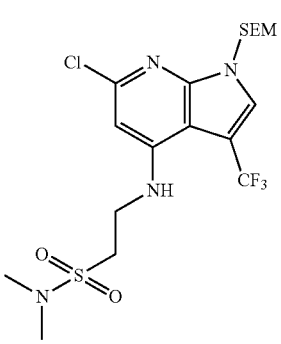 [SMILES: CN(C)S(=O)(=O)CCNc1cc(Cl)nc2c1c(C(F)(F)F)cn2COCC[Si](C)(C)C]

<Preparation Example 4-18> Preparation of 2-((6-chloro-3-(trifluoromethyl)-1-((2-(trimethylsilyl)ethoxy)methyl)-1H-pyrrolo[2,3-b]pyridin-4-yl)amino-N,N-dimethylethane-1-sulfonamide The title compound was prepared in a manner similar to Preparation Example 4-1. (Yield: 15%)

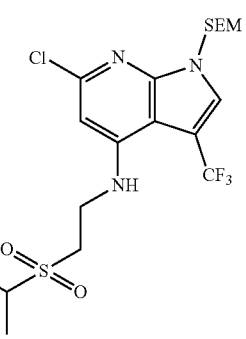

<Preparation Example 5-1> Preparation of 6-chloro-4-cyclopropyl-3-(trifluoromethyl)-1-((2-(trimethylsilyl)ethoxy)methyl)-1H-pyrrolo[2,3-b]pyridine The title compound was prepared by the method shown in Scheme 5 below.

[Scheme 5]

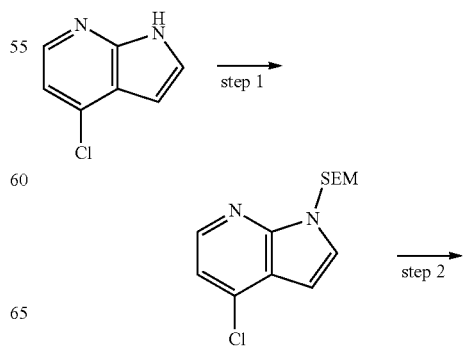

-continued

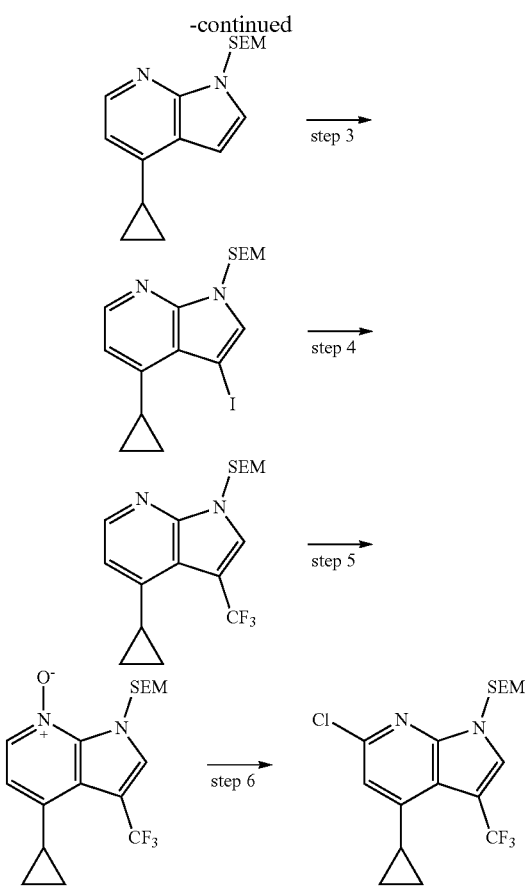

Step 1: 4-chloro-1H-pyrrolo[2,3-b]pyridine (1.0 eq) was dissolved in DMF (0.5 M) under nitrogen, and then NaH (1.2 eq) was slowly added thereto at 0° C. The reaction mixture was reacted at 0° C. for 30 minutes, and then stirred at 25° C. for 2 hours after further adding (2-(chloromethoxy) ethyl)trimethylsilane (1.2 eq). Distilled water was added to the reactant, and then an organic material was extracted with ethyl acetate (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 81%)

Step 2: 4-chloro-1-((2-(trimethylsilyl)ethoxy)methyl)-1H-pyrrolo[2,3-b]pyridine (1.0 eq), cyclopropylboronic acid (2.0 eq) and cesium carbonate (2.0 eq) were dissolved in toluene (0.5 M), and then sonicated for 1 minute to remove gas. Pd$_2$(dba)$_3$ (0.15 eq) and Xantphos (0.1 eq) were added thereto under nitrogen, and then reacted at 120° C. for 16 hours. The reaction mixture was filtered through Celite and washed with DCM. The resulting filtrate was concentrated and then purified through MPLC (EtOAc:Hex) to obtain the target compound as a white solid. (Yield: 75%)

Step 3: 4-cyclopropyl-1-((2-(trimethylsilyl)ethoxy)methyl)-1H-pyrrolo[2,3-b]pyridine (1.0 eq) wad dissolved in DMF (1.5 M) under nitrogen, and then NIS (1.5 eq) was slowly added thereto at 0° C. The reaction mixture was reacted at 0° C. for 10 minutes and stirred at room temperature for 2 hours. After adding ice water to the reactant, the resulting solid target compound was filtered. The filtered target compound was washed with n-Hexane to obtain the target compound as a light brown solid. (Yield: 53%)

Step 4: CuI (5.0 eq) and KF (5.0 eq) were maintained at a temperature of 200° C. under reduced pressure near vacuum for 2 hours to remove moisture. After the reactant was cooled to room temperature, TMS-CF$_3$ (5.0 eq) was dissolved in DMF and NMP (1:1 ratio, total 1.0 M) under nitrogen, and then slowly added thereto through a syringe. The reaction mixture was reacted for 1 hour at room temperature, and 4-cyclopropyl-3-iodo-1-((2-(trimethylsilyl)ethoxy)methyl)-1H-pyrrolo[2,3-b]pyridine (1.0 eq) was further dissolved in DMF and NMP (1:1 ratio, total 1.0 M), and then slowly added thereto through a syringe. The reaction mixture was stirred at 50° C. for 16 hours. Distilled water was added to the reactant, and then an organic material was extracted with ethyl acetate (x3). The collected organic layers were washed with brine, and then concentrated under reduced pressure while the remaining water was removed using Na$_2$SO$_4$. The concentrated mixture was purified through MPLC (EtOAc:Hex) to obtain the target compound as a white solid. (Yield: 90%)

Step 5: 4-cyclopropyl-3-(trifluoromethyl)-1-((2-(trimethylsilyl)ethoxy)methyl)-1H-pyrrolo[2,3-b]pyridine (1.0 eq) was dissolved in chloroform (0.25 M), and then 3-chloroperbenzoic acid (3.0 eq) was added thereto, and the reaction was carried out at 75° C. for 16 hours using a reflux device. The reaction was terminated by adding Na$_2$S$_2$O$_3$ and water to the reactant at 0° C., and an organic material was extracted with DCM (x3). The collected organic layers were washed with brine, and then concentrated under reduced pressure while the remaining water was removed using Na$_2$SO$_4$. The concentrated mixture was used in the next step without further purification. (Yield: 105%)

Step 6: 4-(cyclopropyl-3-(trifluoromethyl)-1-((2-(trimethylsilyl)ethoxy)methyl)-1H-pyrrolo[2,3-b]pyridine 7-oxide (1.0 eq) was dissolved in DMF (0.3 M), and then methanesulfonyl chloride (4.0 eq) was added thereto and reacted at 80° C. for 30 minutes. The reaction was terminated by adding water to the reactant at 0° C., and an organic material was extracted EtOAc (x3) after titration to pH 8 further using aq. NaHCO$_3$. The collected organic layers were washed with brine, and then the remaining water was removed using Na$_2$SO$_4$. The reactant was purified through MPLC (EtOAc:Hex) to obtain the target compound as an ivory solid. (yield: 38%).

<Preparation Example 6-1> Preparation of 6-chloro-4-cyclopropyl-1-((2-(trimethylsilyl)ethoxy)methyl)-1H-pyrrolo[2,3-b]pyridine-3-carbonitrile The title compound was prepared by the method shown in Scheme 6 below.

[Scheme 6]

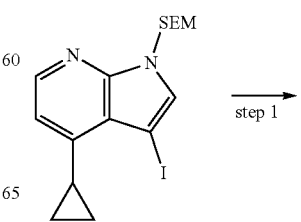

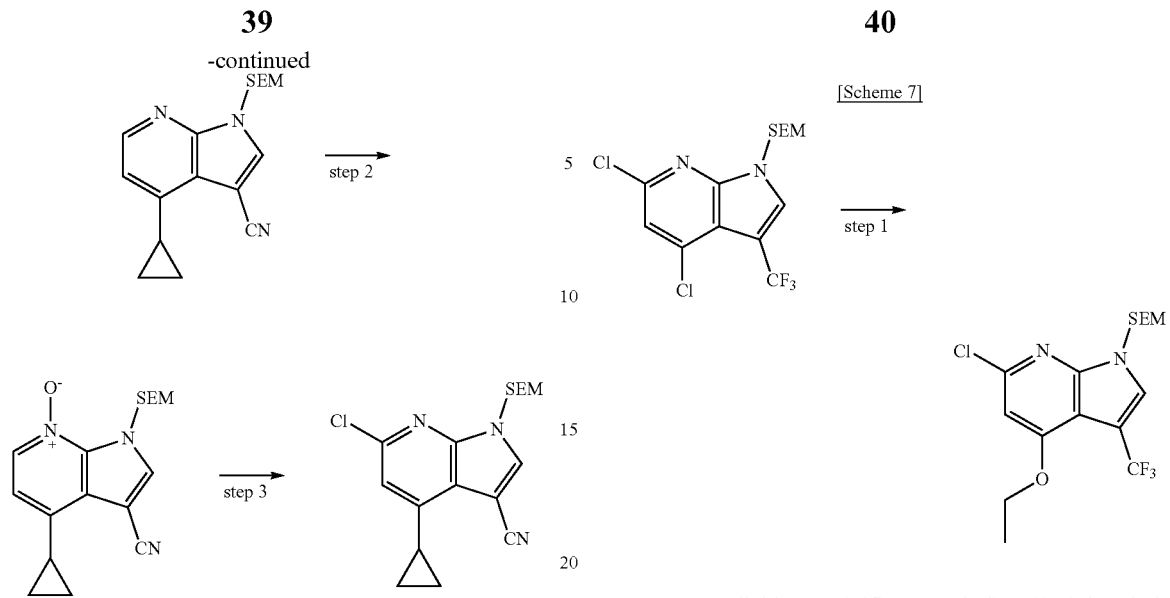

Step 1: 4-cyclopropyl-3-iodo-1-((2-(trimethylsilyl)ethoxy)methyl)-1H-pyrrolo[2,3-b]pyridine (1.0 eq) was dissolved in DMF (0.5 M), and then CuI (0.7 eq) and CuCN (2.0 eq) were slowly added thereto. Pd(PPh₃)₄ (0.5 eq) was added thereto at 50° C. under nitrogen and stirred at 80° C. for 16 hours. Distilled water was added to the reactant, and then an organic material was extracted with EtOAc (x3). The collected organic layers were washed with brine, and then concentrated under reduced pressure while the remaining water was removed using Na₂SO₄. The concentrated mixture was purified through MPLC (EtOAc:Hex) to obtain the target compound as a white solid. (Yield: 76%)

Step 2: 4-cyclopropyl-1-((2-(trimethylsilyl)ethoxy)methyl)-1H-pyrrolo[2,3-b]pyridine-3-carbonitrile (1.0 eq) was dissolved in chloroform (0.18 M), and then 3-chloroperbenzoic acid (3.0 eq) was added thereto, and the reaction was carried out at 75° C. for 16 hours using a reflux device. The reaction was terminated by adding Na₂S₂O₃ and water to the reactant at 0° C., and an organic material was extracted with DCM (x3). The collected organic layers were washed with brine, and then concentrated under reduced pressure while the remaining water was removed using Na₂SO₄. The concentrated mixture was used in the next step without further purification. (Yield: 110%)

Step 3: 3-cyano-4-cyclopropyl-1-((2-(trimethylsilyl)ethoxy)methyl)-1H-pyrrolo[2,3-b]pyridine-7-oxide (1.0 eq) was dissolved in DMF (0.3 M), and then methanesulfonyl chloride (4.0 eq) was added thereto and reacted at 80° C. for 30 minutes. The reaction was terminated by adding water to the reactant at 0° C., and an organic material was extracted with EtOAc (x3) after titration to pH 8 further using aq. NaHCO₃. The collected organic layer was washed with brine, and then the remaining water was removed using Na₂SO₄. The reactant was purified through MPLC (EtOAc:Hex) to obtain the target compound as a white solid. (Yield: 49%)

<Preparation Example 7-1> Preparation of 6-chloro-4-ethoxy-3-(trifluoromethyl)-1-((2-(trimethylsilyl)ethoxy)methyl)-1H-pyrrolo[2,3-b]pyridine The title compound was prepared by the method shown in Scheme 7 below.

Step 1: 4,6-dichloro-3-(trifluoromethyl)-1-((2-(trimethylsilyl)ethoxy)methyl)-1H-pyrrolo[2,3-b]pyridine (1.0 eq) was dissolved in THF (1.0 M) under nitrogen, and then NaH (1.1 eq) and 33% ethanol (1.5 eq) were slowly added thereto. The reaction mixture was stirred at room temperature for 16 hours. Distilled water was added to the reactant, and then an organic material was extracted with EtOAc (x3). The collected organic layers were washed with brine, and then concentrated under reduced pressure while the remaining water was removed using Na₂SO₄. The concentrated mixture was purified through MPLC (EtOAc:Hex) to obtain the target compound as a white solid. (Yield: 19%)

<Example 1> Preparation 1 of the Compound According to the Present Invention

A pyrrolopyridine derivative compound according to the present invention was prepared in the same manner as shown in Scheme 8 below.

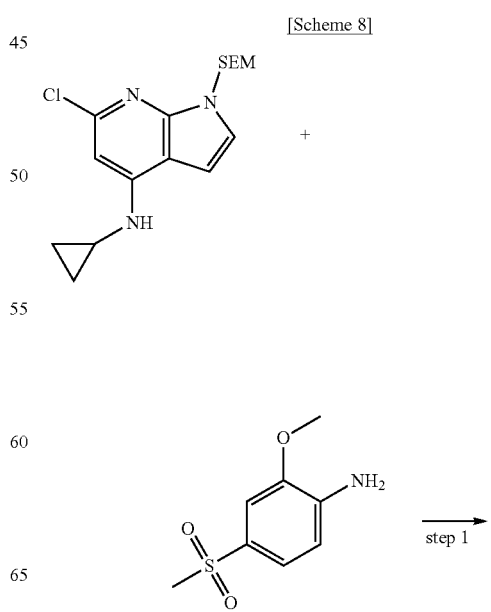

-continued

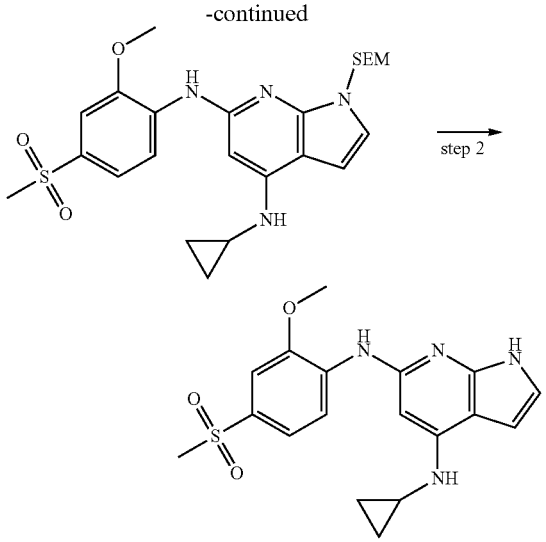

Step 1: The compound (1.0 eq) prepared in Step 2 of Scheme 1, 2-methoxy-4-(methylsulfonyl)aniline (1.2 eq) and K$_2$CO$_3$ (5.0 eq) were added to sec-BuOH (0.1 M) and dissolved, and then sonicated for 1 minute to remove gas. Pd$_2$(dba)$_3$ (0.1 eq) and Xphos (0.1 eq) were added to the reaction mixture at 80° C. under nitrogen, and then stirred at 100° C. for 2 hours. The reaction mixture was filtered through celite and washed with ethyl acetate. After concentration of the resulting filtrate, the mixture of the resulting liquids was used in the next step without further purification. (Yield: 104%)

Step 2: N$^4$-Cyclopropyl-N$^6$-(2-methoxy-4-(methylsulfonyl)phenyl)-1-((2-(trimethylsilyl)ethoxy)methyl)-1H-pyrrolo[2,3-b]pyridine-4,6-diamine (1.0 eq) was dissolved in CH$_2$Cl$_2$ (0.1 M), and then TFA (73 eq) was added at room temperature. After reaction for 2 hours, the solvent was removed. The concentrated mixture was again dissolved in 1,4-dioxane (0.1 M), and then NH$_4$OH (0.1 M) was added thereto, and the mixture was reacted at 60° C. for 2 hours. After the reaction, the solvent was removed by concentration under reduced pressure. The concentrated mixture was purified through Pre-HPLC to obtain the target compound as a solid. (Yield: 86%)

Examples 2 to 267 were prepared in a manner similar to that of Example 1, and the chemical structures, compound names, and NMR, mass and HPLC analysis results of Examples 1 to 267 were summarized and shown in Table 1 below.

TABLE 1

| Compound of Example | Structure | Compound Name | $^1$H NMR, MS | Yield (%) | HPLC r.t. (min), Purity |
|---|---|---|---|---|---|
| 1 | 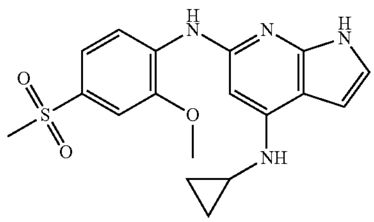 [SMILES: COc1cc(S(C)(=O)=O)ccc1Nc1cc(NC2CC2)c2cc[nH]c2n1] | N$^4$-cyclopropyl-N$^6$-(2-methoxy-4-(methylsulfonyl)phenyl)-1H-pyrrolo[2,3-b]pyridine-4,6-diamine | $^1$H NMR (400 MHZ, MeOD) δ 7.97 (d, J = 8.3 Hz, 1H), 7.56 (dt, J = 5.8, 1.9 Hz, 2H), 7.34 (dd, J = 8.3, 2.0 Hz, 1H), 7.29 (d, J = 2.0 Hz, 1H), 7.00 (d, J = 3.5 Hz, 1H), 6.61 (d, J = 3.5 Hz, 1H), 4.05 (s, 3H), 3.94 (s, 2H), 3.17 (s, 3H), 3.07 (s, 2H), 1.29 (ddd, J = 12.6, 9.9, 7.1 Hz, 3H), 0.91 (dt, J = 6.6, 5.1 Hz, 2H), 0.73-0.68 (m, 2H).; 373.3[M + H]$^+$ | 86 | 1.14 |
| 2 | 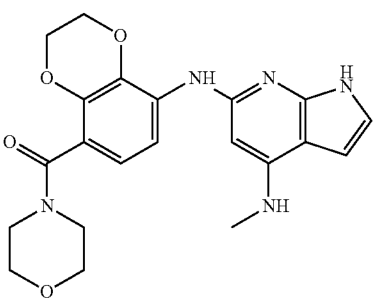 [SMILES: CNc1cc(Nc2ccc(C(=O)N3CCOCC3)c3c2OCCO3)nc2[nH]ccc12] | (8-((4-(Methylamino)-1H-pyrrolo[2,3-b]pyridine-6-yl)amino)-2,3-dihydrobenzo[b][1,4]dioxin-5-yl)(morpholino)methanone | 410.3[M + H]$^+$ | 2 | 1.01 |
| 3 | 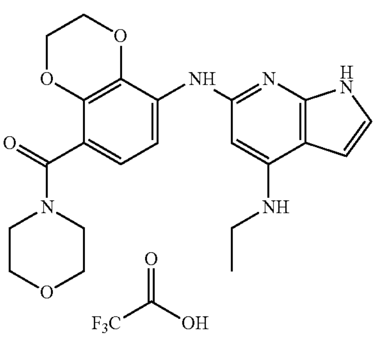 [SMILES: CCNc1cc(Nc2ccc(C(=O)N3CCOCC3)c3c2OCCO3)nc2[nH]ccc12 ; O=C(O)C(F)(F)F] | (8-((4-(ethylamino)-1H-pyrrolo[2,3-b]pyridin-6-yl)amino)-2,3-dihydrobenzo[b][1,4]dioxin-5-yl)(morpholino)methanone 2,2,2-trifluoroacetate | $^1$H NMR (400 MHZ, MeOD) δ 7.09 (d, J = 8.2 Hz, 1H), 7.00 (dd, J = 15.6, 5.9 Hz, 2H), 6.72 (d, J = 3.5 Hz, 1H), 5.93 (s, 1H), 4.41 (d, J = 25.3 Hz, 6H), 3.73 (s, 10H), 3.46 (s, 5H), 1.46-1.32 (m, 7H). 424.3 [M + H]$^+$ | 20 | 1.02 |

TABLE 1-continued

| Compound of Example | Structure | Compound Name | ¹H NMR, MS | Yield (%) | HPLC r.t. (min), Purity |
|---|---|---|---|---|---|
| 4 | 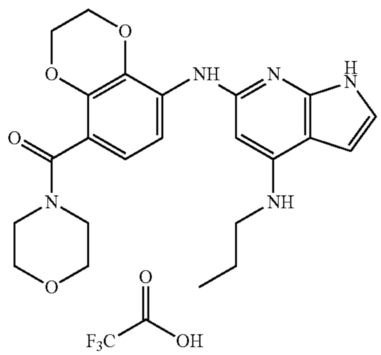 | morpholino(8-((4-(propylamino)-1H-pyrrolo[2,3-b]pyridin-6-yl)amino)-2,3-dihydrobenzo [b][1,4]dioxin-5-yl)(morpholino) methanone 2,2,2-trifluoroacetate | ¹H NMR (400 MHZ, MeOD) δ 7.08 (d, J = 8.2 Hz, 1H), 7.00 (dd, J = 16.2, 5.8 Hz, 2H), 6.72 (d, J = 3.4 Hz, 1H), 5.93 (s, 1H), 4.44 (s, 6H), 3.78 (d, J = 44.3 Hz, 10H), 3.49 (d, J = 20.3 Hz, 3H), 1.81 (dq, J = 14.5, 7.3 Hz, 3H), 1.42-1.29 (m, 4H), 1.09 (dd, J = 17.1, 9.7 Hz, 4H), 0.97 (d, J = 7.9 Hz, 2H). 438.3 [M + H]⁺ | 20 | 1.14 |
| 5 | 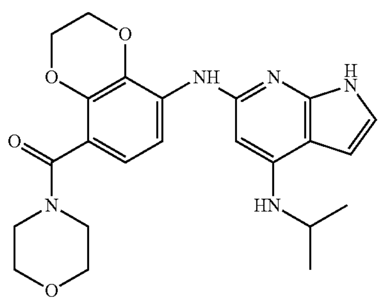 [SMILES: CC(C)Nc1cc(Nc2ccc(C(=O)N3CCOCC3)c3c2OCCO3)nc2[nH]ccc12] | (8-((4-(isopropylamino)-1H-pyrrolo[2,3-b]pyridin-6-yl)amino)-2,3-dihydrobenzo[b][1,4]dioxin-5-yl)(morpholino) methanone | 438.3[M + H]⁺ | 11 | 1.09 |
| 6 | 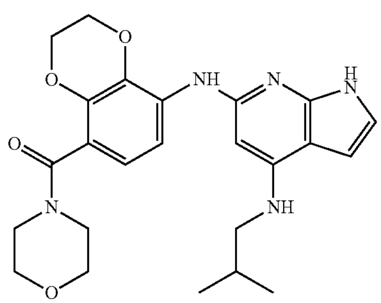 [SMILES: CC(C)CNc1cc(Nc2ccc(C(=O)N3CCOCC3)c3c2OCCO3)nc2[nH]ccc12] | (8-((4-(isobutylamino)-1H-pyrrolo[2,3-b]pyridin-6-yl)amino)-2,3-dihydrobenzo [b][1,4]dioxin-5-yl)(morpholino) methanone | 452.3[M + H]⁺ | 42 | 1.20 |
| 7 | 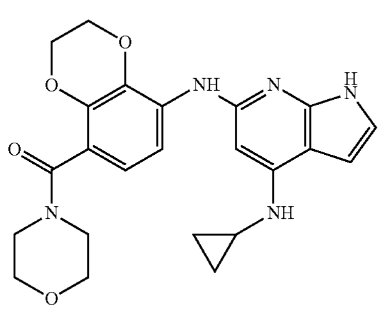 [SMILES: O=C(c1ccc(Nc2cc(NC3CC3)c3cc[nH]c3n2)c2c1OCCO2)N1CCOCC1] | (8-((4-(cyclopropylamino)-1H-pyrrolo[2,3-b]pyridin-6-yl)amino)-2,3-dihydrobenzo [b][1,4]dioxin-5-yl)(morpholino) methanone | ¹H NMR (400 MHZ, MeOD) δ 7.65 (d, J = 8.4 Hz, 1H), 6.95 (d, J = 3.5 Hz, 1H), 6.87 (d, J = 8.4 Hz, 1H), 6.52 (d, J = 3.5 Hz, 1H), 6.34 (s, 1H), 4.42 (dd, J = 12.1, 3.8 Hz, 4H), 3.81 (s, 4H), 3.72 (dd, J = 10.7, 4.7 Hz, 2H), 3.48 (d, J = 23.8 Hz, 2H), 2.67-2.58 (m, 1H), 0.92-0.85 (m, 2H), 0.73-0.65 (m, 2H).; 436.3[M + H]⁺ | 69 | 1.05 |

TABLE 1-continued

| Compound of Example | Structure | Compound Name | ¹H NMR, MS | Yield (%) | HPLC r.t. (min), Purity |
|---|---|---|---|---|---|
| 8 | 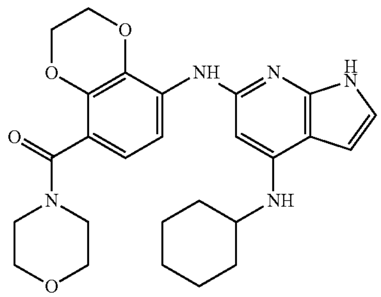 [SMILES: O=C(c1ccc(Nc2cc(NC3CCCCC3)c3cc[nH]c3n2)c2c1OCCO2)N1CCOCC1] | (8-((4-(cyclohexylamino)-1H-pyrrolo[2,3-b]pyridin-6-yl)amino)-2,3-dihydrobenzo[b][1,4]dioxin-5-yl)(morpholino)methanone | ¹H NMR (400 MHZ, MeOD) δ 10.84 (s, 1H), 8.09 (s, 1H), 7.70 (s, 1H), 6.81-6.78 (m, 1H), 6.69 (d, J = 8.5 Hz, 1H), 6.50 (dd, J = 3.3, 2.1 Hz, 1H), 6.15 (s, 1H), 6.01 (s, 1H), 4.33 (dd, J = 16.4, 4.1 Hz, 4H), 3.57 (d, J = 23.5 Hz, 6H), 3.27 (s, 2H), 2.02 (s, 1H), 1.78 (d, J = 12.9 Hz, 2H), 1.43-1.21 (m, 7H).; 478.3[M + H]⁺ | 92 | 1.28 |
| 9 | 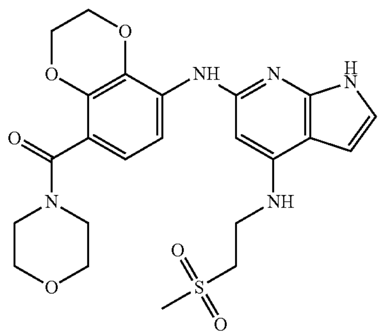 [SMILES: CS(=O)(=O)CCNc1cc(Nc2ccc(C(=O)N3CCOCC3)c3c2OCCO3)nc2[nH]ccc12] | (8-((4-((2-(methylsulfonyl)ethyl)amino)-1H-pyrrolo[2,3-b]pyridin-6-yl)amino)-2,3-dihydrobenzo[b][1,4]dioxin-5-yl)(morpholino)methanone | 502.3[M + H]⁺ | 2 | 0.95 |
| 10 | 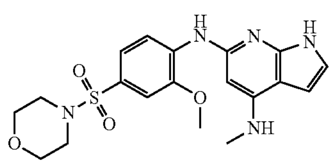 [SMILES: CNc1cc(Nc2ccc(S(=O)(=O)N3CCOCC3)cc2OC)nc2[nH]ccc12] | N⁶-(2-methoxy-4-(morpholinosulfonyl)phenyl)-N⁴-methyl-1H-pyrrolo[2,3-b]pyridine-4,6-diamine | 418.3[M + H]⁺ | 5 | 1.11 |
| 11 | 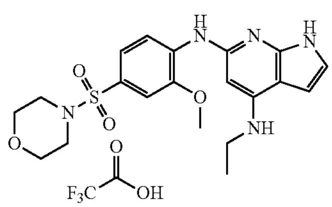 | N⁴-ethyl-N⁶-(2-methoxy-4-(morpholinosulfonyl)phenyl)-1H-pyrrolo[2,3-b]pyridine-4,6-diamine 2,2,2-trifluoroacetate | ¹H NMR (400 MHZ, MeOD) δ 7.66 (d, J = 8.3 Hz, 1H), 7.53 7.45 (m, 2H), 7.09 (d, J = 3.5 Hz, 1H), 6.77 (d, J = 3.5 Hz, 1H), 6.16 (s, 1H), 4.09 (s, 3H), 3.84-3.78 (m, 4H), 3.51 (dd, J = 14.2, 7.0 Hz, 2H), 3.13-3.07 (m, 4H), 1.39 (dt, J = 21.5, 7.7 Hz, 5H) 432.3[M + H]⁺ | 12 | 1.20 |
| 12 | 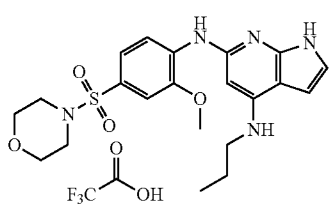 | N⁶-(2-methoxy-4-(morpholinosulfonyl)phenyl)-N⁴-propyl-1H-pyrrolo[2,3-b]pyridine-4,6-diamine 2,2,2-trifluoroacetate | ¹H NMR (400 MHZ, MeOD) δ 7.64 (d, J = 8.3 Hz, 1H), 7.53 7.44 (m, 2H), 7.10 (d, J = 3.5 Hz, 1H), 6.78 (t, J = 4.9 Hz, 1H), 6.15 (s, 1H), 4.09 (d, J = 7.4 Hz, 4H), 3.83-3.75 (m, 5H), 3.43 (s, 2H), 3.13-3.06 (m, 5H), 1.89-1.77 (m, 2H), 1.39 (d, J = 20.7 Hz, 1H), 1.11 (t, J = 7.4 Hz, 4H). 446.3 [M + H]⁺ | 20 | 1.27 |
| 13 | 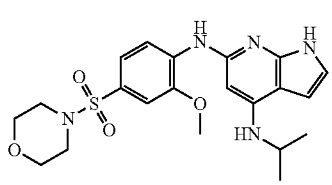 [SMILES: COc1cc(S(=O)(=O)N2CCOCC2)ccc1Nc1cc(NC(C)C)c2cc[nH]c2n1] | N⁴-isopropyl-N⁶-(2-methoxy-4-(morpholinosulfonyl)phenyl)-1H-pyrrolo[2,3-b]pyridine-4,6-diamine | 446.3[M + H]⁺ | 28 | 1.23 |

TABLE 1-continued

| Compound of Example | Structure | Compound Name | $^1$H NMR, MS | Yield (%) | HPLC r.t. (min), Purity |
|---|---|---|---|---|---|
| 14 | 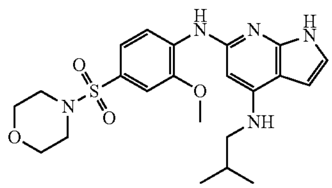 [SMILES: COc1cc(S(=O)(=O)N2CCOCC2)ccc1Nc1cc(NCC(C)C)c2cc[nH]c2n1] | $N^4$-isobutyl-$N^6$-(2-methoxy-4-(morpholinosulfonyl)phenyl)-1H-pyrrolo[2,3-b]pyridine-4,6-diamine | 460.3[M + H]$^+$ | 50 | 1.31 |
| 15 | 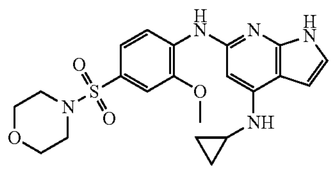 [SMILES: COc1cc(S(=O)(=O)N2CCOCC2)ccc1Nc1cc(NC2CC2)c2cc[nH]c2n1] | $N^4$-cyclopropyl-$N^6$-(2-methoxy-4-(morpholinosulfonyl)phenyl)-1H-pyrrolo[2,3-b]pyridine-4,6-diamine | $^1$H NMR (400 MHZ, MeOD) δ 7.72 (d, J = 8.3 Hz, 1H), 7.45 (dd, J = 8.3, 1.9 Hz, 1H), 7.41 (d, J = 1.8 Hz, 1H), 7.19 (dd, J = 8.3, 2.0 Hz, 1H), 7.11 (d, J = 1.9 Hz, 1H), 7.03 (d, J = 3.6 Hz, 2H), 6.81 (d, J = 8.3 Hz, 1H), 6.69 (d, J = 3.5 Hz, 1H), 6.44 (s, 1H), 4.04 (s, 3H), 3.92 (s, 2H), 3.78-3.68 (m, 9H), 3.34 (dt, J = 3.3, 1.6 Hz, 4H), 3.07-3.02 (m, 4H), 2.97-2.91 (m, 4H), 2.75-2.68 (m, 1H), 1.33-1.23 (m, 8H), 1.02-0.86 (m, 6H), 0.73 (dd, J = 3.6, 2.2 Hz, 2H).; 444.3[M + H]$^+$ | 66 | 1.23 |
| 16 | 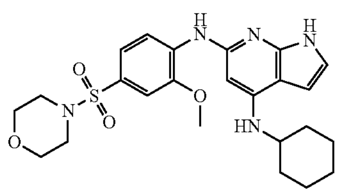 [SMILES: COc1cc(S(=O)(=O)N2CCOCC2)ccc1Nc1cc(NC2CCCCC2)c2cc[nH]c2n1] | $N^4$-cyclohexyl-$N^6$-(2-methoxy-4-(morpholinosulfonyl)phenyl)-1H-pyrrolo[2,3-b]pyridine-4,6-diamine | $^1$H NMR (400 MHZ, DMSO) δ 10.90 (s, 1H), 8.88 (s, 1H), 8.08 (s, 1H), 7.23 (dd, J = 8.6, 2.0 Hz, 1H), 7.13 (d, J = 1.9 Hz, 1H), 6.88-6.83 (m, 1H), 6.55-6.50 (m, 1H), 6.15 (s, 1H), 3.97 (s, 3H), 3.66-3.61 (m, 4H), 2.91-2.84 (m, 4H), 2.02 (d, J = 11.2 Hz, 2H), 1.79 (d, J = 12.9 Hz, 2H), 1.67 (d, J = 13.0 Hz, 1H), 1.44-1.12 (m, 7H), 0.85 (ddd, J = 10.6, 9.6, 5.1 Hz, 1H).; 486.3[M + H]$^+$ | 98 | 1.35 |
| 17 | 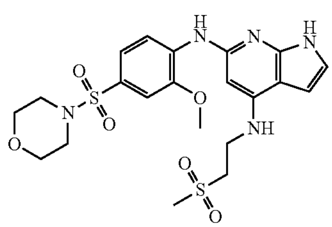 [SMILES: COc1cc(S(=O)(=O)N2CCOCC2)ccc1Nc1cc(NCCS(C)(=O)=O)c2cc[nH]c2n1] | $N^6$-(2-methoxy-4-(morpholinosulfonyl)phenyl)-$N^4$-(2-(methylsulfonyl)ethyl)-1H-pyrrolo[2,3-b]pyridine-4,6-diamine | 510.3[M + H]$^+$ | 14 | 1.10 |
| 18 | 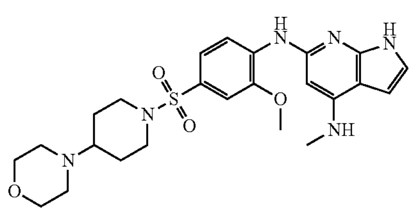 [SMILES: CNc1cc(Nc2ccc(S(=O)(=O)N3CCC(N4CCOCC4)CC3)cc2OC)nc2[nH]ccc12] | $N^6$-(2-methoxy-4-((4-morpholinopiperidin-1-yl)sulfonyl)phenyl)-$N^4$-methyl-1H-pyrrolo[2,3-b]pyridine-4,6-diamine | 501.3[M + H]$^+$ | 26 | 0.95 |
| 19 | 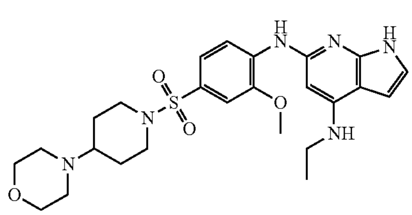 [SMILES: CCNc1cc(Nc2ccc(S(=O)(=O)N3CCC(N4CCOCC4)CC3)cc2OC)nc2[nH]ccc12] | $N^4$-ethyl-$N^6$-(2-methoxy-4-((4-morpholinopiperidin-1-yl)sulfonyl)phenyl)-1H-pyrrolo[2,3-b]pyridine-4,6-diamine | 515.4[M + H]$^+$ | 20 | 1.02 |

TABLE 1-continued

| Compound of Example | Structure | Compound Name | ¹H NMR, MS | Yield (%) | HPLC r.t. (min), Purity |
|---|---|---|---|---|---|
| 20 | 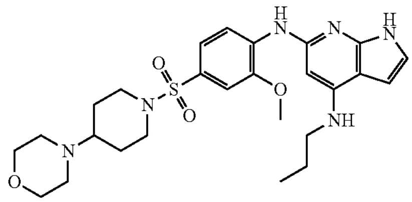 [SMILES: CCCNc1cc(Nc2ccc(S(=O)(=O)N3CCC(N4CCOCC4)CC3)cc2OC)nc2[nH]ccc12] | $N^6$-(2-methoxy-4-((4-morpholinopiperidin-1-yl)sulfonyl)phenyl)-$N^4$-propyl-1H-pyrrolo[2,3-b]pyridine-4,6-diamine | 529.3[M + H]⁺ | 47 | 1.06 |
| 21 | 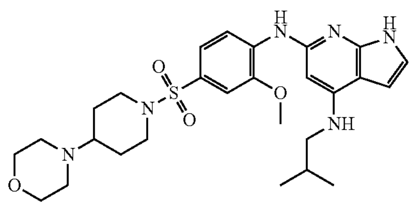 [SMILES: COc1cc(S(=O)(=O)N2CCC(N3CCOCC3)CC2)ccc1Nc1cc(NCC(C)C)c2cc[nH]c2n1] | $N^4$-isobutyl-$N^6$-(2-methoxy-4-((4-morpholinopiperidin-1-yl)sulfonyl)phenyl)-1H-pyrrolo[2,3-b]pyridine-4,6-diamine | ¹H NMR (400 MHZ, MeOD) δ 7.61-7.35 (m, 4H), 7.03 (s, 1H), 6.73 (d, J = 3.2 Hz, 1H), 4.12-3.96 (m, 7H), 3.86 (t, J = 11.6 Hz, 2H), 3.53 (d, J = 11.6 Hz, 2H), 3.20 (s, 4H), 2.57 (t, J = 11.3 Hz, 2H), 2.29 (d, J = 9.5 Hz, 2H), 2.16-1.97 (m, 1H), 1.85 (d, J = 8.7 Hz, 2H), 1.31 (s, 2H), 1.05 (d, J = 6.3 Hz, 7H).; 543.4[M + H]⁺ | 83 | 1.09 |
| 22 | 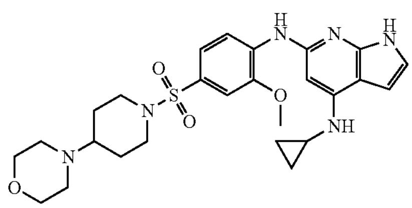 [SMILES: COc1cc(S(=O)(=O)N2CCC(N3CCOCC3)CC2)ccc1Nc1cc(NC2CC2)c2cc[nH]c2n1] | $N^4$-cyclopropyl-$N^6$-(2-methoxy-4-((4-morpholinopiperidin-1-yl)sulfonyl)phenyl)-1H-pyrrolo[2,3-b]pyridine-4,6-diamine | ¹H NMR (400 MHZ, MeOD) δ 7.50 (d, J = 8.1 Hz, 1H), 7.36 (d, J = 8.3 Hz, 1H), 7.32 (s, 1H), 6.91 (d, J = 3.3 Hz, 1H), 6.55 (s, 1H), 3.92 (s, 7H), 3.75 (t, J = 11.8 Hz, 2H), 3.41 (d, J = 12.3 Hz, 2H), 3.21 (dt, J = 3.3, 1.6 Hz, 3H), 2.59 (s, 1H), 2.45 (t, J = 11.6 Hz, 2H), 2.19 (d, J = 11.6 Hz, 2H), 1.74 (qd, J = 12.3, 4.1 Hz, 2H), 1.19 (s, 1H), 0.83 (d, J = 5.7 Hz, 2H), 0.66-0.59 (m, 2H).; 527.4[M + H]⁺ | 62 | 1.00 |
| 23 | 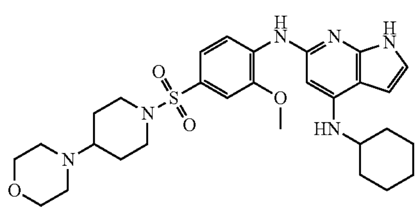 [SMILES: COc1cc(S(=O)(=O)N2CCC(N3CCOCC3)CC2)ccc1Nc1cc(NC2CCCCC2)c2cc[nH]c2n1] | $N^4$-cyclohexyl-$N^6$-(2-methoxy-4-((4-morpholinopiperidin-1-yl)sulfonyl)phenyl)-1H-pyrrolo[2,3-b]pyridine-4,6-diamine | ¹H NMR (400 MHZ, DMSO) δ 10.87 (s, 1H), 8.88 (d, J = 8.6 Hz, 1H), 8.02 (s, 1H), 7.22 (dd, J = 8.6, 1.9 Hz, 1H), 7.13 (d, J = 2.0 Hz, 1H), 6.84 (dd, J = 3.2, 2.5 Hz, 1H), 6.51 (dd, J = 3.3, 2.1 Hz, 1H), 6.13 (s, 1H), 6.08 (d, J = 8.0 Hz, 1H), 3.96 (s, 3H), 3.64 (d, J = 11.6 Hz, 2H), 3.52 (s, 5H), 3.42-3.26 (m, 5H), 2.39 (s, 5H), 2.23 (d, J = 10.6 Hz, 2H), 2.02 (d, J = 11.3 Hz, 2H), 1.91 (s, 2H), 1.84-1.74 (m, 4H), 1.67 (d, J = 12.6 Hz, 1H), 1.47-1.15 (m, 9H).; 569.4[M + H]⁺ | 84 | 1.14 |
| 24 | 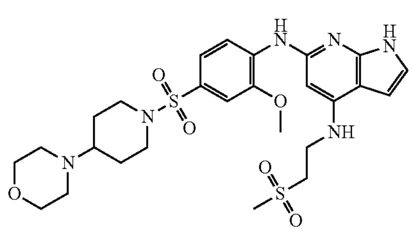 [SMILES: COc1cc(S(=O)(=O)N2CCC(N3CCOCC3)CC2)ccc1Nc1cc(NCCS(C)(=O)=O)c2cc[nH]c2n1] | $N^6$-(2-methoxy-4-((4-morpholinopiperidin-1-yl)sulfonyl)phenyl)-$N^4$-(2-(methylsulfonyl)ethyl)-1H-pyrrolo[2,3-b]pyridine-4,6-diamine | 593.4[M + H]⁺ | 26 | 0.91 |
| 25 | 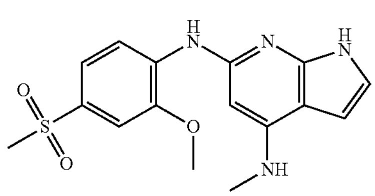 [SMILES: CNc1cc(Nc2ccc(S(C)(=O)=O)cc2OC)nc2[nH]ccc12] | $N^6$-(2-methoxy-4-(methylsulfonyl)phenyl)-$N^4$-methyl-1H-pyrrolo[2,3-b]pyridine-4,6-diamine | 347.2[M + H]⁺ | 16 | 1.01 |

TABLE 1-continued

| Compound of Example | Structure | Compound Name | ¹H NMR, MS | Yield (%) | HPLC r.t. (min), Purity |
|---|---|---|---|---|---|
| 26 | 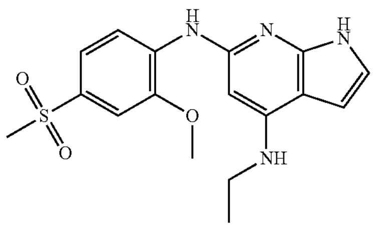 [SMILES: CCNc1cc(Nc2ccc(S(C)(=O)=O)cc2OC)nc2[nH]ccc12] | $N^4$-ethyl-$N^6$-(2-methoxy-4-(methylsulfonyl)phenyl)-1H-pyrrolo[2,3-b]pyridine-4,6-diamine | 361.3[M + H]⁺ | 23 | 1.07 |
| 27 | 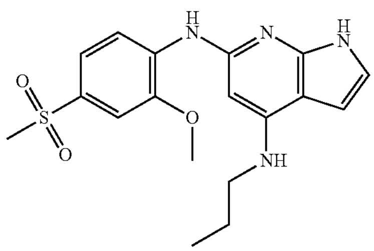 [SMILES: CCCNc1cc(Nc2ccc(S(C)(=O)=O)cc2OC)nc2[nH]ccc12] | $N^6$-(2-methoxy-4-(methylsulfonyl)phenyl)-$N^4$-propyl-1H-pyrrolo[2,3-b]pyridine-4,6-diamine | 375.3[M + H]⁺ | 24 | 1.15 |
| 28 | 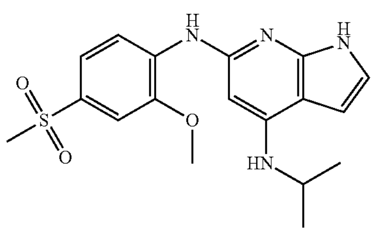 | $N^4$-isopropyl-$N^6$-(2-methoxy-4-(methylsulfonyl)phenyl)-1H-pyrrolo[2,3-b]pyridine-4,6-diamine | 366.3[M + H]⁺ | 10 | 1.15 |
| 29 | 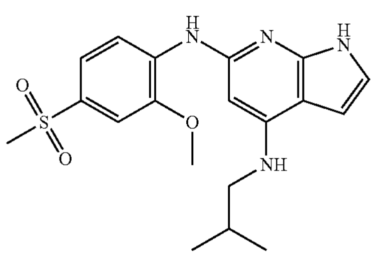 | $N^4$-isobutyl-$N^6$-(2-methoxy-4-(methylsulfonyl)phenyl)-1H-pyrrolo[2,3-b]pyridine-4,6-diamine | 424.3[M + H]⁺ | 34 | 1.08 |
| 30 | 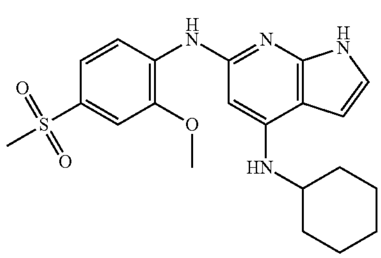 [SMILES: COc1cc(S(C)(=O)=O)ccc1Nc1cc(NC2CCCCC2)c2cc[nH]c2n1] | $N^4$-cyclohexyl-$N^6$-(2-methoxy-4-(methylsulfonyl)phenyl)-1H-pyrrolo[2,3-b]pyridine-4,6-diamine | ¹H NMR (400 MHZ, DMSO) δ 10.91 (s, 1H), 8.87 (d, J = 8.2 Hz, 1H), 8.05 (s, 1H), 7.43-7.31 (m, 2H), 6.85 (dd, J = 3.2, 2.5 Hz, 1H), 6.52 (dd, J = 3.3, 2.1 Hz, 1H), 6.14 (s, 2H), 3.98 (s, 3H), 3.16 (s, 3H), 2.02 (d, J = 11.5 Hz, 2H), 1.83-1.73 (m, 2H), 1.67 (d, J = 12.7 Hz, 1H), 1.45-1.11 (m, 6H).; 415.3[M + H]⁺ | 84 | 1.32 |
| 31 | 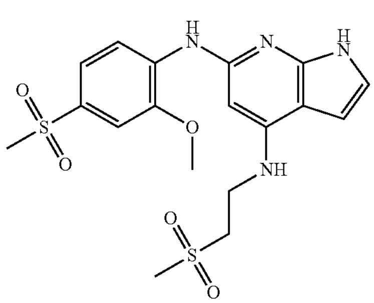 [SMILES: COc1cc(S(C)(=O)=O)ccc1Nc1cc(NCCS(C)(=O)=O)c2cc[nH]c2n1] | $N^6$-(2-methoxy-4-(methylsulfonyl)phenyl)-$N^4$-(2-(methylsulfonyl)ethyl)-1H-pyrrolo[2,3-b]pyridine-4,6-diamine | ¹H NMR (400 MHZ, MeOD) δ 7.80 (d, J = 8.7 Hz, 1H), 7.61 (dd, J = 6.6, 2.0 Hz, 2H), 7.05 (d, J = 3.5 Hz, 1H), 6.65 (d, J = 3.5 Hz, 1H), 6.18 (s, 1H), 4.04 (s, 3H), 3.96-3.89 (m, 2H), 3.53 (t, J = 6.7 Hz, 2H), 3.17 (s, 3H), 3.05 (s, 4H), 1.31 (s, 6H), 0.91 (d, J = 7.1 Hz, 1H).; 439.2[M + H]⁺ | 48 | 0.98 |

TABLE 1-continued

| Compound of Example | Structure | Compound Name | $^1$H NMR, MS | Yield (%) | HPLC r.t. (min), Purity |
|---|---|---|---|---|---|
| 32 | 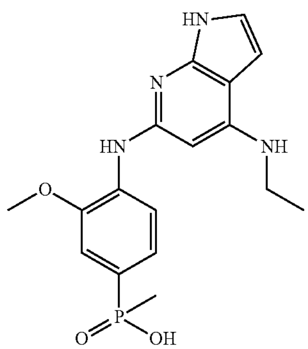 [SMILES: CCNc1cc(Nc2ccc(P(C)(=O)O)cc2OC)nc2[nH]ccc12] | (4-((4-(ethylamino)-1H-pyrrolo[2,3-b]pyridin-6-yl)amino)-3-methoxyphenyl)(methyl)phosphinic acid | 361.3[M + H]$^+$ | 20 | 0.99 |
| 33 | 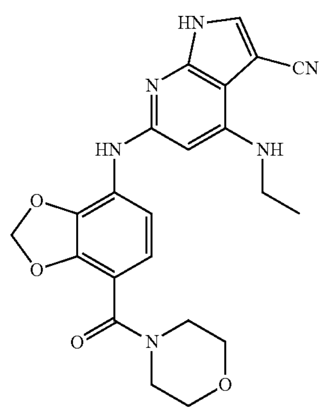 [SMILES: CCNc1cc(Nc2ccc(C(=O)N3CCOCC3)c3c2OCO3)nc2[nH]cc(C#N)c12] | 4-(ethylamino)-6-((7-(morpholine-4-carbonyl)benzo[d][1,3]dioxin-4-yl)amino)-1H-pyrrolo[2,3-b]pyridine-3-carbonitrile | $^1$H NMR (400 MHZ, DMSO-d$_6$) δ 12.09 (s, 1H), 8.65 (s, 1H), 8.30 (s, 1H), 7.83 (s, 1H), 7.45 (s, 1H), 6.87-6.80 (m, 1H), 6.14 (s, 1H), 6.10 (s, 2H), 3.60 (s, 6H), 3.43 (s, 2H), 3.24 (s, 2H), 1.25 (s, 3H).; 435.3 [M + H]$^+$ | 92 | 1.13 |
| 34 | 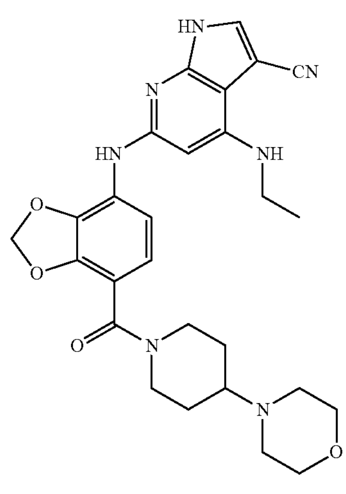 [SMILES: CCNc1cc(Nc2ccc(C(=O)N3CCC(N4CCOCC4)CC3)c3c2OCO3)nc2[nH]cc(C#N)c12] | 4-(ethylamino)-6-((7-(4-morpholinopiperidine-1-carbonyl)benzo[d][1,3]dioxol-4-yl)amino)-1H-pyrrolo[2,3-b]pyridine-3-carbonitrile | $^1$H NMR (400 MHZ, DMSO-d$_6$) δ 12.13 (s, 1H), 8.50 (s, 1H), 7.87 (d, J = 8.8 Hz, 1H), 7.80 (s, 1H), 7.68 (s, 1H), 6.78 (s, 1H), 6.15 (s, 1H), 6.08 (s, 2H), 3.56 (s, 5H), 3.23 (s, 5H), 2.45 (s, 5H), 1.65 (s, 4H), 1.24 (s, 3H).; 518.4 [M + H]$^+$ | 18 | 0.96 |

TABLE 1-continued

| Compound of Example | Structure | Compound Name | $^1$H NMR, MS | Yield (%) | HPLC r.t. (min), Purity |
|---|---|---|---|---|---|
| 35 | 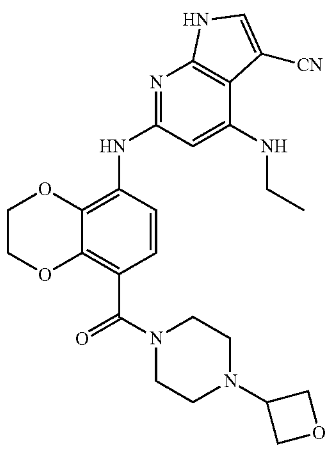 | 4-(ethylamino)-6-((8-(4-(oxetan-3-yl)piperazine-1-carbonyl)-2,3-dihydrobenzo[b][1,4]dioxin-5-yl)amino)-1H-pyrrolo[2,3-b]pyridine-3-carbonitrile | $^1$H NMR (400 MHZ, DMSO) δ 12.07 (s, 1H), 8.16-8.08 (m, 1H), 7.95 (s, 1H), 7.81 (s, 1H), 6.71-6.63 (m, 1H), 6.26 (s, 1H), 5.29 (s, 1H), 4.53 (d, J = 3.3 Hz, 2H), 4.43 (d, J = 3.0 Hz, 2H), 4.32 (d, J = 21.6 Hz, 4H), 3.61 (s, 2H), 3.42 (d, J = 4.4 Hz, 1H), 3.25 (d, J = 3.8 Hz, 4H), 2.34-2.11 (m, 4H), 1.25 (d, J = 3.3 Hz, 3H).; 504.4 [M + H]$^+$ | 57 | 0.96 |
| 36 | 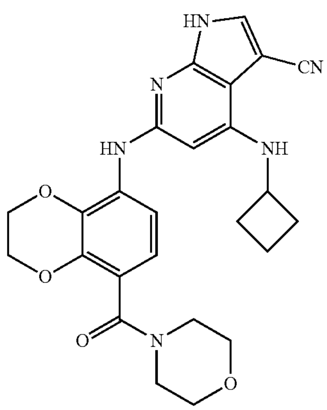 [SMILES: N#Cc1c[nH]c2nc(Nc3ccc(C(=O)N4CCOCC4)c4c3OCCO4)cc(NC3CCC3)c12] | 4-(cyclobutylamino)-6-((8-(morpholine-4-carbonyl)-2,3-dihydrobenzo[b][1,4]dioxin-5-yl)amino)-1H-pyrrolo[2,3-b]pyridine-3-carbonitrile | 493.4[M + H]$^+$ | 20 | 0.97 |
| 37 | 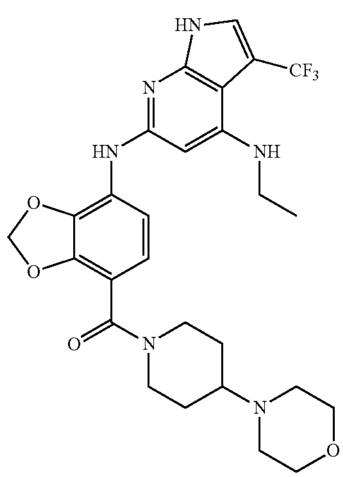 | (7-((4-(ethylamino)-3-(trifluoromethyl)-1H-pyrrolo[2,3-b]pyridin-6-yl)amino)benzo[d][1,3]dioxol-4-yl)(4-morpholinopiperidin-1-yl)methanone | 561.4[M + H]$^+$ | 15 | 1.09 |

TABLE 1-continued

| Compound of Example | Structure | Compound Name | ¹H NMR, MS | Yield (%) | HPLC r.t. (min), Purity |
|---|---|---|---|---|---|
| 38 | 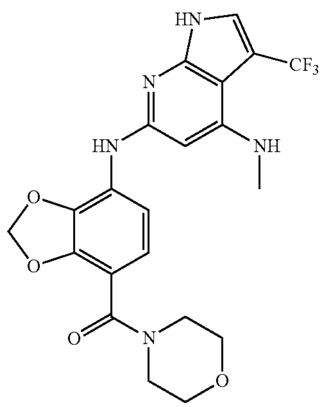 [SMILES: CNc1cc(Nc2ccc(C(=O)N3CCOCC3)c3c2OCO3)nc2[nH]cc(C(F)(F)F)c12] | (7-((4-(methylamino)-3-(trifluoromethyl)-1H-pyrrolo[2,3-b]pyridin-6-yl)amino)benzo[d][1,3]dioxol-4-yl)(morpholino)methanone | 464.2[M + H]⁺ | 7 | 1.23 |
| 39 | 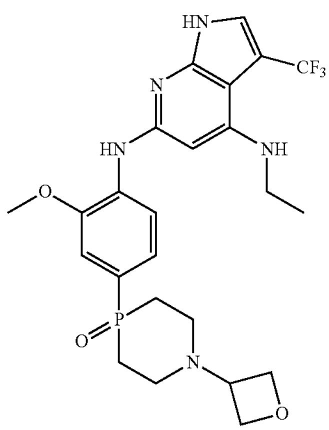 [SMILES: CCNc1cc(Nc2ccc(P3(=O)CCN(C4COC4)CC3)cc2OC)nc2[nH]cc(C(F)(F)F)c12] | 4-(4-((4-(ethylamino)-3-(trifluoromethyl)-1H-pyrrolo[2,3-b]pyridin-6-yl)amino)-3-methoxyphenyl)-1-(oxetan-3-yl)-1,4-azaphosphinane 4-oxide | ¹H NMR (400 MHZ, DMSO) δ 11.83 (s, 1H), 8.78 (d, J = 5.8 Hz, 1H), 8.15 (s, 1H), 7.54 (s, 1H), 7.28 (d, J = 11.4 Hz, 2H), 7.08 (s, 2H), 6.71 (d, J = 5.0 Hz, 1H), 6.33 (s, 1H), 5.35 (s, 3H), 4.55 (d, J = 4.9 Hz, 6H), 4.44 (s, 5H), 3.96 (s, 3H), 3.82 (s, 6H), 3.58 (s, 3H), 2.18 (s, 3H), 1.82 (d, J = 15.1 Hz, 5H).; 524.3 [M + H]⁺ | 12 | 1.23 |
| 40 | 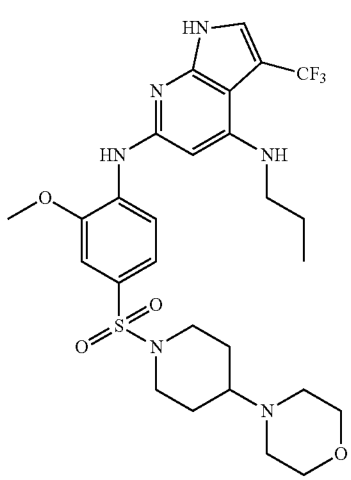 [SMILES: CCCNc1cc(Nc2ccc(S(=O)(=O)N3CCC(N4CCOCC4)CC3)cc2OC)nc2[nH]cc(C(F)(F)F)c12] | N⁶-(2-methoxy-4-((4-morpholinopiperidin-1-yl)sulfonyl)phenyl)-N⁴-propyl-3-(trifluoromethyl)-1H-pyrrolo[2,3-b]pyridine-4,6-diamine | ¹H NMR (400 MHZ, MeOD, TFA) δ 8.12-8.00 (m, 1H), 7.54 (s, 1H), 7.45 (dd, J = 8.4, 1.8 Hz, 1H), 7.40 (s, 1H), 4.16-3.97 (m, 7H), 3.86-3.70 (m, 2H), 3.58-3.42 (m, 2H), 3.38 (t, J = 7.0 Hz, 2H), 3.29-3.13 (m, 3H), 2.47 (t, J = 11.6 Hz, 2H), 2.26 (d, J = 11.4 Hz, 2H), 1.89-1.71 (m, 4H), 1.07 (t, J = 7.4 Hz, 3H); 597.34 [M + H]⁺ | 46.5 | 1.44 |

TABLE 1-continued

| Compound of Example | Structure | Compound Name | ¹H NMR, MS | Yield (%) | HPLC r.t. (min), Purity |
|---|---|---|---|---|---|
| 41 | 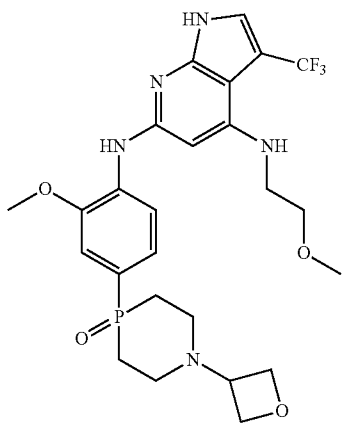 | 4-(3-methoxy-4-((4-((2-methoxyethyl)amino)-3-(trifluoromethyl)-1H-pyrrolo[2,3-b]pyridin-6-yl)amino)phenyl)-1-(oxetan-3-yl)-1,4-azaphosphinane 4-oxide | 554.3[M + H]⁺ | 21 | 1.23 |
| 42 | 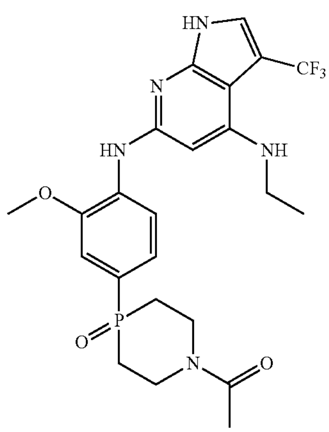 [SMILES: CCNc1cc(Nc2ccc(P3(=O)CCN(C(C)=O)CC3)cc2OC)nc2[nH]cc(C(F)(F)F)c12] | 1-(4-(4-((4-(ethylamino)-3-(trifluoromethyl)-1H-pyrrolo[2,3-b]pyridin-6-yl)amino)-3-methoxyphenyl)-4-oxido-1,4-azaphosphinan-1-yl)ethan-1-one | ¹H NMR (400 MHZ, DMSO) δ 11.82 (s, 1H), 8.78 (dd, J = 8.1, 3.2 Hz, 1H), 8.16 (s, 1H), 7.54 (s, 1H), 7.30 (d, J = 11.7 Hz, 2H), 6.34 (s, 1H), 4.74 (s, 1H), 4.25-4.12 (m, 1H), 3.96 (s, 3H), 3.82 (s, 2H), 3.42-3.37 (m, 1H), 3.26 (d, J = 6.9 Hz, 2H), 2.11 (s, 3H), 1.25 (t, J = 7.1 Hz, 4H).; 510.3[M + H]⁺ | 6 | 1.32 |
| 43 | 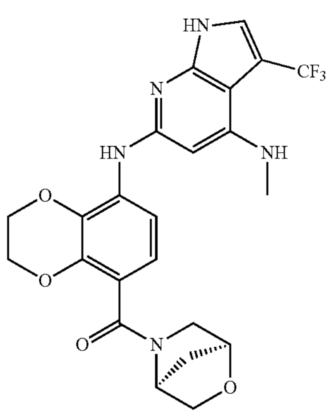 [SMILES: CNc1cc(Nc2ccc(C(=O)N3C[C@@H]4C[C@H]3CO4)c3c2OCCO3)nc2[nH]cc(C(F)(F)F)c12] | ((1S,4S)-2-oxa-5-azabicyclo[2.2.1]heptan-5-yl)(8-((4-(methylamino)-3-(trifluoromethyl)-1H-pyrrolo[2,3-b]pyridin-6-yl)amino)-2,3-dihydrobenzo[b][1,4]dioxin-5-yl)methanone | 490.3[M + H]⁺ | 11 | 1.20 |

TABLE 1-continued

| Compound of Example | Structure | Compound Name | ¹H NMR, MS | Yield (%) | HPLC r.t. (min), Purity |
|---|---|---|---|---|---|
| 44 | 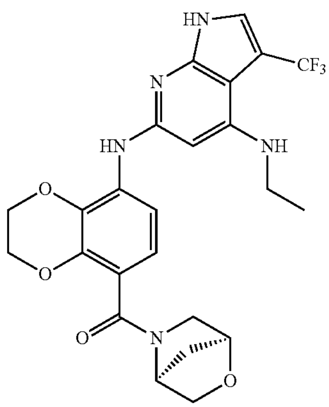 [SMILES: CCNc1cc(Nc2ccc(C(=O)N3C[C@@H]4C[C@H]3CO4)c3c2OCCO3)nc2[nH]cc(C(F)(F)F)c12] | ((1S,4S)-2-oxa-5-azabicyclo[2.2.1]heptan-5-yl)(8-((4-(ethylamino)-3-(trifluoromethyl)-1H-pyrrolo[2,3-b]pyridin-6-yl)amino)-2,3-dihydrobenzo[b][1,4]dioxin-5-yl)methanone | 504.3[M + H]⁺ | 11 | 1.29 |
| 45 | 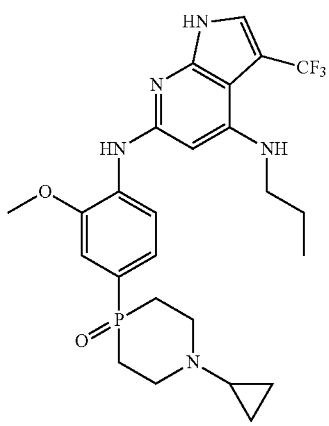 [SMILES: CCCNc1cc(Nc2ccc(P3(=O)CCN(C4CC4)CC3)cc2OC)nc2[nH]cc(C(F)(F)F)c12] | 1-cyclopropyl-4-(3-methoxy-4-((4-(propylamino)-3-(trifluoromethyl)-1H-pyrrolo[2,3-b]pyridin-6-yl)amino)phenyl)-1,4-azaphosphinane 4-oxide | 522.3[M + H]⁺ | 21 | 1.33 |
| 46 | 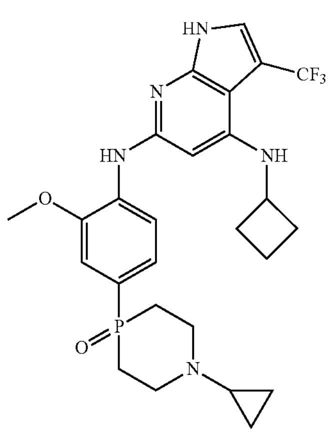 [SMILES: COc1cc(P2(=O)CCN(C3CC3)CC2)ccc1Nc1cc(NC2CCC2)c2c(C(F)(F)F)c[nH]c2n1] | 4-(4-((4-(cyclobutylamino)-3-(trifluoromethyl)-1H-pyrrolo[2,3-b]pyridin-6-yl)amino)-3-methoxyphenyl)-1-cyclopropyl-1,4-azaphosphinane 4-oxide | 534.3[M + H]⁺ | 12 | 1.44 |

TABLE 1-continued

| Compound of Example | Structure | Compound Name | ¹H NMR, MS | Yield (%) | HPLC r.t. (min), Purity |
|---|---|---|---|---|---|
| 47 | 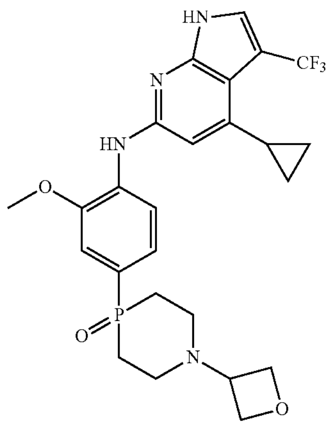 [SMILES: COc1cc(P2(=O)CCN(C3COC3)CC2)ccc1Nc1cc(C2CC2)c2c(C(F)(F)F)c[nH]c2n1] | 4-(4-((4-cyclopropyl-3-(trifluoromethyl)-1H-pyrrolo[2,3-b]pyridin-6-yl)amino)-3-methoxyphenyl)-1-(oxetan-3-yl)-1,4-azaphosphinane 4-oxide | ¹H NMR (400 MHZ, MeOD) δ 8.93 (dd, J = 8.3, 3.8 Hz, 1H), 7.59 (s, 1H), 7.45-7.38 (m, 1H), 7.38-7.33 (m, 1H), 6.57 (s, 1H), 4.89 (dd, J = 13.8, 6.9 Hz, 5H), 4.55 (p, J = 6.5 Hz, 1H), 4.04 (s, 4H), 3.69 (t, J = 11.3 Hz, 2H), 3.62 (s, 1H), 3.54 (dd, J = 22.5, 10.8 Hz, 3H), 2.78 (t, J = 13.2 Hz, 3H), 2.41 (d, J = 17.0 Hz, 2H), 1.14-1.08 (m, 2H), 0.94-0.87 (m, 2H).; 521.3[M + H]⁺ | 11 | 1.47 |
| 48 | 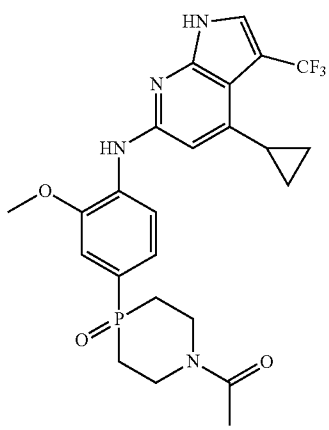 [SMILES: COc1cc(P2(=O)CCN(C(C)=O)CC2)ccc1Nc1cc(C2CC2)c2c(C(F)(F)F)c[nH]c2n1] | 1-(4-(4-((4-cyclopropyl-3-(trifluoromethyl)-1H-pyrrolo[2,3-b]pyridin-6-yl)amino)-3-methoxyphenyl)-4-oxido-1,4-azaphosphinan-1-yl)ethan-1-one | ¹H NMR (400 MHZ, DMSO) δ 12.06 (d, J = 2.5 Hz, 1H), 8.78 (d, J = 8.2, 3.3 Hz, 1H), 8.38 (S, 1H), 7.74 (d, J = 1.7 Hz, 1H), 7.40-7.29 (m, 3H), 7.12 (ddd, J = 12.0, 5.0, 2.8 Hz, 2H), 6.80-6.73 (m, 1H), 6.72 (dd, J = 7.9, 3.4 Hz, 1H), 5.38 (s, 1H), 4.18 (dd, J = 20.3, 14.9 Hz, 2H), 3.96 (s, 4H), 3.82 (s, 3H), 3.77-3.63 (m, 2H), 3.42-3.38 (m, 1H), 3.34 (s, 7H), 2.10 (d, J = 8.1 Hz, 7H), 1.99 (s, 1H), 1.24 (d, J = 1.1 Hz, 3H), 1.18 (t, J = 7.1 Hz, 1H), 1.10-1.03 (m, 3H), 0.89-0.84 (m, 5H).; 507.5[M + H]⁺ | 17 | 1.59 |
| 49 | 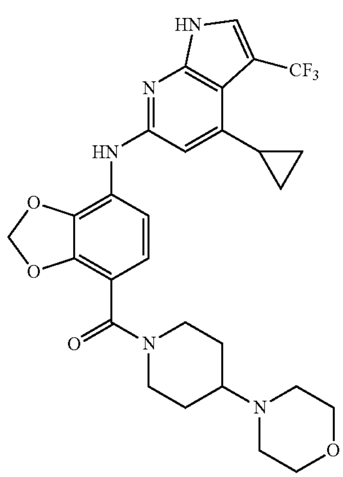 [SMILES: O=C(c1ccc(Nc2cc(C3CC3)c3c(C(F)(F)F)c[nH]c3n2)c2c1OCO2)N1CCC(N2CCOCC2)CC1] | (7-((4-cyclopropyl-3-(trifluoromethyl)-1H-pyrrolo[2,3-b]pyridin-6-yl)amino)benzo[d][1,3]dioxol-4-yl)(4-morpholinopiperidin-1-yl)methanone | ¹H NMR (400 MHZ, MeOD) δ 8.06 (d, J = 8.8 Hz, 1H), 7.58 (s, 1H), 6.94 (d, J = 8.8 Hz, 1H), 6.46 (s, 1H), 6.12 (s, 2H), 4.70 (d, J = 11.8 Hz, 1H), 3.94 (d, J = 11.9 Hz, 1H), 3.83-3.71 (m, 4H), 3.67 (s, 1H), 3.21 (t, J = 11.8 Hz, 1H), 2.97-2.80 (m, 1H), 2.66 (s, 4H), 2.60-2.48 (m, 1H), 2.43-2.35 (m, 1H), 2.09 (s, 1H), 2.03-1.92 (m, 1H), 1.54 (d, J = 10.6 Hz, 2H), 1.19-1.09 (m, 2H), 0.95-0.88 (m, 2H).; 547.3[M + H]⁺ | 11 | 1.07 |

TABLE 1-continued

| Compound of Example | Structure | Compound Name | ¹H NMR, MS | Yield (%) | HPLC r.t. (min), Purity |
|---|---|---|---|---|---|
| 50 | 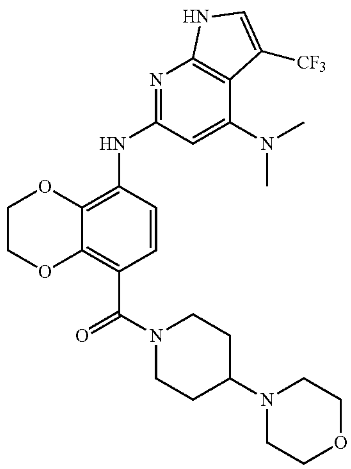 [SMILES: CN(C)c1cc(Nc2ccc(C(=O)N3CCC(N4CCOCC4)CC3)c3c2OCCO3)nc2[nH]cc(C(F)(F)F)c12] | (8-((4-(dimethylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | 575.4[M + H]⁺ | 61.7 | 1.20 |
| 51 | 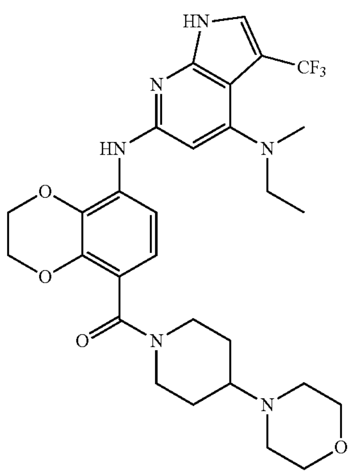 [SMILES: CCN(C)c1cc(Nc2ccc(C(=O)N3CCC(N4CCOCC4)CC3)c3c2OCCO3)nc2[nH]cc(C(F)(F)F)c12] | (8-((4-(ethyl(methyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | 589.4[M + H]⁺ | 40 | 1.34 |
| 52 | 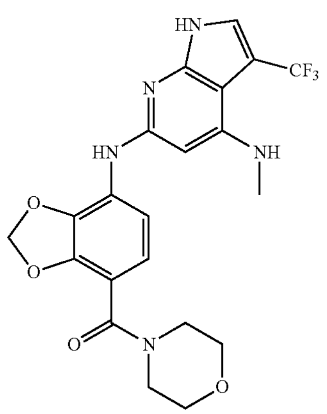 [SMILES: CNc1cc(Nc2ccc(C(=O)N3CCOCC3)c3c2OCO3)nc2[nH]cc(C(F)(F)F)c12] | (7-((4-(methylamino)-3-(trifluoromethyl)-1H-pyrrolo[2,3-b]pyridin-6-yl)amino)-2,3-dihydrobenzofuran-4-yl)(morpholino)methanone | ¹H NMR (400 MHZ, DMSO) δ 11.74 (s, 1H), 8.34 (d, J = 8.3 Hz, 1H), 8.09 (s, 1H), 7.46 (s, 1H), 6.75 (d, J = 8.3 Hz, 1H), 6.19 (s, 1H), 4.98 (d, J = 3.1 Hz, 1H), 4.63 (t, J = 8.8 Hz, 2H), 3.55 (d, J= 40.6 Hz, 8H), 3.21 (t, J = 8.7 Hz, 2H), 2.87 (d, J = 4.8 Hz, 3H).; 462.3 [M + H]⁺ | 21 | 1.22 |

TABLE 1-continued

| Compound of Example | Structure | Compound Name | $^1$H NMR, MS | Yield (%) | HPLC r.t. (min), Purity |
|---|---|---|---|---|---|
| 53 | 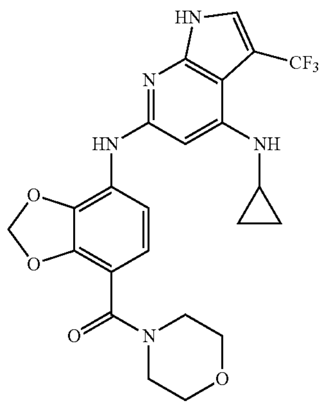 [SMILES: O=C(c1ccc(Nc2cc(NC3CC3)c3c(C(F)(F)F)c[nH]c3n2)c2c1OCO2)N1CCOCC1] | (7-((4-(cyclopropylamino)-3-(trifluoromethyl)-1H-pyrrolo[2,3-b]pyridin-6-yl)amino)-2,3-dihydrobenzofuran-4-yl)(morpholino)methanone | $^1$H NMR (400 MHZ, DMSO) δ 11.87 (s, 1H), 8.64 (s, 1H), 8.03 (s, 1H), 7.53 (s, 1H), 6.79 (d, J = 8.2 Hz, 1H), 6.52 (s, 1H), 5.23 (s, 1H), 4.63 (t, J = 8.8 Hz, 2H), 3.64-3.42 (m, 10H), 3.22 (t, J = 8.7 Hz, 2H), 2.57 (s, 1H), 0.87-0.80 (m, 2H), 0.59-0.52 (m, 2H).; 488.3[M + H]$^+$ | 17 | 1.36 |
| 54 | 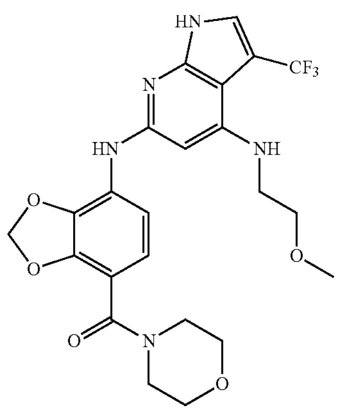 [SMILES: COCCNc1cc(Nc2ccc(C(=O)N3CCOCC3)c3c2OCO3)nc2[nH]cc(C(F)(F)F)c12] | (7-((4-((2-methoxyethyl)amino)-3-(trifluoromethyl)-1H-pyrrolo[2,3-b]pyridin-6-yl)amino)-2,3-dihydrobenzofuran-4-yl)(morpholino)methanone | $^1$H NMR (400 MHZ, DMSO) δ 11.76 (s, 1H), 8.34 (d, J = 8.3 Hz, 1H), 8.09 (s, 1H), 7.49 (s, 1H), 6.75 (d, J = 8.3 Hz, 1H), 6.26 (s, 1H), 5.00 (d, J = 1.6 Hz, 1H), 4.63 (t, J = 8.7 Hz, 2H), 3.61 (t, J = 5.3 Hz, 5H), 3.50 (s, 4H), 3.39 (s, 1H), 3.36-3.33 (m, 2H), 3.32 (s, 3H), 3.21 (t, J = 8.7 Hz, 2H), 1.89 (s, 1H).; 506.3 [M + H]$^+$ | 11 | 1.29 |
| 55 | 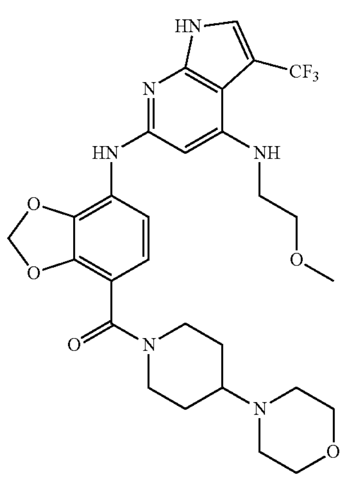 [SMILES: COCCNc1cc(Nc2ccc(C(=O)N3CCC(N4CCOCC4)CC3)c3c2OCO3)nc2[nH]cc(C(F)(F)F)c12] | (7-((4-((2-methoxyethyl)amino)-3-(trifluoromethyl)-1H-pyrrolo[2,3-b]pyridin-6-yl)amino)-2,3-dihydrobenzofuran-4-yl)(4-morpholinopiperidin-1-yl)methanone | $^1$H NMR (400 MHZ, DMSO) δ 11.82 (s, 1H), 10.17 (s, 1H), 8.35-8.15 (m, 2H), 7.52 (s, 1H), 6.77 (d, J = 8.3 Hz, 1H), 6.24 (s, 1H), 5.11 (s, 1H), 4.63 (t, J = 8.8 Hz, 2H), 4.02 (dd, J = 9.6, 4.4 Hz, 3H), 3.73-3.64 (m, 3H), 3.61 (t, J = 5.4 Hz, 3H), 3.50-3.41 (m, 3H), 3.40-3.34 (m, 3H), 3.20 (t, J = 8.7 Hz, 3H), 3.13 (d, J = 12.4 Hz, 2H), 2.10 (t, J = 10.3 Hz, 2H), 1.55 (qd, J = 12.5, 4.1 Hz, 2H).; 589.4[M + H]$^+$ | 21 | 1.13 |

TABLE 1-continued

| Compound of Example | Structure | Compound Name | ¹H NMR, MS | Yield (%) | HPLC r.t. (min), Purity |
|---|---|---|---|---|---|
| 56 | 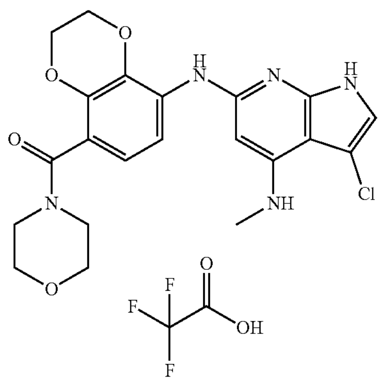 | (8-((3-chloro-4-(methylamino)-1H-pyrrolo[2,3-b]pyridin-6-yl)amino)-2,3-dihydrobenzo[b][1,4]dioxin-5-yl)(morpholino)methanone 2,2,2-trifluoroacetate | 444.3[M + H]⁺ | 6 | 1.07 |
| 57 | 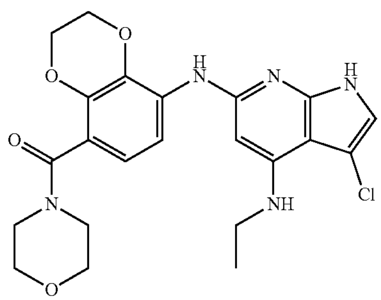 [SMILES: CCNc1cc(Nc2ccc(C(=O)N3CCOCC3)c3c2OCCO3)nc2[nH]cc(Cl)c12] | (8-((3-chloro-4-(ethylamino)-1H-pyrrolo[2,3-b]pyridin-6-yl)amino)-2,3-dihydrobenzo[b][1,4]dioxin-5-yl)(morpholino)methanone | 1H NMR (400 MHZ, Methanol-d4) δ 7.91-7.82 (m, 1H), 7.46-7.37 (m, 1H), 6.78 (dd, J = 21.4, 6.0 Hz, 2H), 5.90 (d, J = 4.1 Hz, 1H), 4.38 (s, 3H), 4.34 (s, 3H), 3.65 (s, 2H), 1.29 (s, 3H). 458.3[M + H]⁺ | 33 | 1.17 |
| 58 | 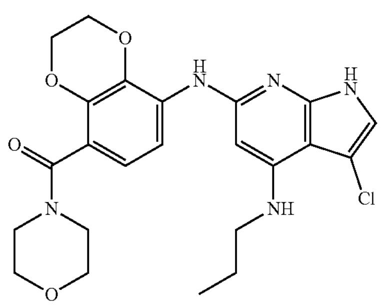 [SMILES: CCCNc1cc(Nc2ccc(C(=O)N3CCOCC3)c3c2OCCO3)nc2[nH]cc(Cl)c12] | (8-((3-chloro-4-(propylamino)-1H-pyrrolo[2,3-b]pyridin-6-yl)amino)-2,3-dihydrobenzo[b][1,4]dioxin-5-yl)(morpholino)methanone | 1H NMR (400 MHZ, Methanol-d4) δ 8.66 (t, J = 6.6 Hz, 1H), 7.30 (d, J = 8.8 Hz, 1H), 7.21 (d, J = 4.1 Hz, 1H), 6.86 (d, J = 4.0 Hz, 1H), 6.01 (d, J = 4.1 Hz, 1H), 4.00 (d, J = 4.1 Hz, 2H), 3.81 (q, J = 6.1 Hz, 1H), 3.71 (d, J = 5.1 Hz, 4H), 2.97 (d, J = 5.5 Hz, 4H), 1.97 (d, J = 4.1 Hz, 4H), 1.32 (s, 3H). 472.3 [M + H]⁺ | 32 | 1.26 |
| 59 | 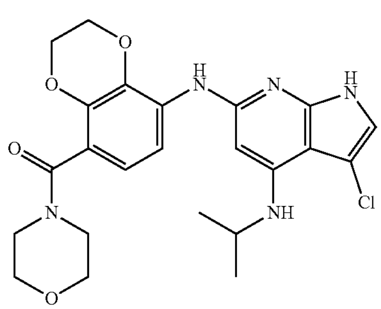 [SMILES: CC(C)Nc1cc(Nc2ccc(C(=O)N3CCOCC3)c3c2OCCO3)nc2[nH]cc(Cl)c12] | (8-((3-chloro-4-(isopropylamino)-1H-pyrrolo[2,3-b]pyridin-6-yl)amino)-2,3-dihydrobenzo[b][1,4]dioxin-5-yl)(morpholino)methanone | 1H NMR (400 MHZ, Methanol-d4) δ 7.87 (d, J = 6.8 Hz, 1H), 6.81 (s, 1H), 6.76 (d, J = 8.5 Hz, 1H), 5.92 (d, J = 4.2 Hz, 1H), 4.36 (d, J = 16.8 Hz, 8H), 3.68-3.59 (m, 4H), 3.52 (d, J = 4.4 Hz, 1H), 1.31 (d, J = 5.4 Hz, 6H).472.3 [M + H]⁺ | 10 | 1.29 |

TABLE 1-continued

| Compound of Example | Structure | Compound Name | 1H NMR, MS | Yield (%) | HPLC r.t. (min), Purity |
|---|---|---|---|---|---|
| 60 | 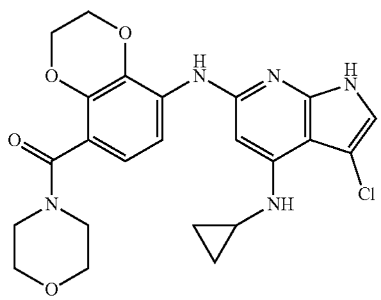 [SMILES: O=C(c1ccc(Nc2cc(NC3CC3)c3c(Cl)c[nH]c3n2)c2c1OCCO2)N1CCOCC1] | (8-((3-chloro-4-(cyclopropylamino)-1H-pyrrolo[2,3-b]pyridin-6-yl)amino)-2,3-dihydrobenzo[b][1,4]dioxin-5-yl)(morpholino)methanone | $^1$H NMR (400 MHZ, DMSO-d6) 811.19 (s, 1H), 8.11 (d, J = 7.9 Hz, 1H), 7.84 (s, 1H), 6.94 (s, 1H), 6.69 (d, J = 7.9 Hz, 1H), 6.39 (s, 1H), 5.87 (s, 1H), 4.33 (d, J = 15.7 Hz, 4H), 3.60 (s, 4H), 3.54 (s, 2H), 3.26 (s, 2H), 1.28 (s, 1H), 0.80 (d, J = 6.1 Hz, 2H), 0.57 (s, 2H). 470.2[M + H]$^+$ | 14 | 1.22 |
| 61 | 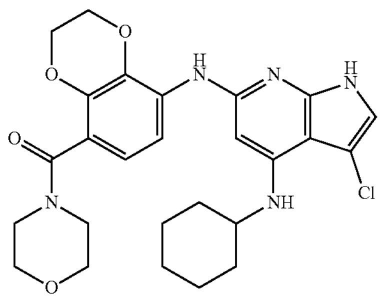 [SMILES: O=C(c1ccc(Nc2cc(NC3CCCCC3)c3c(Cl)c[nH]c3n2)c2c1OCCO2)N1CCOCC1] | (8-((3-chloro-4-(cyclohexylamino)-1H-pyrrolo[2,3-b]pyridin-6-yl)amino)-2,3-dihydrobenzo[b][1,4]dioxin-5-yl)(morpholino)methanone | $^1$H NMR (400 MHZ, DMSO) δ 11.17 (d, J = 2.4 Hz, 1H), 8.19 (d, J = 8.5 Hz, 1H), 7.80 (s, 1H), 6.94 (d, J = 2.6 Hz, 1H), 6.68 (d, J = 8.5 Hz, 1H), 6.16 (s, 1H), 5.33 (d, J = 7.7 Hz, 1H), 4.33 (dd, J = 18.6, 4.0 Hz, 4H), 3.57 (d, J = 25.0 Hz, 6H), 3.43-3.35 (m, 1H), 3.25 (s, 2H), 2.07-1.97 (m, 2H), 1.67 (ddd, J = 44.2, 8.6, 3.7 Hz, 3H), 1.47-1.20 (m, 6H).; 512.3[M + H]$^+$ | 85 | 1.47 |
| 62 | 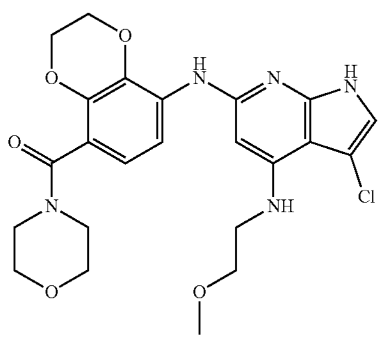 [SMILES: COCCNc1cc(Nc2ccc(C(=O)N3CCOCC3)c3c2OCCO3)nc2[nH]cc(Cl)c12] | (8-((3-chloro-4-((2-methoxyethyl)amino)-1H-pyrrolo[2,3-b]pyridin-6-yl)amino)-2,3-dihydrobenzo[b][1,4]dioxin-5-yl)(morpholino)methanone | $^1$H NMR (400 MHz, DMSO) δ 11.35 (s, 1H), 8.21 (s, 1H), 7.85 (s, 1H), 7.01 (d, J = 1.5 Hz, 1H), 6.73 (d, J = 8.4 Hz, 1H), 6.06 (s, 2H), 4.33 (d, J = 6.8 Hz, 4H), 3.58 (dd, J = 15.0, 9.5 Hz, 10H), 3.39 (d, J = 4.8 Hz, 3H), 3.26 (d, J = 6.7 Hz, 2H).; 488.2[M + H]$^+$ | 59 | 1.14 |
| 63 | 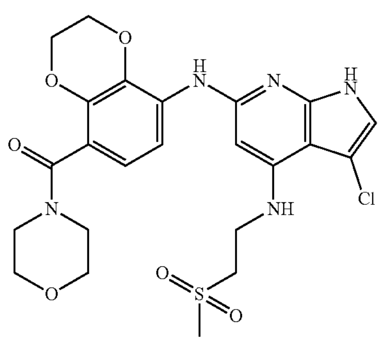 [SMILES: CS(=O)(=O)CCNc1cc(Nc2ccc(C(=O)N3CCOCC3)c3c2OCCO3)nc2[nH]cc(Cl)c12] | (8-((3-chloro-4-((2-(methylsulfonyl)ethyl)amino)-1H-pyrrolo[2,3-b]pyridin-6-yl)amino)-2,3-dihydrobenzo[b][1,4]dioxin-5-yl)(morpholino)methanone | 1H NMR (400 MHZ, Methanol-d4) δ 7.97 (d, J = 9.3 Hz, 1H), 7.76-7.59 (m, 2H), 7.57-7.01 (m, 4H), 6.83 (d, J = 4.0 Hz, 1H), 6.77 (d, J = 8.7 Hz, 1H), 5.99 (d, J = 4.2 Hz, 1H), 5.49 (d, J = 4.0 Hz, 1H), 4.36 (d, J = 17.2 Hz, 4H), 4.21 (d, J = 5.5 Hz, 2H), 4.13-4.06 (m, 1H), 3.73 (s, 3H), 3.04 (d, J = 4.0 Hz, 2H). 536.3 [M + H]$^+$ | 15 | 1.03 |
| 64 | 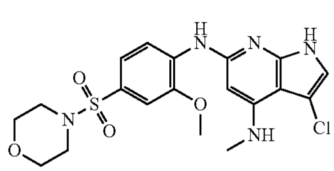 [SMILES: CNc1cc(Nc2ccc(S(=O)(=O)N3CCOCC3)cc2OC)nc2[nH]cc(Cl)c12] | 3-chloro-N$^6$-(2-methoxy-4-(morpholinosulfonyl)phenyl)-N$^4$-methyl-1H-pyrrolo[2,3-b]pyridine-4,6-diamine | 1H NMR (400 MHZ, Methanol-d4) δ 8.75 (s, 1H), 7.39 (s, 1H), 7.30 (s, 1H), 6.93 (d, J = 3.6 Hz, 1H), 6.04 (s, 1H), 5.42 (s, 1H), 4.70 (s, 2H), 4.09 (d, J = 3.6 Hz, 2H), 3.80 (s, 4H), 3.56 (d, J = 3.5 Hz, 1H), 3.21 (s, 1H), 3.05 (d, J = 7.1 Hz, 4H). 452.2[M + H]$^+$ | 77 | 1.32 |

TABLE 1-continued

| Compound of Example | Structure | Compound Name | 1H NMR, MS | Yield (%) | HPLC r.t. (min), Purity |
|---|---|---|---|---|---|
| 65 | 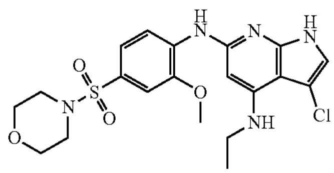 [SMILES: CCNc1cc(Nc2ccc(S(=O)(=O)N3CCOCC3)cc2OC)nc2[nH]cc(Cl)c12] | 3-chloro-N⁴-ethyl-N⁶-(2-methoxy-4-(morpholinosulfonyl)phenyl)-1H-pyrrolo[2,3-b]pyridine-4,6-diamine | 1H NMR (400 MHZ, Methanol-d4) δ 8.68-8.59 (m, 1H), 7.30 (d, J = 9.0 Hz, 1H), 7.21 (d, J = 4.0 Hz, 1H), 6.86 (d, J = 4.1 Hz, 1H), 5.99 (d, J = 4.1 Hz, 1H), 4.00 (d, J = 3.9 Hz, 3H), 3.71 (d, J = 5.3 Hz, 4H), 2.97 (d, J = 6.1 Hz, 4H), 1.35-1.31 (m, 3H), 1.28 (s, 2H). 466.2[M + H]⁺ | 45 | 1.46 |
| 66 | 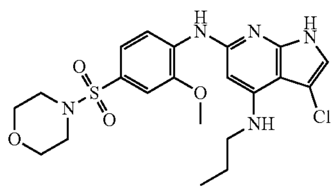 [SMILES: CCCNc1cc(Nc2ccc(S(=O)(=O)N3CCOCC3)cc2OC)nc2[nH]cc(Cl)c12] | 3-chloro-N⁶-(2-methoxy-4-(morpholinosulfonyl)phenyl)-N⁴-propyl-1H-pyrrolo[2,3-b]pyridine-4,6-diamine | 1H NMR (400 MHZ, Methanol-d4) δ 8.76 (s, 1H), 7.47 (d, J = 9.0 Hz, 1H), 7.41 (s, 1H), 7.37-7.19 (m, 2H), 7.14 (s, 1H), 6.89 (s, 1H), 6.09 (d, J = 4.0 Hz, 1H), 4.03 (d, J = 4.1 Hz, 2H), 3.85 (d, J = 5.8 Hz, 1H), 3.68-3.42 (m, 1H), 3.10 (d, J = 4.0 Hz, 3H), 3.06 (d, J = 4.0 Hz, 3H). 480.3[M + H]⁺ | 16 | 1.54 |
| 67 | 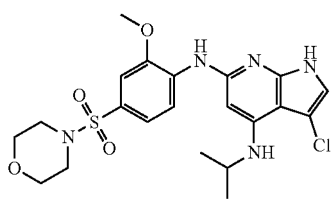 [SMILES: COc1cc(S(=O)(=O)N2CCOCC2)ccc1Nc1cc(NC(C)C)c2c(Cl)c[nH]c2n1] | 3-chloro-N⁴-isopropyl-N⁶-(2-methoxy-4-(morpholinosulfonyl)phenyl)-1H-pyrrolo[2,3-b]pyridine-4,6-diamine | 1H NMR (400 MHZ, Methanol-d4) δ 8.65 (d, J = 9.7 Hz, 1H), 7.30 (d, J = 8.9 Hz, 1H), 7.21 (d, J = 3.9 Hz, 1H), 6.86 (d, J = 3.9 Hz, 1H), 5.99 (d, J = 4.1 Hz, 1H), 4.00 (d, J = 4.0 Hz, 3H), 3.71 (d, J = 5.2 Hz, 4H), 2.97 (d, J = 5.1 Hz, 4H), 1.74 (p, J = 6.7 Hz, 2H), 1.29 (s, 2H), 1.05 (dd, J = 8.3, 4.7 Hz, 3H). 480.3[M + H]⁺ | 35 | 1.56 |
| 68 | 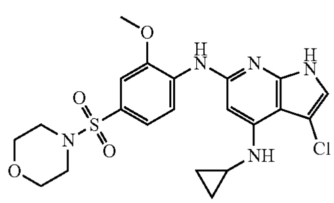 [SMILES: COc1cc(S(=O)(=O)N2CCOCC2)ccc1Nc1cc(NC2CC2)c2c(Cl)c[nH]c2n1] | 3-chloro-N⁴-cyclopropyl-N⁶-(2-methoxy-4-(morpholinosulfonyl)phenyl)-1H-pyrrolo[2,3-b]pyridine-4,6-diamine | 1H NMR (400 MHZ, DMSO-d₆) δ 11.29 (s, 1H), 8.85 (d, J = 8.5 Hz, 1H), 8.33 (s, 1H), 7.24 (d, J = 8.7 Hz, 1H), 7.15 (s, 1H), 7.02 (s, 1H), 6.52 (s, 1H), 5.96 (s, 1H), 3.98 (s, 3H), 3.64 (s, 4H), 2.87 (s, 4H), 0.88-0.78 (m, 4H), 0.59 (s, 1H). 478.2[M + H]⁺ | 8 | 1.56 |
| 69 | 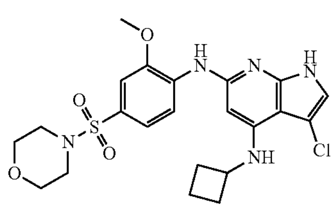 [SMILES: COc1cc(S(=O)(=O)N2CCOCC2)ccc1Nc1cc(NC2CCC2)c2c(Cl)c[nH]c2n1] | 3-chloro-N⁴-cyclobutyl-N⁶-(2-methoxy-4-(morpholinosulfonyl)phenyl)-1H-pyrrolo[2,3-b]pyridine-4,6-diamine | ¹H NMR (400 MHZ, MeOD) δ 11.28 (d, J = 2.4 Hz, 1H), 8.87 (d, J = 8.5 Hz, 1H), 8.23 (s, 1H), 7.39 (dt, J = 6.3, 2.0 Hz, 2H), 7.02 (d, J = 2.6 Hz, 1H), 6.27 (s, 1H), 5.76 (s, 1H), 5.41 (d, J = 7.8 Hz, 1H), 3.99 (s, 3H), 3.16 (s, 3H), 2.08-1.99 (m, 2H), 1.68 (ddd, J = 44.6, 8.8, 4.0 Hz, 4H), 1.48-1.22 (m, 7H).; 492.2[M + H]⁺ | 67 | 1.61 |
| 70 | 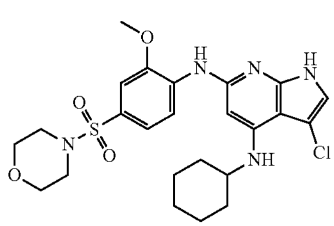 [SMILES: COc1cc(S(=O)(=O)N2CCOCC2)ccc1Nc1cc(NC2CCCCC2)c2c(Cl)c[nH]c2n1] | 3-chloro-N⁴-cyclohexyl-N⁶-(2-methoxy-4-(morpholinosulfonyl)phenyl)-1H-pyrrolo[2,3-b]pyridine-4,6-diamine | ¹H NMR (400 MHZ, DMSO) δ 11.39 (s, 1H), 8.97 (d, J = 8.6 Hz, 1H), 8.35 (s, 1H), 7.31 (d, J = 8.6 Hz, 1H), 7.22 (s, 1H), 7.10 (s, 1H), 6.37 (s, 1H), 5.49 (d, J = 7.6 Hz, 1H), 4.06 (s, 3H), 3.71 (s, 4H), 3.43 (s, 8H), 2.95 (s, 4H), 2.58 (s, 5H), 2.11 (d, J = 11.1 Hz, 2H), 1.76 (dd, J = 43.0, 12.7 Hz, 4H), 1.57-1.28 (m, 6H).; 520.3[M + H]⁺ | 25 | 1.81 |

TABLE 1-continued

| Compound of Example | Structure | Compound Name | $^1$H NMR, MS | Yield (%) | HPLC r.t. (min), Purity |
|---|---|---|---|---|---|
| 71 | 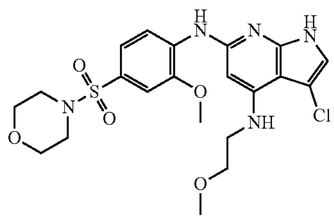 [SMILES: COCCNc1cc(Nc2ccc(S(=O)(=O)N3CCOCC3)cc2OC)nc2[nH]cc(Cl)c12] | 3-chloro-N$^6$-(2-methoxy-4-(morpholinosulfonyl)phenyl)-N$^4$-(2-methoxyethyl)-1H-pyrrolo[2,3-b]pyridine-4,6-diamine | 496.3[M + H]$^+$ | 27 | 1.39 |
| 72 | 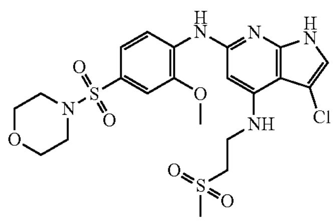 [SMILES: COc1cc(S(=O)(=O)N2CCOCC2)ccc1Nc1cc(NCCS(C)(=O)=O)c2c(Cl)c[nH]c2n1] | 3-chloro-N$^6$-(2-methoxy-4-(morpholinosulfonyl)phenyl)-N$^4$-(2-(methylsulfonyl)ethyl)-1H-pyrrolo[2,3-b]pyridine-4,6-diamine | 1H NMR (400 MHZ, Methanol-d4) δ 8.69 (d, J = 7.8 Hz, 1H), 7.67 (d, J = 33.8 Hz, 1H), 7.46-7.19 (m, 4H), 6.89 (d, J = 4.1 Hz, 1H), 6.09 (d, J = 4.3 Hz, 1H), 4.01 (d, J = 4.3 Hz, 3H), 3.72 (s, 5H), 3.06 (d, J = 4.0 Hz, 3H), 2.98 (s, 4H). 544.2[M + H]$^+$ | 33 | 1.30 |
| 73 | 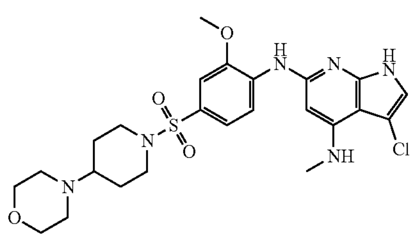 [SMILES: CNc1cc(Nc2ccc(S(=O)(=O)N3CCC(N4CCOCC4)CC3)cc2OC)nc2[nH]cc(Cl)c12] | 3-chloro-N$^6$-(2-methoxy-4-((morpholinopiperidin-1-yl)sulfonyl)phenyl)-N$^4$-methyl-1H-pyrrolo[2,3-b]pyridine-4,6-diamine | 1H NMR (400 MHZ, DMSO-d$_6$) δ 11.24 (s, 1H), 8.86 (d, J = 8.6 Hz, 1H), 8.19 (s, 1H), 7.22 (d, J = 8.7 Hz, 1H), 7.14 (s, 1H), 6.99 (d, J = 2.5 Hz, 1H), 6.14 (s, 1H), 5.95 (d, J = 5.4 Hz, 1H), 3.96 (d, J = 1.7 Hz, 3H), 3.64 (d, J = 11.5 Hz, 2H), 3.51 (t, J = 4.4 Hz, 4H), 2.85 (d, J = 4.8 Hz, 3H), 2.38 (s, 4H), 2.24 (t, J = 11.7 Hz, 2H), 2.10 (d, J = 11.2 Hz, 1H), 1.80 (d, J = 12.4 Hz, 2H), 1.45-1.37 (m, 2H). 535.3[M + H]$^+$ | 27 | 1.08 |
| 74 | 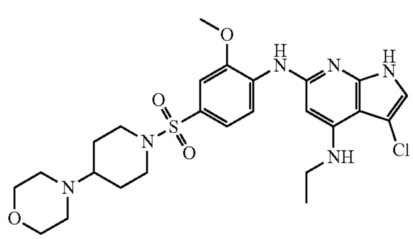 [SMILES: CCNc1cc(Nc2ccc(S(=O)(=O)N3CCC(N4CCOCC4)CC3)cc2OC)nc2[nH]cc(Cl)c12] | 3-chloro-N$^4$-ethyl-N$^6$-(2-methoxy-4-((morpholinopiperidin-1-yl)sulfonyl)phenyl)-1H-pyrrolo[2,3-b]pyridine-4,6-diamine | 1H NMR (400 MHZ, DMSO-d$_6$) δ 11.25 (s, 1H), 8.86 (d, J = 8.6 Hz, 1H), 8.21 (s, 1H), 7.87-7.78 (m, 1H), 7.14 (d, J = 2.4 Hz, 1H), 7.00 (d, J = 2.5 Hz, 1H), 6.22 (s, 1H), 5.77-5.74 (m, 1H), 3.96 (s, 3H), 3.64 (d, J = 11.3 Hz, 2H), 3.52 (s, 4H), 3.26 (t, J = 6.9 Hz, 2H), 2.39 (s, 4H), 2.24 (t, J = 11.7 Hz, 2H), 2.11 (s, 1H), 1.80 (d, J = 12.4 Hz, 2H), 1.47-1.38 (m, 2H), 1.24 (t, J = 7.0 Hz, 3H). 549.3[M + H]$^+$ | 45 | 1.18 |
| 75 | 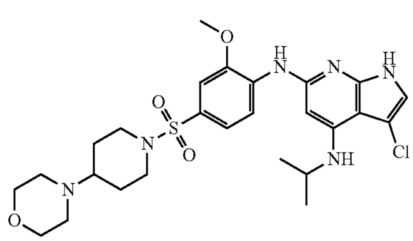 [SMILES: COc1cc(S(=O)(=O)N2CCC(N3CCOCC3)CC2)ccc1Nc1cc(NC(C)C)c2c(Cl)c[nH]c2n1] | 3-chloro-N$^4$-isopropyl-N$^6$-(2-methoxy-4-((morpholinopiperidin-1-yl)sulfonyl)phenyl)-1H-pyrrolo[2,3-b]pyridine-4,6-diamine | $^1$H NMR (400 MHZ, Methanol-d4) δ 8.65 (d, J = 8.5 Hz, 1H), 7.30 (d, J = 9.0 Hz, 1H), 7.22 (d, J = 3.9 Hz, 1H), 6.86 (d, J = 3.9 Hz, 1H), 6.00 (d, J = 4.1 Hz, 1H), 3.99 (d, J = 4.1 Hz, 3H), 3.89-3.72 (m, 4H), 3.67 (d, J = 5.9 Hz, 4H), 2.58 (s, 4H), 2.34 (t, J = 12.1 Hz, 2H), 2.22 (s, 1H), 1.54 (d, J = 12.6 Hz, 2H), 1.31 (d, J = 5.5 Hz, 6H), 0.91 (s, 1H). 563.4[M + H]$^+$ | 12 | 1.3 |

TABLE 1-continued

| Compound of Example | Structure | Compound Name | $^1$H NMR, MS | Yield (%) | HPLC r.t. (min), Purity |
|---|---|---|---|---|---|
| 76 | 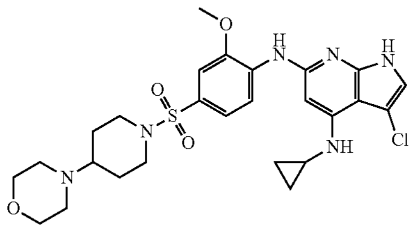 [SMILES: COc1cc(S(=O)(=O)N2CCC(N3CCOCC3)CC2)ccc1Nc1cc(NC2CC2)c2c(Cl)c[nH]c2n1] | 3-chloro-$N^4$-cyclopropyl-$N^6$-(2-methoxy-4-((morpholinopiperidin-1-yl)sulfonyl)phenyl)-1H-pyrrolo[2,3-b]pyridine-4,6-diamine | 1H NMR (400 MHZ, DMSO-$d_6$) δ 11.28 (s, 1H), 8.82 (dd, J = 8.7, 1.8 Hz, 1H), 8.29 (s, 1H), 7.23 (d, J = 8.6 Hz, 1H), 7.15 (d, J = 2.1 Hz, 1H), 7.01 (t, J = 2.3 Hz, 1H), 6.51 (d, J = 1.9 Hz, 1H), 5.95 (s, 1H), 3.96 (d, J = 1.8 Hz, 3H), 3.64 (d, J = 11.3 Hz, 2H), 3.51 (d, J = 4.8 Hz, 4H), 2.39 (t, J = 4.3 Hz, 3H), 2.24 (t, J = 11.7 Hz, 2H), 2.12 (t, J = 10.9 Hz, 1H), 1.80 (d, J = 12.4 Hz, 2H), 1.43 (t, J = 11.7 Hz, 2H), 1.23 (s, 2H), 0.82 (d, J = 6.6 Hz, 2H), 0.62-0.56 (m, 2H). 561.3[M + H]$^+$ | 15 | 1.25 |
| 77 | 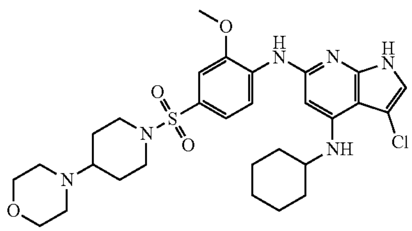 [SMILES: COc1cc(S(=O)(=O)N2CCC(N3CCOCC3)CC2)ccc1Nc1cc(NC2CCCCC2)c2c(Cl)c[nH]c2n1] | 3-chloro-$N^4$-cyclohexyl-$N^6$-(2-methoxy-4-((morpholinopiperidin-1-yl)sulfonyl)phenyl)-1H-pyrrolo[2,3-b]pyridine-4,6-diamine | $^1$H NMR (400 MHZ, DMSO) δ 11.41 (s, 1H), 8.96 (d, J = 8.6 Hz, 1H), 8.33 (s, 1H), 7.32 (d, J = 8.6 Hz, 1H), 7.24 (s, 1H), 7.12 (s, 1H), 6.37 (s, 1H), 5.51 (d, J = 7.6 Hz, 1H), 4.07 (s, 3H), 3.74 (d, J = 10.7 Hz, 3H), 3.61 (s, 6H), 2.48 (s, 5H), 2.34 (t, J = 11.6 Hz, 3H), 2.20 (d, J = 10.8 Hz, 1H), 2.13 (d, J = 11.3 Hz, 2H), 1.97-1.78 (m, 5H), 1.76 (s, 3H), 1.60-1.30 (m, 12H).; 603.4[M + H]$^+$ | 12 | 1.43 |
| 78 | 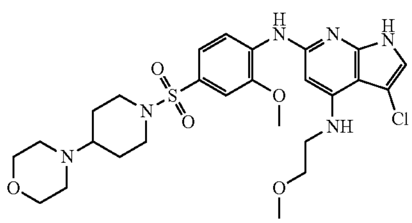 [SMILES: COCCNc1cc(Nc2ccc(S(=O)(=O)N3CCC(N4CCOCC4)CC3)cc2OC)nc2[nH]cc(Cl)c12] | 3-chloro-$N^6$-(2-methoxy-4-((morpholinopiperidin-1-yl)sulfonyl)phenyl)-$N^4$-(2-methoxyethyl)-1H-pyrrolo[2,3-b]pyridine-4,6-diamine | 579.4[M + H]$^+$ | 13 | 1.22 |
| 79 | 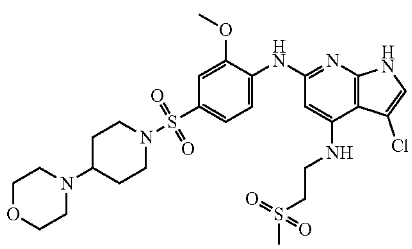 [SMILES: COc1cc(S(=O)(=O)N2CCC(N3CCOCC3)CC2)ccc1Nc1cc(NCCS(C)(=O)=O)c2c(Cl)c[nH]c2n1] | 3-chloro-$N^6$-(2-methoxy-4-((morpholinopiperidin-1-yl)sulfonyl)phenyl)-$N^4$-(2-(methylsulfonyl)ethyl)-1H-pyrrolo[2,3-b]pyridine-4,6-diamine | 1H NMR (400 MHZ, DMSO-$d_6$) δ 11.32 (s, 1H), 8.93-8.75 (m, 1H), 8.24 (s, 1H), 7.23 (d, J = 8.7 Hz, 1H), 7.15 (s, 1H), 7.03 (d, J = 2.5 Hz, 1H), 6.27 (s, 1H), 6.15 (t, J = 5.7 Hz, 1H), 3.97 (d, J = 1.9 Hz, 3H), 3.66 (dd, J = 16.7, 9.2 Hz, 4H), 3.52 (d, J = 6.5 Hz, 6H), 3.09 (d, J = 1.9 Hz, 3H), 2.38 (s, 4H), 2.24 (t, J = 11.7 Hz, 2H), 2.11 (s, 1H), 1.80 (d, J = 12.2 Hz, 2H), 1.41 (d, J = 12.5 Hz, 2H). 627.3[M + H]$^+$ | 44 | 1.08 |
| 80 | 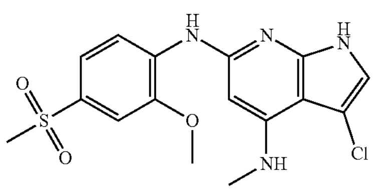 [SMILES: CNc1cc(Nc2ccc(S(C)(=O)=O)cc2OC)nc2[nH]cc(Cl)c12] | 3-chloro-$N^6$-(2-methoxy-4-(methylsulfonyl)phenyl)-$N^4$-methyl-1H-pyrrolo[2,3-b]pyridine-4,6-diamine | 1H NMR (400 MHZ, Methanol-d4) δ 8.68 (d, J = 7.0 Hz, 1H), 7.41 (s, 2H), 6.85 (d, J = 3.9 Hz, 1H), 5.95 (d, J = 4.1 Hz, 1H), 4.02 (d, J = 4.1 Hz, 3H), 3.10 (d, J = 3.7 Hz, 3H), 2.95 (d, J = 4.0 Hz, 3H). 381.2[M + H]$^+$ | 42 | 1.22 |
| 81 | 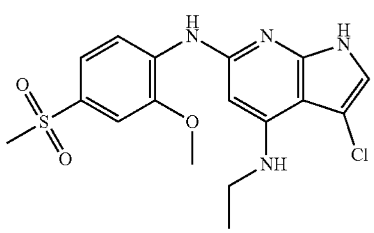 [SMILES: CCNc1cc(Nc2ccc(S(C)(=O)=O)cc2OC)nc2[nH]cc(Cl)c12] | 3-chloro-$N^4$-ethyl-$N^6$-(2-methoxy-4-(methylsulfonyl)phenyl)-1H-pyrrolo[2,3-b]pyridine-4,6-diamine | 1H NMR (400 MHZ, Methanol-d4) δ 8.64 (d, J = 8.0 Hz, 1H), 7.46 (d, J = 9.6 Hz, 2H), 6.86 (d, J = 4.1 Hz, 1H), 5.98 (d, J = 4.2 Hz, 1H), 4.02 (d, J = 4.3 Hz, 3H), 3.34 (d, J = 6.2 Hz, 2H), 3.10 (d, J = 4.2 Hz, 3H), 1.33 (d, J = 6.1 Hz, 3H). 395.2[M + H]$^+$ | 44 | 1.36 |

TABLE 1-continued

| Compound of Example | Structure | Compound Name | ¹H NMR, MS | Yield (%) | HPLC r.t. (min), Purity |
|---|---|---|---|---|---|
| 82 | 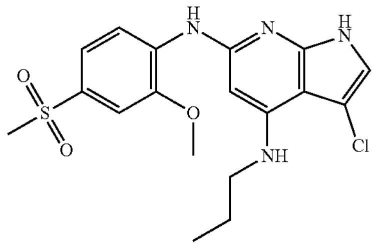 [SMILES: CCCNc1cc(Nc2ccc(S(C)(=O)=O)cc2OC)nc2[nH]cc(Cl)c12] | 3-chloro-N⁶-(2-methoxy-4-(methylsulfonyl)phenyl)-N⁴-propyl-1H-pyrrolo[2,3-b]pyridine-4,6-diamine | 1H NMR (400 MHZ, Methanol-d4) δ 8.67 (d, J = 6.3 Hz, 1H), 7.46 (d, J = 9.1 Hz, 1H), 7.40 (d, J = 4.0 Hz, 1H), 6.86 (d, J = 4.0 Hz, 1H), 5.99 (d, J = 4.1 Hz, 1H), 4.02 (d, J = 4.3 Hz, 3H), 3.10 (d, J = 4.0 Hz, 3H), 1.73 (q, J = 6.8 Hz, 2H), 1.29 (s, 2H), 1.05 (dd, J= 8.5, 4.5 Hz, 3H). 409.2[M + H]⁺ | 14 | 1.46 |
| 83 | 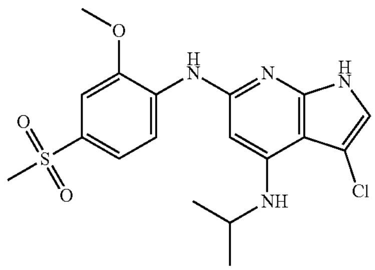 [SMILES: COc1cc(S(C)(=O)=O)ccc1Nc1cc(NC(C)C)c2c(Cl)c[nH]c2n1] | 3-chloro-N⁴-isopropyl-N⁶-(2-methoxy-4-(methylsulfonyl)phenyl)-1H-pyrrolo[2,3-b]pyridine-4,6-diamine | H NMR (400 MHZ, Methanol-d4) δ 8.67 (d, J = 6.8 Hz, 1H), 7.46 (d, J = 9.0 Hz, 1H), 7.40 (d, J = 3.9 Hz, 1H), 6.86 (d, J = 3.9 Hz, 1H), 6.01 (d, J = 4.1 Hz, 1H), 4.02 (d, J = 4.1 Hz, 3H), 3.80 (h, J = 6.1 Hz, 1H), 3.10 (d, J = 3.8 Hz, 3H), 1.31 (d, J = 5.3 Hz, 6H). 409.2[M + H]⁺ | 13 | 1.46 |
| 84 | 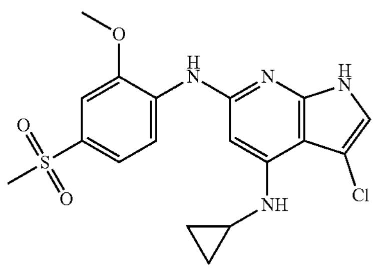 [SMILES: COc1cc(S(C)(=O)=O)ccc1Nc1cc(NC2CC2)c2c(Cl)c[nH]c2n1] | 3-chloro-N⁴-cyclopropyl-N⁶-(2-methoxy-4-(methylsulfonyl)phenyl)-1H-pyrrolo[2,3-b]pyridine-4,6-diamine | ¹H NMR (400 MHZ, DMSO-d₆) 811.30 (s, 1H), 8.82 (d, J = 8.5 Hz, 1H), 8.30 (s, 1H), 7.40 (d, J = 12.4 Hz, 2H), 7.02 (d, 1H), 6.51 (s, 1H), 5.95 (s, 1H), 5.76 (s, 1H), 3.98 (s, 3H), 3.17 (s, 3H), 1.23 (s, 1H), 0.82 (d, J = 6.4 Hz, 2H), 0.59 (s, 2H). 407.2[M + H]⁺ | 8 | 1.44 |
| 85 | 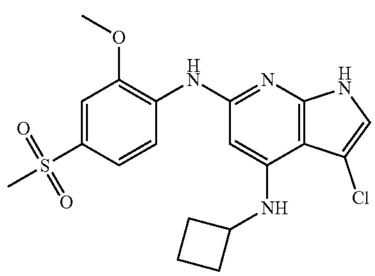 [SMILES: COc1cc(S(C)(=O)=O)ccc1Nc1cc(NC2CCC2)c2c(Cl)c[nH]c2n1] | 3-chloro-N⁴-cyclobutyl-N⁶-(2-methoxy-4-(methylsulfonyl)phenyl)-1H-pyrrolo[2,3-b]pyridine-4,6-diamine | ¹H NMR (400 MHZ, DMSO) δ 11.29 (d, J = 2.1 Hz, 1H), 8.85 (d, J = 8.5 Hz, 1H), 8.25 (s, 1H), 7.43-7.36 (m, 2H), 7.02 (d, J = 2.6 Hz, 1H), 6.15 (s, 1H), 5.71 (d, J = 6.6 Hz, 1H), 3.99 (s, 5H), 3.17 (s, 4H), 2.45 (dd, J = 7.6, 2.4 Hz, 2H), 2.03-1.89 (m, 2H), 1.75 (ddd, J = 14.6, 12.5, 5.6 Hz, 2H).; 421.2[M + H]⁺ | 37 | 1.52 |
| 86 | 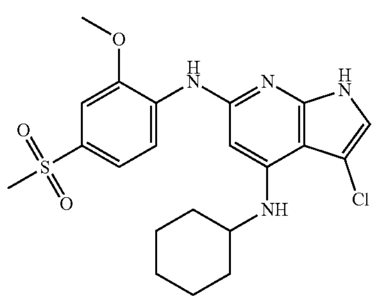 [SMILES: COc1cc(S(C)(=O)=O)ccc1Nc1cc(NC2CCCCC2)c2c(Cl)c[nH]c2n1] | 3-chloro-N⁴-cyclohexyl-N⁶-(2-methoxy-4-(methylsulfonyl)phenyl)-1H-pyrrolo[2,3-b]pyridine-4,6-diamine | ¹H NMR (400 MHZ, DMSO) δ 11.28 (d, J = 2.4 Hz, 1H), 8.87 (d, J = 8.5 Hz, 1H), 8.23 (s, 1H), 7.39 (dt, J = 6.3, 2.0 Hz, 2H), 7.02 (d, J = 2.6 Hz, 1H), 6.27 (s, 1H), 5.76 (s, 1H), 5.41 (d, J = 7.8 Hz, 1H), 3.99 (s, 3H), 3.16 (s, 3H), 2.08-1.99 (m, 2H), 1.68 (ddd, J = 44.6, 8.8, 4.0 Hz, 4H), 1.48-1.22 (m, 7H).; 449.2[M + H]⁺ | 63 | 1.73 |

TABLE 1-continued

| Compound of Example | Structure | Compound Name | $^1$H NMR, MS | Yield (%) | HPLC r.t. (min), Purity |
|---|---|---|---|---|---|
| 87 | 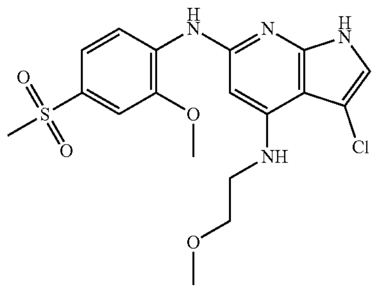 [SMILES: COCCNc1cc(Nc2ccc(S(C)(=O)=O)cc2OC)nc2[nH]cc(Cl)c12] | 3-chloro-$N^6$-(2-methoxy-4-(methylsulfonyl)phenyl)-$N^4$-(2-methoxyethyl)-1H-pyrrolo[2,3-b]pyridine-4,6-diamine | $^1$H NMR (400 MHZ, DMSO) δ 11.31 (d, J = 2.3 Hz, 1H), 8.86 (d, J = 8.5 Hz, 1H), 8.21 (s, 1H), 7.44-7.34 (m, 2H), 7.02 (d, J = 2.6 Hz, 1H), 6.26 (s, 1H), 5.83 (t, J = 5.5 Hz, 1H), 3.99 (s, 3H), 3.60 (t, J = 5.6 Hz, 2H), 3.42-3.35 (m, 2H), 3.17 (s, 3H).; 425.2[M + H]$^+$ | 71 | 1.30 |
| 88 | 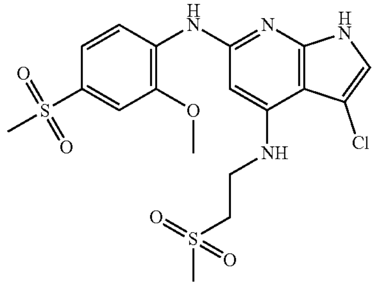 [SMILES: COc1cc(S(C)(=O)=O)ccc1Nc1cc(NCCS(C)(=O)=O)c2c(Cl)c[nH]c2n1] | 3-chloro-$N^6$-(2-methoxy-4-(methylsulfonyl)phenyl)-$N^4$-(2-(methylsulfonyl)ethyl)-1H-pyrrolo[2,3-b]pyridine-4,6-diamine | 1H NMR (400 MHZ, Methanol-d4) δ 8.76 (s, 1H), 7.47 (d, J = 9.0 Hz, 1H), 7.41 (s, 1H), 7.37-7.19 (m, 2H), 7.14 (s, 1H), 6.89 (s, 1H), 6.09 (d, J = 4.0 Hz, 1H), 4.03 (d, J = 4.1 Hz, 2H), 3.85 (d, J = 5.8 Hz, 1H), 3.68-3.42 (m, 1H), 3.10 (d, J = 4.0 Hz, 3H), 3.06 (d, J = 4.0 Hz, 3H). 473.3[M + H]$^+$ | 15 | 1.19 |
| 89 | 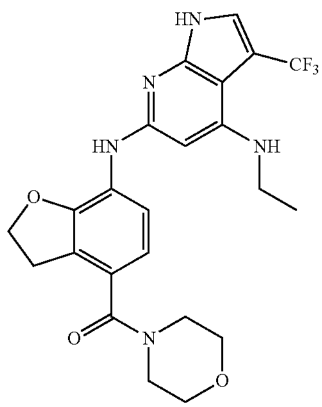 [SMILES: CCNc1cc(Nc2ccc(C(=O)N3CCOCC3)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(morpholino)methanone | 1H NMR (400 MHZ, DMSO) δ 11.78 (s, 1H), 8.25 (d, J = 30.8 Hz, 2H), 7.50 (s, 1H), 6.79-6.70 (m, 1H), 6.24 (s, 1H), 4.77 (s, 1H), 4.63 (s, 2H), 3.55 (d, J = 40.7 Hz, 8H), 3.23 (d, J = 7.4 Hz, 4H), 1.24 (d, J = 5.4 Hz, 3H). 476.3[M + H]$^+$ | 72 | 1.29 |
| 90 | 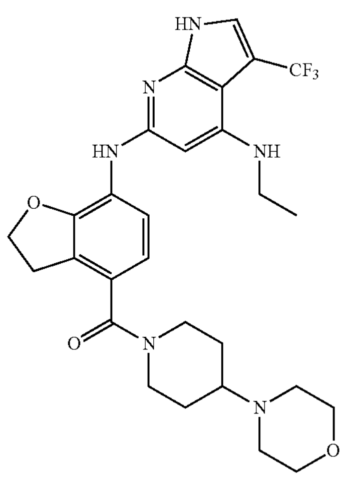 | (7-((4-(ethylamino)-3-(trifluoromethyl)-1H-pyrrolo[2,3-b]pyridin-6-yl)amino)-2,3-dihydrobenzofuran-4-yl)(4-morpholinopiperidin-1-yl)methanone | $^1$H NMR (400 MHZ, DMSO) δ 11.78 (s, 1H), 8.25 (d, J = 30.8 Hz, 2H), 7.50 (s, 1H), 6.79-6.70 (m, 1H), 6.24 (s, 1H), 4.77 (s, 1H), 4.63 (s, 2H), 3.55 (d, J = 40.7 Hz, 8H), 3.23 (d, J = 7.4 Hz, 4H), 1.24 (d, J = 5.4 Hz, 3H).; 473.3 [M + H]$^+$ | 99 | 1.1 |

TABLE 1-continued

| Compound of Example | Structure | Compound Name | ¹H NMR, MS | Yield (%) | HPLC r.t. (min), Purity |
|---|---|---|---|---|---|
| 91 | 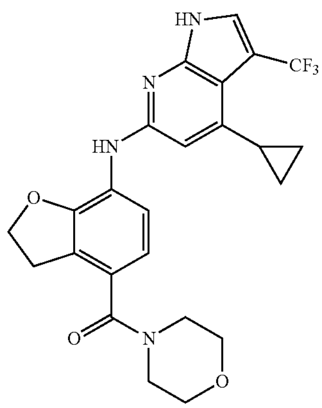 [SMILES: O=C(c1ccc(Nc2cc(C3CC3)c3c(C(F)(F)F)c[nH]c3n2)c2c1CCO2)N1CCOCC1] | (7-((4-cyclopropyl-3-(trifluoromethyl)-1H-pyrrolo[2,3-b]pyridin-6-yl)amino)-2,3-dihydrobenzofuran-4-yl)(morpholino)methanone | 473.3[M + H]⁺ | 11 | 1.71 |
| 92 | 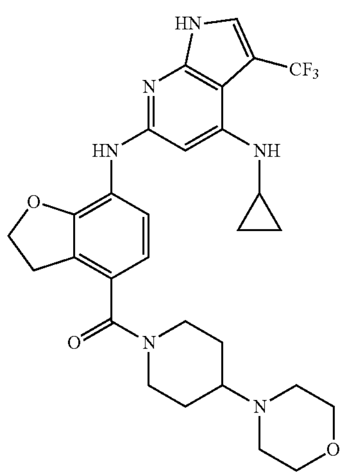 [SMILES: O=C(c1ccc(Nc2cc(NC3CC3)c3c(C(F)(F)F)c[nH]c3n2)c2c1CCO2)N1CCC(N2CCOCC2)CC1] | (7-((4-(cyclopropylamino)-3-(trifluoromethyl)-1H-pyrrolo[2,3-b]pyridin-6-yl)amino)-2,3-dihydrobenzofuran-4-yl)(4-morpholinopiperidin-1-yl)methanone | ¹H NMR (400 MHZ, DMSO) δ 11.77 (d, J = 2.4 Hz, 1H), 8.27 (s, 1H), 7.50 (d, J = 1.0 Hz, 1H), 6.75 (d, J = 8.3 Hz, 1H), 6.60 (s, 1H), 5.00 (s, 1H), 4.63 (t, J = 8.7 Hz, 2H), 3.99 (s, 3H), 3.72 (s, 3H), 3.38 (d, J = 10.0 Hz, 8H), 3.20 (t, J = 8.7 Hz, 3H), 2.09 (s, 2H), 1.52 (dd, J = 23.5, 8.3 Hz, 2H), 0.83 (dd, J = 6.6, 4.9 Hz, 2H), 0.55-0.50 (m, 2H).; 571.4[M + H]⁺ | 21 | 1.15 |
| 93 | 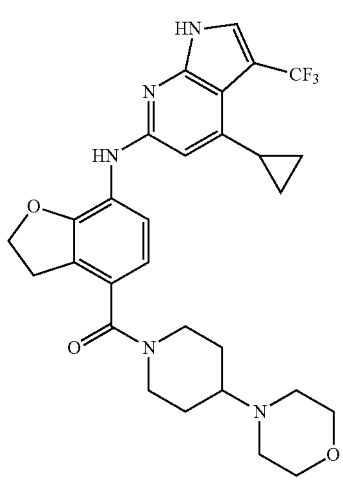 [SMILES: O=C(c1ccc(Nc2cc(C3CC3)c3c(C(F)(F)F)c[nH]c3n2)c2c1CCO2)N1CCC(N2CCOCC2)CC1] | (7-((4-cyclopropyl-3-(trifluoromethyl)-1H-pyrrolo[2,3-b]pyridin-6-yl)amino)-2,3-dihydrobenzofuran-4-yl)(4-morpholinopiperidin-1-yl)mthanone | 556.4[M + H]⁺ | 11 | 1.36 |

TABLE 1-continued

| Compound of Example | Structure | Compound Name | ¹H NMR, MS | Yield (%) | HPLC r.t. (min), Purity |
|---|---|---|---|---|---|
| 94 | 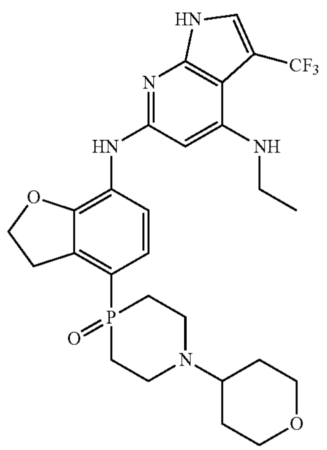 | 4-(4-((4-(ethylamino)-3-(trifluoromethyl)-1H-pyrrolo[2,3-b]pyridin-6-yl)amino)-3-methoxyphenyl)-1-(tetrahydro-2H-pyran-4-yl)-1,4-azaphosphinane 4-oxide | ¹H NMR (400 MHZ, DMSO) δ 11.86 (s, 1H), 8.85 (d, J = 5.6 Hz, 1H), 8.22 (s, 1H), 7.55 (d, J = 1.2 Hz, 1H), 7.41-7.27 (m, 2H), 6.36 (s, 1H), 4.76 (s, 1H), 3.96 (s, 6H), 3.82 (s, 2H), 3.29 (dd, J = 7.0, 5.5 Hz, 4H), 2.70 (dd, J = 23.9, 22.1 Hz, 3H), 1.96 (d, J = 40.2 Hz, 6H), 1.74 (s, 3H), 1.25 (t, J = 7.1 Hz, 3H).; 552.3[M + H]⁺ | 21 | 1.24 |
| 95 | 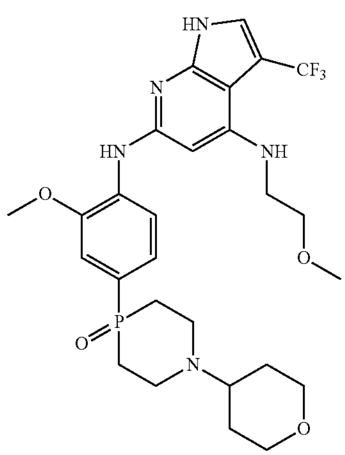 | 4-(3-methoxy-4-((4-((2-methoxyethyl)amino)-3-(trifluoromethyl)-1H-pyrrolo[2,3-b]pyridin-6-yl)amino)phenyl)-1-(tetrahydro-2H-pyran-4-yl)-1,4-azaphosphinane 4-oxide | ¹H NMR (400 MHZ, DMSO) δ 11.89 (s, 1H), 8.86 (dd, J = 8.4, 3.1 Hz, 1H), 8.21 (s, 1H), 7.56 (d, J = 1.2 Hz, 1H), 7.39-7.29 (m, 2H), 6.38 (s, 1H), 5.07 (s, 1H), 3.96 (s, 5H), 3.82 (s, 2H), 3.62 (t, J = 5.3 Hz, 3H), 3.33 (s, 5H), 2.70 (dd, J = 22.6, 20.7 Hz, 3H), 2.31-1.97 (m, 6H), 1.75 (ddd, J = 14.9, 12.5, 4.8 Hz, 4H), 1.24 (d, J= 1.1 Hz, 2H), 0.85 (ddd, J = 10.6, 7.8, 4.4 Hz, 2H). 582.3[M + H]⁺ | 22 | 1.21 |
| 96 | 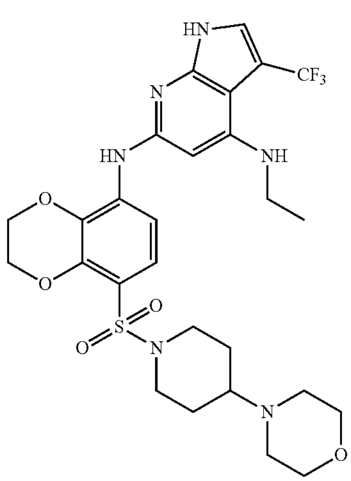 [SMILES: CCNc1cc(Nc2ccc(S(=O)(=O)N3CCC(N4CCOCC4)CC3)c3c2OCCO3)nc2[nH]cc(C(F)(F)F)c12] | N⁴-ethyl-N⁶-(8-((4-morpholonopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine | ¹H NMR (400 MHZ, DMSO) δ 11.82 (d, J = 2.5 Hz, 1H), 8.34 (d, J = 9.0 Hz, 1H), 8.22 (s, 1H), 7.55 (s, 1H), 7.16 (d, J = 9.0 Hz, 1H), 6.38 (s, 1H), 4.45-4.34 (m, 5H), 4.27 (s, 2H), 3.64 (d, J = 12.2 Hz, 3H), 3.57-3.49 (m, 7H), 3.27 (dd, J = 7.0, 5.5 Hz, 3H), 2.41 (s, 7H), 1.25 (t, J = 7.1 Hz, 4H).; 611.3[M + H]⁺ | 11 | 1.34 |

TABLE 1-continued

| Compound of Example | Structure | Compound Name | $^1$H NMR, MS | Yield (%) | HPLC r.t. (min), Purity |
|---|---|---|---|---|---|
| 97 | 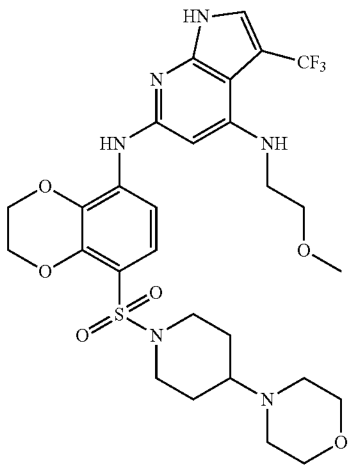 [SMILES: COCCNc1cc(Nc2ccc(S(=O)(=O)N3CCC(N4CCOCC4)CC3)c3c2OCCO3)nc2[nH]cc(C(F)(F)F)c12] | $N^4$-(2-methoxyethyl)-$N^6$-(8-((4-morpholonopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine | $^1$H NMR (400 MHZ, DMSO) δ 11.85 (d, J = 2.6 Hz, 1H), 8.34 (d, J = 9.0 Hz, 1H), 8.20 (s, 1H), 7.57 (d, J = 1.2 Hz, 1H), 7.16 (d, J = 9.0 Hz, 1H), 6.40 (s, 1H), 5.07 (d, J = 1.7 Hz, 1H), 4.45-4.33 (m, 4H), 4.27 (s, 1H), 3.65-3.60 (m, 3H), 3.57-3.51 (m, 4H), 3.41-3.36 (m, 3H), 3.33 (s, 4H), 2.42 (s, 4H), 2.20 (d, J = 10.4 Hz, 1H), 1.79 (d, J = 10.9 Hz, 2H), 1.44-1.30 (m, 2H).; 641.4[M + H]$^+$ | 11 | 1.31 |
| 98 | 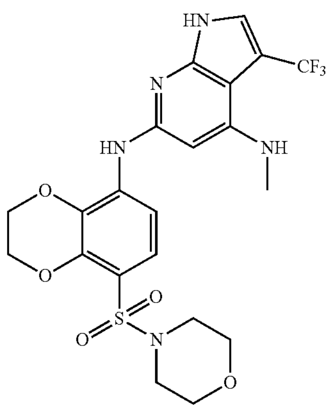 [SMILES: CNc1cc(Nc2ccc(S(=O)(=O)N3CCOCC3)c3c2OCCO3)nc2[nH]cc(C(F)(F)F)c12] | $N^4$-methyl-$N^6$-(8-(morpholonosulfonyl)-2,3-dihydrobenzo[b][1,4]dioxin-5-yl)-3-(trifluoromethyl)-1H-pyrrolo[2,3-b]pyridine-4,6-diamine | $^1$H NMR (400 MHZ, DMSO) δ 11.81 (d, J = 2.6 Hz, 1H), 8.37 (d, J = 9.0 Hz, 1H), 8.24 (s, 1H), 7.54 (d, J = 1.3 Hz, 1H), 7.17 (d, J = 9.0 Hz, 1H), 6.33 (s, 1H), 5.08 (d, J = 3.1 Hz, 1H), 4.47-4.35 (m, 4H), 3.67-3.56 (m, 4H), 3.05-3.00 (m, 4H), 2.90 (d, J = 4.8 Hz, 3H).; 514.2[M + H]$^+$ | 11 | 1.46 |
| 99 | 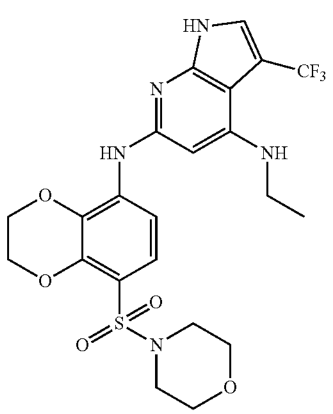 [SMILES: CCNc1cc(Nc2ccc(S(=O)(=O)N3CCOCC3)c3c2OCCO3)nc2[nH]cc(C(F)(F)F)c12] | $N^4$-ethyl-$N^6$-(8-(morpholonosulfonyl)-2,3-dihydrobenzo[b][1,4]dioxin-5-yl)-3-(trifluoromethyl)-1H-pyrrolo[2,3-b]pyridine-4,6-diamine | $^1$H NMR (400 MHZ, DMSO) δ 11.83 (d, J = 2.3 Hz, 1H), 8.37 (d, J = 9.0 Hz, 1H), 8.26 (s, 1H), 7.56 (s, 1H), 7.17 (d, J = 9.0 Hz, 1H), 6.39 (s, 1H), 4.47-4.35 (m, 4H), 3.65-3.59 (m, 4H), 3.32-3.24 (m, 2H), 3.05-2.98 (m, 4H), 1.25 (t, J = 7.1 Hz, 4H).; 528.2[M + H]$^+$ | 21 | 1.59 |

TABLE 1-continued

| Compound of Example | Structure | Compound Name | $^1$H NMR, MS | Yield (%) | HPLC r.t. (min), Purity |
|---|---|---|---|---|---|
| 100 | 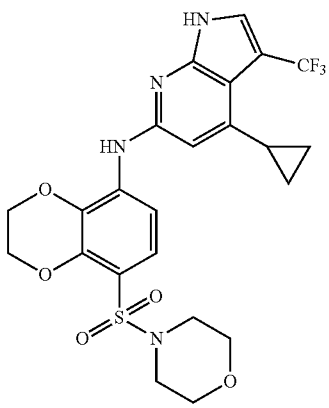 [SMILES: O=S(=O)(c1ccc(Nc2cc(C3CC3)c3c(C(F)(F)F)c[nH]c3n2)c2c1OCCO2)N1CCOCC1] | 4-cyclopropyl-N-(8-(morpholinosulfonyl)-2,3-dihydrobenzo[b][1,4]dioxin-5-yl)-3-(trifluoromethyl)-1H-pyrrolo[2,3-b]pyridine-6-amine | $^1$H NMR (400 MHZ, DMSO) δ 12.08 (s, 1H), 8.47 (s, 1H), 8.36 (d, J = 9.0 Hz, 1H), 7.77 (s, 1H), 7.20 (d, J = 9.0 Hz, 1H), 6.82 (s, 1H), 5.68 (s, 1H), 4.46-4.38 (m, 5H), 3.65-3.60 (m, 5H), 3.06-3.00 (m, 5H), 2.25-2.16 (m, 1H), 1.12-1.02 (m, 2H), 0.88-0.81 (m, 2H).; 525.2[M + H]$^+$ | 12 | 1.81 |
| 101 | 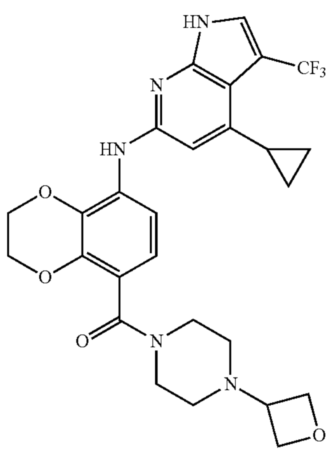 [SMILES: O=C(c1ccc(Nc2cc(C3CC3)c3c(C(F)(F)F)c[nH]c3n2)c2c1OCCO2)N1CCN(C2COC2)CC1] | (8-((4-cyclopropyl-3-(trifluoromethyl)-1H-pyrrolo[2,3-b]pyridin-6-yl)amino)-2,3-dihydrobenzo[b][1,4]dioxin-5-yl)(4-(oxetan-3-yl)piperazin-1-yl)methanone | $^1$H NMR (400 MHZ, MeOD) δ 8.27 (d, J = 8.5 Hz, 1H), 7.57 (s, 1H), 6.83 (d, J = 8.5 Hz, 1H), 6.51 (s, 1H), 4.78-4.61 (m, 8H), 4.47-4.31 (m, 8H), 3.84 (d, J = 21.0 Hz, 4H), 3.55 (ddd, J = 27.4, 16.7, 10.7 Hz, 6H), 2.36 (dd, J = 24.5, 19.0 Hz, 9H), 1.17-1.09 (m, 3H), 1.08-0.87 (m, 5H).; 544.3[M + H]$^+$ | 21 | 1.41 |
| 102 | 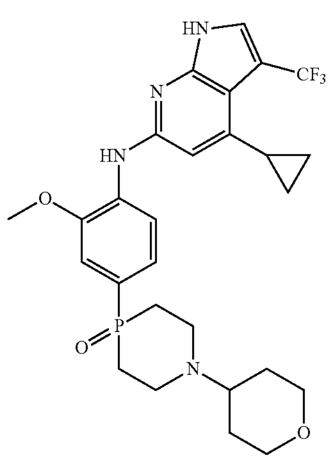 [SMILES: COc1cc(P2(=O)CCN(C3CCOCC3)CC2)ccc1Nc1cc(C2CC2)c2c(C(F)(F)F)c[nH]c2n1] | 4-(4-((4-cyclopropyl-3-(trifluoromethyl)-1H-pyrrolo[2,3-b]pyridin-6-yl)amino)-3-methoxyphenyl)-1-(tetrahydro-2H-pyran-4-yl)-1,4-azaphosphinane 4-oxide | 549.3[M + H]$^+$ | 7 | 1.39 |

TABLE 1-continued

| Compound of Example | Structure | Compound Name | $^1$H NMR, MS | Yield (%) | HPLC r.t. (min), Purity |
|---|---|---|---|---|---|
| 103 | 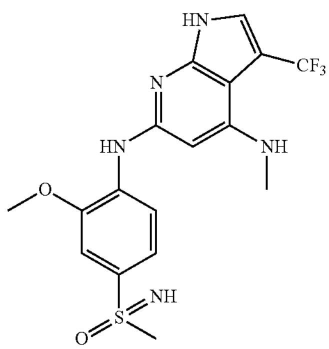 [SMILES: CNc1cc(Nc2ccc(S(C)(=N)=O)cc2OC)nc2[nH]cc(C(F)(F)F)c12] | N$^6$-(2-methoxy-4-(s-methylsulfonylimidoyl)phenyl)-N$^4$-methyl-3-(trifluoromethyl)-1H-pyrrolo[2,3-b]pyridine-4,6-diamine | $^1$H NMR (400 MHZ, DMSO) δ 9.07 (d, J = 8.6 Hz, 1H), 8.51 (s, 1H), 7.93 (s, 1H), 7.62 (d, J = 8.7 Hz, 1H), 7.58 (s, 1H), 6.51 (s, 1H), 4.12 (s, 3H), 3.18 (s, 3H), 3.05 (d, J = 4.6 Hz, 4H).; 414.2[M + H]$^+$ | 11 | 1.26 |
| 104 | 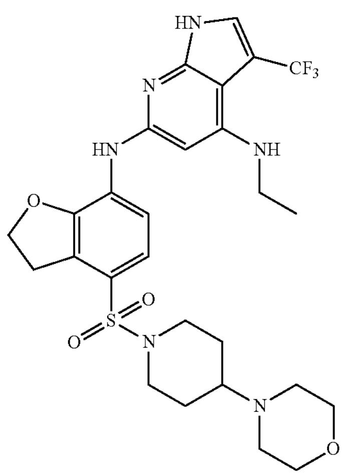 [SMILES: CCNc1cc(Nc2ccc(S(=O)(=O)N3CCC(N4CCOCC4)CC3)c3c2OCC3)nc2[nH]cc(C(F)(F)F)c12] | N$^4$-ethyl-N$^6$-(4-((4-morpholinopiperidin-1-yl)sulfonyl)-2,3-dihydrobenzofuran-7-yl)-3-(trifluoromethyl)-1H-pyrrolo[2,3-b]pyridine-4,6-diamine | $^1$H NMR (400 MHZ, DMSO-d$_6$) δ 11.82 (s, 1H), 8.63 (d, J = 8.7 Hz, 1H), 8.43 (s, 1H), 7.54 (s, 1H), 7.09 (d, J = 8.7 Hz, 1H), 6.38 (s, 1H), 4.78 (q, J = 5.0 Hz, 1H), 4.69 (t, J = 8.8 Hz, 2H), 3.63 (d, J = 11.7 Hz, 2H), 3.52 (s, 2H), 3.47 (s, 2H), 3.26 (d, J = 1.9 Hz, 2H), 2.39 (t, J = 4.6 Hz, 4H), 2.15 (dd, J = 12.8, 9.4 Hz, 1H), 1.86 (s, 4H), 1.81 (d, J = 13.5 Hz, 2H), 1.41 (tt, J = 13.5, 6.8 Hz, 2H), 1.24 (t, J = 7.1 Hz, 3H). 595.5[M + H]$^+$ | 57 | 1.38 |
| 105 | 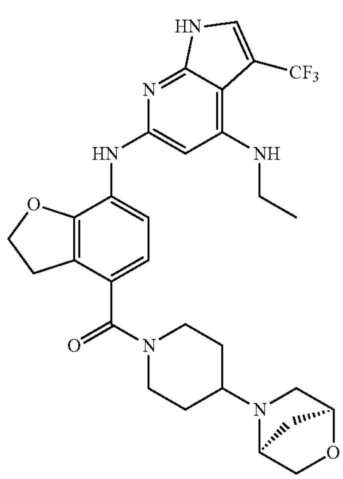 [SMILES: CCNc1cc(Nc2ccc(C(=O)N3CCC(N4C[C@@H]5C[C@H]4CO5)CC3)c3c2OCC3)nc2[nH]cc(C(F)(F)F)c12] | (4-((1S,4S)-2-oxa-5-azabicyclo[2.2.1]heptan-5-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone | $^1$H NMR (400 MHZ, Methanol-d4) δ 7.40 (d, J = 1.6 Hz, 1H), 7.13 (d, J = 8.1 Hz, 1H), 6.86 (d, J = 8.1 Hz, 1H), 4.61 (t, J = 8.9 Hz, 4H), 4.22 (d, J = 10.7 Hz, 1H), 4.03 (d, J = 10.0 Hz, 1H), 3.91-3.73 (m, 2H), 3.65 (d, J = 11.6 Hz, 1H), 3.51 (d, J = 11.3 Hz, 1H), 3.34 (q, J = 7.1 Hz, 2H), 2.85 (s, 1H), 2.25-2.08 (m, 3H), 2.06 (s, 3H), 1.67 (s, 3H), 1.25 (t, J = 7.2 Hz, 3H), 1.20 (s, 6H). 571.5[M + H]$^+$ | 45 | 1.18 |

TABLE 1-continued

| Compound of Example | Structure | Compound Name | ¹H NMR, MS | Yield (%) | HPLC r.t. (min), Purity |
|---|---|---|---|---|---|
| 106 | 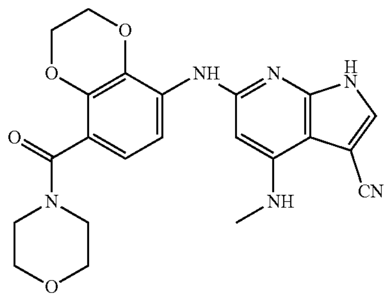 [SMILES: CNc1cc(Nc2ccc(C(=O)N3CCOCC3)c3c2OCCO3)nc2[nH]cc(C#N)c12] | 4-(methylamino)-6-((8-(morpholine-4-carbonyl)-2,3-dihydrobenzo[b][1,4]dioxin-5-yl)amino)-1H-pyrrolo[2,3-b]pyridine-3-carbonitrile | ¹H NMR (400 MHZ, DMSO) δ 12.06 (s, 1H), 8.14 (d, J = 8.5 Hz, 1H), 7.94 (s, 1H), 7.81 (s, 1H), 6.70 (d, J = 8.4 Hz, 1H), 6.20 (s, 1H), 5.52 (d, J = 4.4 Hz, 1H), 4.33 (d, J = 14.9 Hz, 4H), 3.57 (d, J = 26.2 Hz, 7H), 3.32 (d, J = 47.1 Hz, 6H), 2.85 (d, J = 4.0 Hz, 3H).; 435.3[M + H]⁺ | 24 | 1.06 |
| 107 | 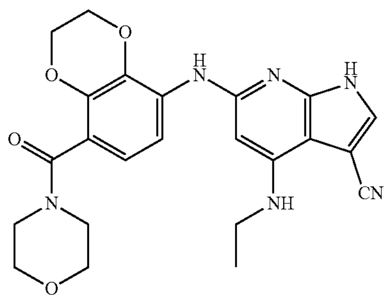 [SMILES: CCNc1cc(Nc2ccc(C(=O)N3CCOCC3)c3c2OCCO3)nc2[nH]cc(C#N)c12] | 4-(ethylamino)-6-((8-(morpholine-4-carbonyl)-2,3-dihydrobenzo[b][1,4]dioxin-5-yl)amino)-1H-pyrrolo[2,3-b]pyridine-3-carbonitrile | 1H NMR (400 MHZ, DMSO-d₆) δ 12.06 (s, 1H), 8.13 (dd, J = 8.5, 1.8 Hz, 1H), 7.95 (s, 1H), 7.80 (d, J = 2.4 Hz, 1H), 6.69 (dd, J = 8.6, 1.8 Hz, 1H), 6.26 (d, J = 1.8 Hz, 1H), 5.28 (t, J = 5.0 Hz, 1H), 4.37-4.29 (m, 4H), 3.60 (s, 3H), 3.53 (s, 2H), 3.24 (p, J = 6.6 Hz, 4H), 1.28-1.22 (m, 4H). 449.3[M + H]⁺ | 26 | 1.02 |
| 108 | 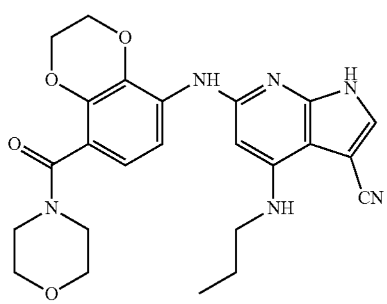 [SMILES: CCCNc1cc(Nc2ccc(C(=O)N3CCOCC3)c3c2OCCO3)nc2[nH]cc(C#N)c12] | 6-((8-(morpholine-4-carbonyl)-2,3-dihydrobenzo[b][1,4]dioxin-5-yl)amino)-4-(propylamino)-1H-pyrrolo[2,3-b]pyridine-3-carbonitrile | ¹H NMR (400 MHZ, MeOD) δ 7.92 (d, J = 7.0 Hz, 1H), 7.47 (s, 1H), 6.67 (d, J = 8.5 Hz, 1H), 5.93 (s, 1H), 4.36-4.15 (m, 5H), 3.63 (s, 5H), 3.54 (d, J = 15.8 Hz, 2H), 3.31 (d, J = 25.9 Hz, 2H), 3.15 (t, J = 7.0 Hz, 2H), 1.65 (dq, J = 14.5, 7.3 Hz, 3H), 0.96 (t, J = 7.4 Hz, 4H).463.3[M + H]⁺ | 38 | 1.25 |
| 109 | 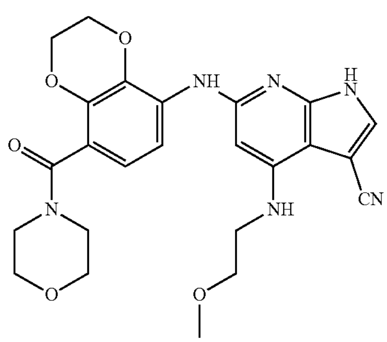 [SMILES: COCCNc1cc(Nc2ccc(C(=O)N3CCOCC3)c3c2OCCO3)nc2[nH]cc(C#N)c12] | 4-((2-methoxyethyl)amino)-6-((8-(morpholine-4-carbonyl)-2,3-dihydrobenzo[b][1,4]dioxin-5-yl)amino)-1H-pyrrolo[2,3-b]pyridine-3-carbonitrile | ¹H NMR (400 MHZ, DMSO) δ 12.10 (s, 1H), 8.06 (s, 2H), 7.83 (d, J = 2.2 Hz, IH), 6.71 (d, J = 8.5 Hz, 1H), 6.28 (s, 1H), 5.44 (s, 1H), 4.34 (dd, J = 15.3, 3.9 Hz, 4H), 3.66-3.48 (m, 8H), 3.39 (d, J = 4.1 Hz, 4H), 3.26 (s, 2H), 1.28-1.12 (m, 2H).; 479.4[M + H]⁺ | 76 | 1.13 |

TABLE 1-continued

| Compound of Example | Structure | Compound Name | ¹H NMR, MS | Yield (%) | HPLC r.t. (min), Purity |
|---|---|---|---|---|---|
| 110 | 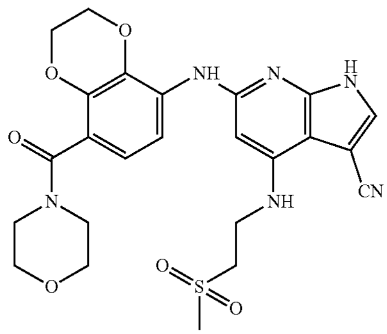 [SMILES: CS(=O)(=O)CCNc1cc(Nc2ccc(C(=O)N3CCOCC3)c3c2OCCO3)nc2[nH]cc(C#N)c12] | 4-((2-(methylsulfonyl)ethyl)amino)-6-((8-(morpholine-4-carbonyl)-2,3-dihydrobenzo[b][1,4]dioxin-5-yl)amino)-1H-pyrrolo[2,3-b]pyridine-3-carbonitrile | 1H NMR (400 MHZ, DMSO-$d_6$) δ 12.20 (s, 2H), 8.35 (s, 1H), 8.22 (d, J = 6.9 Hz, 1H), 7.88 (s, 3H), 6.83 (d, J = 7.0 Hz, 1H), 6.75 (s, 1H), 6.73 (s, 1H), 6.24 (s, 2H), 4.35 (s, 4H), 4.33 (s, 4H), 3.11 (s, 4H), 1.09 (t, J = 7.0 Hz, 2H). 527.3[M + H]$^+$ | 65 | 1.06 |
| 111 | 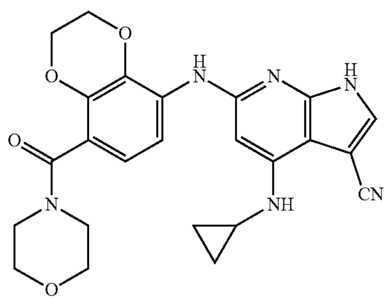 [SMILES: N#Cc1c[nH]c2nc(Nc3ccc(C(=O)N4CCOCC4)c4c3OCCO4)cc(NC3CC3)c12] | 4-(cyclopropylamino)-6-((8-(morpholine-4-carbonyl)-2,3-dihydrobenzo[b][1,4]dioxin-5-yl)amino)-1H-pyrrolo[2,3-b]pyridine-3-carbonitrile | 1H NMR (400 MHz, DMSO-$d_6$) δ 12.07 (s, 1H), 8.09-8.02 (m, 2H), 7.80 (t, J = 2.4 Hz, 1H), 6.70 (d, J = 8.5 Hz, 1H), 6.55 (s, 1H), 5.64 (s, 1H), 4.33 (d, J = 17.1 Hz, 4H), 3.57 (d, J = 26.3 Hz, 6H), 2.54 (d, J = 1.7 Hz, 3H), 0.82 (d, J = 6.7 Hz, 2H), 0.56 (s, 2H). 461.3[M + H]$^+$ | 49 | 1.26 |
| 112 | 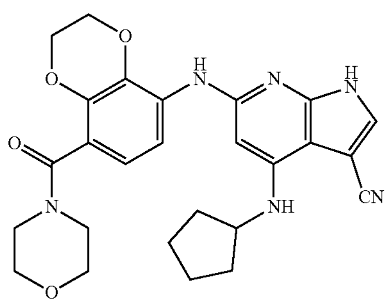 [SMILES: N#Cc1c[nH]c2nc(Nc3ccc(C(=O)N4CCOCC4)c4c3OCCO4)cc(NC3CCCC3)c12] | 4-(cyclopentylamino)-6-((8-(morpholine-4-carbonyl)-2,3-dihydrobenzo[b][1,4]dioxin-5-yl)amino)-1H-pyrrolo[2,3-b]pyridine-3-carbonitrile | 1H NMR (400 MHz, Methanol-$d_4$) δ 8.03-7.89 (m, 1H), 7.57 (d, J = 3.9 Hz, 1H), 6.77 (t, J = 6.3 Hz, 1H), 6.07 (d, J = 4.0 Hz, 1H), 4.36 (d, J = 17.9 Hz, 6H), 3.96 (t, J = 5.9 Hz, 1H), 3.73 (s, 4H), 2.11 (dd, J = 11.9, 5.7 Hz, 2H), 1.70 (s, 8H) 489.3[M + H]$^+$ | 18 | 1.38 |
| 113 | 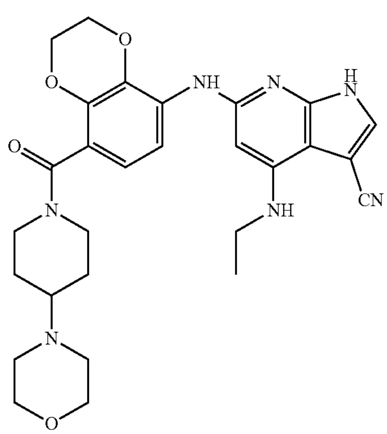 [SMILES: CCNc1cc(Nc2ccc(C(=O)N3CCC(N4CCOCC4)CC3)c3c2OCCO3)nc2[nH]cc(C#N)c12] | 4-(ethylamino)-6-((8-(4-morpholinopiperidine-1-carbonyl)-2,3-dihydrobenzo [b][1,4]dioxin-5-yl)amino)-1H-pyrrolo[2,3-b]pyridine-3-carbonitrile | ¹H NMR (400 MHZ, DMSO) δ 12.08 (s, 1H), 10.12 (s, 1H), 8.08 (d, J = 7.7 Hz, 2H), 7.82 (s, 1H), 6.70 (s, 1H), 6.25 (s, 1H), 5.38 (s, 1H), 4.64 (d, J = 11.6 Hz, 1H), 4.34 (d, J = 21.9 Hz, 5H), 4.02 (d, J = 11.3 Hz, 3H), 3.68 (s, 5H), 3.45 (s, 4H), 3.25 (d, J = 6.6 Hz, 2H), 3.11 (s, 3H), 2.95 (s, 1H), 2.70 (s, 1H), 2.17 (s, 1H).; 532.4[M+H] | 53 | 0.97 |

TABLE 1-continued

| Compound of Example | Structure | Compound Name | $^1$H NMR, MS | Yield (%) | HPLC r.t. (min), Purity |
|---|---|---|---|---|---|
| 114 | 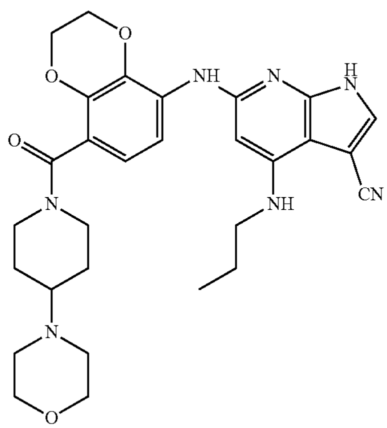 [SMILES: CCCNc1cc(Nc2ccc(C(=O)N3CCC(N4CCOCC4)CC3)c3c2OCCO3)nc2[nH]cc(C#N)c12] | 6-((8-(4-morpholinopiperidine-1-carbonyl)-2,3-dihydrobenzo [b] [1,4]dioxin-5-yl)amino)-4-(propylamino)-1H-pyrrolo[2,3-b]pyridine-3-carbonitrile | $^1$H NMR (400 MHZ, DMSO) δ 12.08 (s, 1H), 10.22 (s, 1H), 8.12-8.01 (m, 2H), 7.82 (d, J = 1.4 Hz, 1H), 6.70 (s, 1H), 6.26 (s, 1H), 5.37 (s, 1H), 4.64 (d, J = 12.0 Hz, 1H), 4.34 (d, J = 21.3 Hz, 5H), 4.09-3.93 (m, 3H), 3.78-3.57 (m, 4H), 3.45 (s, 4H), 3.18 (d, J = 6.9 Hz, 2H), 3.11 (s, 3H), 2.70 (dd, J = 16.3, 7.2 Hz, 1H), 2.17 (s, 1H), 1.72-1.61 (m, 3H), 1.53 (s, 2H), 0.98 (t, J = 7.4 Hz, 3H).; 546.4[M + H]$^+$ | 70 | 1.05 |
| 115 | 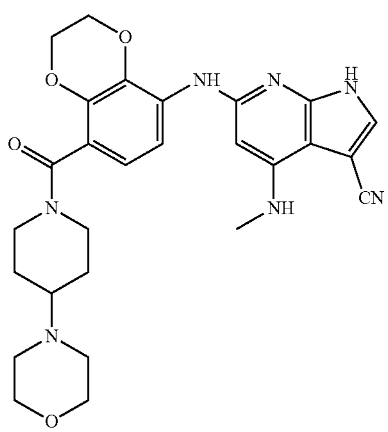 [SMILES: CNc1cc(Nc2ccc(C(=O)N3CCC(N4CCOCC4)CC3)c3c2OCCO3)nc2[nH]cc(C#N)c12] | 4-(methylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile | $^1$H NMR (400 MHZ, DMSO) δ 12.14 (s, 1H), 10.30 (s, 1H), 8.16 (s, 1H), 7.99 (s, 1H), 7.83 (s, 1H), 7.34-7.00 (m, 1H), 6.71 (s, 1H), 6.17 (s, 1H), 5.69 (s, 1H), 4.64 (d, J = 11.9 Hz, 2H), 4.34 (d, J = 19.8 Hz, 5H), 4.09-3.92 (m, 3H), 3.67 (d, J = 7.7 Hz, 4H), 3.45 (s, 5H), 3.11 (s, 4H), 2.85 (d, J = 8.3 Hz, 3H), 2.70 (s, 1H), 2.17 (s, 1H), 1.53 (s, 3H).; 518.4[M + H]$^+$ | 78 | 0.88 |
| 116 | 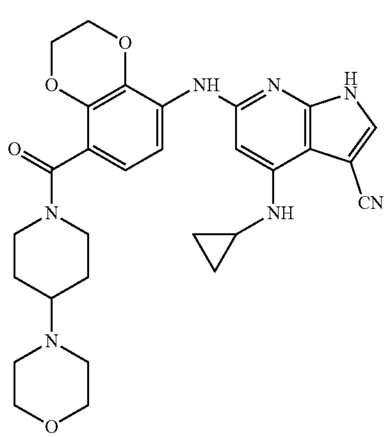 [SMILES: N#Cc1c[nH]c2nc(Nc3ccc(C(=O)N4CCC(N5CCOCC5)CC4)c4c3OCCO4)cc(NC3CC3)c12] | 4-(cyclopropylamino)-6-((8-(4-morpholinopiperidine-1-carbonyl)-2,3-dihydrobenzo [b] [1,4]dioxin-5-yl)amino)-1H-pyrrolo[2,3-b]pyridine-3-carbonitrile | $^1$H NMR (400 MHZ, DMSO) δ 12.05 (s, 1H), 8.03 (s, 1H), 7.80 (d, J = 2.0 Hz, 1H), 6.68 (s, 1H), 6.55 (s, 1H), 5.64 (s, 1H), 4.56 (s, 1H), 4.33 (d, J = 23.3 Hz, 5H), 3.62 (s, 5H), 3.14-2.86 (m, 3H), 2.72 (t, J = 12.0 Hz, 2H), 1.91 (s, 1H), 0.86-0.79 (m, 2H), 0.60-0.52 (m, 2H).; 544.4[M + H]$^+$ | 57 | 1.02 |

TABLE 1-continued

| Compound of Example | Structure | Compound Name | ¹H NMR, MS | Yield (%) | HPLC r.t. (min), Purity |
|---|---|---|---|---|---|
| 117 | 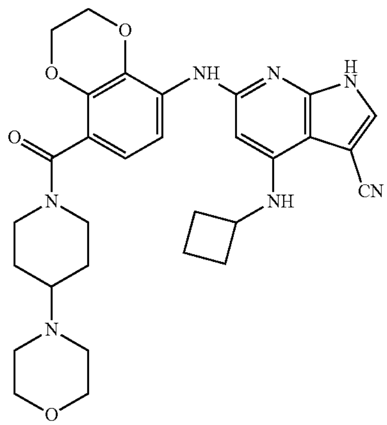 [SMILES: N#Cc1c[nH]c2nc(Nc3ccc(C(=O)N4CCC(N5CCOCC5)CC4)c4c3OCCO4)cc(NC3CCC3)c12] | 4-(cyclobutylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile | ¹H NMR (400 MHZ, MeOD) δ 8.00 (d, J = 6.5 Hz, 1H), 7.59 (s, 1H), 6.75 (dd, J = 30.8, 8.3 Hz, 1H), 5.97 (s, 1H), 4.69 (d, J = 13.1 Hz, 1H), 4.36 (d, J = 23.5 Hz, 4H), 4.09 (p, J = 7.5 Hz, 1H), 3.73 (s, 5H), 3.23-2.94 (m, 1H), 2.82 (d, J = 8.1 Hz, 1H), 2.65 (s, 4H), 2.59-2.46 (m, 3H), 1.89 (ddd, J = 10.3, 6.0, 3.0 Hz, 3H).; 558.4[M + H]⁺ | 33 | 1.02 |
| 118 | 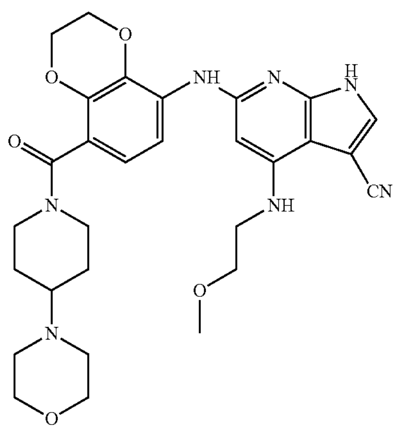 [SMILES: COCCNc1cc(Nc2ccc(C(=O)N3CCC(N4CCOCC4)CC3)c3c2OCCO3)nc2[nH]cc(C#N)c12] | 4-((2-methoxyethyl)amino)-6-((8-(4-morpholinopiperidine-1-carbonyl)-2,3-dihydrobenzo [b][1,4]dioxin-5-yl)amino)-1H-pyrrolo[2,3-b]pyridine-3-carbonitrile | ¹H NMR (400 MHZ, DMSO) δ 12.11 (s, 1H), 10.07 (s, 1H), 8.08 (d, J = 8.7 Hz, 2H), 7.84 (s, 1H), 7.31-6.97 (m, 1H), 6.70 (s, 1H), 6.29 (s, 1H), 5.44 (s, 1H), 4.64 (d, J = 12.0 Hz, 1H), 4.34 (d, J = 22.2 Hz, 4H), 4.02 (d, J = 12.3 Hz, 3H), 3.73-3.55 (m, 6H), 3.45 (s, 2H), 3.39 (s, 3H), 3.33 (s, 3H), 3.11 (s, 2H), 2.70 (s, 1H), 2.17 (s, 1H), 1.53 (s, 2H).; 562.4[M + H]⁺ | 20 | 0.96 |
| 119 | 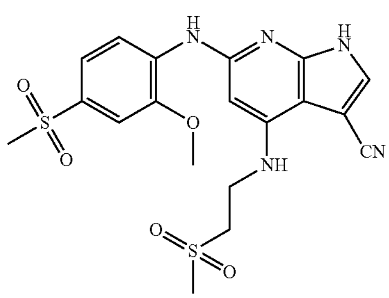 [SMILES: COc1cc(S(C)(=O)=O)ccc1Nc1cc(NCCS(C)(=O)=O)c2c(C#N)c[nH]c2n1] | 6-((2-methoxy-4-(methylsulfonyl)phenyl)amino)-4-((2-(methylsulfonyl)ethyl)amino)-1H-pyrrolo[2,3-b]pyridine-3-carbonitrile | 1H NMR (400 MHZ, DMSO) δ 12.23 (s, 1H), 8.85 (d, J = 8.6 Hz, 1H), 8.42 (s, 1H), 7.91 (s, 1H), 7.42 (d, J = 9.6 Hz, 2H), 6.46 (s, 1H), 5.85 (t, J = 5.2 Hz, 1H), 4.00 (s, 3H), 3.72-3.67 (m, 2H), 3.53 (t, J = 6.5 Hz, 2H), 3.18 (s, 3H), 3.10 (s, 3H). 464.2[M + H]⁺ | 46 | 1.24 |
| 120 | 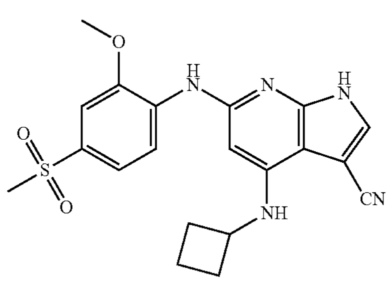 [SMILES: COc1cc(S(C)(=O)=O)ccc1Nc1cc(NC2CCC2)c2c(C#N)c[nH]c2n1] | 4-(cyclobutylamino)-6-((2-methoxy-4-(methylsulfonyl)phenyl)amino)-1H-pyrrolo[2,3-b]pyridine-3-carbonitrile | 412.2[M + H]⁺ | 3 | 1.55 |

TABLE 1-continued

| Compound of Example | Structure | Compound Name | $^1$H NMR, MS | Yield (%) | HPLC r.t. (min), Purity |
|---|---|---|---|---|---|
| 121 | 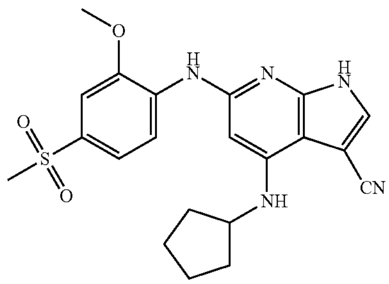 [SMILES: COc1cc(S(C)(=O)=O)ccc1Nc1cc(NC2CCCC2)c2c(C#N)c[nH]c2n1] | 4-(cyclopentylamino)-6-((2-methoxy-4-(methylsulfonyl)phenyl)amino)-1H-pyrrolo[2,3-b]pyridine-3-carbonitrile | 1H NMR (400 MHZ, Methanol-d4) δ 8.92-8.62 (m, 1H), 7.60 (s, 1H), 7.44 (d, J = 8.7 Hz, 1H), 7.38 (d, J = 4.0 Hz, 1H), 6.15 (s, 1H), 3.99 (d, J = 4.1 Hz, 3H), 3.07 (s, 3H), 2.17-2.06 (m, 2H), 1.82-1.56 (m, 6H), 1.25 (s, 3H). 426.3[M + H]$^+$ | 13 | 1.68 |
| 122 | 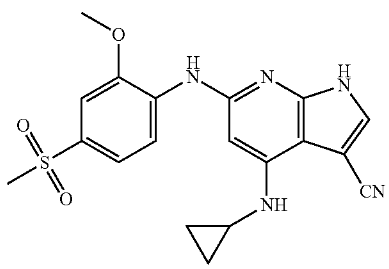 [SMILES: COc1cc(S(C)(=O)=O)ccc1Nc1cc(NC2CC2)c2c(C#N)c[nH]c2n1] | 4-(cyclopropylamino)-6-((2-methoxy-4-(methylsulfonyl)phenyl)amino)-1H-pyrrolo[2,3-b]pyridine-3-carbonitrile | 1H NMR (400 MHZ, DMSO) δ 12.17 (s, 1H), 8.80 (d, J = 8.4 Hz, 1H), 8.47 (s, 1H), 7.88 (s, 1H), 7.40 (s, 2H), 6.69 (s, 1H), 5.74 (s, 1H), 3.99 (s, 3H), 3.18 (s, 3H), 1.16 (d, J = 6.3 Hz, 1H), 0.84 (d, J = 6.3 Hz, 2H), 0.58 (s, 2H). 398.3[M + H]$^+$ | 64 | 1.53 |
| 123 | 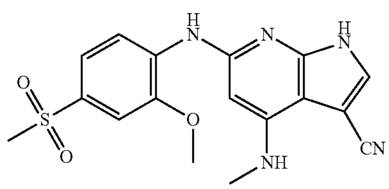 [SMILES: CNc1cc(Nc2ccc(S(C)(=O)=O)cc2OC)nc2[nH]cc(C#N)c12] | 6-((2-methoxy-4-(morpholinosulfonyl)phenyl)amino)-4-(methylamino)-1H-pyrrolo[2,3-b]pyridine-3-carbonitrile | $^1$H NMR (400 MHZ, DMSO) δ 12.20 (s, 1H), 8.85 (d, J = 8.4 Hz, 1H), 8.37 (s, 1H), 7.88 (s, 1H), 7.41 (d, J = 12.2 Hz, 2H), 6.34 (s, 1H), 5.62 (d, J = 4.5 Hz, 1H), 3.99 (s, 3H), 3.17 (s, 3H), 2.88 (d, J = 4.3 Hz, 3H).; 372.2[M+H] | 57 | 1.29 |
| 124 | 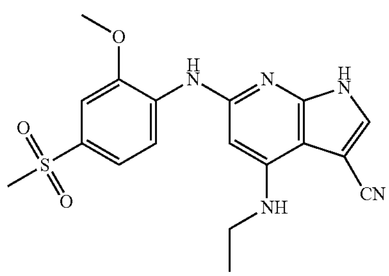 [SMILES: CCNc1cc(Nc2ccc(S(C)(=O)=O)cc2OC)nc2[nH]cc(C#N)c12] | 4-(ethylamino)-6-((2-methoxy-4-(methylsulfonyl)phenyl)amino)-1H-pyrrolo[2,3-b]pyridine-3-carbonitrile | 1H NMR (400 MHZ, DMSO) δ 12.16 (s, 1H), 8.84 (d, J = 8.3 Hz, 1H), 8.38 (s, 1H), 7.88 (s, 1H), 7.41 (d, J = 10.7 Hz, 2H), 6.40 (s, 1H), 5.38 (d, J = 5.1 Hz, 1H), 3.99 (s, 3H), 3.30-3.25 (m, 2H), 3.17 (s, 3H), 1.27 (d, J = 7.4 Hz, 3H). 386.3[M + H]$^+$ | 53 | 1.4 |
| 125 | 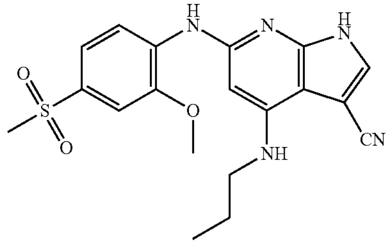 [SMILES: CCCNc1cc(Nc2ccc(S(C)(=O)=O)cc2OC)nc2[nH]cc(C#N)c12] | 6-((2-methoxy-4-(methylsulfonyl)phenyl)amino)-4-(propylamino)-1H-pyrrolo[2,3-b]pyridine-3-carbonitrile | $^1$H NMR (400 MHZ, DMSO) δ 8.84 (d, J = 8.4 Hz, 1H), 8.37 (s, 1H), 7.87 (s, 1H), 7.41 (d, J = 10.9 Hz, 2H), 6.40 (s, 1H), 5.37 (t, J = 4.9 Hz, 1H), 3.99 (s, 3H), 3.24-3.18 (m, 2H), 3.17 (s, 3H), 1.73-1.65 (m, 2H), 0.99 (t, J = 7.2 Hz, 3H).; 400.3[M + H]$^+$ | 23 | 1.52 |

TABLE 1-continued

| Compound of Example | Structure | Compound Name | ¹H NMR, MS | Yield (%) | HPLC r.t. (min), Purity |
|---|---|---|---|---|---|
| 126 | 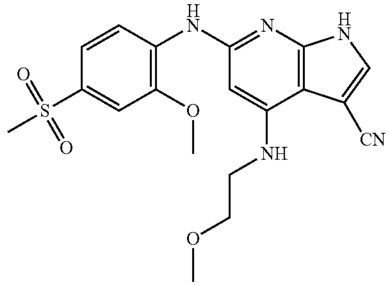 [SMILES: COCCNc1cc(Nc2ccc(S(C)(=O)=O)cc2OC)nc2[nH]cc(C#N)c12] | 6-((2-methoxy-4-(methylsulfonyl)phenyl)amino)-4-((2-methoxyethyl)amino)-1H-pyrrolo[2,3-b]pyridine-3-carbonitrile | ¹H NMR (400 MHZ, DMSO) δ 12.19 (d, J = 2.5 Hz, 1H), 8.84 (d, J = 8.4 Hz, 1H), 8.36 (s, 1H), 7.89 (d, J = 2.9 Hz, 1H), 7.41 (dt, J = 5.8, 2.0 Hz, 2H), 6.43 (s, 1H), 5.45 (t, J = 5.4 Hz, 1H), 3.99 (s, 3H), 3.62 (t, J = 5.5 Hz, 2H), 3.41 (q, J = 5.5 Hz, 2H), 3.34 (s, 3H), 3.17 (s, 3H).; 416.3[M + H]⁺ | 80 | 1.37 |
| 127 | 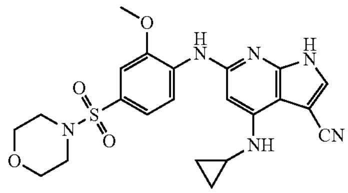 [SMILES: COc1cc(S(=O)(=O)N2CCOCC2)ccc1Nc1cc(NC2CC2)c2c(C#N)c[nH]c2n1] | 4-(cyclopropylamino)-6-((2-methoxy-4-(morpholinosulfonyl)phenyl)amino)-1H-pyrrolo[2,3-b]pyridine-3-carbonitrile | 1H NMR (400 MHZ, DMSO) δ 12.16 (s, 1H), 8.83 (d, J = 8.5 Hz, 1H), 8.50 (s, 1H), 7.88 (s, 1H), 7.25 (d, J = 8.7 Hz, 1H), 7.16 (s, 1H), 6.70 (s, 1H), 5.75 (d, J = 4.7 Hz, 1H), 3.98 (s, 3H), 3.64 (s, 4H), 2.87 (s, 4H), 2.54 (s, 1H), 0.85 (d, J = 6.5 Hz, 2H), 0.58 (s, 2H). 469.3[M + H]⁺ | 39 | 1.62 |
| 128 | 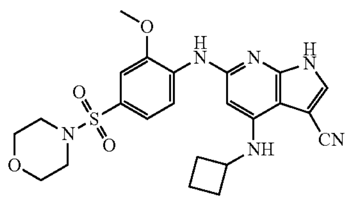 [SMILES: COc1cc(S(=O)(=O)N2CCOCC2)ccc1Nc1cc(NC2CCC2)c2c(C#N)c[nH]c2n1] | 4-(cyclobutylamino)-6-((2-methoxy-4-(morpholinosulfonyl)phenyl)amino)-1H-pyrrolo[2,3-b]pyridine-3-carbonitrile | ¹H NMR (400 MHZ, MeOD) δ 8.77 (d, J = 8.6 Hz, 1H), 7.62 (s, 1H), 7.30 (dd, J = 8.6, 2.0 Hz, 1H), 7.22 (d, J = 1.9 Hz, 1H), 6.04 (s, 1H), 4.10 (dd, J = 7.4, 4.8 Hz, 1H), 4.00 (s, 3H), 3.70 (dd, J = 10.4, 5.7 Hz, 5H), 3.00-2.93 (m, 4H), 2.58-2.49 (m, 2H), 2.04-1.84 (m, 5H).; 483.3[M + H]⁺ | 35 | 1.57 |
| 129 | 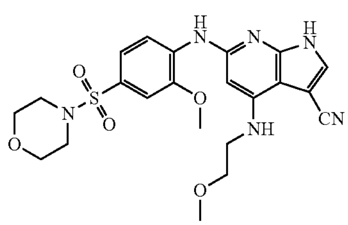 [SMILES: COCCNc1cc(Nc2ccc(S(=O)(=O)N3CCOCC3)cc2OC)nc2[nH]cc(C#N)c12] | 6-((2-methoxy-4-(morpholinosulfonyl)phenyl)amino)-4-((2-methoxyethyl)amino)-1H-pyrrolo[2,3-b]pyridine-3-carbonitrile | ¹H NMR (400 MHZ, DMSO) 12.18 (d, J = 2.5 Hz, 1H), 8.86 (d, J = 8.6 Hz, 1H), 8.39 (s, 1H), 7.90 (d, J = 2.9 Hz, 1H), 7.26 (dd, J = 8.6, 1.9 Hz, 1H), 7.17 (d, J = 2.0 Hz, 1H), 6.45 (s, 1H), 5.46 (t, J = 5.4 Hz, 1H), 3.99 (s, 3H), 3.63 (dd, J = 11.0, 5.4 Hz, 6H), 3.42 (q, J = 5.5 Hz, 2H), 3.34 (s, 3H), 2.91 2.84 (m, 4H).; 487.3[M + H]⁺ | 51 | 1.48 |
| 130 | 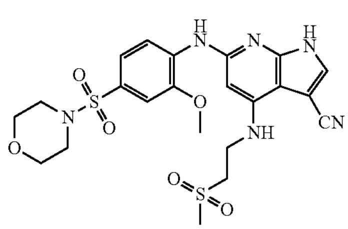 [SMILES: COc1cc(S(=O)(=O)N2CCOCC2)ccc1Nc1cc(NCCS(C)(=O)=O)c2c(C#N)c[nH]c2n1] | 6-((2-methoxy-4-(morpholinosulfonyl)phenyl)amino)-4-((2-(methylsulfonyl)ethyl)amino)-1H-pyrrolo[2,3-b]pyridine-3-carbonitrile | 535.3[M + H]⁺ | 2 | 1.36 |
| 131 | 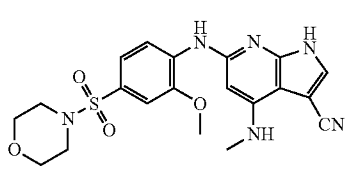 [SMILES: CNc1cc(Nc2ccc(S(=O)(=O)N3CCOCC3)cc2OC)nc2[nH]cc(C#N)c12] | 6-((2-methoxy-4-(morpholinosulfonyl)phenyl)amino)-4-(methylamino)-1H-pyrrolo[2,3-b]pyridine-3-carbonitrile | 443.3[M + H]⁺ | 21 | 1.41 |

TABLE 1-continued

| Compound of Example | Structure | Compound Name | ¹H NMR, MS | Yield (%) | HPLC r.t. (min), Purity |
|---|---|---|---|---|---|
| 132 | 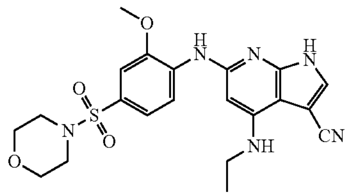 [SMILES: CCNc1cc(Nc2ccc(S(=O)(=O)N3CCOCC3)cc2OC)nc2[nH]cc(C#N)c12] | 4-(ethylamino)-6-((2-methoxy-4-(morpholinosulfonyl)phenyl)amino)-1H-pyrrolo[2,3-b]pyridine-3-carbonitrile | 1H NMR (400 MHZ, DMSO) δ 12.15 (s, 1H), 8.87 (d, J = 8.5 Hz, 1H), 8.41 (s, 1H), 7.88 (s, 1H), 7.24 (d, J = 8.5 Hz, 1H), 7.16 (s, 1H), 6.41 (s, 1H), 5.39 (d, J = 5.5 Hz, 1H), 3.98 (s, 4H), 3.63 (s, 6H), 3.30-3.26 (m, 2H), 2.87 (s, 4H). 457.3[M + H]⁺ | 49 | 1.54 |
| 133 | 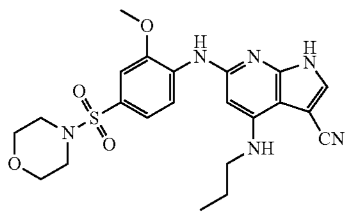 [SMILES: CCCNc1cc(Nc2ccc(S(=O)(=O)N3CCOCC3)cc2OC)nc2[nH]cc(C#N)c12] | 6-((2-methoxy-4-(morpholinosulfonyl)phenyl)amino)-4-(propylamino)-1H-pyrrolo[2,3-b]pyridine-3-carbonitrile | 1H NMR (400 MHZ, DMSO) δ 12.15 (s, 1H), 8.86 (d, J = 8.5 Hz, 1H), 8.41 (s, 1H), 7.88 (s, 1H), 7.24 (d, J = 8.6 Hz, 1H), 7.16 (s, 1H), 6.41 (s, 1H), 5.39 (s, 1H), 3.98 (s, 3H), 3.63 (s, 4H), 3.20 (dd, J = 12.3, 6.0 Hz, 2H), 2.87 (s, 4H), 2.35 (dd, J = 13.7, 6.5 Hz, 2H), 0.99 (t, J = 7.2 Hz, 3H). 471.3[M + H]⁺ | 52 | 1.65 |
| 134 | 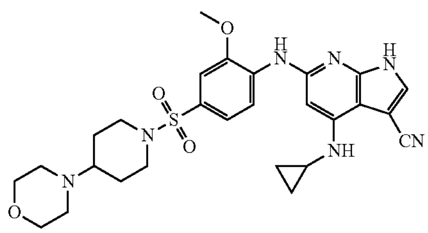 [SMILES: COc1cc(S(=O)(=O)N2CCC(N3CCOCC3)CC2)ccc1Nc1cc(NC2CC2)c2c(C#N)c[nH]c2n1] | 4-(cyclopropylamino)-6-((2-methoxy-4-((4-morpholinopiperidin-1-yl)sulfonyl)phenyl)amino)-1H-pyrrolo[2,3-b]pyridine-3-carbonitrile | 1H NMR (400 MHZ, DMSO) δ 12.15 (s, 1H), 8.80 (d, J = 9.0 Hz, 1H), 8.46 (s, 1H), 7.88 (s, 1H), 7.24 (d, J = 8.6 Hz, 1H), 7.16 (s, 1H), 6.68 (s, 1H), 5.74 (s, 1H), 3.97 (s, 3H), 3.64 (d, J = 10.9 Hz, 2H), 3.51 (s, 4H), 3.31-3.28 (m, 1H), 2.38 (s, 4H), 2.25 (t, J = 11.3 Hz, 2H), 2.12 (t, J = 10.6 Hz, 1H), 1.80 (d, J = 11.8 Hz, 2H), 1.41 (d, J = 12.2 Hz, 2H), 0.84 (d, J = 6.6 Hz, 2H), 0.57 (s, 2H). 552.4[M + H]⁺ | 53 | 1.31 |
| 135 | 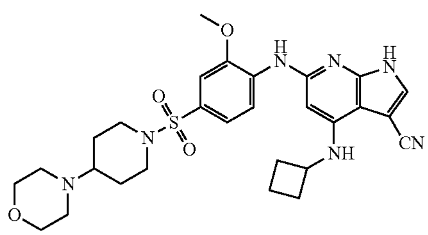 [SMILES: COc1cc(S(=O)(=O)N2CCC(N3CCOCC3)CC2)ccc1Nc1cc(NC2CCC2)c2c(C#N)c[nH]c2n1] | 4-(cyclobutylamino)-6-((2-methoxy-4-((4-morpholinopiperidin-1-yl)sulfonyl)phenyl)amino)-1H-pyrrolo[2,3-b]pyridine-3-carbonitrile | 566.4[M + H]⁺ | 7 | 1.28 |
| 136 | 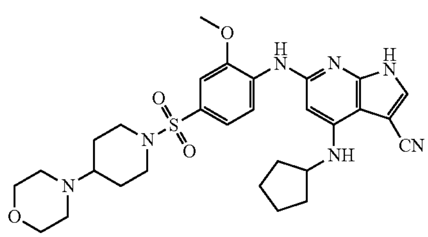 [SMILES: COc1cc(S(=O)(=O)N2CCC(N3CCOCC3)CC2)ccc1Nc1cc(NC2CCCC2)c2c(C#N)c[nH]c2n1] | 4-(cyclopentylamino)-6-((2-methoxy-4-((4-morpholinopiperidin-1-yl)sulfonyl)phenyl)amino)-1H-pyrrolo[2,3-b]pyridine-3-carbonitrile | ¹H NMR (400 MHZ, DMSO-d₆) δ12.15 (s, 1H), 8.84 (d, J = 8.1 Hz, 1H), 8.41 (s, 1H), 7.87 (s, 1H), 7.23 (d, J = 8.6 Hz, 1H), 7.16 (s, 1H), 6.43 (s, 1H), 5.17 (d, J = 6.3 Hz, 1H), 3.97 (s, 3H), 3.87 (dd, J = 12.2, 6.1 Hz, 1H), 3.64 (d, J = 11.7 Hz, 2H), 3.51 (s, 4H), 2.38 (s, 4H), 2.24 (t, J = 11.2 Hz, 2H), 2.18-2.06 (m, 4H), 1.83-1.70 (m, 4H), 1.68-1.58 (m, 2H), 1.56-1.48 (m, 2H), 1.41 (d, J = 10.1 Hz, 1H). 580.4[M + H]⁺ | 34 | 1.35 |
| 137 | 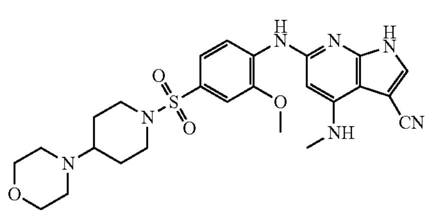 [SMILES: CNc1cc(Nc2ccc(S(=O)(=O)N3CCC(N4CCOCC4)CC3)cc2OC)nc2[nH]cc(C#N)c12] | 6-((2-methoxy-4-((4-morpholinopiperidin-1-yl)sulfonyl)phenyl)amino)-4-(methylamino)-1H-pyrrolo[2,3-b]pyridine-3-carbonitrile | ¹H NMR (400 MHZ, DMSO) δ 12.15 (d, J = 2.5 Hz, 1H), 8.88 (d, J = 8.6 Hz, 1H), 8.39 (s, 1H), 7.88 (d, J = 2.8 Hz, 1H), 7.27 (dd, J = 8.6, 1.9 Hz, 1H), 7.19 (d, J = 1.9 Hz, 1H), 6.34 (s, 1H), 3.98 (s, 4H), 3.79 (d, J = 11.7 Hz, 3H), 3.54 (s, 8H), 3.38 (d, J = 12.6 Hz, 3H), 3.03 (s, 3H), 2.88 (s, 3H), 2.24 (t, J = 11.5 Hz, 3H), 2.18-2.05 (m, 4H), 1.69 (dt, J = 20.3, 10.0 Hz, 3H).; 526.3[M + H]⁺ | 53 | 1.15 |

TABLE 1-continued

| Compound of Example | Structure | Compound Name | ¹H NMR, MS | Yield (%) | HPLC r.t. (min), Purity |
|---|---|---|---|---|---|
| 138 | 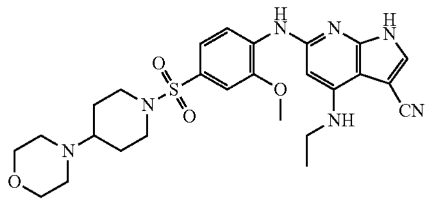 [SMILES: CCNc1cc(Nc2ccc(S(=O)(=O)N3CCC(N4CCOCC4)CC3)cc2OC)nc2[nH]cc(C#N)c12] | 4-(ethylamino)-6-((2-methoxy-4-((4-morpholinopiperidin-1-yl)sulfonyl)phenyl)amino)-1H-pyrrolo[2,3-b]pyridine-3-carbonitrile | 540.4 [M + H]⁺ | 10 | 1.25 |
| 139 | 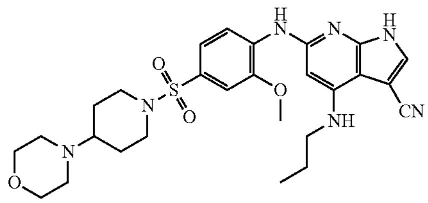 [SMILES: CCCNc1cc(Nc2ccc(S(=O)(=O)N3CCC(N4CCOCC4)CC3)cc2OC)nc2[nH]cc(C#N)c12] | 6-((2-methoxy-4-((4-morpholinopiperidin-1-yl)sulfonyl)phenyl)amino)-4-(propylamino)-1H-pyrrolo[2,3-b]pyridine-3-carbonitrile | ¹H NMR (400 MHZ, DMSO) δ 12.14 (s, 1H), 8.84 (d, J = 8.7 Hz, 1H), 8.37 (s, 1H), 7.88 (s, 1H), 7.27-7.20 (m, 1H), 7.16 (s, 1H), 7.07 (d, J = 8.2 Hz, 1H), 6.96 (s, 1H), 6.72 (d, J = 7.9 Hz, 1H), 6.40 (s, 1H), 5.70 (s, 1H), 5.38 (s, 1H), 3.97 (s, 3H), 3.82 (s, 2H), 3.65 (d, J = 9.9 Hz, 2H), 3.52 (s, 5H), 3.18 (dd, J = 12.8, 5.8 Hz, 3H), 2.39 (s, 5H), 2.28-2.11 (m, 5H), 1.79 (s, 4H), 1.68 (dd, J = 14.1, 7.0 Hz, 2H), 1.41 (s, 5H), 0.99 (t, J = 7.2 Hz, 3H).; 554.4[M + H]⁺ | 3 | 1.33 |
| 140 | 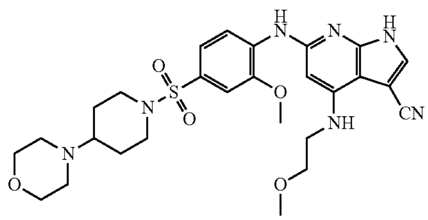 [SMILES: COCCNc1cc(Nc2ccc(S(=O)(=O)N3CCC(N4CCOCC4)CC3)cc2OC)nc2[nH]cc(C#N)c12] | 6-((2-methoxy-4-((4-morpholinopiperidin-1-yl)sulfonyl)phenyl)amino)-4-((2-methoxyethyl)amino)-1H-pyrrolo[2,3-b]pyridine-3-carbonitrile | ¹H NMR (400 MHZ, DMSO) δ 12.18 (s, 1H), 8.84 (d, J = 8.5 Hz, 1H), 8.36 (s, 1H), 7.90 (s, 1H), 7.25 (d, J = 8.6 Hz, 1H), 7.17 (s, 1H), 6.44 (s, 1H), 5.46 (s, 1H), 3.97 (s, 3H), 3.63 (dd, J = 13.6, 8.5 Hz, 4H), 3.53 (s, 4H), 3.41 (d, J = 5.1 Hz, 2H), 2.40 (s, 4H), 2.25 (t, J = 11.6 Hz, 2H), 2.13 (s, 1H), 1.81 (d, J = 11.1 Hz, 2H), 1.42 (d, J = 10.9 Hz, 2H).; 570.4[M + H]⁺ | 68 | 1.21 |
| 141 | 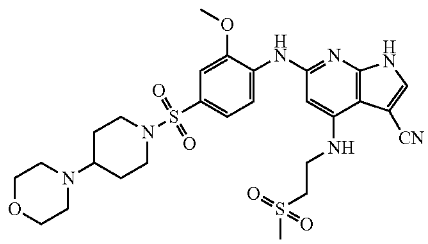 [SMILES: COc1cc(S(=O)(=O)N2CCC(N3CCOCC3)CC2)ccc1Nc1cc(NCCS(C)(=O)=O)c2c(C#N)c[nH]c2n1] | 6-((2-methoxy-4-((4-morpholinopiperidin-1-yl)sulfonyl)phenyl)amino)-4-((2-(methylsulfonyl)ethyl)amino)-1H-pyrrolo[2,3-b]pyridine-3-carbonitrile | 1H NMR (400 MHZ, DMSO-d₆) δ 12.20 (s, 1H), 8.84 (dd, J = 8.6, 1.9 Hz, 1H), 8.41 (s, 1H), 7.91 (d, J = 2.5 Hz, 1H), 7.24 (d, J = 8.6 Hz, 1H), 7.16 (d, J = 2.4 Hz, 1H), 6.45 (d, J = 1.9 Hz, 1H), 5.84 (d, J = 5.9 Hz, 1H), 3.98 (d, J = 1.9 Hz, 3H), 3.74-3.59 (m, 4H), 3.52 (q, J = 6.4, 5.1 Hz, 5H), 3.10 (d, J = 1.8 Hz, 3H), 2.38 (s, 3H), 2.24 (t, J = 11.7 Hz, 2H), 2.10 (d, J = 11.1 Hz, 1H), 1.80 (d, J = 12.4 Hz, 2H), 1.48-1.35 (m, 2H), 1.26 (d, J = 17.2 Hz, 1H), 0.87 (d, J = 6.8 Hz, 1H). 618.4[M + H]⁺ | 58 | 1.10 |
| 142 | 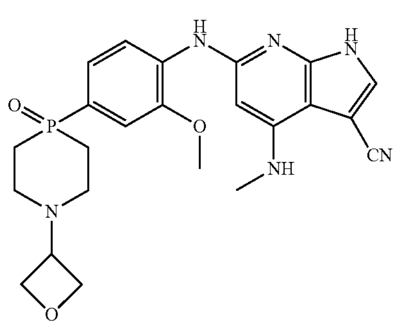 [SMILES: CNc1cc(Nc2ccc(P3(=O)CCN(C4COC4)CC3)cc2OC)nc2[nH]cc(C#N)c12] | 6-((2-methoxy-4-(1-(oxetan-3-yl)-4-oxido-1,4-azaphosphinan-4-yl)phenyl)amino)-4-(methylamino)-1H-pyrrolo[2,3-b]pyridine-3-carbonitrile | ¹H NMR (400 MHZ, DMSO) δ 12.11 (s, 1H), 8.76 (d, J = 6.3 Hz, 1H), 8.19 (s, 1H), 7.85 (d, J = 2.3 Hz, 1H), 7.28 (d, J = 11.5 Hz, 2H), 7.07 (d, J = 12.6 Hz, 1H), 6.28 (s, 1H), 5.57 (s, 1H), 4.60 (s, 7H), 3.96 (s, 4H), 3.82 (s, 3H), 3.39 (s, 7H), 2.87 (d, J = 3.4 Hz, 4H), 2.33 (s, 3H), 1.99 (s, 3H).; 467.3[M + H]⁺ | 35 | 0.99 |

TABLE 1-continued

| Compound of Example | Structure | Compound Name | ¹H NMR, MS | Yield (%) | HPLC r.t. (min), Purity |
|---|---|---|---|---|---|
| 143 | 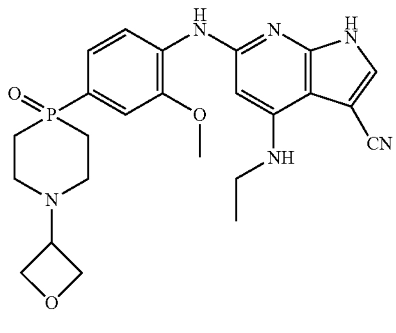 [SMILES: CCNc1cc(Nc2ccc(P3(=O)CCN(C4COC4)CC3)cc2OC)nc2[nH]cc(C#N)c12] | 4-(ethylamino)-6-((2-methoxy-4-(1-(oxetan-3-yl)-4-oxido-1,4-azaphosphinan-4-yl)phenyl)amino)-1H-pyrrolo[2,3-b]pyridine-3-carbonitrile | ¹H NMR (400 MHZ, DMSO) δ 12.12 (s, 1H), 8.73 (d, J = 5.9 Hz, 1H), 8.17 (s, 1H), 7.84 (d, J = 2.6 Hz, 1H), 7.28 (d, J = 11.5 Hz, 1H), 6.33 (s, 1H), 5.32 (t, J = 5.2 Hz, 1H), 4.56 (t, J = 6.2 Hz, 2H), 4.44 (s, 2H), 3.95 (s, 3H), 3.59 (s, 1H), 3.39 (s, 1H), 3.26 (d, J = 6.3 Hz, 2H), 2.75-2.55 (m, 3H), 2.26 (s, 2H), 1.89 (d, J = 14.5 Hz, 2H), 1.26 (t, J = 7.1 Hz, 4H).; 481.3[M + H]⁺ | 58 | 1.11 |
| 144 | 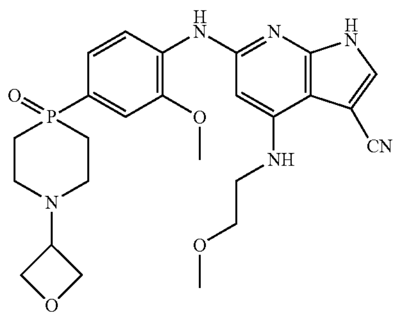 [SMILES: COCCNc1cc(Nc2ccc(P3(=O)CCN(C4COC4)CC3)cc2OC)nc2[nH]cc(C#N)c12] | 6-((2-methoxy-4-(1-(oxetan-3-yl)-4-oxido-1,4-azaphosphinan-4-yl)phenyl)amino)-4-((2-methoxyethyl)amino)-1H-pyrrolo[2,3-b]pyridine-3-carbonitrile | ¹H NMR (400 MHZ, DMSO) δ 12.14 (s, 1H), 8.72 (d, J = 5.8 Hz, 1H), 8.16 (s, 1H), 7.86 (d, J = 2.5 Hz, 1H), 7.28 (d, J = 11.4 Hz, 2H), 7.06 (d, J = 12.2 Hz, 2H), 6.71 (dd, J = 7.8, 3.0 Hz, 1H), 6.37 (s, 1H), 5.41 (s, 1H), 5.34 (s, 2H), 4.55 (q, J = 6.1 Hz, 4H), 4.43 (dd, J = 13.4, 6.3 Hz, 6H), 3.95 (s, 2H), 3.82 (s, 4H), 3.59 (dt, J = 13.6, 6.0 Hz, 4H), 3.40 (t, J = 5.4 Hz, 4H), 3.17 (d, J = 5.2 Hz, 2H), 2.63 (dd, J = 24.0, 9.7 Hz, 6H), 2.29 (d, J = 30.5 Hz, 2H), 2.14 (t, J = 18.8 Hz, 3H), 1.94-1.70 (m, 5H).; 511.3[M + H]⁺ | 76 | 1.06 |
| 145 | 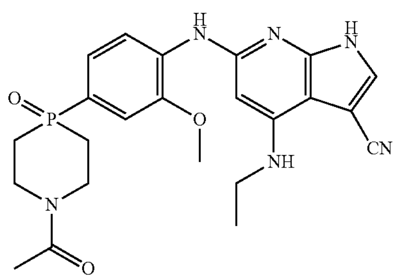 [SMILES: CCNc1cc(Nc2ccc(P3(=O)CCN(C(C)=O)CC3)cc2OC)nc2[nH]cc(C#N)c12] | 6-((4-(1-acetyl-4-oxido-1,4-azaphosphinan-4-yl)-2-methoxyphenyl)amino)-4-(ethylamino)-1H-pyrrolo[2,3-b]pyridine-3-carbonitrile | ¹H NMR (400 MHZ, DMSO) δ 12.10 (s, 1H), 8.74 (dd, J = 8.1, 2.9 Hz, 1H), 8.19 (s, 1H), 7.85 (d, J = 2.6 Hz, 1H), 7.31 (t, J = 9.8 Hz, 2H), 6.34 (s, 1H), 5.33 (t, J = 5.4 Hz, 1H), 4.17 (dd, J = 21.2, 14.1 Hz, 1H), 3.95 (s, 3H), 3.82 (s, 1H), 3.42-3.37 (m, 1H), 3.26 (dd, J = 13.1, 6.6 Hz, 2H), 2.10 (s, 3H), 1.26 (t, J = 7.1 Hz, 4H).; 467.3[M + H]⁺ | 78 | 1.16 |
| 146 | 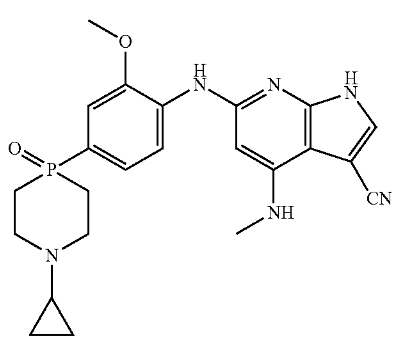 [SMILES: CNc1cc(Nc2ccc(P3(=O)CCN(C4CC4)CC3)cc2OC)nc2[nH]cc(C#N)c12] | 6-((4-(1-cyclopropyl-4-oxido-1,4-azaphosphinan-4-yl)-2-methoxyphenyl)amino)-4-(methylamino)-1H-pyrrolo[2,3-b]pyridine-3-carbonitrile | 1H NMR (400 MHZ, DMSO-d₆) δ 12.14 (s, 1H), 8.73 (s, 1H), 8.17 (s, 1H), 7.84 (s, 1H), 7.27 (s, 2H), 6.27 (s, 1H), 5.57 (s, 1H), 3.94 (s, 3H), 2.90 (d, J = 31.9 Hz, 7H), 2.18 (s, 2H), 1.91 (s, 1H), 1.84 (s, 2H), 0.41 (d, J = 48.9 Hz, 4H). 451.4[M + H]⁺ | 36 | 0.96 |

TABLE 1-continued

| Compound of Example | Structure | Compound Name | $^1$H NMR, MS | Yield (%) | HPLC r.t. (min), Purity |
|---|---|---|---|---|---|
| 147 | 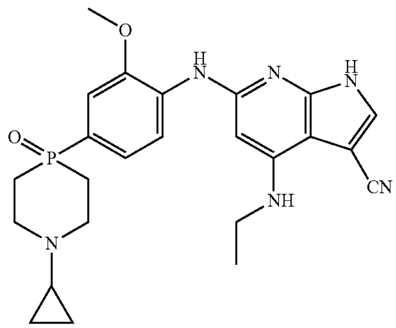 [SMILES: CCNc1cc(Nc2ccc(P3(=O)CCN(C4CC4)CC3)cc2OC)nc2[nH]cc(C#N)c12] | 6-((4-(1-cyclopropyl-4-oxido-1,4-azaphosphinan-4-yl)-2-methoxyphenyl)amino)-4-(ethylamino)-1H-pyrrolo[2,3-b]pyridine-3-carbonitrile | 1H NMR (400 MHZ, DMSO) δ 12.14 (s, 1H), 8.73 (s, 1H), 8.19 (s, 1H), 7.85 (s, 1H), 7.27 (s, 2H), 6.34 (s, 1H), 5.33 (s, 1H), 3.95 (s, 3H), 3.27 (d, J = 5.0 Hz, 2H), 2.95 (s, 3H), 2.18 (s, 2H), 1.88 (d, J = 25.9 Hz, 3H), 1.26 (d, J = 5.5 Hz, 4H), 0.42 (d, J = 49.1 Hz, 4H). 465.4[M + H]$^+$ | 53 | 1.08 |
| 148 | 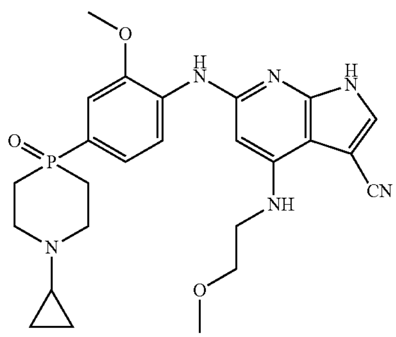 [SMILES: COCCNc1cc(Nc2ccc(P3(=O)CCN(C4CC4)CC3)cc2OC)nc2[nH]cc(C#N)c12] | 6-((4-(1-cyclopropyl-4-oxido-1,4-azaphosphinan-4-yl)-2-methoxyphenyl)amino)-4-((2-methoxyethyl)amino)-1H-pyrrolo[2,3-b]pyridine-3-carbonitrile | 1H NMR (400 MHZ, DMSO) δ 8.71 (s, 1H), 8.16 (s, 1H), 7.86 (s, 1H), 7.25 (d, J = 10.3 Hz, 2H), 6.37 (s, 1H), 5.40 (s, 1H), 3.95 (s, 3H), 3.61 (d, J = 3.7 Hz, 2H), 3.39 (s, 3H), 2.96 (s, 3H), 2.18 (s, 2H), 1.84 (d, J = 14.2 Hz, 3H), 1.75 (s, 2H), 0.47 (s, 2H), 0.35 (s, 2H). 495.3[M + H]$^+$ | 21 | 1.06 |
| 149 | 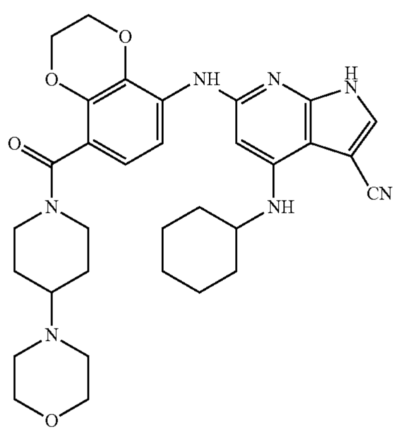 [SMILES: N#Cc1c[nH]c2nc(Nc3ccc(C(=O)N4CCC(N5CCOCC5)CC4)c4c3OCCO4)cc(NC3CCCCC3)c12] | 4-(cyclohexylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile | $^1$H NMR (400 MHZ, Methanol-$d_4$) δ 7.99 (d, J = 8.8 Hz, 1H), 7.60 (s, 1H), 6.76 (d, J = 21.3 Hz, 1H), 6.10 (s, 1H), 4.42-4.39 (m, 2H), 4.37-4.33 (m, 2H), 3.80-3.71 (m, 6H), 3.59-3.48 (m, 2H), 2.85 (t, J = 12.7 Hz, 1H), 2.73-2.64 (m, 5H), 2.60-2.55 (m, 1H), 2.13-2.06 (m, 3H), 1.86-1.79 (m, 2H), 1.72-1.59 (m, 2H), 1.59-1.47 (m, 4H), 1.45-1.36 (m, 4H); 586.3[M + H]$^+$ | 47 | 1.22 |
| 150 | 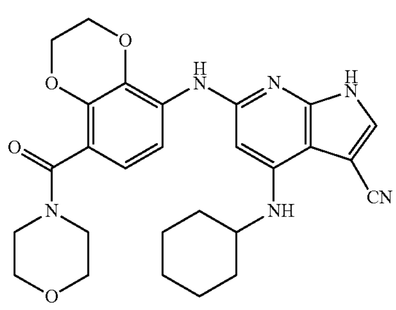 [SMILES: N#Cc1c[nH]c2nc(Nc3ccc(C(=O)N4CCOCC4)c4c3OCCO4)cc(NC3CCCCC3)c12] | N$^4$-(cyclohexylamino)-N$^6$-((8-(morpholine-4-carbonyl)-2,3-dihydrobenzo[b][1,4]dioxin-5-yl)amino)-1H-pyrrolo[2,3-b]pyridine-3-carbonitrile | 503.4[M + H]$^+$ | 73.5 | 1.41 |

TABLE 1-continued

| Compound of Example | Structure | Compound Name | ¹H NMR, MS | Yield (%) | HPLC r.t. (min), Purity |
|---|---|---|---|---|---|
| 151 | 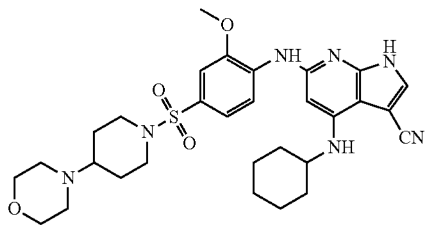 [SMILES: COc1cc(S(=O)(=O)N2CCC(N3CCOCC3)CC2)ccc1Nc1cc(NC2CCCCC2)c2c(C#N)c[nH]c2n1] | $N^4$-(cyclohexylamino)-$N^6$-((2-methoxy-4-((4-morpholinopiperidin-1-yl)sulfonyl)phenyl)amino)-1H-pyrrolo[2,3-b]pyridine-3-carbonitrile | 594.4[M + H]⁺ | 75 | 1.46 |
| 152 | 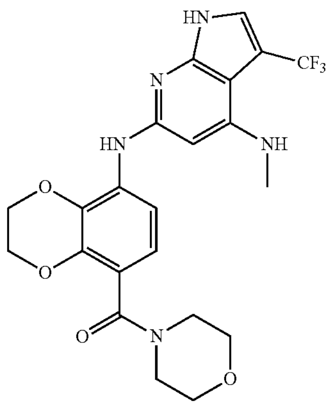 [SMILES: CNc1cc(Nc2ccc(C(=O)N3CCOCC3)c3c2OCCO3)nc2[nH]cc(C(F)(F)F)c12] | (8-((4-(methylamino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHZ, MeOD) δ 7.50 (d, J = 1.4 Hz, 1H), 7.13 (d, J = 8.2 Hz, 1H), 6.95 (d, J = 8.2 Hz, 1H), 4.39 (s, 4H), 3.78 (s, 4H), 3.68 (s, 2H), 3.43 (d, J = 17.2 Hz, 2H), 3.07 (s, 3H); 478.3[M + H]⁺ | 54 | 1.22 |
| 153 | 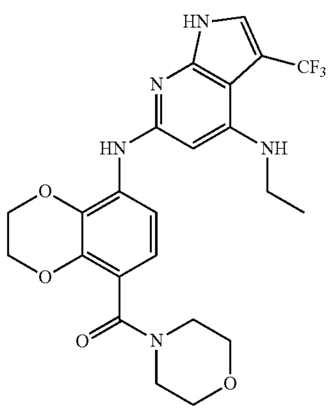 [SMILES: CCNc1cc(Nc2ccc(C(=O)N3CCOCC3)c3c2OCCO3)nc2[nH]cc(C(F)(F)F)c12] | (8-((4-(ethylamino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHZ, MeOD) δ 7.52 (d, J = 1.4 Hz, 1H), 7.10 (d, J = 8.2 Hz, 1H), 6.95 (d, J = 8.2 Hz, 1H), 4.39 (s, 4H), 3.78 (s, 4H), 3.74-3.62 (m, 2H), 3.50-3.38 (m, 4H), 1.36 (t, J = 7.2 Hz, 3H); 492.3 [M + H]⁺ | 63 | 1.30 |
| 154 | 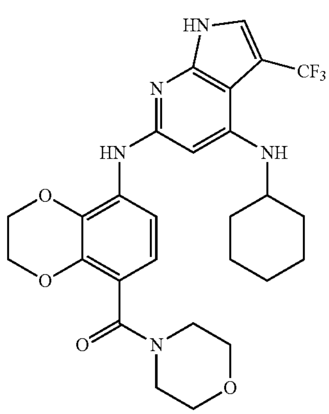 [SMILES: O=C(c1ccc(Nc2cc(NC3CCCCC3)c3c(C(F)(F)F)c[nH]c3n2)c2c1OCCO2)N1CCOCC1] | (8-((4-(cyclohexylamino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHZ, MeOD) δ 7.51 (s, 1H), 7.16 (d, J = 8.0 Hz, 1H), 6.93 (d, J = 8.2 Hz, 1H), 4.39 (s, 4H), 3.86-3.73 (m, 4H), 3.73-3.57 (m, 3H), 3.43 (d, J = 18.1 Hz, 2H), 2.09 (d, J = 13.0 Hz, 2H), 1.86-1.76 (m, 2H), 1.68 (s, 1H), 1.59-1.38 (m, 5H); 546.4[M + H]⁺ | 49 | 1.59 |

TABLE 1-continued

| Compound of Example | Structure | Compound Name | ¹H NMR, MS | Yield (%) | HPLC r.t. (min), Purity |
|---|---|---|---|---|---|
| 155 | 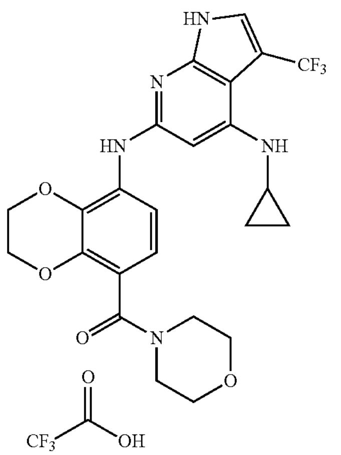 | (8-((4-(cyclopropylamino)-3-(trifluoromethyl)-1H-pyrrolo[2,3-b]pyridin-6-yl)amino)-2,3-dihydrobenzo[b][1,4]dioxin-5-yl)(morpholino)methanone 2,2,2-trifluoroacetate | ¹H NMR (400 MHZ, MeOD, TFA) δ 7.49 (d, J = 1.2 Hz, 1H), 7.13 (d, J = 8.2 Hz, 1H), 6.93 (d, J = 8.2 Hz, 1H), 4.37 (s, 4H), 3.83-3.70 (m, 4H), 3.65 (dd, J = 10.3, 4.6 Hz, 2H), 3.48-3.33 (m, 2H), 2.74-2.63 (m, 1H), 0.99-0.92 (m, 2H), 0.73-0.65 (m, 2H); 504.3[M + H]⁺ | 50 | 1.39 |
| 156 | 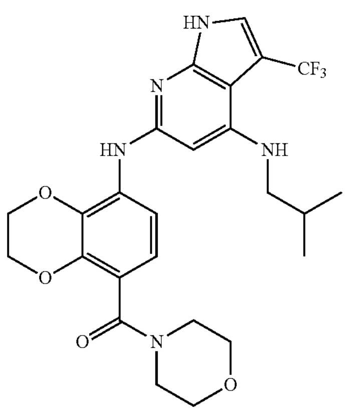 [SMILES: CC(C)CNc1cc(Nc2ccc(C(=O)N3CCOCC3)c3c2OCCO3)nc2[nH]cc(C(F)(F)F)c12] | (8-((4-(isobutylamino)-3-(trifluoromethyl)-1H-pyrrolo[2,3-b]pyridin-6-yl)amino)-2,3-dihydrobenzo[b][1,4]dioxin-5-yl)(morpholino)methanone | 1H NMR (400 MHZ, CDCl₃) δ 9.18 (s, 1H), 7.86 (d, J = 8.5 Hz, 1H), 7.15 (s, 1H), 6.84 (d, J = 8.5 Hz, 1H), 6.71 (s, 1H), 4.90 (s, 1H), 4.43-4.28 (m, 4H), 3.87-3.70 (m, 4H), 3.70-3.55 (m, 2H), 3.45-3.29 (m, 2H), 3.11-3.00 (m, 2H), 2.08-1.91 (m, 1H), 1.05 (s, 3H), 1.03 (s, 3H); 520.3[M + H]⁺ | 53.9 | 1.45 |
| 157 | 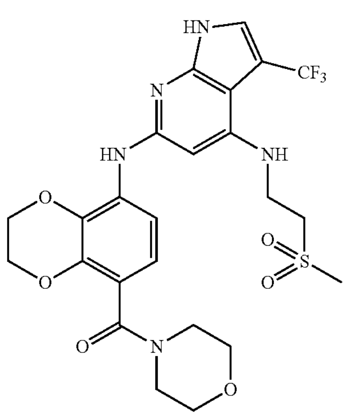 [SMILES: CS(=O)(=O)CCNc1cc(Nc2ccc(C(=O)N3CCOCC3)c3c2OCCO3)nc2[nH]cc(C(F)(F)F)c12] | (8-((4-((2-(methylsulfonyl)ethyl)amino)-3-(trifluoromethyl)-1H-pyrrolo[2,3-b]pyridin-6-yl)amino)-2,3-dihydrobenzo [b][1,4]dioxin-5-yl)(morpholino)methanone | ¹H NMR (400 MHZ, CDCl₃) δ 9.21 (s, 1H), 7.92 (d, J = 8.5 Hz, 1H), 7.22 (s, 1H), 6.86 (d, J = 8.5 Hz, 1H), 6.80 (s, 1H), 5.15 (s, 1H), 4.45-4.27 (m, 4H), 3.93-3.84 (m, 2H), 3.84-3.71 (m, 4H), 3.67-3.55 (m, 2H), 3.38 (t, J = 6.2 Hz, 4H), 2.98 (s, 3H); 570.3[M + H]⁺ | 33 | 1.15 |

TABLE 1-continued

| Compound of Example | Structure | Compound Name | ¹H NMR, MS | Yield (%) | HPLC r.t. (min), Purity |
|---|---|---|---|---|---|
| 158 | 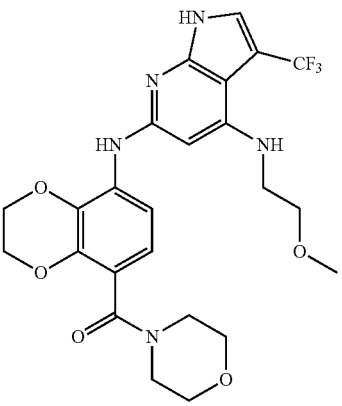 [SMILES: COCCNc1cc(Nc2ccc(C(=O)N3CCOCC3)c3c2OCCO3)nc2[nH]cc(C(F)(F)F)c12] | (8-((4-((2-methoxyethyl)amino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHz, CD$_3$OD_SPE) δ 8.00 (d, J = 8.5 Hz, 1H), 7.33 (d, J = 1.4 Hz, 1H), 6.77 (d, J = 8.5 Hz, 1H), 4.40-4.35 (m, 2H), 4.35-4.31 (m, 2H), 3.76-3.70 (m, 4H), 3.70-3.61 (m, 4H), 3.47-3.36 (m, 7H); 522.3 [M + H]⁺ | 40 | 1.28 |
| 159 | 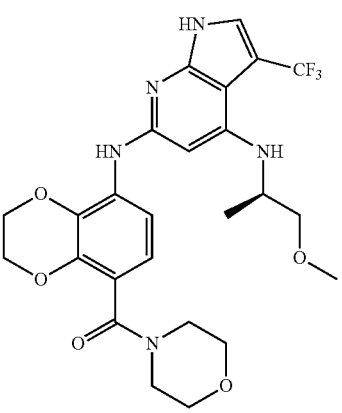 [SMILES: COC[C@@H](C)Nc1cc(Nc2ccc(C(=O)N3CCOCC3)c3c2OCCO3)nc2[nH]cc(C(F)(F)F)c12] | (R)-(8-((4-((1-methoxypropan-2-yl)amino)-3-(trifluoromethyl)-1H-pyrrolo[2,3-b]pyridin-6-yl)amino)-2,3-dihydrobenzo[b][1,4]dioxin-5-yl)(morpholino)methanone | 1H NMR (400 MHZ, DMSO-d$_6$) δ 11.80 (s, 1H), 8.22-8.15 (m, 1H), 7.95 (s, 1H), 7.50 (s, 1H), 6.74-6.65 (m, 1H), 6.33 (s, 1H), 4.86 (s, 1H), 4.34 (d, J = 19.7 Hz, 4H), 3.76 (s, 1H), 3.57 (d, J = 25.3 Hz, 6H), 3.46 (s, 2H), 3.27 (s, 2H), 1.29-1.19 (m, 5H). 536.3[M + H]⁺ | 34 | 1.37 |
| 160 | 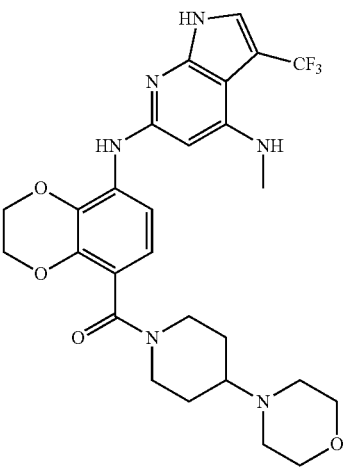 [SMILES: CNc1cc(Nc2ccc(C(=O)N3CCC(N4CCOCC4)CC3)c3c2OCCO3)nc2[nH]cc(C(F)(F)F)c12] | (8-((4-(methylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.86 (s, 1H), 10.29 (s, 1H), 8.18 (s, 1H), 8.00 (s, 1H), 7.51 (s, 1H), 6.72 (s, 1H), 6.15 (s, 1H), 5.20 (s, 1H), 4.64 (d, J = 12.0 Hz, 1H), 4.34 (d, J = 19.1 Hz, 4H), 4.11-3.89 (m, 3H), 3.46 (s, 7H), 3.11 (s, 3H), 2.90 (s, 3H), 2.69 (d, J = 11.7 Hz, 1H), 2.17 (s, 1H).; 561.4[M + H]⁺ | 81 | 1.02 |

TABLE 1-continued

| Compound of Example | Structure | Compound Name | ¹H NMR, MS | Yield (%) | HPLC r.t. (min), Purity |
|---|---|---|---|---|---|
| 161 | 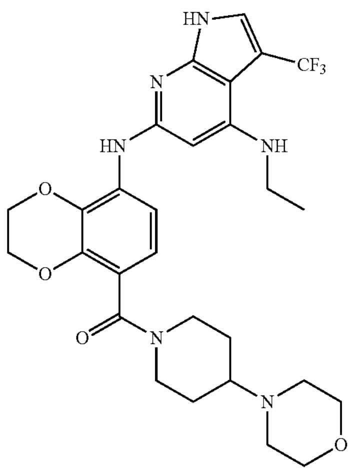 [SMILES: CCNc1cc(Nc2ccc(C(=O)N3CCC(N4CCOCC4)CC3)c3c2OCCO3)nc2[nH]cc(C(F)(F)F)c12] | (8-((4-(ethylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.82 (s, 1H), 10.23 (s, 1H), 8.09 (s, 2H), 7.52 (s, 1H), 6.70 (s, 1H), 6.25 (s, 1H), 4.81 (s, 1H), 4.64 (d, J = 11.9 Hz, 1H), 4.35 (d, J = 22.6 Hz, 4H), 4.13-3.92 (m, 3H), 3.68 (s, 4H), 3.44 (d, J = 5.8 Hz, 3H), 3.27 (d, J = 5.1 Hz, 2H), 3.11 (s, 2H), 2.95 (s, 1H), 2.70 (s, 1H), 2.17 (s, 1H), 1.53 (s, 2H), 1.24 (t, J = 6.8 Hz, 3H).; 575.4[M + H]⁺ | 75 | 1.13 |
| 162 | 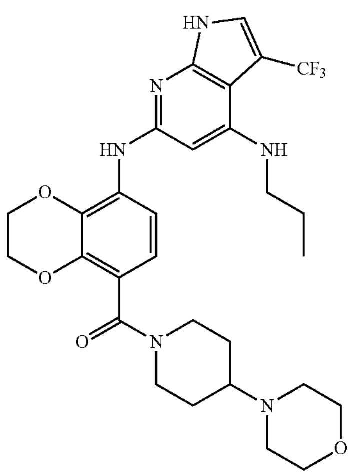 [SMILES: CCCNc1cc(Nc2ccc(C(=O)N3CCC(N4CCOCC4)CC3)c3c2OCCO3)nc2[nH]cc(C(F)(F)F)c12] | (4-morpholinopiperidin-1-yl)(8-((4-(propylamino)-3-(trifluoromethyl)-1H-pyrrolo[2,3-b]pyridin-6-yl)amino)-2,3-dihydrobenzo[b][1,4]dioxin-5-yl)methanone | ¹H NMR (400 MHZ, DMSO) δ 11.87 (s, 1H), 10.17 (s, 1H), 8.21 (s, 1H), 7.98 (s, 1H), 7.53 (s, 1H), 6.73 (d, J = 10.3 Hz, 1H), 6.22 (s, 1H), 4.96 (s, 1H), 4.64 (d, J = 12.6 Hz, 1H), 4.34 (d, J = 19.4 Hz, 5H), 4.11-3.93 (m, 4H), 3.69 (s, 6H), 3.46 (d, J = 6.0 Hz, 4H), 3.22 (dd, J = 10.8, 6.5 Hz, 3H), 3.11 (s, 3H), 2.82-2.62 (m, 1H), 2.17 (s, 1H), 1.72-1.58 (m, 3H), 1.24 (d, J = 1.1 Hz, 1H), 0.97 (t, J = 7.4 Hz, 4H), 0.90-0.79 (m, 1H).; 589.4[M + H]⁺ | 62 | 1.19 |
| 163 | 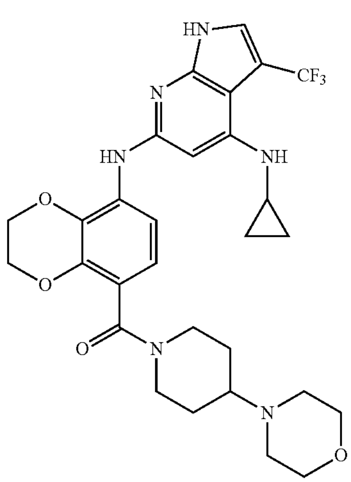 [SMILES: O=C(c1ccc(Nc2cc(NC3CC3)c3c(C(F)(F)F)c[nH]c3n2)c2c1OCCO2)N1CCC(N2CCOCC2)CC1] | (8-((4-(cyclopropylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.88 (s, 1H), 10.15 (s, 1H), 8.27 (s, 1H), 7.96 (d, J = 7.7 Hz, 1H), 7.54 (s, 1H), 6.72 (s, 1H), 6.55 (s, 1H), 5.15 (s, 1H), 4.65 (d, J = 12.3 Hz, 1H), 4.35 (d, J = 19.7 Hz, 5H), 4.03 (dd, J = 14.2, 7.1 Hz, 4H), 3.68 (s, 5H), 3.44 (d, J = 6.8 Hz, 4H), 3.12 (s, 3H), 2.69 (d, J = 13.7 Hz, 1H), 2.62-2.52 (m, 1H), 2.50 (dt, J = 3.6, 1.8 Hz, 5H), 2.17 (s, 1H), 1.24 (s, 1H), 0.89-0.80 (m, 3H), 0.59-0.51 (m, 2H).; 587.4 [M + H]⁺ | 97 | 1.16 |

TABLE 1-continued

| Compound of Example | Structure | Compound Name | ¹H NMR, MS | Yield (%) | HPLC r.t. (min), Purity |
|---|---|---|---|---|---|
| 164 | 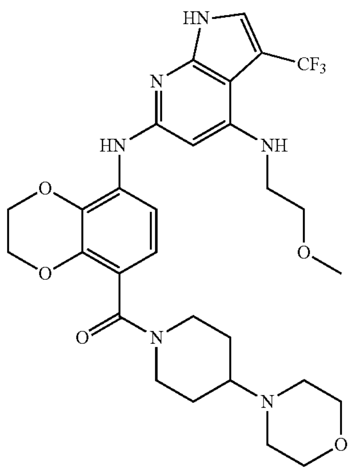 [SMILES: COCCNc1cc(Nc2ccc(C(=O)N3CCC(N4CCOCC4)CC3)c3c2OCCO3)nc2[nH]cc(C(F)(F)F)c12] | (8-((4-((2-methoxyethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.93 (s, 1H), 10.43 (s, 1H), 8.19 (s, 1H), 8.00 (d, J = 7.1 Hz, 1H), 7.54 (s, 1H), 6.72 (s, 1H), 6.25 (s, 1H), 5.18 (s, 1H), 4.65 (d, J = 12.2 Hz, 1H), 4.35 (d, J = 19.6 Hz, 5H), 4.03 (dd, J = 14.2, 7.1 Hz, 3H), 3.69 (d, J = 12.6 Hz, 3H), 3.62 (t, J = 5.3 Hz, 3H), 3.52-3.43 (m, 2H), 3.44-3.35 (m, 3H), 3.33 (s, 3H), 3.13 (d, J = 15.9 Hz, 3H), 2.72 (d, J = 10.9 Hz, 1H), 2.18 (s, 1H), 1.56 (d, J = 12.9 Hz, 2H).; 605.4[M + H]⁺ | 32 | 1.09 |
| 165 | 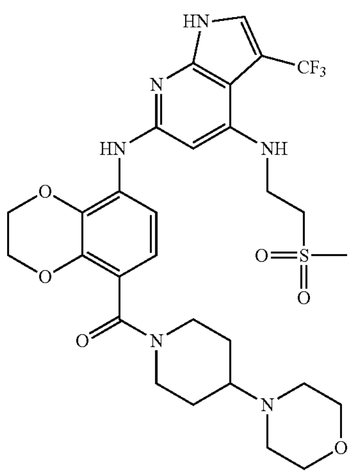 [SMILES: CS(=O)(=O)CCNc1cc(Nc2ccc(C(=O)N3CCC(N4CCOCC4)CC3)c3c2OCCO3)nc2[nH]cc(C(F)(F)F)c12] | (8-((4-((2-(methylsulfonyl)ethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.81 (s, 1H), 8.20 (d, J = 8.5 Hz, 1H), 7.96 (s, 1H), 7.51 (s, 1H), 6.69 (s, 1H), 6.33 (s, 1H), 5.26 (s, 1H), 4.56 (d, J = 8.7 Hz, 1H), 4.35 (d, J = 27.2 Hz, 4H), 3.72 (dd, J = 12.2, 6.1 Hz, 4H), 3.60 (d, J = 12.6 Hz, 2H), 3.52 (t, J = 6.3 Hz, 3H), 3.34 (d, J = 6.7 Hz, 4H), 3.07 (s, 4H), 2.79-2.65 (m, 2H).; 653.4[M + H]⁺ | 25 | 0.98 |
| 166 | 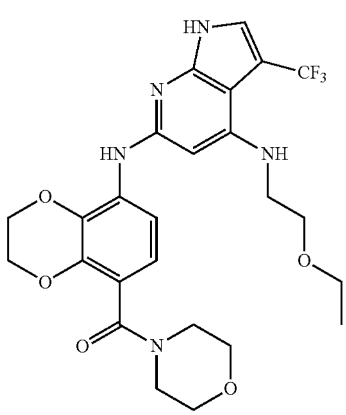 [SMILES: CCOCCNc1cc(Nc2ccc(C(=O)N3CCOCC3)c3c2OCCO3)nc2[nH]cc(C(F)(F)F)c12] | (8-((4-((2-ethoxyethyl)amino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHZ, DMSO) δ 11.81 (s, 1H), 8.18 (d, J = 8.5 Hz, 1H), 7.89 (s, 1H), 7.51 (s, 1H), 6.70 (d, J = 8.5 Hz, 1H), 6.28 (s, 1H), 5.08 (s, 1H), 4.34 (d, J = 16.4 Hz, 4H), 3.69-3.44 (m, 11H), 3.34 (d, J = 4.5 Hz, 4H), 1.14 (t, J = 6.9 Hz, 3H) ; 536.3[M + H]⁺. | 12 | 1.37 |

TABLE 1-continued

| Compound of Example | Structure | Compound Name | ¹H NMR, MS | Yield (%) | HPLC r.t. (min), Purity |
|---|---|---|---|---|---|
| 167 | 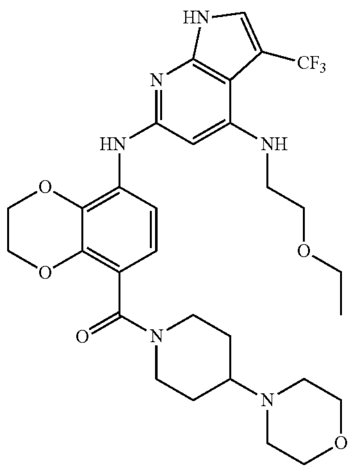 [SMILES: CCOCCNc1cc(Nc2ccc(C(=O)N3CCC(N4CCOCC4)CC3)c3c2OCCO3)nc2[nH]cc(C(F)(F)F)c12] | (8-((4-((2-ethoxyethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, DMSO) δ 11.78 (s, 1H), 8.14 (d, J = 8.4 Hz, 1H), 7.87 (s, 1H), 7.50 (s, 1H), 6.73-6.59 (m, 1H), 6.26 (s, 1H), 5.08 (s, 1H), 4.46 (s, 1H), 4.32 (d, J = 24.4 Hz, 4H), 3.65 (d, J = 4.5 Hz, 2H), 3.60-3.44 (m, 7H), 3.33 (s, 7H), 2.95 (d, J = 43.0 Hz, 1H), 2.73 (t, J = 11.9 Hz, 1H), 2.45 (s, 4H), 1.84 (d, J = 12.4 Hz, 1H), 1.72 (s, 1H), 1.14 (t, J = 6.9 Hz, 3H).; 619.4[M + H]⁺ | 46 | 1.19 |
| 168 | 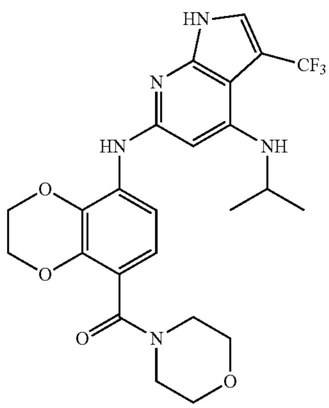 [SMILES: CC(C)Nc1cc(Nc2ccc(C(=O)N3CCOCC3)c3c2OCCO3)nc2[nH]cc(C(F)(F)F)c12] | (8-((4-(isopropylamino)-3-(trifluoromethyl)-1H-pyrrolo[2,3-b]pyridin-6-yl)amino)-2,3-dihydrobenzo[b][1,4]dioxin-5-yl)(morpholino)methanone | ¹H NMR (400 MHZ, CDCl₃) δ 9.77 (s, 1H), 7.69 (d, J = 8.4 Hz, 1H), 7.14 (s, 1H), 6.83 (d, J = 8.4 Hz, 1H), 6.71 (s, 1H), 4.77 (s, 1H), 4.42-4.28 (m, 4H), 3.86-3.69 (m, 5H), 3.69-3.52 (m, 2H), 3.47-3.29 (m, 2H), 3.26-2.90 (m, 1H), 1.31 (s, 3H), 1.29 (s, 3H); 506.4[M + H]⁺ | 51 | 1.39 |
| 169 | 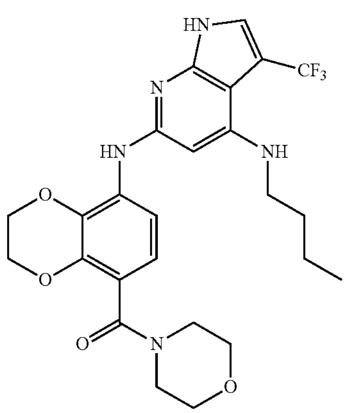 [SMILES: CCCCNc1cc(Nc2ccc(C(=O)N3CCOCC3)c3c2OCCO3)nc2[nH]cc(C(F)(F)F)c12] | (8-((4-(butylamino)-3-(trifluoromethyl)-1H-pyrrolo[2,3-b]pyridin-6-yl)amino)-2,3-dihydrobenzo[b][1,4]dioxin-5-yl)(morpholino)methanone | 520.3[M + H]⁺ | 20 | 1.46 |

TABLE 1-continued

| Compound of Example | Structure | Compound Name | ¹H NMR, MS | Yield (%) | HPLC r.t. (min), Purity |
|---|---|---|---|---|---|
| 170 | 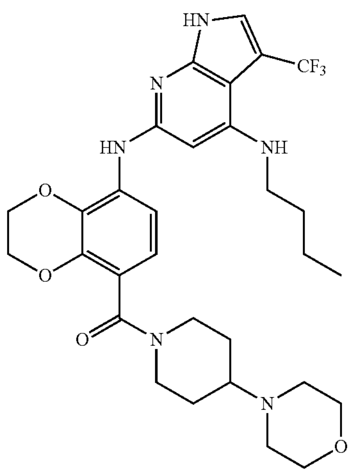 [SMILES: CCCCNc1cc(Nc2ccc(C(=O)N3CCC(N4CCOCC4)CC3)c3c2OCCO3)nc2[nH]cc(C(F)(F)F)c12] | (8-((4-(butylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | 603.4[M + H]⁺ | 55 | 1.28 |
| 171 | 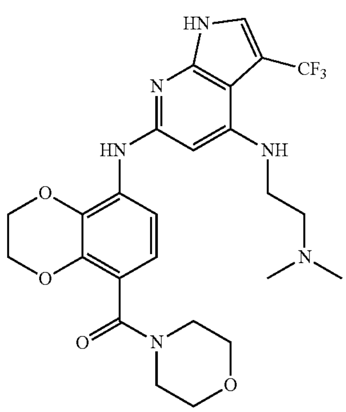 [SMILES: CN(C)CCNc1cc(Nc2ccc(C(=O)N3CCOCC3)c3c2OCCO3)nc2[nH]cc(C(F)(F)F)c12] | (8-((4-((2-(dimethylamino)ethyl)amino)-3-(trifluoromethyl)-1H-pyrrolo[2,3-b]pyridin-6-yl)amino)-2,3-dihydrobenzo [b][1,4]dioxin-5-yl)(morpholino)methanone | ¹H NMR (400 MHZ, MeOD) δ 8.08 (d, J = 8.5 Hz, 1H), 7.44 (d, J = 1.0 Hz, 1H), 6.82 (d, J = 8.5 Hz, 1H), 6.20 (s, 1H), 4.44-4.33 (m, 4H), 3.82 (t, J = 6.4 Hz, 2H), 3.76 (s, 4H), 3.67 (d, J = 15.2 Hz, 2H), 3.49 (t, J = 6.4 Hz, 3H), 3.00 (s, 6H).; 535.3[M + H]⁺ | 75 | 0.97 |
| 172 | 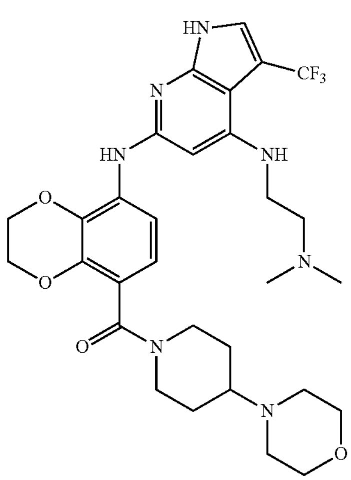 [SMILES: CN(C)CCNc1cc(Nc2ccc(C(=O)N3CCC(N4CCOCC4)CC3)c3c2OCCO3)nc2[nH]cc(C(F)(F)F)c12] | (8-((4-((2-(dimethylamino)ethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | 618.5[M + H]⁺ | 15 | 0.80 |

TABLE 1-continued

| Compound of Example | Structure | Compound Name | ¹H NMR, MS | Yield (%) | HPLC r.t. (min), Purity |
|---|---|---|---|---|---|
| 173 | 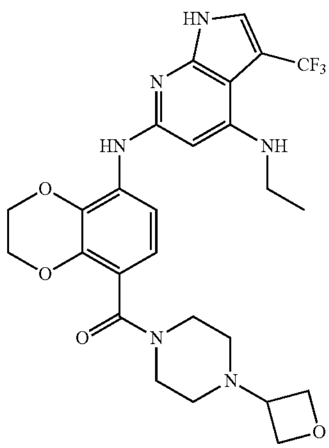 [SMILES: CCNc1cc(Nc2ccc(C(=O)N3CCN(C4COC4)CC3)c3c2OCCO3)nc2[nH]cc(C(F)(F)F)c12] | (8-((4-(ethylamino)-3-(trifluoromethyl)-1H-pyrrolo[2,3-b]pyridin-6-yl)amino)-2,3-dihydrobenzo[b][1,4]dioxin-5-yl)(4-(oxetan-3-yl)piperazin-1-yl)methanone | ¹H NMR (400 MHZ, MeOD, TFA) δ 7.50 (s, 1H), 7.11 (d, J = 8.2 Hz, 1H), 6.95 (d, J = 8.3 Hz, 1H), 4.87-4.73 (m, 4H), 4.45-4.32 (m, 4H), 4.32-4.17 (m, 1H), 4.10-3.91 (m, 2H), 3.77-3.57 (m, 2H), 3.42 (q, J = 7.2 Hz, 2H), 3.20-2.96 (m, 4H), 1.33 (t, J = 7.2 Hz, 3H); 547.25 [M + H]⁺ | 69 | 1.13 |
| 174 | 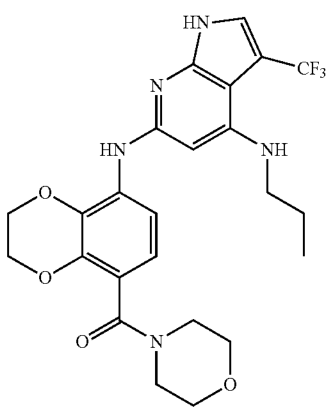 [SMILES: CCCNc1cc(Nc2ccc(C(=O)N3CCOCC3)c3c2OCCO3)nc2[nH]cc(C(F)(F)F)c12] | morpholino(8-((4-(propylamino)-3-(trifluoromethyl)-1H-pyrrolo[2,3-b]pyridin-6-yl)amino)-2,3-dihydrobenzo[b][1,4]dioxin-5-yl)methanone | ¹H NMR (400 MHZ, CDCl₃) δ 8.96 (s, 1H), 7.21 (s, 1H), 6.76-6.67 (m, 2H), 5.45 (s, 1H), 4.55-4.39 (m, 1H), 4.38-4.20 (m, 3H), 3.96-3.84 (m, 1H), 3.84-3.73 (m, 4H), 3.73-3.54 (m, 3H), 3.54-3.44 (m, 1H), 3.32-3.23 (m, 2H), 1.82-1.72 (m, 2H), 1.06 (t, J = 7.4 Hz, 3H); 506.31 [M + H]⁺ | 40 | 1.30 |
| 175 | 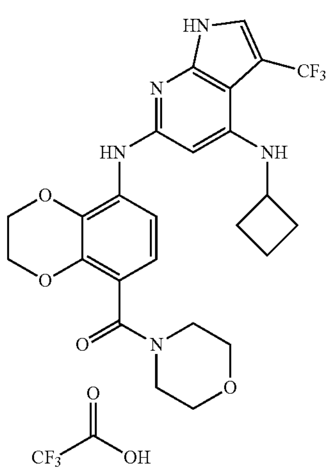 | (8-((4-(cyclobutylamino)-3-(trifluoromethyl)-1H-pyrrolo[2,3-b]pyridin-6-yl)amino)-2,3-dihydrobenzo[b][1,4]dioxin-5-yl)(morpholino)methanone 2,2,2-trifluoroacetate | ¹H NMR (400 MHZ, MeOD, TFA) δ 7.43 (s, 1H), 7.06 (d, J = 8.2 Hz, 1H), 6.84 (d, J = 8.2 Hz, 1H), 4.29 (s, 4H), 4.12-4.01 (m, 1H), 3.73-3.63 (m, 4H), 3.62-3.52 (m, 2H), 3.40-3.27 (m, 2H), 2.51-2.39 (m, 2H), 2.02-1.90 (m, 2H), 1.90-1.79 (m, 2H); 518.31 [M + H]⁺ | 29 | 1.32 |

TABLE 1-continued

| Compound of Example | Structure | Compound Name | ¹H NMR, MS | Yield (%) | HPLC r.t. (min), Purity |
|---|---|---|---|---|---|
| 176 | 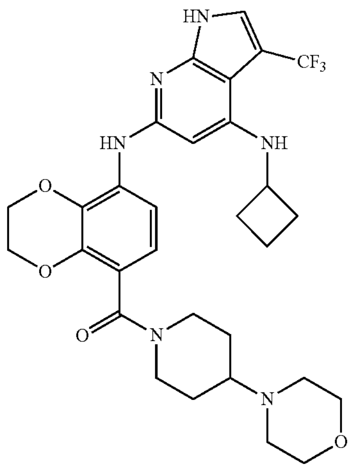 [SMILES: O=C(c1ccc(Nc2cc(NC3CCC3)c3c(C(F)(F)F)c[nH]c3n2)c2c1OCCO2)N1CCC(N2CCOCC2)CC1] | (8-((4-(cyclobutylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | ¹H NMR (400 MHZ, CDCl₃) δ 9.77 (s, 1H), 7.72 (s, 1H), 7.15 (s, 1H), 6.79 (s, 1H), 6.67 (s, 1H), 5.05-4.97 (m, 1H), 4.82-4.71 (m, 1H), 4.41-4.27 (m, 4H), 4.06-3.96 (m, 1H), 3.78-3.67 (m, 5H), 3.09-2.88 (m, 1H), 2.83-2.72 (m, 1H), 2.60-2.45 (m, 6H), 2.45-2.34 (m, 1H), 2.01-1.72 (m, 7H); 601.45 [M + H]⁺ | 38 | 1.20 |
| 177 | 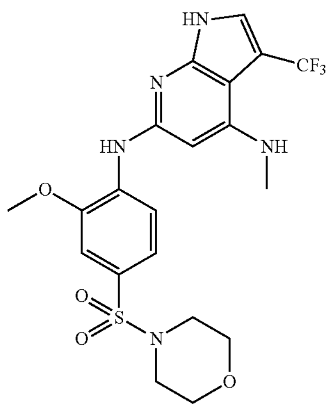 [SMILES: CNc1cc(Nc2ccc(S(=O)(=O)N3CCOCC3)cc2OC)nc2[nH]cc(C(F)(F)F)c12] | N⁶-(2-methoxy-4-(morpholinosulfonyl)phenyl)-N⁴-methyl-3-(trifluoromethyl)-1H-pyrrolo[2,3-b]pyridine-4,6-diamine | ¹H NMR (400 MHZ, MeOD) δ 7.91 (d, J = 8.3 Hz, 1H), 7.54 (d, J = 1.3 Hz, 1H), 7.46 (dd, J = 8.3, 2.0 Hz, 1H), 7.42 (d, J = 1.9 Hz, 1H), 6.14 (s, 1H), 4.03 (s, 3H), 3.78-3.72 (m, 4H), 3.09 (s, 3H), 3.07-3.02 (m, 4H); 486.2[M + H]⁺ | 52 | 1.57, |
| 178 | 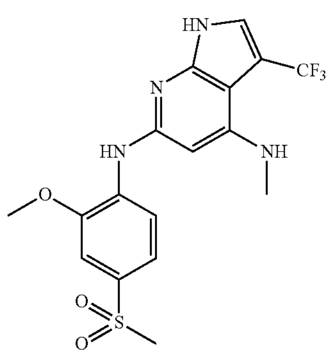 [SMILES: CNc1cc(Nc2ccc(S(C)(=O)=O)cc2OC)nc2[nH]cc(C(F)(F)F)c12] | N⁶-(2-methoxy-4-(methylsulfonyl)phenyl)-N⁴-methyl-3-(trifluoromethyl)-1H-pyrrolo[2,3-b]pyridine-4,6-diamine | ¹H NMR (400 MHZ, MeOD) δ 8.09 (d, J = 8.6 Hz, 1H), 7.69-7.66 (m, 2H), 7.58 (d, J = 1.3 Hz, 1H), 6.20 (s, 1H), 4.10 (s, 3H), 3.24 (s, 3H), 3.13 (s, 3H); 415.2[M + H]⁺ | 28 | 1.47 |

TABLE 1-continued

| Compound of Example | Structure | Compound Name | $^1$H NMR, MS | Yield (%) | HPLC r.t. (min), Purity |
|---|---|---|---|---|---|
| 179 | 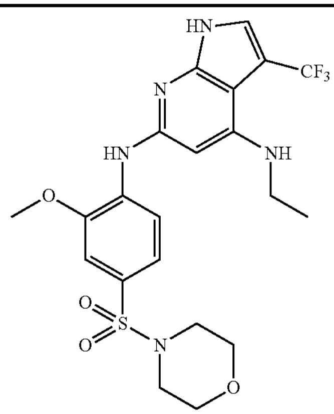 | N$^4$-ethyl-N$^6$-(2-methoxy-4-(morpholinosulfonyl)phenyl)-3-(trifluoromethyl)-1H-pyrrolo[2,3-b]pyridine-4,6-diamine | $^1$H NMR (400 MHZ, MeOD) δ 7.91 (d, J = 6.1 Hz, 1H), 7.41 (d, J = 1.2 Hz, 1H), 7.32 (dd, J = 8.4, 2.0 Hz, 1H), 7.27 (d, J = 1.9 Hz, 1H), 6.03 (s, 1H), 3.91 (s, 3H), 3.67-3.59 (m, 4H), 3.39-3.27 (m, 2H), 2.96-2.86 (m, 4H), 1.28 1.20 (m, 3H); 500.2[M + H]$^+$ | 63 | 1.72 |
| 180 | 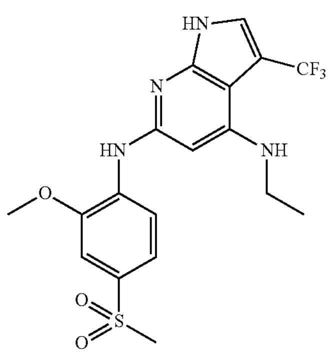 [SMILES: CCNc1cc(Nc2ccc(S(C)(=O)=O)cc2OC)nc2[nH]cc(C(F)(F)F)c12] | N$^4$-ethyl-N$^6$-(2-methoxy-4-(methylsulfonyl)phenyl)-3-(trifluoromethyl)-1H-pyrrolo[2,3-b]pyridine-4,6-diamine | $^1$H NMR (400 MHZ, MeOD) o 7.98 (d, J = 8.7 Hz, 1H), 7.62 (dd, J = 6.6, 2.1 Hz, 2H), 7.54 (d, J = 1.2 Hz, 1H), 6.16 (s, 1H), 4.04 (s, 3H), 3.51-3.41 (m, 2H), 3.18 (s, 3H), 1.37 (t, J = 7.2 Hz, 3H); 429.2[M + H]$^+$ | 67 | 1.64 |
| 181 | 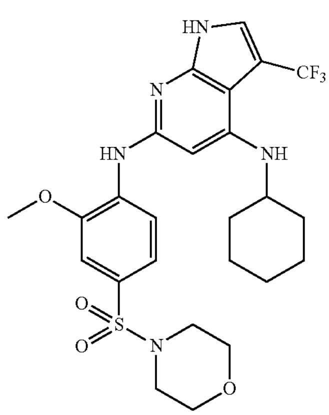 [SMILES: COc1cc(S(=O)(=O)N2CCOCC2)ccc1Nc1cc(NC2CCCCC2)c2c(C(F)(F)F)c[nH]c2n1] | N$^4$-cyclohexyl-N$^6$-(2-methoxy-4-(morpholinosulfonyl)phenyl)-3-(trifluoromethyl)-1H-pyrrolo[2,3-b]pyridine-4,6-diamine | $^1$H NMR (400 MHZ, MeOD) δ 7.87 (d, J = 8.2 Hz, 1H), 7.45 (d, J = 1.3 Hz, 1H), 7.35 (dd, J = 8.3, 1.9 Hz, 1H), 7.31 (d, J = 1.9 Hz, 1H), 6.08 (s, 1H), 3.93 (s, 3H), 3.69-3.62 (m, 4H), 3.54 (t, J = 9.0 Hz, 1H), 2.98-2.90 (m, 4H), 2.06-1.95 (m, 2H), 1.72 (dd, J = 9.4, 4.0 Hz, 2H), 1.65-1.55 (m, 1H), 1.49-1.28 (m, 5H); 554.3[M + H]$^+$ | 67 | 2.04 |
| 182 | 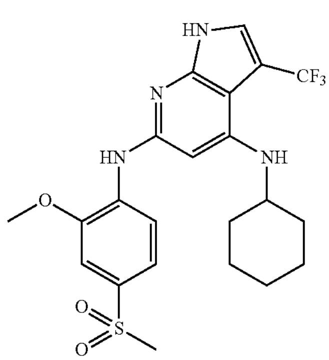 [SMILES: COc1cc(S(C)(=O)=O)ccc1Nc1cc(NC2CCCCC2)c2c(C(F)(F)F)c[nH]c2n1] | N$^4$-cyclohexyl-N$^6$-(2-methoxy-4-(methylsulfonyl)phenyl)-3-(trifluoromethyl)-1H-pyrrolo[2,3-b]pyridine-4,6-diamine | $^1$H NMR (400 MHZ, MeOD) δ 8.06 (d, J = 8.7 Hz, 1H), 7.62-7.58 (m, 2H), 7.53 (d, J = 1.3 Hz, 1H), 6.20 (s, 1H), 4.04 (s, 3H), 3.64 (dd, J = 10.9, 7.1 Hz, 1H), 3.16 (d, J = 9.6 Hz, 3H), 2.14-2.05 (m, 2H), 1.82 (dd, J = 9.3, 3.8 Hz, 2H), 1.74-1.62 (m, 1H), 1.59-1.37 (m, 5H); 483.3[M + H]$^+$ | 44 | 1.98 |

TABLE 1-continued

| Compound of Example | Structure | Compound Name | $^1$H NMR, MS | Yield (%) | HPLC r.t. (min), Purity |
|---|---|---|---|---|---|
| 183 | 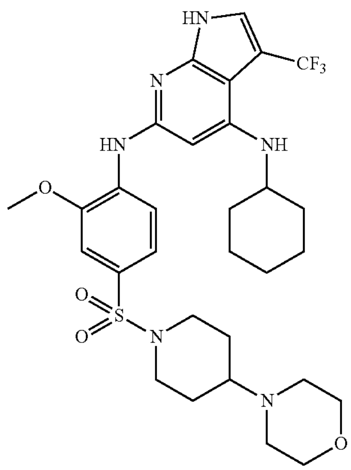 [SMILES: COc1cc(S(=O)(=O)N2CCC(N3CCOCC3)CC2)ccc1Nc1cc(NC2CCCCC2)c2c(C(F)(F)F)c[nH]c2n1] | N$^4$-cyclohexyl-N$^6$-(2-methoxy-4-((4-morpholinopiperidin-1-yl)sulfonyl)phenyl)-3-(trifluoromethyl)-1H-pyrrolo[2,3-b]pyridine-4,6-diamine | $^1$H NMR (400 MHZ, MeOD) δ 8.28-8.13 (m, 1H), 7.52 (s, 1H), 7.43 (dt, J = 8.5, 2.1 Hz, 1H), 7.38 (d, J = 1.8 Hz, 1H), 4.01 (d, J = 13.0 Hz, 7H), 3.81 (d, J = 23.3 Hz, 2H), 3.62 (s, 1H), 3.56-3.38 (m, 2H), 3.27-3.17 (m, 2H), 2.47 (t, J = 12.2 Hz, 2H), 2.26 (d, J = 12.3 Hz, 2H), 2.11 (d, J = 9.7 Hz, 2H), 1.88-1.75 (m, 4H), 1.75-1.65 (m, 1H), 1.60-1.36 (m, 5H); 637.4[M + H]$^+$ | 72 | 1.60 |
| 184 | 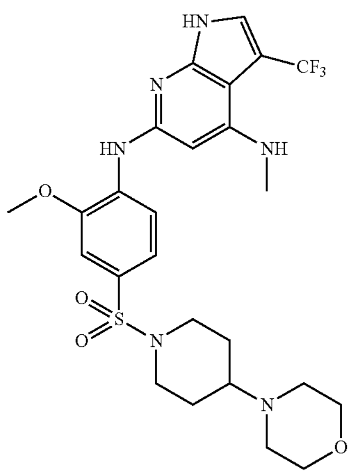 [SMILES: CNc1cc(Nc2ccc(S(=O)(=O)N3CCC(N4CCOCC4)CC3)cc2OC)nc2[nH]cc(C(F)(F)F)c12] | N$^6$-(2-methoxy-4-((4-morpholinopiperidin-1-yl)sulfonyl)phenyl)-N$^4$-methyl-3-(trifluoromethyl)-1H-pyrrolo[2,3-b]pyridine-4,6-diamine | $^1$H NMR (400 MHZ, MeOD) δ 8.45 (d, J = 8.6 Hz, 1H), 7.52 (d, J = 1.4 Hz, 1H), 7.47 (dd, J = 8.5, 2.0 Hz, 1H), 7.40 (d, J = 1.9 Hz, 1H), 4.22-3.99 (m, 7H), 3.93-3.73 (m, 2H), 3.58-3.46 (m, 2H), 3.31-3.20 (m, 3H), 3.09 (s, 3H), 2.51 (t, J = 11.4 Hz, 2H), 2.31 (d, J = 11.7 Hz, 2H), 1.86 (tt, J 12.4, 6.2 Hz, 2H); 569.3[M + H]$^+$ | 71 | 1.27 |
| 185 | 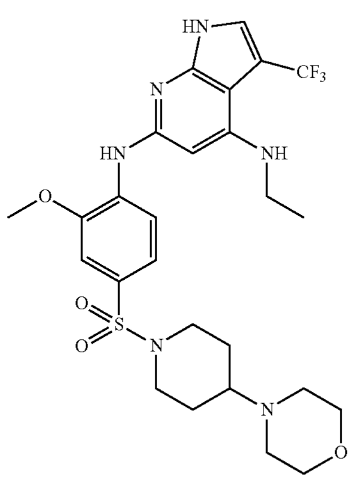 [SMILES: CCNc1cc(Nc2ccc(S(=O)(=O)N3CCC(N4CCOCC4)CC3)cc2OC)nc2[nH]cc(C(F)(F)F)c12] | N$^4$-ethyl-N$^6$-(2-methoxy-4-((4-morpholinopiperidin-1-yl)sulfonyl)phenyl)-3-(trifluoromethyl)-1H-pyrrolo[2,3-b]pyridine-4,6-diamine | $^1$H NMR (400 MHZ, MeOD) δ 8.26 (d, J = 17.4 Hz, 1H), 7.50 (s, 1H), 7.43 (dd, J = 8.5, 1.9 Hz, 1H), 7.37 (d, J = 1.9 Hz, 1H), 4.15-3.96 (m, 7H), 3.87-3.70 (m, 2H), 3.53-3.38 (m, 4H), 3.27-3.18 (m, 3H), 2.47 (t, J = 11.6 Hz, 2H), 2.26 (d, J = 11.8 Hz, 2H), 1.81 (qd, J = 12.2, 4.1 Hz, 2H), 1.36 (t, J = 7.2 Hz, 3H); 583.4[M + H]$^+$ | 72 | 1.36 |

TABLE 1-continued

| Compound of Example | Structure | Compound Name | $^1$H NMR, MS | Yield (%) | HPLC r.t. (min), Purity |
|---|---|---|---|---|---|
| 186 | 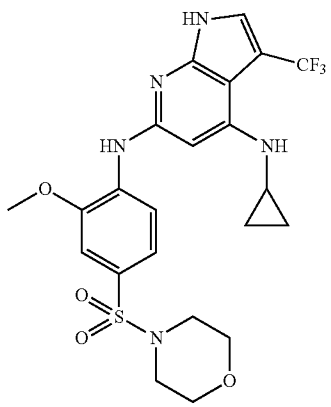 [SMILES: COc1cc(S(=O)(=O)N2CCOCC2)ccc1Nc1cc(NC2CC2)c2c(C(F)(F)F)c[nH]c2n1] | N$^4$-cyclopropyl-N$^6$-(2-methoxy-4-(morpholinosulfonyl)phenyl)-3-(trifluoromethyl)-1H-pyrrolo[2,3-b]pyridine-4,6-diamine | $^1$H NMR (400 MHZ, MeOD) δ 8.10 (d, J = 7.8 Hz, 1H), 7.53 (d, J = 1.2 Hz, 1H), 7.45 (dd, J = 8.4, 1.9 Hz, 1H), 7.40 (d, J = 1.9 Hz, 1H), 4.04 (s, 3H), 3.78-3.71 (m, 4H), 3.06-3.00 (m, 4H), 2.77-2.68 (m, 1H), 1.02-0.92 (m, 2H), 0.73-0.65 (m, 2H); 512.3[M + H]$^+$ | 56 | 1.81 |
| 187 | 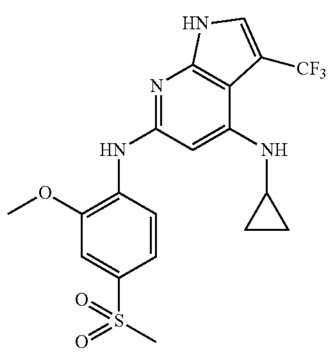 [SMILES: COc1cc(S(C)(=O)=O)ccc1Nc1cc(NC2CC2)c2c(C(F)(F)F)c[nH]c2n1] | N$^4$-cyclopropyl-N$^6$-(2-methoxy-4-(methylsulfonyl)phenyl)-3-(trifluoromethyl)-1H-pyrrolo[2,3-b]pyridine-4,6-diamine | $^1$H NMR (400 MHZ, MeOD) δ 8.16 (d, J = 7.6 Hz, 1H), 7.64-7.58 (m, 2H), 7.52 (d, J = 1.2 Hz, 1H), 4.05 (s, 3H), 3.20-3.15 (m, 3H), 2.77-2.66 (m, 1H), 1.03-0.90 (m, 2H), 0.75-0.64 (m, 2H); 441.2[M + H]$^+$ | 61 | 1.74 |
| 188 | 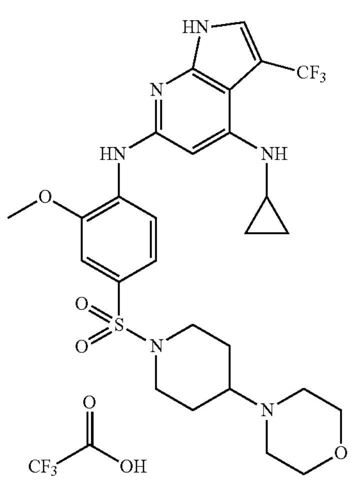 | N$^4$-cyclopropyl-N$^6$-(2-methoxy-4-((4-morpholinopiperidin-1-yl)sulfonyl)phenyl)-3-(trifluoromethyl)-1H-pyrrolo[2,3-b]pyridine-4,6-diamine 2,2,2-trifluoroacetate | $^1$H NMR (400 MHZ, MeOD, TFA) & 8.19 (s, 1H), 7.47 (d, J = 19.3 Hz, 1H), 7.42 (d, J = 8.5 Hz, 1H), 7.36 (s, 1H), 4.16-3.93 (m, 7H), 3.84-3.59 (m, 2H), 3.56-3.38 (m, 2H), 3.26-3.09 (m, 3H), 2.73-2.62 (m, 1H), 2.44 (t, J = 11.9 Hz, 2H), 2.24 (d, J = 11.8 Hz, 2H), 1.79 (td, J = 12.2, 8.6 Hz, 2H), 0.98-0.88 (m, 2H), 0.71-0.62 (m, 2H); 595.4[M + H]$^+$ | 71 | 1.41 |

TABLE 1-continued

| Compound of Example | Structure | Compound Name | $^1$H NMR, MS | Yield (%) | HPLC r.t. (min), Purity |
|---|---|---|---|---|---|
| 189 | 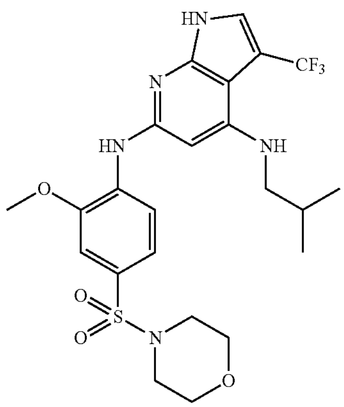 [SMILES: COc1cc(S(=O)(=O)N2CCOCC2)ccc1Nc1cc(NCC(C)C)c2c(C(F)(F)F)c[nH]c2n1] | N$^4$-isobutyl-N$^6$-(2-methoxy-4-(morpholinosulfonyl)phenyl)-3-(trifluoromethyl)-1H-pyrrolo[2,3-b]pyridine-4,6-diamine | $^1$H NMR (400 MHZ, MeOD-d4) δ 8.76 (d, J = 8.6 Hz, 1H), 7.38 (s, 1H), 7.31 (d, J = 8.6 Hz, 1H), 7.22 (s, 1H), 6.13 (s, 1H), 4.00 (s, 3H), 3.76-3.65 (m, 4H), 3.13 (d, J = 6.2 Hz, 2H), 2.99-2.93 (m, 4H), 2.07-1.92 (m, 6.6 Hz, 1H), 1.06 (s, 3H), 1.04 (s, 3H); 528.3[M + H]$^+$ | 15 | 1.92 |
| 190 | 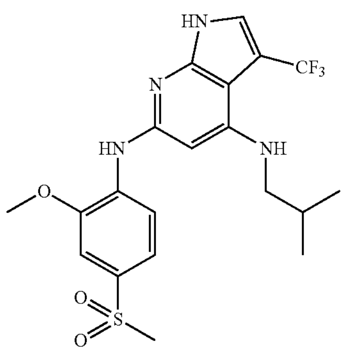 [SMILES: COc1cc(S(C)(=O)=O)ccc1Nc1cc(NCC(C)C)c2c(C(F)(F)F)c[nH]c2n1] | N$^4$-isobutyl-N$^6$-(2-methoxy-4-(methylsulfonyl)phenyl)-3-(trifluoromethyl)-1H-pyrrolo[2,3-b]pyridine-4,6-diamine | $^1$H NMR (400 MHZ, MeOD-d$_6$) δ 8.79 (d, J = 8.7 Hz, 1H), 7.47 (d, J = 8.7 Hz, 1H), 7.40 (d, J = 8.6 Hz, 2H), 6.14 (s, 1H), 4.02 (s, 3H), 3.13 (d, J = 6.1 Hz, 2H), 3.10 (s, 3H), 2.08-1.96 (m, 1H), 1.06 (s, 3H), 1.04 (s, 3H); 457.2[M + H]$^+$ | 42 | 1.82 |
| 191 | 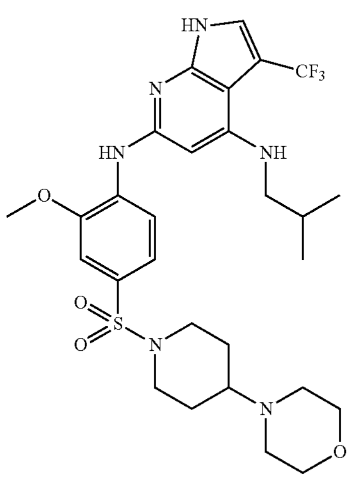 [SMILES: COc1cc(S(=O)(=O)N2CCC(N3CCOCC3)CC2)ccc1Nc1cc(NCC(C)C)c2c(C(F)(F)F)c[nH]c2n1] | N$^4$-isobutyl-N$^6$-(2-methoxy-4-((4-morpholinopiperidin-1-yl)sulfonyl)phenyl)-3-(trifluoromethyl)-1H-pyrrolo[2,3-b]pyridine-4,6-diamine | $^1$H NMR (400 MHZ, CDCl$_3$) δ 8.83 (s, 1H), 8.62 (d, J = 8.6 Hz, 1H), 7.36 (dd, J = 8.6, 1.9 Hz, 1H), 7.24 (s, 1H), 7.21-7.16 (m, 2H), 4.94 (s, 1H), 3.99 (s, 3H), 3.82 (d, J = 11.7 Hz, 2H), 3.73-3.64 (m, 4H), 3.09 (dd, J = 6.5, 5.3 Hz, 2H), 2.52-2.45 (m, 4H), 2.31 (t, J = 10.9 Hz, 2H), 2.16-1.96 (m, 2H), 1.87 (d, J = 11.7 Hz, 2H), 1.68-1.55 (m, 4H), 1.07 (s, 3H), 1.05 (s, 3H); 611.4[M + H]$^+$ | 82 | 1.49 |

TABLE 1-continued

| Compound of Example | Structure | Compound Name | ¹H NMR, MS | Yield (%) | HPLC r.t. (min), Purity |
|---|---|---|---|---|---|
| 192 | 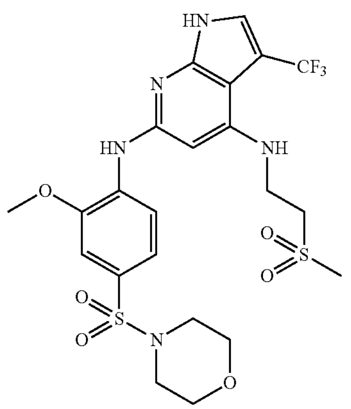 | N⁶-(2-methoxy-4-(morpholinosulfonyl)phenyl)-N⁴-(2-(methylsulfonyl)ethyl)-3-(trifluoromethyl)-1H-pyrrolo[2,3-b]pyridine-4,6-diamine | ¹H NMR (400 MHZ, CDCl₃) δ 8.73-8.66 (m, 2H), 7.39 (dd, J = 8.6, 1.9 Hz, 1H), 7.31 (d, J = 8.1 Hz, 2H), 7.20 (d, J = 1.9 Hz, 1H), 4.02 (s, 3H), 3.93 (q, J = 6.2 Hz, 2H), 3.81-3.71 (m, 4H), 3.41 (t, J = 6.3 Hz, 2H), 3.05-3.01 (m, 4H), 3.00 (s, 3H); 578.3[M + H]⁺ | 26 | 1.47 |
| 193 | 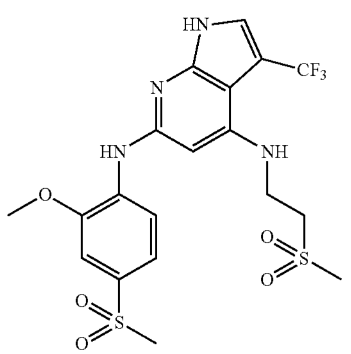 | N⁶-(2-methoxy-4-(methylsulfonyl)phenyl)-N⁴-(2-(methylsulfonyl)ethyl)-3-(trifluoromethyl)-1H-pyrrolo[2,3-b]pyridine-4,6-diamine | 507.2[M + H]⁺ | 13 | 1.39 |
| 194 | 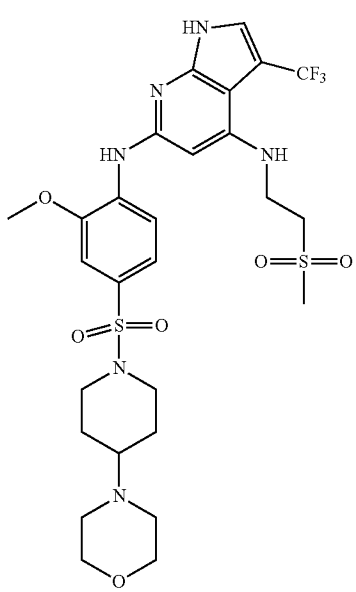 [SMILES: COc1cc(S(=O)(=O)N2CCC(N3CCOCC3)CC2)ccc1Nc1cc(NCCS(C)(=O)=O)c2c(C(F)(F)F)c[nH]c2n1] | N⁶-(2-methoxy-4-((4-morpholinopiperidin-1-yl)sulfonyl)phenyl)-N⁴-(2-(methylsulfonyl)ethyl)-3-(trifluoromethyl)-1H-pyrrolo[2,3-b]pyridine-4,6-diamine | ¹H NMR (400 MHZ, CDCl₃) δ 8.93 (s, 1H), 8.67 (d, J = 8.6 Hz, 1H), 7.37 (d, J = 8.6 Hz, 1H), 7.28 (s, 2H), 7.21 (d, J = 1.8 Hz, 1H), 5.26-5.11 (m, 1H), 3.99 (s, 3H), 3.91 (q, J = 6.2 Hz, 2H), 3.82 (d, J = 11.4 Hz, 2H), 3.76-3.64 (m, 4H), 3.41 (t, J = 6.3 Hz, 2H), 3.00 (s, 3H), 2.53-2.46 (m, 4H), 2.32 (t, J = 11.1 Hz, 2H), 1.87 (d, J = 11.7 Hz, 2H), 1.68-1.54 (m, 2H); 661.4[M + H]⁺ | 39 | 1.22 |

TABLE 1-continued

| Compound of Example | Structure | Compound Name | ¹H NMR, MS | Yield (%) | HPLC r.t. (min), Purity |
|---|---|---|---|---|---|
| 195 | 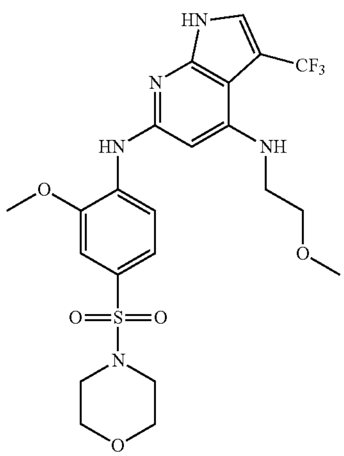 | N⁶-(2-methoxy-4-(morpholinosulfonyl)phenyl)-N⁴-(2-methoxyethyl)-3-(trifluoromethyl)-1H-pyrrolo[2,3-b]pyridine-4,6-diamine | ¹H NMR (400 MHZ, MeOD-d₆) δ 8.78 (d, J = 8.4 Hz, 1H), 7.38 (s, 1H), 7.31 (d, J = 8.5 Hz, 1H), 7.22 (s, 1H), 6.15 (s, 1H), 4.01 (s, 3H), 3.75-3.65 (m, 6H), 3.47-3.43 (m, 2H), 3.42 (s, 3H), 3.01-2.91 (m, 4H); 530.3[M + H]⁺ | 38 | 1.64 |
| 196 | 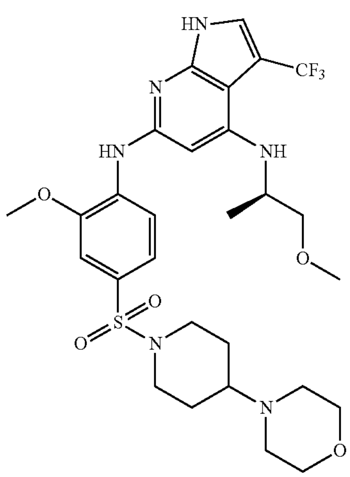 [SMILES: COC[C@@H](C)Nc1cc(Nc2ccc(S(=O)(=O)N3CCC(N4CCOCC4)CC3)cc2OC)nc2[nH]cc(C(F)(F)F)c12] | (R)-N⁶-(2-methoxy-4-((4-morpholinopiperidin-1-yl)sulfonyl)phenyl)-N⁴-(1-methoxypropan-2-yl)-3-(trifluoromethyl)-1H-pyrrolo[2,3-b]pyridine-4,6-diamine | ¹H NMR (400 MHZ, DMSO-d₆) δ 11.87 (s, 1H), 8.88 (d, J = 8.1 Hz, 1H), 8.36 (s, 1H), 7.58 (s, 1H), 7.24 (d, J = 7.5 Hz, 1H), 7.16 (s, 1H), 6.46 (s, 1H), 4.93 (s, 1H), 3.97 (s, 3H), 3.79 (s, 1H), 3.64 (d, J = 10.2 Hz, 2H), 3.49 (d, J = 13.6 Hz, 6H), 2.38 (s, 4H), 2.24 (t, J = 11.1 Hz, 2H), 2.11 (s, 1H), 1.90 (s, 1H), 1.80 (d, J = 11.7 Hz, 2H), 1.41 (d, J = 11.3 Hz, 2H), 1.24 (s, 4H). 627.5[M + H]⁺ | 42 | 1.43 |
| 197 | 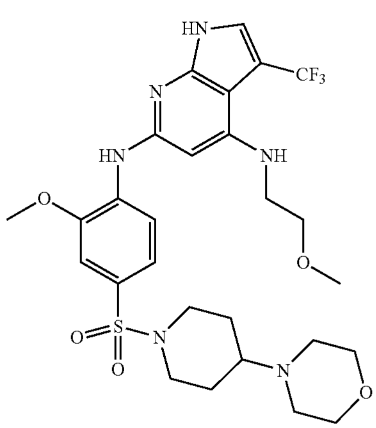 [SMILES: COCCNc1cc(Nc2ccc(S(=O)(=O)N3CCC(N4CCOCC4)CC3)cc2OC)nc2[nH]cc(C(F)(F)F)c12] | N⁶-(2-methoxy-4-((4-morpholinopiperidin-1-yl)sulfonyl)phenyl)-N⁴-(2-methoxyethyl)-3-(trifluoromethyl)-1H-pyrrolo[2,3-b]pyridine-4,6-diamine | ¹H NMR (400 MHz, DMSO) δ 11.93 (s, 1H), 8.88 (d, J = 8.6 Hz, 1H), 8.31 (s, 1H), 7.58 (s, 1H), 7.25 (dd, J = 8.6, 1.8 Hz, 1H), 7.16 (d, J = 1.8 Hz, 1H), 6.41 (s, 1H), 5.08 (s, 1H), 3.97 (s, 3H), 3.63 (dd, J = 12.4, 7.2 Hz, 4H), 3.56-3.46 (m, 4H), 3.39 (d, J = 5.3 Hz, 5H), 2.38 (s, 4H), 2.25 (t, J = 11.2 Hz, 2H), 2.11 (t, J = 11.0 Hz, 1H), 1.80 (d, J = 11.4 Hz, 2H), 1.48-1.34 (m, 2H).; 613.4[M + H]⁺ | 31 | 1.28 |

TABLE 1-continued

| Compound of Example | Structure | Compound Name | ¹H NMR, MS | Yield (%) | HPLC r.t. (min), Purity |
|---|---|---|---|---|---|
| 198 | 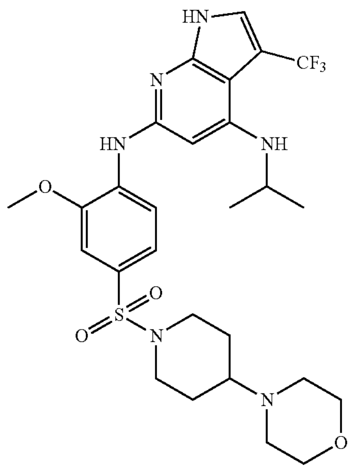 [SMILES: COc1cc(S(=O)(=O)N2CCC(N3CCOCC3)CC2)ccc1Nc1cc(NC(C)C)c2c(C(F)(F)F)c[nH]c2n1] | N⁴-isopropyl-N⁶-(2-methoxy-4-((4-morpholinopiperidin-1-yl)sulfonyl)phenyl)-3-(trifluoromethyl)-1H-pyrrolo[2,3-b]pyridine-4,6-diamine | ¹H NMR (400 MHZ, CDCl₃) δ 8.86 (s, 1H), 8.57 (d, J = 8.6 Hz, 1H), 7.36 (dd, J = 8.6, 1.9 Hz, 1H), 7.23 (s, 1H), 7.21 (d, J = 1.9 Hz, 1H), 7.17 (s, 1H), 5.85 (s, 1H), 4.77 (d, J = 4.5 Hz, 1H), 4.00 (s, 3H), 3.86-3.74 (m, 3H), 3.72-3.65 (m, 4H), 2.54-2.44 (m, 4H), 2.31 (dd, J = 11.8, 10.2 Hz, 2H), 2.18-2.07 (m, 1H), 1.87 (d, J = 11.3 Hz, 2H), 1.62 (qd, J = 12.2, 3.9 Hz, 2H), 1.33 (d, J = 3.6 Hz, 3H), 1.32 (s, 3H); 597.4[M + H]⁺ | 55 | 1.44 |
| 199 | 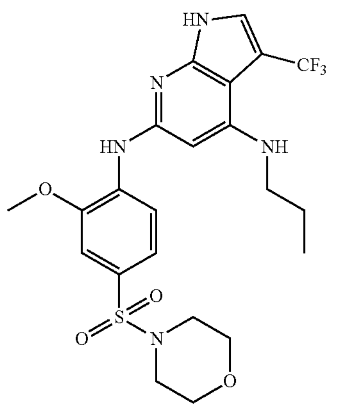 [SMILES: CCCNc1cc(Nc2ccc(S(=O)(=O)N3CCOCC3)cc2OC)nc2[nH]cc(C(F)(F)F)c12] | N⁶-(2-methoxy-4-(morpholinosulfonyl)phenyl)-N⁴-propyl-3-(trifluoromethyl)-1H-pyrrolo[2,3-b]pyridine-4,6-diamine | ¹H NMR (400 MHZ, DMSO) δ 11.88 (s, 1H), 8.91 (d, J = 8.6 Hz, 1H), 8.39 (s, 1H), 7.58 (s, 1H), 7.25 (d, J = 8.6 Hz, 1H), 7.16 (s, 1H), 6.42 (s, 1H), 4.83 (s, 1H), 3.99 (s, 3H), 3.64 (s, 4H), 3.23 (dd, J = 12.0, 5.9 Hz, 2H), 2.88 (s, 4H), 1.69-1.62 (m, 2H), 0.98 (t, J = 7.2 Hz, 3H).; 514.3 [M + H]⁺ | 34 | 1.74 |
| 200 | 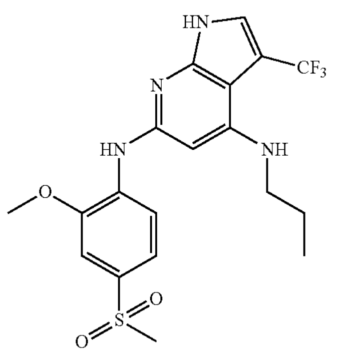 [SMILES: CCCNc1cc(Nc2ccc(S(C)(=O)=O)cc2OC)nc2[nH]cc(C(F)(F)F)c12] | N⁶-(2-methoxy-4-(methylsulfonyl)phenyl)-N⁴-propyl-3-(trifluoromethyl)-1H-pyrrolo[2,3-b]pyridine-4,6-diamine | ¹H NMR (400 MHZ, DMSO) δ 11.88 (s, 1H), 8.88 (d, J = 8.6 Hz, 1H), 8.36 (s, 1H), 7.57 (s, 1H), 7.41 (d, J = 13.4 Hz, 1H), 6.40 (s, 1H), 4.82 (s, 1H), 3.99 (s, 3H), 3.22 (dd, J = 12.3, 6.2 Hz, 2H), 3.17 (s, 3H), 1.66 (dd, J = 14.2, 7.2 Hz, 2H), 1.20 (dd, J = 32.8, 6.7 Hz, 3H), 0.98 (t, J = 7.3 Hz, 3H).; 443.2[M + H]⁺ | 4 | 1.66 |
| 201 | 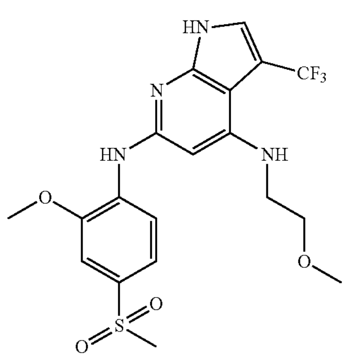 | N⁶-(2-methoxy-4-(methylsulfonyl)phenyl)-N⁴-(2-methoxyethyl)-3-(trifluoromethyl)-1H-pyrrolo[2,3-b]pyridine-4,6-diamine | ¹H NMR (400 MHZ, DMSO) δ 11.90 (s, 1H), 8.88 (d, J = 8.5 Hz, 1H), 8.33 (s, 1H), 7.58 (s, 1H), 7.44-7.38 (m, 2H), 6.42 (s, 1H), 5.09 (s, 1H), 3.99 (s, 3H), 3.62 (s, 2H), 3.39 (d, J = 4.7 Hz, 2H), 3.17 (s, 3H).; 459.2[M + H]⁺ | 46 | 1.50 |

TABLE 1-continued

| Compound of Example | Structure | Compound Name | ¹H NMR, MS | Yield (%) | HPLC r.t. (min), Purity |
|---|---|---|---|---|---|
| 202 | 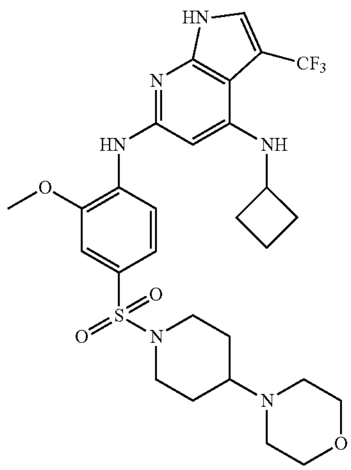 [SMILES: COc1cc(S(=O)(=O)N2CCC(N3CCOCC3)CC2)ccc1Nc1cc(NC2CCC2)c2c(C(F)(F)F)c[nH]c2n1] | $N^4$-cyclobutyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine | ¹H NMR (400 MHZ, TFA salt, MeOD-d$_6$) δ 8.24 (d, J = 8.2 Hz, 1H), 7.48 (s, 1H), 7.40 (d, J = 8.6 Hz, 1H), 7.33 (s, 1H), 4.19-4.02 (m, 2H), 4.02-3.93 (m, J = 14.6 Hz, 5H), 3.83-3.64 (m, 2H), 3.55-3.35 (m, 2H), 3.25-3.09 (m, J = 26.9, 15.5 Hz, 3H), 2.59-2.49 (m, J = 5.8 Hz, 2H), 2.43 (t, J = 12.1 Hz, 2H), 2.23 (d, J = 12.0 Hz, 2H), 2.06-1.87 (m, 4H), 1.84-1.72 (m, 2H); 610.4[M + H]⁺ | 79 | 1.40 |
| 203 | 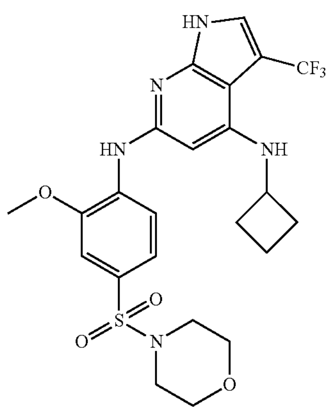 [SMILES: COc1cc(S(=O)(=O)N2CCOCC2)ccc1Nc1cc(NC2CCC2)c2c(C(F)(F)F)c[nH]c2n1] | $N^4$-cyclobutyl-$N^6$-(2-methoxy-4-(morpholinosulfonyl)phenyl)-3-(trifluoromethyl)-1H-pyrrolo[2,3-b]pyridine-4,6-diamine | 526.3[M + H]⁺ | 40 | 1.74 |
| 204 | 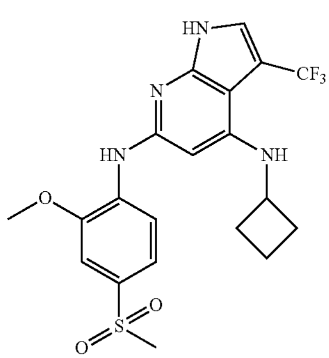 [SMILES: COc1cc(S(C)(=O)=O)ccc1Nc1cc(NC2CCC2)c2c(C(F)(F)F)c[nH]c2n1] | $N^4$-cyclobutyl-$N^6$-(2-methoxy-4-(methylsulfonyl)phenyl)-3-(trifluoromethyl)-1H-pyrrolo[2,3-b]pyridine-4,6-diamine | 455.2[M + H]⁺ | 25 | 1.66 |

TABLE 1-continued

| Compound of Example | Structure | Compound Name | ¹H NMR, MS | Yield (%) | HPLC r.t. (min), Purity |
|---|---|---|---|---|---|
| 205 | 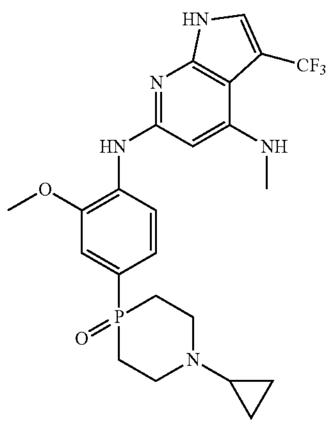 [SMILES: CNc1cc(Nc2ccc(P3(=O)CCN(C4CC4)CC3)cc2OC)nc2[nH]cc(C(F)(F)F)c12] | 1-cyclopropyl-4-(3-methoxy-4-((4-(methylamino)-3-(trifluoromethyl)-1H-pyrrolo[2,3-b]pyridin-6-yl)amino)phenyl)-1,4-azaphosphinane 4-oxide | 1H NMR (400 MHZ, DMSO) δ 11.89 (s, 1H), 8.92 (s, 1H), 8.23 (s, 1H), 7.53 (s, 1H), 7.32 (s, 2H), 6.29 (s, 1H), 5.06 (s, 1H), 3.95 (s, 3H), 3.83 (s, 2H), 3.36 (s, 3H), 3.05 (s, 1H), 2.90 (s, 4H), 2.18 (t, J = 17.6 Hz, 2H), 1.20 (s, 2H), 0.87 (s, 2H). 494.4[M + H]⁺ | 50 | 1.12 |
| 206 | 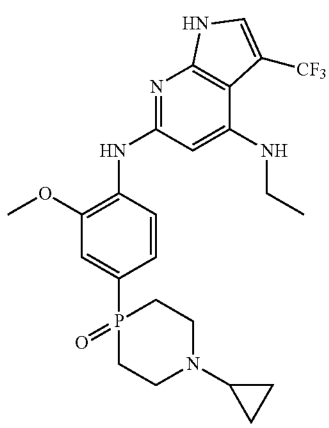 [SMILES: CCNc1cc(Nc2ccc(P3(=O)CCN(C4CC4)CC3)cc2OC)nc2[nH]cc(C(F)(F)F)c12] | 1-cyclopropyl-4-(4-((4-(ethylamino)-3-(trifluoromethyl)-1H-pyrrolo[2,3-b]pyridin-6-yl)amino)-3-methoxyphenyl)-1,4-azaphosphinane 4-oxide | 1H NMR (400 MHZ, DMSO) δ 11.84 (s, 1H), 8.75 (s, 1H), 8.14 (s, 1H), 7.53 (s, 1H), 7.25 (d, J = 11.0 Hz, 2H), 6.33 (s, 1H), 4.74 (s, 1H), 3.95 (s, 3H), 3.30-3.23 (m, 4H), 3.03-2.90 (m, 4H), 2.24-2.12 (m, 2H), 1.84 (d, J = 14.0 Hz, 2H), 0.47 (s, 2H), 0.35 (s, 2H). 508.4[M + H]⁺ | 9 | 1.27 |
| 207 | 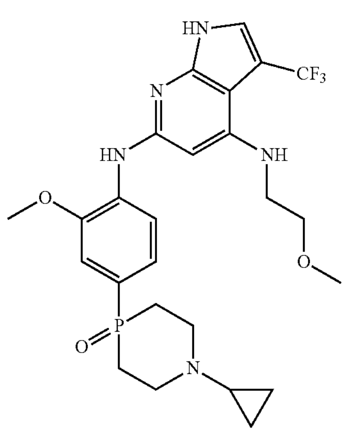 | 1-cyclopropyl-4-(3-methoxy-4-((4-((2-methoxyethyl)amino)-3-(trifluoromethyl)-1H-pyrrolo[2,3-b]pyridin-6-yl)amino)phenyl)-1,4-azaphosphinane 4-oxide | 1H NMR (400 MHZ, DMSO) δ 11.89 (s, 1H), 8.81 (s, 1H), 8.30 (d, J = 28.9 Hz, 2H), 7.45 (s, 2H), 6.38 (s, 1H), 5.09 (s, 1H), 3.96 (s, 3H), 3.78 (s, 2H), 3.62 (d, J = 3.2 Hz, 2H), 3.41 (d, J = 17.3 Hz, 4H), 3.33 (s, 3H), 2.24 (s, 2H), 1.77-1.42 (m, 1H), 1.03-0.91 (m, 2H), 0.85 (s, 4H). 538.3[M + H]⁺ | 90 | 1.21 |

TABLE 1-continued

| Compound of Example | Structure | Compound Name | ¹H NMR, MS | Yield (%) | HPLC r.t. (min), Purity |
|---|---|---|---|---|---|
| 208 | 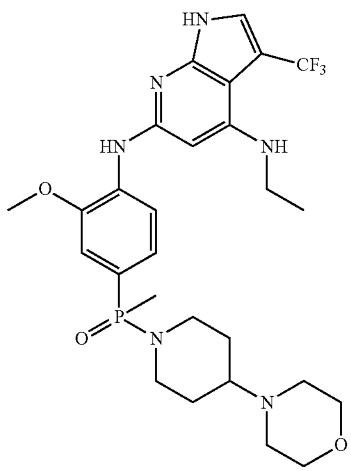 [SMILES: CCNc1cc(Nc2ccc(P(C)(=O)N3CCC(N4CCOCC4)CC3)cc2OC)nc2[nH]cc(C(F)(F)F)c12] | (4-((4-(ethylamino)-3-(trifluoromethyl)-1H-pyrrolo[2,3-b]pyridin-6-yl)amino)-3-methoxyphenyl)(methyl)(4-morpholinopiperidin-1-yl)phosphine oxide | 1H NMR (400 MHZ, DMSO-$d_6$) δ 11.80 (s, 1H), 8.73 (s, 1H), 8.12 (s, 1H), 7.54 (s, 1H), 7.18 (d, J = 10.4 Hz, 2H), 6.32 (s, 1H), 4.73 (s, 1H), 3.92 (s, 3H), 3.55 (s, 4H), 3.28 (d, J = 6.2 Hz, 3H), 2.43 (s, 4H), 2.24 (s, 1H), 1.72 (s, 2H), 1.64 (d, J = 13.4 Hz, 3H), 1.24 (s, 7H), 0.85 (s, 1H). 581.5[M + H]⁺ | 18 | 1.10 |
| 209 | 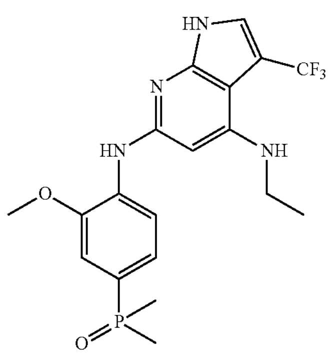 [SMILES: CCNc1cc(Nc2ccc(P(C)(C)=O)cc2OC)nc2[nH]cc(C(F)(F)F)c12] | (4-((4-(ethylamino)-3-(trifluoromethyl)-1H-pyrrolo[2,3-b]pyridin-6-yl)amino)-3-methoxyphenyl)dimethylphosphine oxide | ¹H NMR (400 MHZ, CDCl₃) δ 9.93 (d, J = 56.3 Hz, 1H), 8.37 (s, 1H), 7.39 (dd, J = 12.3, 1.3 Hz, 1H), 7.12-7.04 (m, 2H), 6.99 (d, J = 5.0 Hz, 1H), 4.78 (s, 1H), 4.00 (s, 3H), 3.36-3.24 (m, 2H), 1.73 (s, 3H), 1.70 (s, 3H), 1.36 (t, J = 7.2 Hz, 3H); 427.28 [M + H]⁺ | 20 | 1.32 |
| 210 | 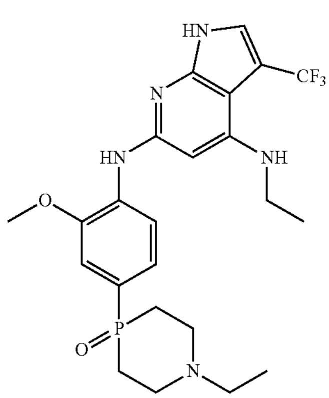 [SMILES: CCNc1cc(Nc2ccc(P3(=O)CCN(CC)CC3)cc2OC)nc2[nH]cc(C(F)(F)F)c12] | 1-ethyl-4-(4-((4-(ethylamino)-3-(trifluoromethyl)-1H-pyrrolo[2,3-b]pyridin-6-yl)amino)-3-methoxyphenyl)-1,4-azaphosphinane 4-oxide | ¹H NMR (400 MHz, CDCl₃) δ 8.20 (s, 1H), 7.36 (d, J = 12.2 Hz, 1H), 7.25-7.17 (m, 2H), 7.13 (d, J = 4.4 Hz, 1H), 4.85 (s, 1H), 3.98 (s, 3H), 3.33-3.12 (m, 4H), 3.01 (s, 2H), 2.73-2.63 (m, 2H), 2.41-2.25 (m, 2H), 2.06-1.98 (m, 2H), 1.35 (t, J = 7.2 Hz, 3H), 1.17 (t, J = 7.2 Hz, 3H); 496.38 [M + H]⁺ | 44 | 1.17 |

TABLE 1-continued

| Compound of Example | Structure | Compound Name | 1H NMR, MS | Yield (%) | HPLC r.t. (min), Purity |
|---|---|---|---|---|---|
| 211 | 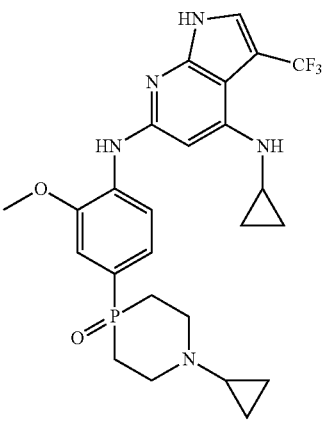 [SMILES: COc1cc(P2(=O)CCN(C3CC3)CC2)ccc1Nc1cc(NC2CC2)c2c(C(F)(F)F)c[nH]c2n1] | 1-cyclopropyl-4-(4-((4-(cyclopropylamino)-3-(trifluoromethyl)-1H-pyrrolo[2,3-b]pyridin-6-yl)amino)-3-methoxyphenyl)-1,4-azaphosphinane 4-oxide | 520.3[M + H]+ | 22 | 1.34 |
| 212 | 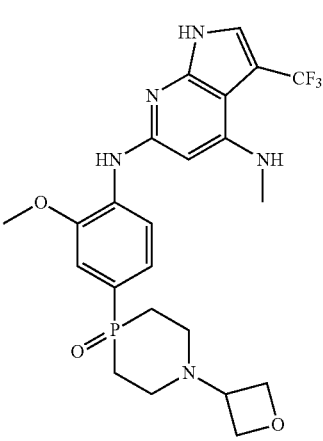 [SMILES: CNc1cc(Nc2ccc(P3(=O)CCN(C4COC4)CC3)cc2OC)nc2[nH]cc(C(F)(F)F)c12] | 4-(3-methoxy-4-((4-(methylamino)-3-(trifluoromethyl)-1H-pyrrolo[2,3-b]pyridin-6-yl)amino)phenyl)-1-(oxetan-3-yl)-1,4-azaphosphinane 4-oxide | 510.3[M + H]+ | 13 | 1.16 |
| 213 | 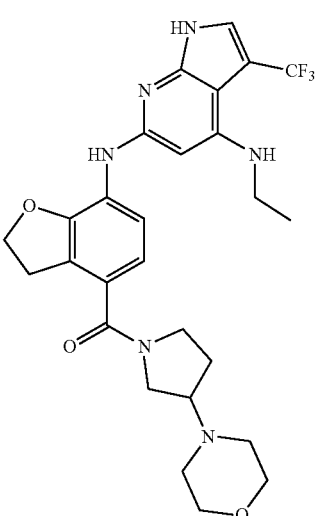 | (R)-(7-((4-(ethylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | 1H NMR (400 MHZ, Methanol-d4) δ 7.44 (d, J = 8.1 Hz, 2H), 7.00 (d, J = 8.2 Hz, 1H), 4.75-4.60 (m, 3H), 4.10 (q, J = 7.2 Hz, 1H), 3.90 (s, 5H), 3.73 (s, 2H), 3.62 (d, J = 21.5 Hz, 2H), 3.39 (q, J = 7.3 Hz, 3H), 2.15 (s, 3H), 1.34 (d, J = 7.2 Hz, 3H), 1.30 (s, 6H). 545.5[M + H]+ | 87 | 1.16 |

TABLE 1-continued

| Compound of Example | Structure | Compound Name | ¹H NMR, MS | Yield (%) | HPLC r.t. (min), Purity |
|---|---|---|---|---|---|
| 214 | 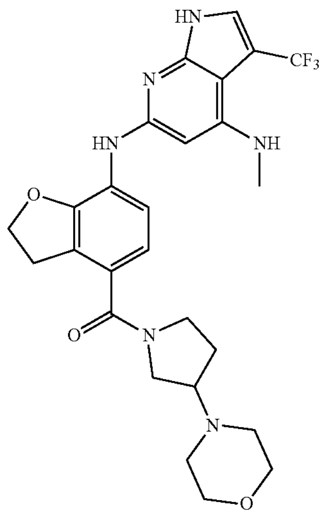 [SMILES: CNc1cc(Nc2ccc(C(=O)N3CCC(N4CCOCC4)C3)c3c2OCC3)nc2[nH]cc(C(F)(F)F)c12] | (R)-(7-((4-(methylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | 531.4[M + H]⁺ | 53 | 1.07 |
| 215 | 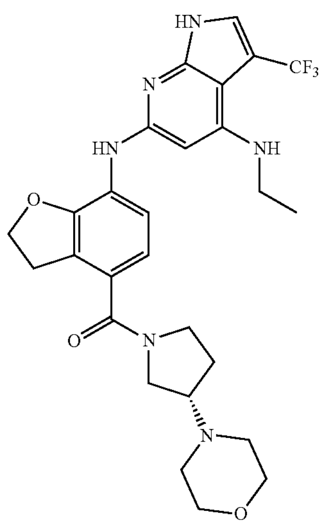 | (S)-(7-((4-(ethylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | ¹H NMR (400 MHZ, Methanol-d4) δ 8.05 (dd, J = 8.3, 3.3 Hz, 1H), 7.21 (s, 1H), 6.78 (t, J = 7.4 Hz, 1H), 5.89 (s, 1H), 4.62-4.50 (m, 2H), 3.80-3.66 (m, 1H), 3.64-3.55 (m, 4H), 3.54-3.38 (m, 2H), 3.28 (d, J = 11.7 Hz, 2H), 3.16-3.07 (m, 1H), 2.88-2.72 (m, 1H), 2.45 (d, J = 13.5 Hz, 3H), 2.29 (d, J = 8.8 Hz, 1H), 2.20-2.11 (m, 1H), 2.05 (s, 1H), 1.71 (dq, J = 21.1, 10.6 Hz, 1H), 1.22 (t, J = 7.2 Hz, 4H). 572.4[M + H]⁺ | 38 | 1.13 |
| 216 | 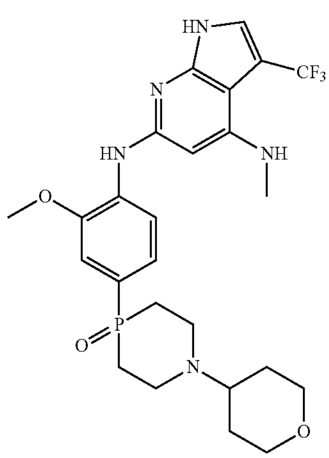 [SMILES: CNc1cc(Nc2ccc(P3(=O)CCN(C4CCOCC4)CC3)cc2OC)nc2[nH]cc(C(F)(F)F)c12] | 4-(3-methoxy-4-((4-(methylamino)-3-(trifluoromethyl)-1H-pyrrolo[2,3-b]pyridin-6-yl)amino)phenyl)-1-(tetrahydro-2H-pyran-4-yl)-1,4-azaphosphinane 4-oxide | ¹H NMR (400 MHZ, DMSO) δ 11.87 (s, 1H), 8.91-8.77 (m, 1H), 8.24 (s, 1H), 7.53 (d, J = 1.2 Hz, 1H), 7.36 (t, J = 5.5 Hz, 4H), 7.23 (s, 2H), 7.10 (s, 2H), 6.29 (s, 1H), 5.07 (s, 1H), 4.84 (s, 1H), 3.96 (s, 6H), 3.41-3.30 (m, 5H), 2.90 (d, J = 3.0 Hz, 3H), 2.80 (d, J = 13.5 Hz, 2H), 2.32-2.15 (m, 2H), 2.03 (s, 3H), 1.79 (s, 2H).; 538.3[M + H]⁺ | 15 | 1.13 |

TABLE 1-continued

| Compound of Example | Structure | Compound Name | ¹H NMR, MS | Yield (%) | HPLC r.t. (min), Purity |
|---|---|---|---|---|---|
| 217 | 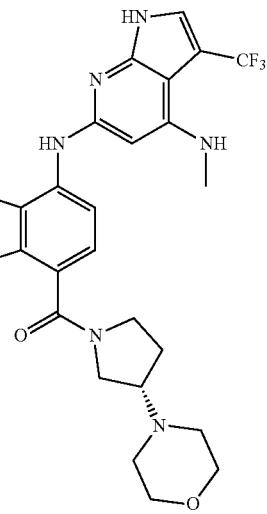 | (S)-(7-((4-(methylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | ¹H NMR (400 MHZ, Methanol-d4) δ 7.51 (s, 1H), 7.25 (d, J = 7.9 Hz, 1H), 7.08 (d, J = 8.1 Hz, 1H), 5.89 (s, 1H), 4.77-4.69 (m, 2H), 3.98 (q, J = 47.1, 40.8 Hz, 9H), 3.64 (d, J = 18.4 Hz, 2H), 3.54-3.39 (m, 3H), 3.08 (s, 3H), 2.54 (s, 1H), 2.30 (d, J = 10.7 Hz, 1H), 1.32 (s, 1H). 531.4[M + H]⁺ | 55 | 1.06 |
| 218 | 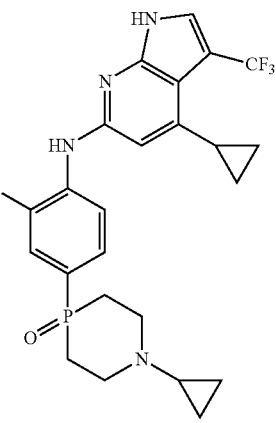 | 1-cyclopropyl-4-(4-((4-cyclopropyl-3-(trifluoromethyl)-1H-pyrrolo[2,3-b]pyridin-6-yl)amino)-3-methoxyphenyl)-1,4-azaphosphinane 4-oxide | 1H NMR (400 MHZ, DMSO) δ 12.09 (s, 1H), 8.75 (s, 1H), 8.37 (s, 1H), 7.73 (s, 1H), 7.28 (d, J = 11.5 Hz, 2H), 6.77 (s, 1H), 3.95 (s, 3H), 3.39 (s, 1H), 2.97 (d, J = 15.6 Hz, 4H), 2.19 (s, 3H), 1.84 (d, J = 12.2 Hz, 4H), 1.06 (s, 2H), 0.48 (s, 2H), 0.36 (s, 2H). 505.5[M + H]⁺ | 29.9 | 1.44 |
| 219 | 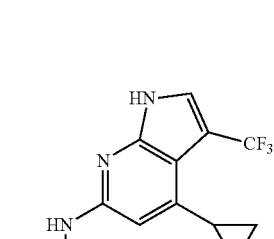 | (4-((4-cyclopropyl-3-(trifluoromethyl)-1H-pyrrolo[2,3-b]pyridin-6-yl)amino)-3-methoxyphenyl) dimethylphosphine oxide | 1H NMR (400 MHZ, DMSO-d₆) δ 12.08 (s, 1H), 8.78-8.70 (m, 1H), 8.33 (s, 1H), 7.73 (s, 1H), 7.29 (d, J = 11.8 Hz, 2H), 6.76 (s, 1H), 3.94 (s, 3H), 2.19 (s, 1H), 1.64 (d, J = 13.0 Hz, 6H), 1.10-1.01 (m, 2H), 0.85 (s, 2H). 424.2[M + H]⁺ | 33 | 1.60 |

TABLE 1-continued

| Compound of Example | Structure | Compound Name | ¹H NMR, MS | Yield (%) | HPLC r.t. (min), Purity |
|---|---|---|---|---|---|
| 220 | 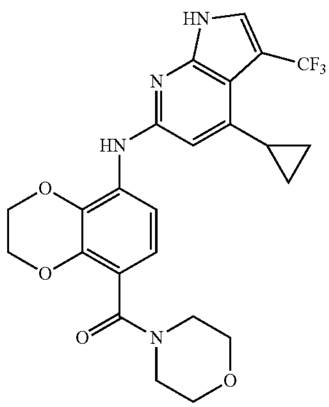 [SMILES: O=C(c1ccc(Nc2cc(C3CC3)c3c(C(F)(F)F)c[nH]c3n2)c2c1OCCO2)N1CCOCC1] | (8-((4-cyclopropyl-3-(trifluoromethyl)-1H-pyrrolo[2,3-b]pyridin-6-yl)amino)-2,3-dihydrobenzo[b][1,4]dioxin-5-yl)(morpholino)methanone | 1H NMR (400 MHZ, cd3od) δ 8.18 (d, J = 8.6 Hz, 1H), 7.49 (s, 1H), 6.77 (dd, J = 8.5, 2.5 Hz, 1H), 6.43 (s, 1H), 4.34 (dd, J = 17.1, 4.0 Hz, 4H), 3.72 (s, 4H), 3.62 (t, J = 8.8 Hz, 2H), 3.39 (d, J = 20.8 Hz, 2H), 2.33-2.25 (m, 1H), 1.07-1.02 (m, 2H), 0.84 (dd, J = 11.3, 4.9 Hz, 2H). 489.3[M + H]⁺ | 29 | 1.69 |
| 221 | 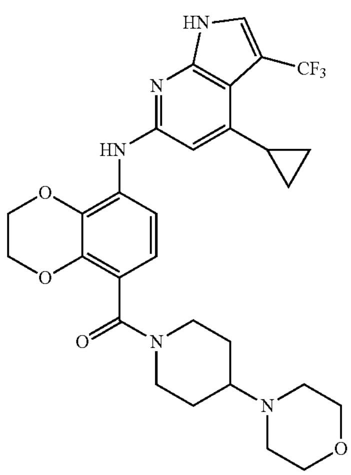 [SMILES: O=C(c1ccc(Nc2cc(C3CC3)c3c(C(F)(F)F)c[nH]c3n2)c2c1OCCO2)N1CCC(N2CCOCC2)CC1] | (8-((4-cyclopropyl-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone | 1H NMR (400 MHZ, DMSO-d₆) δ 12.00 (s, 1H), 8.16-8.07 (m, 2H), 7.68 (s, 1H), 6.70 (s, 2H), 4.32 (d, J = 23.0 Hz, 4H), 3.56 (s, 4H), 3.33 (s, 2H), 3.04-2.89 (m, 1H), 2.73 (t, J = 12.5 Hz, 1H), 2.45 (s, 4H), 2.22-2.13 (m, 1H), 1.84 (d, J = 12.5 Hz, 1H), 1.71 (d, J = 11.1 Hz, 1H), 1.27 (d, J = 19.1 Hz, 3H), 1.04 (d, J = 8.1 Hz, 2H), 0.82 (d, J = 5.7 Hz, 2H). 572.4[M + H]⁺ | 29 | 1.38 |
| 222 | 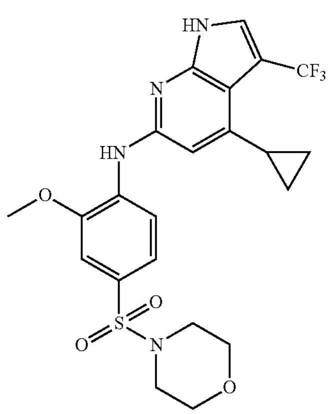 [SMILES: COc1cc(S(=O)(=O)N2CCOCC2)ccc1Nc1cc(C2CC2)c2c(C(F)(F)F)c[nH]c2n1] | 4-cyclopropyl-N-(2-methoxy-4-(morpholinosulfonyl)phenyl)-3-(trifluoromethyl)-1H-pyrrolo[2,3-b]pyridin-6-amine | 1H NMR (400 MHZ, DMSO-d₆) δ 12.11 (s, 1H), 8.90 (dd, J = 8.9, 2.2 Hz, 1H), 8.59 (s, 1H), 7.78 (s, 1H), 7.28 (d, J = 8.6 Hz, 1H), 7.18 (d, J = 2.4 Hz, 1H), 6.84 (s, 1H), 3.99 (s, 3H), 3.67-3.61 (m, 4H), 2.92-2.81 (m, 4H), 2.21 (t, J = 6.7 Hz, 1H), 1.08 (d, J = 7.6 Hz, 2H), 0.86 (s, 2H). 497.3[M + H]⁺ | 32 | 1.86 |

TABLE 1-continued

| Compound of Example | Structure | Compound Name | ¹H NMR, MS | Yield (%) | HPLC r.t. (min), Purity |
|---|---|---|---|---|---|
| 223 | 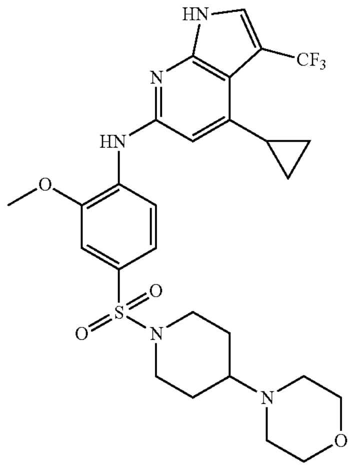 [SMILES: COc1cc(S(=O)(=O)N2CCC(N3CCOCC3)CC2)ccc1Nc1cc(C2CC2)c2c(C(F)(F)F)c[nH]c2n1] | 4-cyclopropyl-N-(2-methoxy-4-((4-morpholinopiperidin-1-yl)sulfonyl)phenyl)-3-(trifluoromethyl)-1H-pyrrolo[2,3-b]pyridin-6-amine | 1H NMR (400 MHZ, DMSO-$d_6$) δ 12.10 (s, 1H), 8.87 (d, J = 8.4 Hz, 1H), 8.55 (s, 1H), 7.77 (s, 1H), 7.27 (d, J = 8.7 Hz, 1H), 7.17 (s, 1H), 6.83 (s, 1H), 3.97 (s, 3H), 3.65 (d, J = 11.5 Hz, 2H), 3.51 (m, 4H), 2.38 (m, 4H), 2.25 (t, J = 11.7 Hz, 3H), 2.10 (d, J = 11.4 Hz, 1H), 1.80 (d, J = 12.5 Hz, 2H), 1.41 (q, J = 12.5, 12.0 Hz, 2H), 1.08 (d, J = 7.7 Hz, 2H), 0.85 (d, J = 5.1 Hz, 2H). 580.3[M + H]⁺ | 18 | 1.50 |
| 224 | 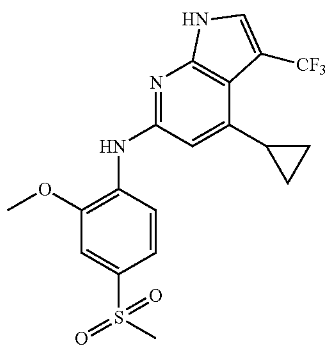 [SMILES: COc1cc(S(C)(=O)=O)ccc1Nc1cc(C2CC2)c2c(C(F)(F)F)c[nH]c2n1] | 4-cyclopropyl-N-(2-methoxy-4-(methylsulfonyl)phenyl)-3-(trifluoromethyl)-1H-pyrrolo[2,3-b]pyridin-6-amine | 1H NMR (400 MHZ, DMSO-$d_6$) δ 12.12 (s, 1H), 8.88 (d, J = 8.6 Hz, 1H), 8.56 (s, 1H), 7.78 (s, 1H), 7.47-7.40 (m, 2H), 6.83 (s, 1H), 3.99 (s, 3H), 3.18 (s, 3H), 2.21 (p, J = 7.6, 6.9 Hz, 1H), 1.11-1.03 (m, 2H), 0.88-0.82 (m, 2H). 426.3[M + H]⁺ | 11 | 1.81 |
| 225 | 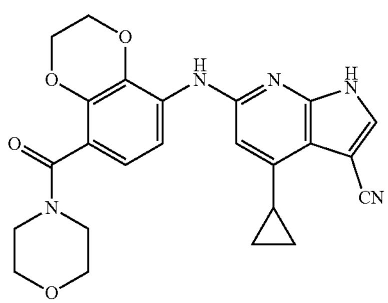 [SMILES: N#Cc1c[nH]c2nc(Nc3ccc(C(=O)N4CCOCC4)c4c3OCCO4)cc(C3CC3)c12] | 4-cyclopropyl-6-((8-(morpholine-4-carbonyl)-2,3-dihydrobenzo[b][1,4]dioxin-5-yl)amino)-1H-pyrrolo[2,3-b]pyridine-3-carbonitrile | 1H NMR (400 MHZ, DMSO-$d_6$) δ 12.29 (s, 1H), 8.20 (s, 1H), 8.12 (d, J = 8.4 Hz, 1H), 8.03 (s, 1H), 6.76-6.65 (m, 2H), 4.33 (d, J = 15.3 Hz, 4H), 3.60 (s, 4H), 3.53 (s, 2H), 3.25 (s, 2H), 2.43 (q, J = 7.1 Hz, 1H), 1.13 (d, J = 8.0 Hz, 2H), 0.85 (d, J = 5.3 Hz, 2H). 446.3[M + H]⁺ | 34 | 1.47 |
| 226 | 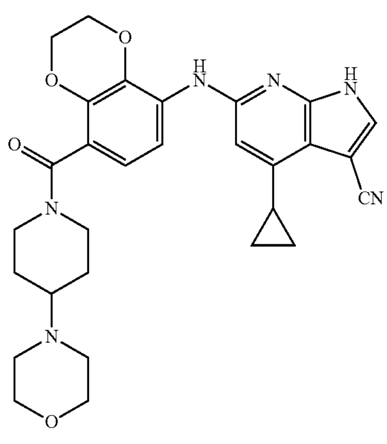 [SMILES: N#Cc1c[nH]c2nc(Nc3ccc(C(=O)N4CCC(N5CCOCC5)CC4)c4c3OCCO4)cc(C3CC3)c12] | 4-cyclopropyl-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile | 1H NMR (400 MHZ, DMSO-$d_6$) δ 12.30 (s, 1H), 8.21 (s, 1H), 8.11 (d, J = 8.5 Hz, 1H), 8.03 (s, 1H), 6.69 (s, 2H), 4.34 (d, J = 21.8 Hz, 4H), 4.02 (s, 2H), 3.76-3.39 (m, 6H), 3.17-2.91 (m, 2H), 2.78-2.64 (m, 1H), 2.46-2.37 (m, 2H), 2.20-1.96 (m, 2H), 1.63-1.35 (m, 2H), 1.24 (s, 1H), 1.13 (d, J = 7.9 Hz, 2H), 0.85 (d, J = 5.5 Hz, 2H). 529.4[M + H]⁺ | 52 | 1.22 |

TABLE 1-continued

| Compound of Example | Structure | Compound Name | ¹H NMR, MS | Yield (%) | HPLC r.t. (min), Purity |
|---|---|---|---|---|---|
| 227 | 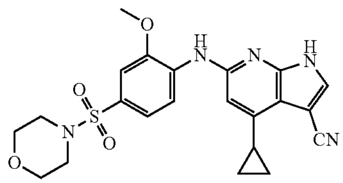 [SMILES: COc1cc(S(=O)(=O)N2CCOCC2)ccc1Nc1cc(C2CC2)c2c(C#N)c[nH]c2n1] | 4-cyclopropyl-6-((2-methoxy-4-(morpholinosulfonyl)phenyl)amino)-1H-pyrrolo[2,3-b]pyridine-3-carbonitrile | 1H NMR (400 MHZ, DMSO-d₆) δ 8.86 (s, 1H), 8.59 (s, 1H), 8.10 (s, 1H), 7.42 (s, 1H), 7.27 (s, 1H), 7.18 (s, 1H), 6.81 (s, 1H), 3.98 (s, 3H), 3.64 (m, 4H), 2.88 (m, 4H), 1.63 (m, 1H), 1.16 (m, 2H), 0.89 (m, 2H). 454.3[M + H]⁺ | 10 | 1.63 |
| 228 | 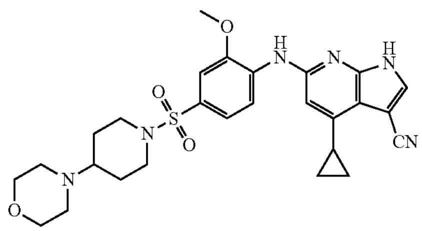 [SMILES: COc1cc(S(=O)(=O)N2CCC(N3CCOCC3)CC2)ccc1Nc1cc(C2CC2)c2c(C#N)c[nH]c2n1] | 4-cyclopropyl-6-((2-methoxy-4-((4-morpholinopiperidin-1-yl)sulfonyl)phenyl)amino)-1H-pyrrolo[2,3-b]pyridine-3-carbonitrile | 1H NMR (400 MHZ, DMSO-d₆) δ 9.91 (s, 1H), 8.86 (d, J = 8.6 Hz, 1H), 8.61 (s, 1H), 8.13 (d, J = 3.0 Hz, 1H), 7.30 (dd, J = 8.6, 2.0 Hz, 1H), 7.21 (d, J = 2.0 Hz, 1H), 6.83 (s, 1H), 3.98 (s, 5H), 3.80 (d, J = 11.3 Hz, 2H), 3.68-3.59 (m, 3H), 3.53-3.49 (m, 2H), 3.38 (d, J = 12.1 Hz, 3H), 2.23 (t, J = 11.7 Hz, 2H), 2.11 (d, J = 11.7 Hz, 2H), 1.73-1.60 (m, 2H), 1.20-1.13 (m, 2H), 0.90-0.84 (m, 2H). 537.3[M + H]⁺ | 79 | 1.26 |
| 229 | 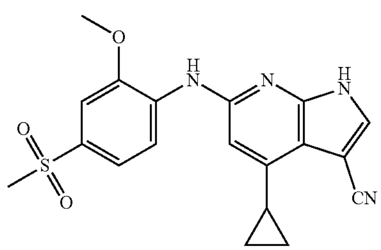 [SMILES: COc1cc(S(C)(=O)=O)ccc1Nc1cc(C2CC2)c2c(C#N)c[nH]c2n1] | 4-cyclopropyl-6-((2-methoxy-4-(methylsulfonyl)phenyl)amino)-1H-pyrrolo[2,3-b]pyridine-3-carbonitrile | 1H NMR (400 MHZ, DMSO-d₆) δ 12.40 (s, 1H), 8.83 (d, J = 6.3 Hz, 1H), 8.57 (s, 1H), 8.10 (t, J = 3.1 Hz, 1H), 7.43 (d, J = 12.3 Hz, 2H), 6.80 (s, 1H), 3.99 (s, 3H), 3.18 (s, 3H), 2.50 (m, 1H), 1.15 (m, 2H), 0.88 (m, 2H). 383.2[M + H]⁺ 383.2[M + H]⁺ | 13 | 1.54 |
| 230 | 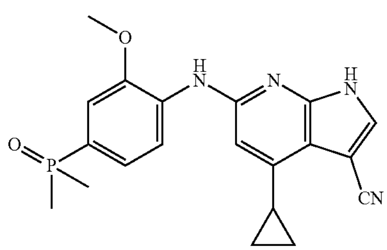 [SMILES: COc1cc(P(C)(C)=O)ccc1Nc1cc(C2CC2)c2c(C#N)c[nH]c2n1] | 4-cyclopropyl-6-((4-(dimethylphosphoryl)-2-methoxyphenyl)amino)-1H-pyrrolo[2,3-b]pyridine-3-carbonitrile | 1H NMR (400 MHZ, DMSO) δ 12.42 (s, 1H), 8.69 (d, J = 3.2 Hz, 1H), 8.36 (s, 1H), 8.07 (s, 1H), 7.30 (d, J = 12.4 Hz, 2H), 6.74 (s, 1H), 3.94 (s, 3H), 2.46 (s, 1H), 1.64 (d, J = 13.1 Hz, 6H), 1.14 (s, 2H), 0.88 (s, 2H). 381.3[M + H]⁺ | 52 | 1.36 |
| 231 | 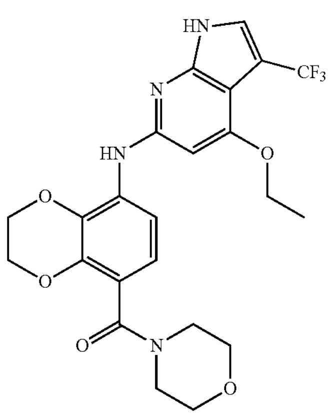 [SMILES: CCOc1cc(Nc2ccc(C(=O)N3CCOCC3)c3c2OCCO3)nc2[nH]cc(C(F)(F)F)c12] | (8-((4-ethoxy-3-(trifluoromethyl)-1H-pyrrolo[2,3-b]pyridin-6-yl)amino)-2,3-dihydrobenzo[b][1,4]dioxin-5-yl)(morpholino)methanone | 493.3[M + H]⁺ | 40 | 1.60 |

TABLE 1-continued

| Compound of Example | Structure | Compound Name | $^1$H NMR, MS | Yield (%) | HPLC r.t. (min), Purity |
|---|---|---|---|---|---|
| 232 | 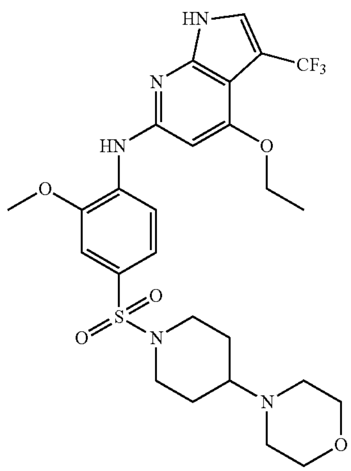 [SMILES: CCOc1cc(Nc2ccc(S(=O)(=O)N3CCC(N4CCOCC4)CC3)cc2OC)nc2[nH]cc(C(F)(F)F)c12] | 4-ethoxy-N-(2-methoxy-4-((4-morpholinopiperidin-1-yl)sulfonyl)phenyl)-3-(trifluoromethyl)-1H-pyrrolo[2,3-b]pyridin-6-amine | $^1$H NMR (400 MHZ, DMSO) δ 11.99 (d, J = 2.6 Hz, 1H), 10.41 (s, 1H), 8.93 (d, J = 8.6 Hz, 1H), 8.59 (s, 1H), 7.60 (d, J = 1.2 Hz, 1H), 7.30 (dd, J = 8.6, 1.9 Hz, 1H), 7.21 (d, J = 1.9 Hz, 1H), 6.84 (s, 1H), 5.74 (s, 1H), 4.19 (q, J = 7.0 Hz, 2H), 4.00 (s, 3H), 3.82-3.61 (m, 18H), 3.37 (s, 9H), 2.12 (d, J = 11.1 Hz, 5H), 1.99 (s, 1H), 1.77-1.53 (m, 4H), 1.41 (t, J = 7.4 Hz, 4H), 1.24 (d, J = 1.4 Hz, 1H), 1.18 (t, J = 7.1 Hz, 1H).; 584.3[M + H]$^+$ | 68 | 1.49 |
| 233 | 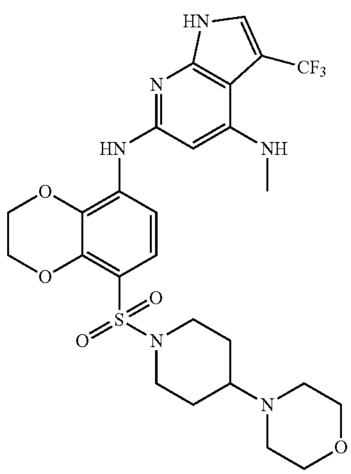 [SMILES: CNc1cc(Nc2ccc(S(=O)(=O)N3CCC(N4CCOCC4)CC3)c3c2OCCO3)nc2[nH]cc(C(F)(F)F)c12] | $N^4$-methyl-$N^6$-(8-((4-morpholinopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine | 597.3[M + H]$^+$ | 21 | 1.21 |
| 234 | 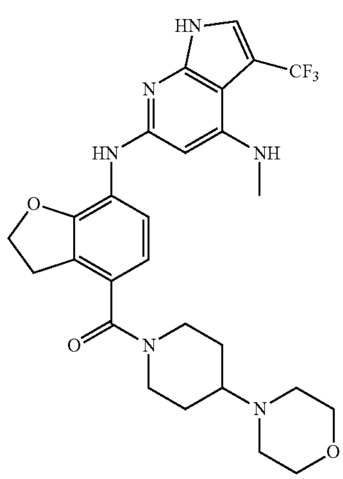 [SMILES: CNc1cc(Nc2ccc(C(=O)N3CCC(N4CCOCC4)CC3)c3c2OCC3)nc2[nH]cc(C(F)(F)F)c12] | (7-((4-(methylamino)-3-(trifluoromethyl)-1H-pyrrolo[2,3-b]pyridin-6-yl)amino)-2,3-dihydrobenzofuran-4-yl)(4-morpholinopiperidin-1-yl)methanone | $^1$H NMR (400 MHZ, MeOD) δ 8.21 (d, J = 8.3 Hz, 1H), 7.40 (d, J = 1.1 Hz, 1H), 6.87 (d, J = 8.3 Hz, 1H), 6.04 (s, 1H), 4.74 (t, J = 8.7 Hz, 2H), 3.90 (s, 5H), 3.39 (dt, J = 3.2, 1.6 Hz, 3H), 3.33 (t, J = 8.7 Hz, 2H), 3.04 (s, 3H), 2.17 (s, 2H), 1.62 (dd, J = 7.1, 4.0 Hz, 2H), 1.36 (s, 1H), 1.31 (t, J = 7.1 Hz, 1H), 0.98 (t, J = 6.8 Hz, 2H).; 545.4[M+H] | 12 | 1.04 |

TABLE 1-continued

| Compound of Example | Structure | Compound Name | ¹H NMR, MS | Yield (%) | HPLC r.t. (min), Purity |
|---|---|---|---|---|---|
| 235 | 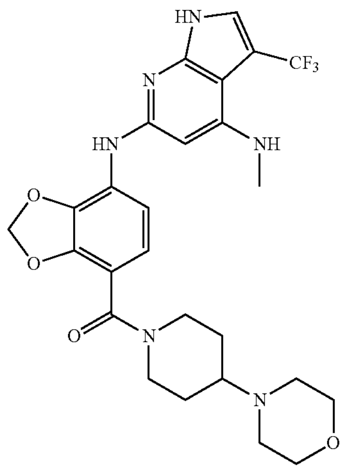 [SMILES: CNc1cc(Nc2ccc(C(=O)N3CCC(N4CCOCC4)CC3)c3c2OCO3)nc2[nH]cc(C(F)(F)F)c12] | (7-((4-(methylamino)-3-(trifluoromethyl)-1H-pyrrolo[2,3-b]pyridin-6-yl)amino)benzo[d][1,3]dioxol-4-yl)(4-morpholinopiperidin-1-yl)methanone | 547.3[M + H]⁺ | 13 | 1.00 |
| 236 | 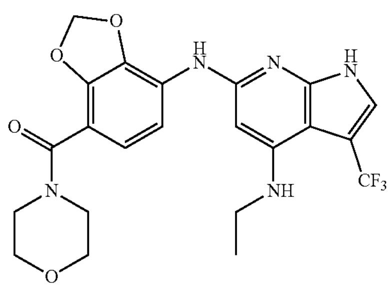 [SMILES: CCNc1cc(Nc2ccc(C(=O)N3CCOCC3)c3c2OCO3)nc2[nH]cc(C(F)(F)F)c12] | (7-((4-(ethylamino)-3-(trifluoromethyl)-1H-pyrrolo[2,3-b]pyridin-6-yl)amino)benzo[d][1,3]dioxol-4-yl)(morpholino)methanone | 478.3[M + H]⁺ | 25 | 1.26 |
| 237 | 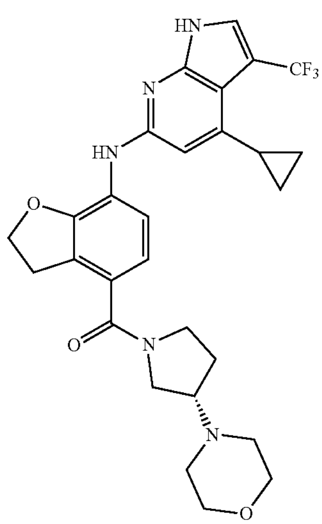 [SMILES: O=C(c1ccc(Nc2cc(C3CC3)c3c(C(F)(F)F)c[nH]c3n2)c2c1CCO2)N1CC[C@H](N2CCOCC2)C1] | (S)-(7-((4-cyclopropyl-3-(trifluoromethyl)-1H-pyrrolo[2,3-b]pyridin-6-yl)amino)-2,3-dihydrobenzofuran-4-yl)(3-morpholinopyrrolidin-1-yl)methanone | ¹H NMR (400 MHZ, Chloroform-d) δ 11.60 (s, 1H), 9.51 (s, 1H), 7.34 (s, 1H), 6.76 (s, 2H), 6.43 (s, 1H), 4.68 (q, J = 9.9 Hz, 2H), 4.32 (m, 2H), 4.14-3.89 (m, 5H), 3.72 (m, J = 10.7 Hz, 2H), 3.51 (m, 2H), 3.42-3.35 (m, 1H), 3.18 (dt, J = 12.6, 8.6 Hz, 1H), 2.95-2.92 (m, 3H), 2.48-2.36 (m, 2H), 1.30 (s, 2H), 1.04 (m, 2H). 542.4 [M + H]⁺ | 62 | 1.53 |

TABLE 1-continued

| Compound of Example | Structure | Compound Name | ¹H NMR, MS | Yield (%) | HPLC r.t. (min), Purity |
|---|---|---|---|---|---|
| 238 | 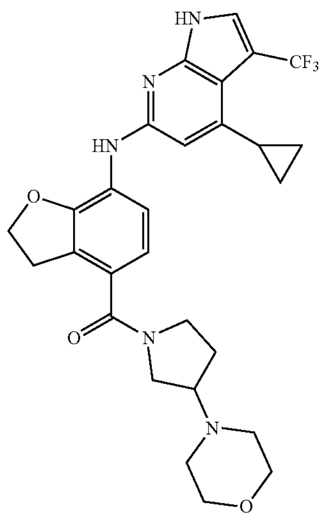 [SMILES: O=C(c1ccc(Nc2cc(C3CC3)c3c(C(F)(F)F)c[nH]c3n2)c2c1CCO2)N1CCC(N2CCOCC2)C1] | (R)-(7-((4-cyclopropyl-3-(trifluoromethyl)-1H-pyrrolo[2,3-b]pyridin-6-yl)amino)-2,3-dihydrobenzofuran-4-yl)(3-morpholinopyrrolidin-1-yl)methanone | ¹H NMR (400 MHZ, Chloroform-d) δ 11.69 (s, 1H), 9.32 (s, 1H), 7.35 (s, 1H), 6.77 (d, J = 5.1 Hz, 2H), 6.41 (s, 1H), 4.74-4.62 (m, 2H), 4.31 (m, 2H), 4.10 (ddd, J = 29.8, 20.8, 11.2 Hz, 3H), 3.98 (m, 2H), 3.74 (m, 2H), 3.49 (m, 2H), 3.44-3.35 (m, 1H), 3.19 (m, 1H), 3.01-2.89 (m, 3H), 2.48-2.38 (m, 2H), 1.30 (m, 2H), 1.04 (m, 2H). 542.4 [M + H]⁺ | 42 | 1.56 |
| 239 | 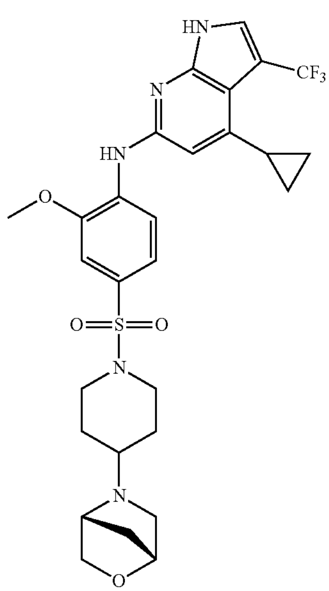 [SMILES: COc1cc(S(=O)(=O)N2CCC(N3C[C@H]4C[C@@H]3CO4)CC2)ccc1Nc1cc(C2CC2)c2c(C(F)(F)F)c[nH]c2n1] | N-(4-((4-((1R,4R)-2-oxa-5-azabicyclo[2.2.1]heptan-5-yl)piperidin-1-yl)sulfonyl)-2-methoxyphenyl)-4-cyclopropyl-3-(trifluoromethyl)-1H-pyrrolo[2,3-b]pyridin-6-amine | ¹H NMR (400 MHZ, Chloroform-d) δ 8.72 (d, J = 8.6 Hz, 1H), 8.61 (s, 1H), 7.48 (s, 1H), 7.40 (dd, J= 8.6, 2.0 Hz, 1H), 7.32 (s, 1H), 7.22 (d, J = 2.0 Hz, 1H), 6.27 (s, 1H), 4.35 (s, 1H), 4.00 (s, 3H), 3.63 (m, 3H), 3.59-3.54 (m, 1H), 3.01 (d, J = 9.7 Hz, 1H), 2.57-2.47 (m, 2H), 2.35 (m, 3H), 1.91-1.76 (m, 4H), 1.73 (d, J = 9.6 Hz, 1H), 1.51 (m, 2H), 1.14-1.11 (m, 2H), 0.88-0.85 (m, 2H). 592.4 [M + H]⁺ | 30 | 1.76 |

TABLE 1-continued

| Compound of Example | Structure | Compound Name | ¹H NMR, MS | Yield (%) | HPLC r.t. (min), Purity |
|---|---|---|---|---|---|
| 240 | 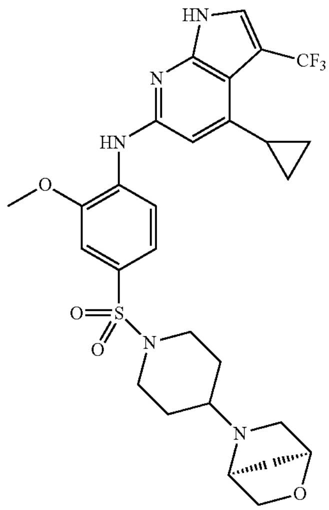 [SMILES: COc1cc(S(=O)(=O)N2CCC(N3C[C@@H]4C[C@H]3CO4)CC2)ccc1Nc1cc(C2CC2)c2c(C(F)(F)F)c[nH]c2n1] | N-(4-((4-((1S,4S)-2-oxa-5-azabicyclo[2.2.1]heptan-5-yl)piperidin-1-yl)sulfonyl)-2-methoxyphenyl)-4-cyclopropyl-3-(trifluoromethyl)-1H-pyrrolo[2,3-b]pyridin-6-amine | ¹H NMR (400 MHZ, Chloroform-d) δ 8.72 (d, J = 8.6 Hz, 1H), 8.67 (s, 1H), 7.48 (s, 1H), 7.40 (dd, J = 8.6, 2.0 Hz, 1H), 7.32 (s, 1H), 7.22 (d, J = 2.0 Hz, 1H), 6.27 (s, 1H), 4.35 (s, 1H), 4.00 (s, 3H), 3.92 (d, J = 7.9 Hz, 1H), 3.66-3.59 (m, 3H), 3.57 (dd, J = 7.9, 1.6 Hz, 1H), 3.01 (dd, J = 10.0, 1.8 Hz, 1H), 2.52 (dd, J = 14.1, 11.4 Hz, 2H), 2.41-2.29 (m, 3H), 1.84 (m, 3H), 1.73 (d, J = 9.6 Hz, 1H), 1.59 (m, 2H), 1.13 (m, 2H), 0.87 (m, 2H). 592.4 [M + H]⁺ | 81 | 1.74 |
| 241 | 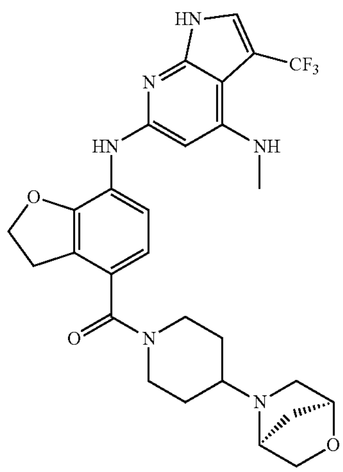 [SMILES: CNc1cc(Nc2ccc(C(=O)N3CCC(N4C[C@@H]5C[C@H]4CO5)CC3)c3c2OCC3)nc2[nH]cc(C(F)(F)F)c12] | (4-((1S,4S)-2-oxa-5-azabicyclo[2.2.1]heptan-5-yl)piperidin-1-yl)(7-((4-(methylamino)-3-(trifluoromethyl)-1H-pyrrolo[2,3-b]pyridin-6-yl)amino)-2,3-dihydrobenzofuran-4-yl)methanone | ¹H NMR (400 MHZ, Chloroform-d) δ 8.91 (s, 1H), 8.09 (d, J = 8.3 Hz, 1H), 7.17 (s, 1H), 6.79 (d, J = 8.3 Hz, 1H), 6.48 (s, 1H), 5.77 (s, 1H), 4.87 (s, 1H), 4.67 (t, J = 8.7 Hz, 2H), 4.41 (s, 1H), 4.05 (d, J = 7.8Hz, 1H), 3.69 (s, 1H), 3.64 (d, J = 7.8 Hz, 1H), 3.32 (t, J = 8.7 Hz, 2H), 3.08 (m, 2H), 2.99 (m, 1H), 2.96 (d, J = 4.9 Hz, 3H), 2.66 (m, 1H), 2.45 (d, J = 9.9 Hz, 1H), 1.90-1.76 (m, 4H), 1.60 (s, 4H). 557.5 [M + H]⁺ | 49 | 1.20 |
| 242 | 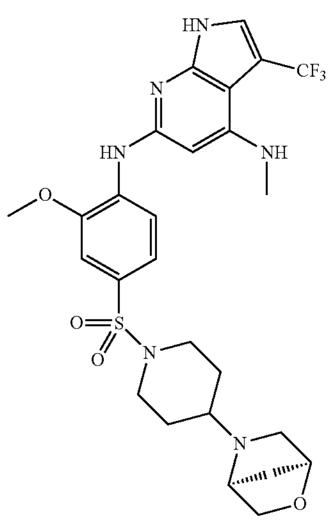 [SMILES: CNc1cc(Nc2ccc(S(=O)(=O)N3CCC(N4C[C@@H]5C[C@H]4CO5)CC3)cc2OC)nc2[nH]cc(C(F)(F)F)c12] | N⁶-(4-((4-((1S,4S)-2-oxa-5-azabicyclo[2.2.1]heptan-5-yl)piperidin-1-yl)sulfonyl)-2-methoxyphenyl)-N⁴-methyl-3-(trifluoromethyl)-1H-pyrrolo[2,3-b]pyridine-4,6-diamine | ¹H NMR (400 MHz, Chloroform-d) δ 11.64 (s, 1H), 8.69 (s, 1H), 7.52 (m, 1H), 7.39 (d, J = 8.0 Hz, 1H), 7.28 (s, 1H), 6.12 (s, 1H), 5.65 (s, 1H), 4.59 (s, 1H), 4.42 (s, 1H), 4.28 (d, J = 10.3 Hz, 1H), 3.92 (s, 3H), 3.81 (dt, J = 21.3, 11.7 Hz, 3H), 3.71 (s, 2H), 3.56 (s, 1H), 3.12 (d, J = 4.9 Hz, 3H), 2.94 (m, 2H), 2.84-2.65 (m, 2H), 2.18 (s, 3H), 1.94 (s, 2H). 581.4 [M + H]⁺ | 66 | 1.43 |

TABLE 1-continued

| Compound of Example | Structure | Compound Name | ¹H NMR, MS | Yield (%) | HPLC r.t. (min), Purity |
|---|---|---|---|---|---|
| 243 | 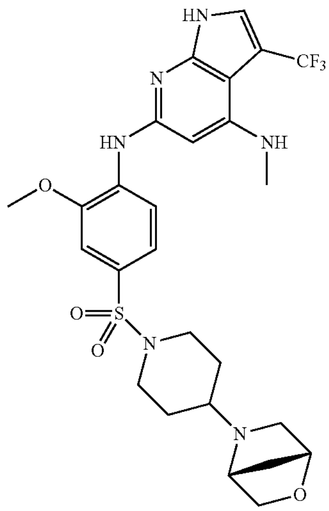 [SMILES: CNc1cc(Nc2ccc(S(=O)(=O)N3CCC(N4C[C@H]5C[C@@H]4CO5)CC3)cc2OC)nc2[nH]cc(C(F)(F)F)c12] | N⁶-(4-((4-((1R,4R)-2-oxa-5-azabicyclo[2.2.1]heptan-5-yl)piperidin-1-yl)sulfonyl)-2-methoxyphenyl)-N⁴-methyl-3-(trifluoromethyl)-1H-pyrrolo[2,3-b]pyridine-4,6-diamine | ¹H NMR (400 MHZ, Chloroform-d) δ 8.78 (s, 1H), 8.65 (d, J = 8.5 Hz, 1H), 7.38 (dd, J = 8.5, 2.0 Hz, 1H), 7.25-7.15 (m, 3H), 5.83 (s, 1H), 4.94 (s, 1H), 4.36 (s, 1H), 4.00 (s, 3H), 3.92 (d, J = 7.9 Hz, 1H), 3.68-3.60 (m, 3H), 3.57 (d, J = 7.8 Hz, 1H), 3.05-2.97 (m, 4H), 2.51 (t, J = 15.0 Hz, 2H), 2.35 (d, J = 9.8 Hz, 2H), 1.87-1.77 (m, 4H), 1.73 (d, J = 9.6 Hz, 2H). 581.4 [M + H]⁺ | 46 | 1.50 |
| 244 | 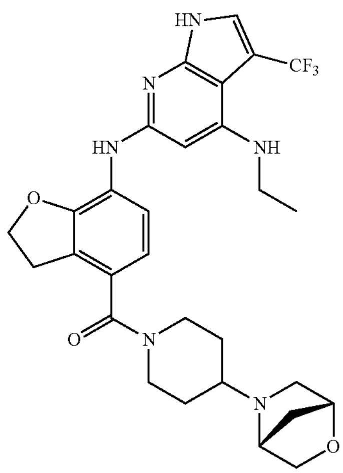 [SMILES: CCNc1cc(Nc2ccc(C(=O)N3CCC(N4C[C@H]5C[C@@H]4CO5)CC3)c3c2OCC3)nc2[nH]cc(C(F)(F)F)c12] | (4-((1R,4R)-2-oxa-5-azabicyclo[2.2.1]heptan-5-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone | 571.5 [M + H]⁺ | 43 | 1.17 |
| 245 | 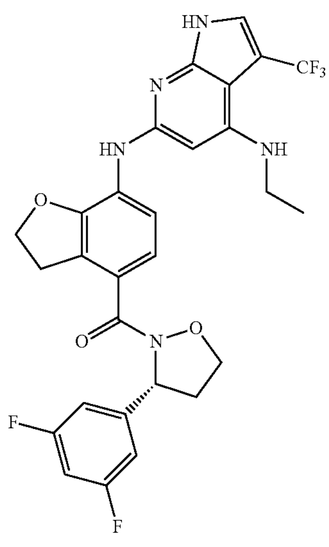 [SMILES: CCNc1cc(Nc2ccc(C(=O)N3OCC[C@@H]3c3cc(F)cc(F)c3)c3c2OCC3)nc2[nH]cc(C(F)(F)F)c12] | (R)-(3-(3,5-difluorophenyl)isoxazolidin-2-yl)(7-((4-(ethylamino)-3-(trifluoromethyl)-1H-pyrrolo[2,3-b]pyridin-6-yl)amino)-2,3-dihydrobenzofuran-4-yl)methanone | ¹H NMR (400 MHZ, DMSO-d6) δ 11.75 (d, J = 2.9 Hz, 1H), 8.39 (d, J = 8.6 Hz, 1H), 8.24 (s, 1H), 7.51 (dd, J = 3.0, 1.6 Hz, 1H), 7.21-7.08 (m, 4H), 6.31 (s, 1H), 5.57 (dd, J = 8.8, 5.8 Hz, 1H), 4.73 (t, J = 4.4 Hz, 1H), 4.69-4.54 (m, 2H), 4.19 (td, J = 7.8, 3.2 Hz, 1H), 3.81-3.73 (m, 1H), 3.50 (dt, J = 16.0, 9.2 Hz, 1H), 3.31-3.18 (m, 3H), 2.88 (dddd, J = 12.1, 9.6, 6.8, 3.1 Hz, 1H), 2.28-2.16 (m, 1H), 1.24 (t, J = 7.1 Hz, 3H). 574.4 [M + H]⁺ | 51 | 1.69 |

TABLE 1-continued

| Compound of Example | Structure | Compound Name | $^1$H NMR, MS | Yield (%) | HPLC r.t. (min), Purity |
|---|---|---|---|---|---|
| 246 | 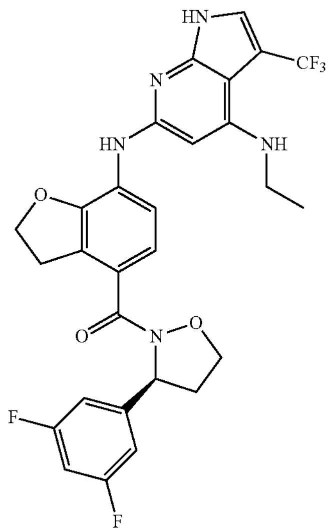 [SMILES: CCNc1cc(Nc2ccc(C(=O)N3OCC[C@H]3c3cc(F)cc(F)c3)c3c2OCC3)nc2[nH]cc(C(F)(F)F)c12] | (S)-(3-(3,5-difluorophenyl)isoxazolidin-2-yl)(7-((4-(ethylamino)-3-(trifluoromethyl)-1H-pyrrolo[2,3-b]pyridin-6-yl)amino)-2,3-dihydrobenzofuran-4-yl)methanone | $^1$H NMR (400 MHZ, DMSO-d6) δ 11.75 (s, 1H), 8.39 (d, J = 8.6 Hz, 1H), 8.23 (s, 1H), 7.51 (d, J = 2.6 Hz, 1H), 7.21-7.08 (m, 4H), 6.31 (s, 1H), 5.57 (dd, J = 8.8, 5.8 Hz, 1H), 4.71 (d, J = 10.4 Hz, 1H), 4.69-4.54 (m, 2H), 4.19 (q, J = 4.9 Hz, 1H), 3.77 (q, J = 8.0 Hz, 1H), 3.50 (dt, J = 17.3, 9.1 Hz, 1H), 3.29-3.20 (m, 3H), 2.93-2.82 (m, 1H), 2.28-2.17 (m, 1H), 1.24 (d, J = 2.6 Hz, 3H). 574.4 [M + H]$^+$ | 9 | 1.69 |
| 247 | 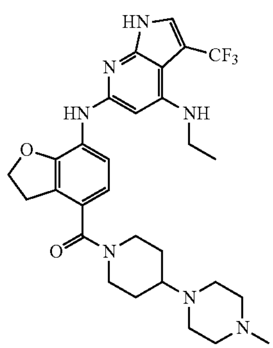 [SMILES: CCNc1cc(Nc2ccc(C(=O)N3CCC(N4CCN(C)CC4)CC3)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(4-(4-methylpiperazin-1-yl)piperidin-1-yl)methanone | $^1$H NMR (400 MHZ, DMSO-d6) δ 12.56-11.61 (m, 3H), 7.60 (s, 1H), 6.85 (d, J = 8.3 Hz, 1H), 6.00 (s, 1H), 4.64 (t, J = 8.7 Hz, 2H), 3.70 (brs, 10H), 3.49 (s, 3H), 3.34 (s, 2H), 3.22 (t, J = 8.9 Hz, 2H), 2.83 (s, 3H), 2.15 (s, 2H), 1.69 (d, J = 13.2 Hz, 2H), 1.27-1.19 (m, 3H), 0.88 (td, J = 29.3, 27.2, 13.8 Hz, 1H). 572.5 [M + H]$^+$ | 75 | 1.09 |
| 248 | 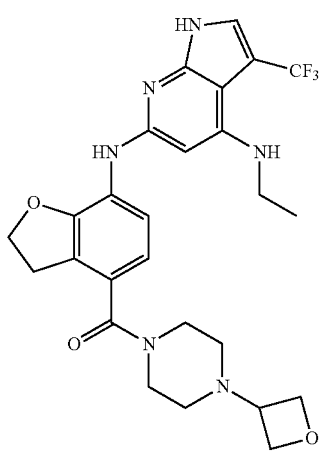 [SMILES: CCNc1cc(Nc2ccc(C(=O)N3CCN(C4COC4)CC3)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(4-(oxetan-3-yl)piperazin-1-yl)methanone | $^1$H NMR (400 MHZ, Chloroform-d) δ 8.01 (q, J = 8.6 Hz, 1H), 7.06 (d, J = 27.5 Hz, 1H), 6.77 (dd, J = 8.2, 6.1 Hz, 1H), 6.45 (s, 1H), 5.78 (s, 1H), 4.74 (s, 1H), 4.72-4.64 (m, 4H), 4.61 (td, J = 6.2, 1.7 Hz, 2H), 3.67 (d, J = 25.0 Hz, 3H), 3.49 (td, J = 6.5, 2.4 Hz, 1H), 3.34 (t, J = 8.7 Hz, 2H), 3.27 (qd, J = 7.2, 4.8 Hz, 2H), 2.29 (s, 3H), 1.61 (s, 3H), 1.34 (t, J = 7.2 Hz, 3H). 531.4 [M + H]$^+$ | 77 | 1.16 |

TABLE 1-continued

| Compound of Example | Structure | Compound Name | $^1$H NMR, MS | Yield (%) | HPLC r.t. (min), Purity |
|---|---|---|---|---|---|
| 249 | 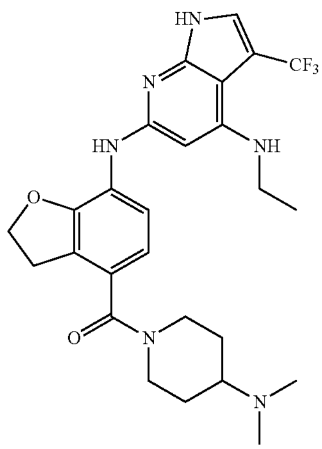 [SMILES: CCNc1cc(Nc2ccc(C(=O)N3CCC(N(C)C)CC3)c3c2OCC3)nc2[nH]cc(C(F)(F)F)c12] | (4-(dimethylamino)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone | $^1$H NMR (400 MHZ, Chloroform-d) δ 9.37 (s, 1H), 8.02 (d, J = 8.3 Hz, 1H), 7.12 (s, 1H), 6.78 (d, J = 8.3 Hz, IH), 6.44 (s, 1H), 5.78 (s, 1H), 4.74 (s, 1H), 4.67 (t, J = 8.7 Hz, 2H), 3.32 (t, J = 8.7 Hz, 2H), 3.29-3.23 (m, 2H), 2.89 (s, 1H), 2.30 (s, 6H), 1.87 (s, 2H), 1.68 (s, 4H), 1.43 (s, 2H), 1.35 (d, J = 7.2 Hz, 3H). 517.4 [M + H]$^+$ | 30 | 1.11 |
| 250 | 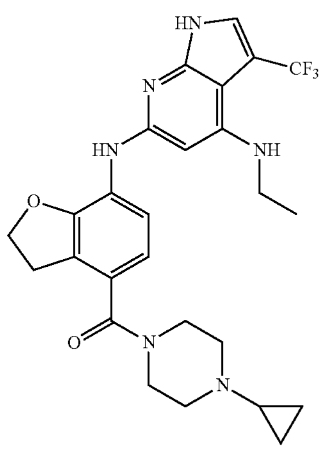 [SMILES: CCNc1cc(Nc2ccc(C(=O)N3CCN(C4CC4)CC3)c3c2OCC3)nc2[nH]cc(C(F)(F)F)c12] | (4-cyclopropylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone | 1H NMR (400 MHZ, DMSO-d6) δ 11.74 (d, J = 2.9 Hz, 1H), 8.32 (d, J = 8.3 Hz, IH), 8.09 (s, 1H), 7.51-7.45 (m, 1H), 6.72 (d, J = 8.3 Hz, 1H), 6.24 (s, 1H), 4.70 (dt, J = 7.2, 3.6 Hz, 1H), 4.62 (t, J= 8.7 Hz, 2H), 3.44 (s, 3H), 3.27-3.17 (m, 4H), 2.50 (t, J = 1.9 Hz, 4H), 1.66 (tt, J = 6.8, 3.6 Hz, 1H), 1.24 (t, J = 7.1 Hz, 3H), 0.43 (dt, J = 6.2, 3.0 Hz, 2H), 0.33 (q, J = 3.4, 3.0 Hz, 2H). 515.4 [M + H]$^+$ | 71 | 1.17 |
| 251 | 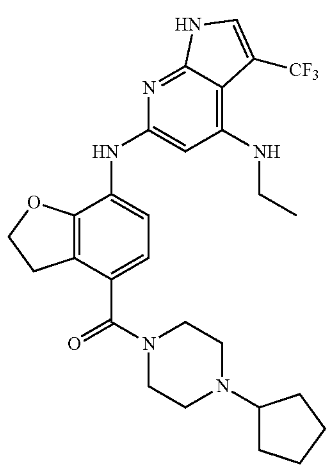 [SMILES: CCNc1cc(Nc2ccc(C(=O)N3CCN(C4CCCC4)CC3)c3c2OCC3)nc2[nH]cc(C(F)(F)F)c12] | (4-cyclopentylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone | $^1$H NMR (400 MHZ, DMSO-d$_6$) δ 11.74 (d, J = 2.9 Hz, 1H), 8.32 (d, J = 8.3 Hz, 1H), 8.09 (s, 1H), 7.50-7.46 (m, 1H), 6.71 (d, J = 8.3 Hz, 1H), 6.24 (s, 1H), 4.69 (q, J = 4.6 Hz, 1H), 4.62 (t, J = 8.7 Hz, 2H), 3.47 (s, 4H), 3.28-3.15 (m, 5H), 2.40 (s, 4H), 1.77 (q, J = 5.1 Hz, 2H), 1.60 (q, J = 7.3, 6.0 Hz, 2H), 1.49 (qd, J = 7.5, 3.6 Hz, 2H), 1.37-1.30 (m, 2H), 1.24 (t, J = 7.1 Hz, 3H). 543.5 [M + H]$^+$ | 64 | 1.21 |

TABLE 1-continued

| Compound of Example | Structure | Compound Name | ¹H NMR, MS | Yield (%) | HPLC r.t. (min), Purity |
|---|---|---|---|---|---|
| 252 | 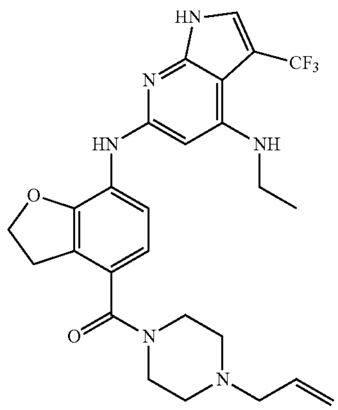 | (4-allylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone | ¹H NMR (400 MHZ, DMSO-$d_6$) δ 11.75 (d, J = 2.8 Hz, 1H), 8.33 (d, J = 8.4 Hz, 1H), 8.12 (s, 1H), 7.48 (dd, J = 2.9, 1.5 Hz, 1H), 6.71 (d, J = 8.3 Hz, 1H), 6.25 (s, 1H), 5.87-5.76 (m, 1H), 5.25-5.09 (m, 2H), 4.70 (s, 1H), 4.62 (t, J = 8.7 Hz, 2H), 3.53 (d, J = 33.7 Hz, 4H), 3.27-3.16 (m, 4H), 3.00-2.94 (m, 2H), 2.36 (s, 3H), 1.24 (t, J = 7.1 Hz, 3H). 519.4 [M + H]⁺ | 69 | 1.13 |
| 253 | 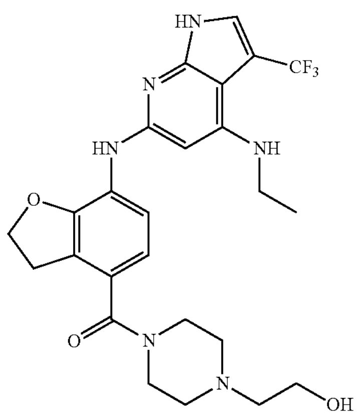 [SMILES: CCNc1cc(Nc2ccc(C(=O)N3CCN(CCO)CC3)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(4-(2-hydroxyethyl)piperazin-1-yl)methanone | ¹H NMR (400 MHZ, DMSO-$d_6$) δ 11.75 (d, J = 2.9 Hz, 1H), 8.33 (d, J = 8.3 Hz, 1H), 8.12 (s, 1H), 7.49 (dt, J = 3.1, 1.5 Hz, 1H), 6.71 (d, J = 8.3 Hz, 1H), 6.25 (s, 1H), 4.70 (s, 1H), 4.62 (t, J = 8.7 Hz, 2H), 4.46 (t, J = 5.3 Hz, 1H), 3.51 (q, J = 6.0 Hz, 4H), 3.29-3.14 (m, 5H), 2.41 (t, J = 5.9 Hz, 6H), 1.24 (t, J = 7.1 Hz, 4H). 519.3 [M + H]⁺ | 66 | 1.10 |
| 254 | 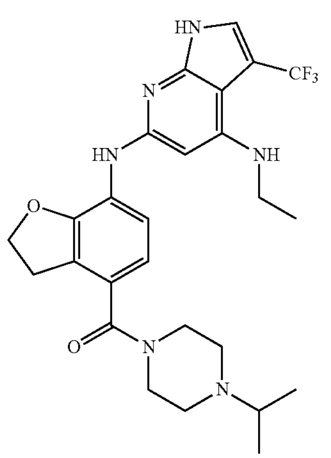 [SMILES: CCNc1cc(Nc2ccc(C(=O)N3CCN(C(C)C)CC3)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(4-isopropylpiperazin-1-yl)methanone | ¹H NMR (400 MHZ, DMSO-$d_6$) δ 11.75 (d, J = 2.9 Hz, 1H), 8.32 (d, J = 8.3 Hz, 1H), 8.11 (s, 1H), 7.54-7.43 (m, 1H), 6.71 (d, J = 8.3 Hz, 1H), 6.24 (s, 1H), 4.70 (s, 1H), 4.62 (t, J = 8.7 Hz, 2H), 3.51 (s, 4H), 3.27-3.15 (m, 4H), 2.68 (p, J = 6.5 Hz, 1H), 2.43 (s, 4H), 1.25 (d, J = 7.1 Hz, 3H), 0.97 (d, J = 6.5 Hz, 6H). 517.4 [M + H]⁺ | 60 | 1.14 |

TABLE 1-continued

| Compound of Example | Structure | Compound Name | ¹H NMR, MS | Yield (%) | HPLC r.t. (min), Purity |
|---|---|---|---|---|---|
| 255 | 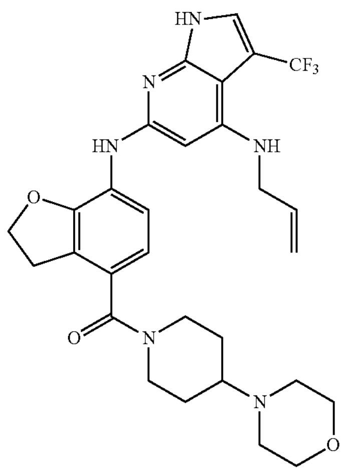 [SMILES: C=CCNc1cc(Nc2ccc(C(=O)N3CCC(N4CCOCC4)CC3)c3c2OCC3)nc2[nH]cc(C(F)(F)F)c12] | (7-((4-(allylamino)-3-(trifluoromethyl)-1H-pyrrolo[2,3-b]pyridin-6-yl)amino)-2,3-dihydrobenzofuran-4-yl)(4-morpholinopiperidin-1-yl)methanone | ¹H NMR (400 MHZ, DMSO-$d_6$) δ 11.76 (d, J = 2.9 Hz, 1H), 8.26 (d, J = 8.3 Hz, 1H), 8.08 (s, 1H), 7.50 (dd, J = 3.1, 1.6 Hz, 1H), 6.72 (d, J = 8.3 Hz, 1H), 6.21 (s, 1H), 5.98 (ddt, J = 17.3, 10.3, 5.1 Hz, 1H), 5.31-5.25 (m, 1H), 5.18 (dq, J = 10.3, 1.6 Hz, 1H), 4.97 (d, J = 6.7 Hz, 1H), 4.61 (t, J = 8.7 Hz, 2H), 3.89 (t, J = 5.5 Hz, 2H), 3.56 (t, J= 4.5 Hz, 4H), 3.18 (t, J = 8.7 Hz, 2H), 2.90 (s, 3H), 2.46 (t, J = 4.6 Hz, 4H), 2.38 (d, J = 10.8 Hz, 1H), 1.80 (s, 2H), 1.32 (t, J = 12.9 Hz, 2H), 1.24 (d, J = 9.7 Hz, 1H). 571.5 [M + H]⁺ | 30 | 1.09 |
| 256 | 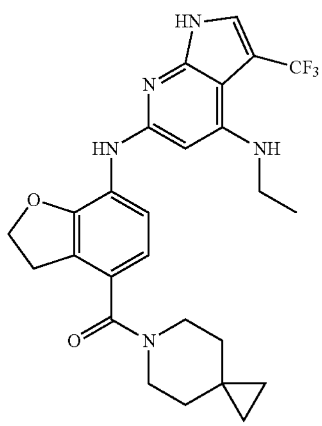 [SMILES: CCNc1cc(Nc2ccc(C(=O)N3CCC4(CC3)CC4)c3c2OCC3)nc2[nH]cc(C(F)(F)F)c12] | (7-((4-(ethylamino)-3-(trifluoromethyl)-1H-pyrrolo[2,3-b]pyridin-6-yl)amino)-2,3-dihydrobenzofuran-4-yl)(6-azaspiro[2.5]octan-6-yl)methanone | ¹H NMR (400 MHZ, DMSO-$d_6$) δ 11.75 (d, J = 2.9 Hz, 1H), 8.31 (d, J = 8.4 Hz, 1H), 8.10 (s, 1H), 7.48 (dt, J = 3.2, 1.5 Hz, 1H), 6.73 (d, J = 8.3 Hz, 1H), 6.24 (s, 1H), 4.70 (s, 1H), 4.62 (t, J = 8.7 Hz, 2H), 3.54 (d, J = 25.0 Hz, 2H), 3.28-3.16 (m, 5H), 1.34 (s, 4H), 1.24 (t, J = 7.1 Hz, 4H), 0.35 (s, 4H). 500.4 [M + H]⁺ | 79 | 1.45 |
| 257 | 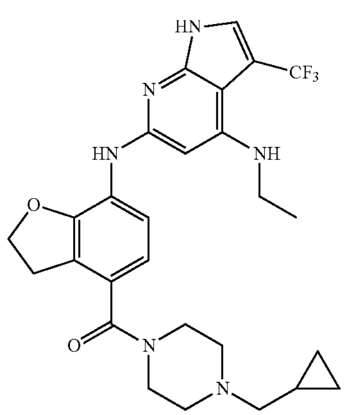 [SMILES: CCNc1cc(Nc2ccc(C(=O)N3CCN(CC4CC4)CC3)c3c2OCC3)nc2[nH]cc(C(F)(F)F)c12] | (4-(cyclopropylmethyl)piperazin-1-yl)(7-((4-(ethylamino)-3-(trifluoromethyl)-1H-pyrrolo[2,3-b]pyridin-6-yl)amino)-2,3-dihydrobenzofuran-4-yl)methanone | ¹H NMR (400 MHz, DMSO-$d_6$) δ 11.73 (d, J = 2.9 Hz, 1H), 8.32 (d, J = 8.3 Hz, 1H), 8.09 (s, 1H), 7.47 (dd, J = 3.1, 1.6 Hz, 1H), 6.71 (d, J = 8.3 Hz, 1H), 6.24 (s, 1H), 4.69 (dt, J = 7.2, 3.6 Hz, 1H), 4.62 (t, J= 8.7 Hz, 2H), 3.67-3.37 (m, 4H), 3.27-3.16 (m, 4H), 2.44 (s, 4H), 2.20 (d, J = 6.6 Hz, 2H), 1.24 (t, J = 7.1 Hz, 3H), 0.88-0.78 (m, 1H), 0.52-0.40 (m, 2H), 0.14-0.02 (m, 2H). 529.3 [M + H]⁺ | 65 | 1.15 |

TABLE 1-continued

| Compound of Example | Structure | Compound Name | ¹H NMR, MS | Yield (%) | HPLC r.t. (min), Purity |
|---|---|---|---|---|---|
| 258 | 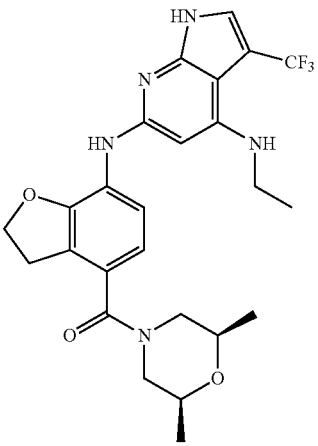 [SMILES: CCNc1cc(Nc2ccc(C(=O)N3C[C@@H](C)O[C@@H](C)C3)c3c2OCC3)nc2[nH]cc(C(F)(F)F)c12] | ((2S,6R)-2,6-dimethylmorpholino)(7-((4-(ethylamino)-3-(trifluoromethyl)-1H-pyrrolo[2,3-b]pyridin-6-yl)amino)-2,3-dihydrobenzofuran-4-yl)methanone | ¹H NMR (400 MHZ, DMSO-$d_6$) δ 11.73 (d, J = 2.7 Hz, 1H), 8.35 (d, J = 8.3 Hz, 1H), 8.11 (s, 1H), 7.48 (d, J = 2.6 Hz, 1H), 6.73 (d, J = 8.3 Hz, 1H), 6.25 (s, 1H), 4.70 (s, 1H), 4.63 (t, J = 8.7 Hz, 2H), 4.09 (q, J = 5.2 Hz, 1H), 3.52 (ddq, J = 10.8, 7.3, 4.6 Hz, 2H), 3.27-3.16 (m, 5H), 2.67 (s, 2H), 1.24 (t, J = 7.1 Hz, 3H), 1.08 (s, 6H). 504.4 [M + H]⁺ | 60 | 1.34 |
| 259 | 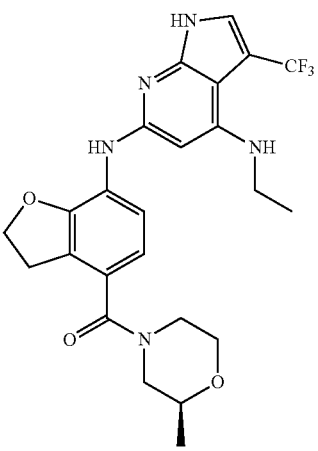 [SMILES: CCNc1cc(Nc2ccc(C(=O)N3CCO[C@@H](C)C3)c3c2OCC3)nc2[nH]cc(C(F)(F)F)c12] | (S)-(7-((4-(ethylamino)-3-(trifluoromethyl)-1H-pyrrolo[2,3-b]pyridin-6-yl)amino)-2,3-dihydrobenzofuran-4-yl)(2-methylmorpholino)methanone | ¹H NMR (400 MHZ, DMSO-$d_6$) δ 11.82-11.67 (m, 1H), 8.35 (d, J= 8.3 Hz, 1H), 8.10 (s, 1H), 7.48 (s, 1H), 6.74 (d, J = 8.4 Hz, 1H), 6.25 (s, 1H), 4.70 (s, 1H), 4.63 (t, J = 8.7 Hz, 2H), 3.82 (d, J = 11.4 Hz, 2H), 3.52-3.39 (m, 2H), 3.27-3.16 (m, 4H), 3.04 (s, 1H), 2.84-2.58 (m, 1H), 1.24 (t, J = 7.1 Hz, 3H), 1.08 (s, 3H), 0.85 (d, J = 4.8 Hz, 1H). 490.4 [M + H]⁺ | 68 | 1.29 |
| 260 | 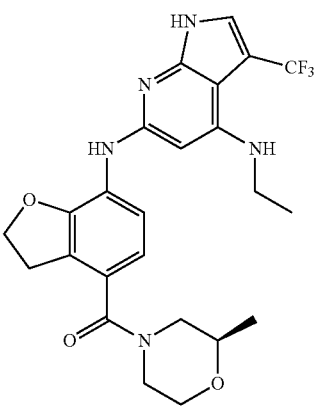 [SMILES: CCNc1cc(Nc2ccc(C(=O)N3CCO[C@H](C)C3)c3c2OCC3)nc2[nH]cc(C(F)(F)F)c12] | (R)-(7-((4-(ethylamino)-3-(trifluoromethyl)-1H-pyrrolo[2,3-b]pyridin-6-yl)amino)-2,3-dihydrobenzofuran-4-yl)(2-methylmorpholino)methanone | ¹H NMR (400 MHZ, DMSO-$d_6$) δ 11.80-11.66 (m, 1H), 8.35 (d, J= 8.3 Hz, 1H), 8.11 (s, 1H), 7.48 (s, 1H), 6.74 (d, J = 8.3 Hz, 1H), 6.25 (s, 1H), 4.70 (d, J = 6.5 Hz, 1H), 4.63 (t, J = 8.7 Hz, 2H), 3.82 (d, J = 11.1 Hz, 2H), 3.52-3.41 (m, 2H), 3.29-3.16 (m, 4H), 3.04 (s, 1H), 2.80-2.59 (m, 1H), 1.24 (t, J = 7.1 Hz, 3H), 1.08 (s, 3H). 490.4 [M + H]⁺ | 48 | 1.30 |

TABLE 1-continued

| Compound of Example | Structure | Compound Name | ¹H NMR, MS | Yield (%) | HPLC r.t. (min), Purity |
|---|---|---|---|---|---|
| 261 | 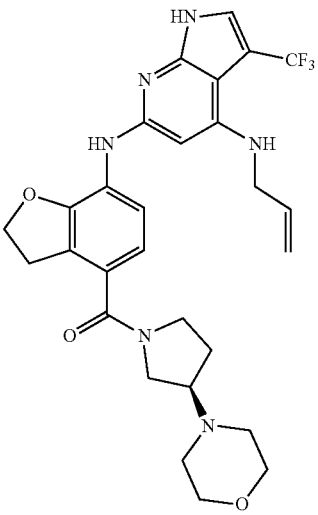 [SMILES: C=CCNc1cc(Nc2ccc(C(=O)N3CC[C@@H](N4CCOCC4)C3)c3c2OCC3)nc2[nH]cc(C(F)(F)F)c12] | (R)-(7-((4-(allylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | 557.5 [M + H]⁺ | 7 | 1.13 |
| 262 | 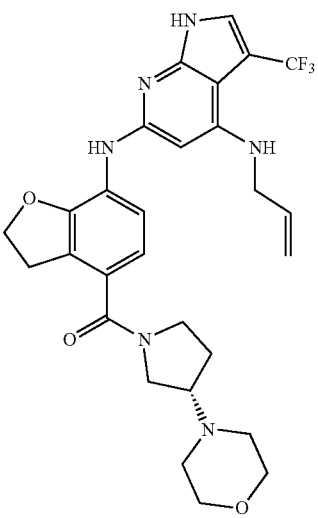 [SMILES: C=CCNc1cc(Nc2ccc(C(=O)N3CC[C@H](N4CCOCC4)C3)c3c2OCC3)nc2[nH]cc(C(F)(F)F)c12] | (S)-(7-((4-(allylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone | 557.5 [M + H]⁺ | 4 | 1.10 |
| 263 | 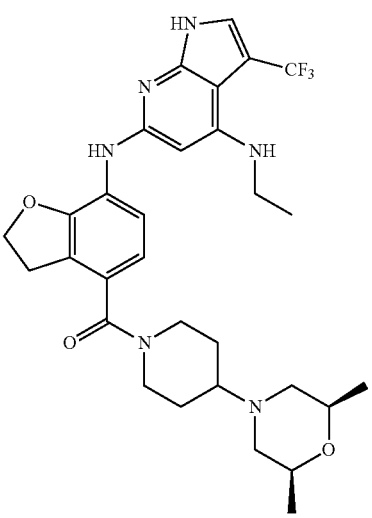 [SMILES: CCNc1cc(Nc2ccc(C(=O)N3CCC(N4C[C@@H](C)O[C@@H](C)C4)CC3)c3c2OCC3)nc2[nH]cc(C(F)(F)F)c12] | (4-((2S,6R)-2,6-dimethylmorpholino)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone | ¹H NMR (400 MHZ, DMSO-d₆) δ 11.73 (d, J = 2.9 Hz, 1H), 8.30 (d, J = 8.3 Hz, 1H), 8.08 (s, 1H), 7.48 (dt, J = 3.2, 1.5 Hz, 1H), 6.72 (d, J = 8.3 Hz, 1H), 6.24 (s, 1H), 4.69 (q, J = 4.6 Hz, 1H), 4.62 (t, J = 8.7 Hz, 2H), 3.50 (ddt, J = 13.6, 7.3, 3.6 Hz, 2H), 3.27-3.15 (m, 4H), 3.02-2.80 (m, 2H), 2.74 (d, J = 10.7 Hz, 2H), 2.39 (d, J = 11.5 Hz, 1H), 1.78 (t, J = 10.5 Hz, 3H), 1.54 (ddd, J = 39.6, 8.5, 4.4 Hz, 1H), 1.33 (t, J = 6.3 Hz, 2H), 1.24 (t, J = 7.1 Hz, 4H), 1.04 (d, J= 6.3 Hz, 6H), 0.86 (td, J = 7.6, 7.1, 3.0 Hz, 1H). 587.4 [M + H]⁺ | 60 | 1.15 |

TABLE 1-continued

| Compound of Example | Structure | Compound Name | ¹H NMR, MS | Yield (%) | HPLC r.t. (min), Purity |
|---|---|---|---|---|---|
| 264 | 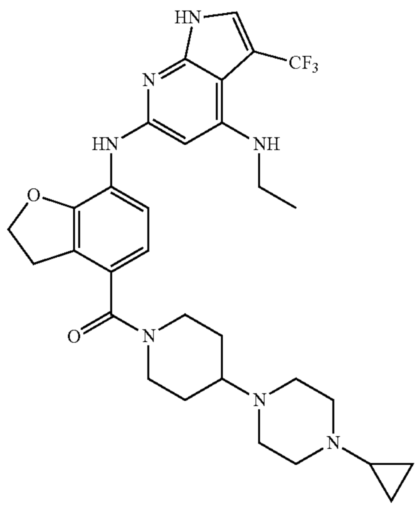 [SMILES: CCNc1cc(Nc2ccc(C(=O)N3CCC(N4CCN(C5CC5)CC4)CC3)c3c2OCC3)nc2[nH]cc(C(F)(F)F)c12] | (4-(4-cyclopropylpiperazin-1-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone | $^1$H NMR (400 MHZ, DMSO-d$_6$) δ 11.73 (d, J = 2.9 Hz, 1H), 8.29 (d, J = 8.3 Hz, 1H), 8.08 (s, 1H), 7.47 (dd, J = 3.0, 1.6 Hz, 1H), 6.71 (d, J = 8.3 Hz, 1H), 6.23 (s, 1H), 4.69 (s, 1H), 4.62 (t, J = 8.7 Hz, 2H), 4.47-4.21 (m, 1H), 3.77 (s, 1H), 3.57 (s, 1H), 3.30-3.11 (m, 5H), 2.89 (s, 2H), 2.42 (d, J = 9.7 Hz, 4H), 1.77 (s, 2H), 1.56 (tt, J = 6.7, 3.6 Hz, 1H), 1.30 (d, J = 11.2 Hz, 2H), 1.24 (t, J = 7.1 Hz, 4H), 0.90-0.77 (m, 1H), 0.38 (dt, J = 6.2, 3.0 Hz, 2H), 0.26 (p, J = 4.0 Hz, 2H). 598.5 [M + H]$^+$ | 43 | 1.13 |
| 265 | 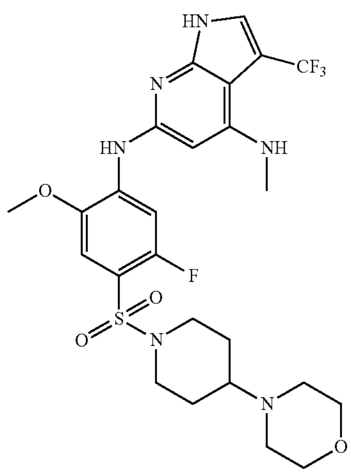 [SMILES: CNc1cc(Nc2cc(F)c(S(=O)(=O)N3CCC(N4CCOCC4)CC3)cc2OC)nc2[nH]cc(C(F)(F)F)c12] | N$^6$-(5-fluoro-2-methoxy-4-((4-morpholinopiperidin-1-yl)sulfonyl)phenyl)-N$^4$-methyl-3-(trifluoromethyl)-1H-pyrrolo[2,3-b]pyridine-4,6-diamine | $^1$H NMR (400 MHZ, DMSO-d$_6$) δ 11.93 (s, 1H), 8.91 (d, J = 14.0 Hz, 1H), 8.58 (d, J = 1.5 Hz, 1H), 7.59 (s, 1H), 7.09 (d, J = 6.5 Hz, 1H), 6.40 (s, 1H), 5.23-5.03 (m, 1H), 3.95 (s, 3H), 3.68 (d, J = 11.9 Hz, 2H), 3.52 (t, J = 4.6 Hz, 4H), 2.91 (d, J = 4.7 Hz, 3H), 2.45 (d, J = 12.0 Hz, 2H), 2.40 (t, J = 4.7 Hz, 4H), 2.19 (td, J = 9.3, 7.6, 5.5 Hz, 1H), 1.81 (d, J = 12.5 Hz, 2H), 1.40 (qd, J = 11.8, 3.7 Hz, 2H). 587.3 [M + H]$^+$ | 72 | 1.38 |
| 266 | 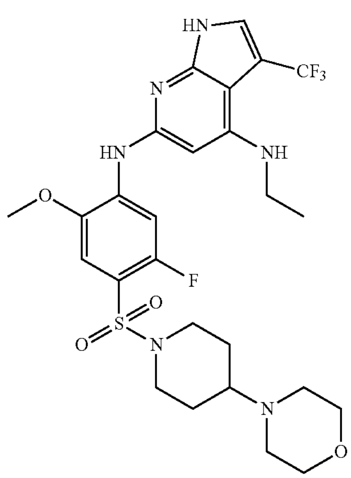 [SMILES: CCNc1cc(Nc2cc(F)c(S(=O)(=O)N3CCC(N4CCOCC4)CC3)cc2OC)nc2[nH]cc(C(F)(F)F)c12] | N$^4$-ethyl-N$^6$-(5-fluoro-2-methoxy-4-((4-morpholinopiperidin-1-yl)sulfonyl)phenyl)-3-(trifluoromethyl)-1H-pyrrolo[2,3-b]pyridine-4,6-diamine | $^1$H NMR (400 MHZ, DMSO-d$_6$) δ 11.94 (s, 1H), 8.90 (d, J = 14.0 Hz, 1H), 8.59 (d, J = 1.6 Hz, 1H), 7.61 (s, 1H), 7.09 (d, J = 6.5 Hz, 1H), 6.47 (s, 1H), 4.84 (s, 1H), 3.95 (s, 3H), 3.68 (d, J = 11.7 Hz, 2H), 3.52 (t, J = 4.5 Hz, 4H), 3.31-3.25 (m, 2H), 2.45 (d, J = 11.7 Hz, 2H), 2.40 (t, J = 4.7 Hz, 4H), 2.23-2.16 (m, 1H), 1.81 (d, J = 12.5 Hz, 2H), 1.47-1.35 (m, 2H), 1.25 (t, J = 7.1 Hz, 3H). 601.4 [M + H]$^+$ | 73 | 1.48 |

TABLE 1-continued

| Compound of Example | Structure | Compound Name | $^1$H NMR, MS | Yield (%) | HPLC r.t. (min), Purity |
|---|---|---|---|---|---|
| 267 | 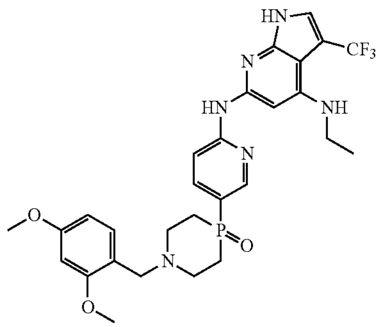 [SMILES: CCNc1cc(Nc2ccc(P3(=O)CCN(Cc4ccc(OC)cc4OC)CC3)cn2)nc2[nH]cc(C(F)(F)F)c12] | 1-(2,4-dimethoxybenzyl)-4-(6-((4-(ethylamino)-3-(trifluoromethyl)-1H-pyrrolo[2,3-b]pyridin-6-yl)amino)pyridin-3-yl)-1,4-azaphosphinane 4-oxide | $^1$H NMR (400 MHZ, Chloroform-d) δ 11.70 (s, 1H), 10.33 (s, 1H), 8.62 (dd, J = 6.1, 2.1 Hz, 1H), 7.90 (td, J = 10.2, 9.4, 2.2 Hz, 1H), 7.79-7.69 (m, 1H), 7.39 (s, 1H), 7.23 (d, J = 8.1 Hz, 1H), 6.51-6.43 (m, 2H), 6.23 (s, 1H), 4.90 (s, 1H), 3.82 (s, 3H), 3.80 (s, 3H), 3.66 (s, 2H), 3.34-3.25 (m, 2H), 3.12-2.98 (m, 4H), 2.25-2.08 (m, 4H), 1.36 (t, J = 7.2 Hz, 3H). 589.4 [M + H]$^+$ | 49 | 1.16 |

<Experimental Example 1> Evaluation 1 of Enzyme Inhibitory Activity of the Compound According to the Present Invention In order to evaluate the inhibitory activity of the compounds according to the present invention on LRRK2, LRRK2 (G2019S), DYRK1, CLK1 and TTK kinases, the following experiment was performed.

1) LRRK2

Example compounds were reacted with the purified human LRRK2 (Invitrogen #PR8604B) enzyme to evaluate the enzyme inhibitory ability as follows. The reaction buffer was used as the composition of 40 mM Tris-HCl pH7.4, 20 mM MgCl$_2$, 0.5 mg/ml BSA and 50 μM DTT, and the reaction of all test materials was performed on the reaction buffer. The compound was diluted with 10 mM DMSO stock in 12 steps by a serial dilution method, and the enzyme activity was measured at the final compound concentrations of 50, 10, 2, 0.4, 0.08, 0.016, 0.0032, 0.00064, 0.000128, 0.0000256, 0.00000512 and 0.000001024 μM. In the test, the human LRRK2 (25 ng) enzyme was reacted with the purified ATP (10 μM) and an enzyme substrate (0.2 g) at 25° C. for 2 hours, and then the enzyme activity was identified using the in vitro ADP-Glo™ kinase assay (promega). The enzyme activity reaction liquid, an ADP-Glo reaction liquid and an enzyme potency detection solution were reacted in a ratio of 2:2:1, and the degree of inhibition of enzyme activity was measured by Luminescence. The degree of inhibition of enzyme activity according to the treatment concentrations of the respective compounds was calculated based on the fluorescence of the enzyme activity of a solvent control group that was not treated with the compound, where the concentration of each compound to inhibit enzyme activity inhibition by 50% was determined as an IC$_{50}$ (nM) value and obtained using Prism (Version 5.01, GraphPad) software. The results were shown in Table 2 below.

2) LRRK2 G2019S

Example compounds were reacted with the purified human LRRK2 G2019S (L10-12GG, SignalChem) enzyme to evaluate the enzyme inhibitory ability as follows. The reaction buffer was used as the composition of 40 mM Tris-HCl pH7.4, 20 mM MgCl$_2$, 0.5 mg/ml BSA and 50 μM DTT, and the reaction of all test materials was performed on the reaction buffer. The compound was diluted with 10 mM DMSO stock in 12 steps by a serial dilution method, and the enzyme activity was measured at the final compound concentrations of 50, 10, 2, 0.4, 0.08, 0.016, 0.0032, 0.00064, 0.000128, 0.0000256, 0.00000512 and 0.000001024 μM. In the test, the human LRRK2 G2019S (16 ng) enzyme was reacted with the purified ATP (25 μM) and an enzyme substrate (0.2 μg) at 25° C. for 2 hours, and then the enzyme activity was identified using the in vitro ADP-Glo™ kinase assay (promega). The enzyme activity reaction liquid, an ADP-Glo reaction liquid and an enzyme potency detection solution were reacted in a ratio of 2:2:1, and the degree of inhibition of enzyme activity was measured by Luminescence. The degree of inhibition of enzyme activity according to the treatment concentrations of the respective compounds was calculated based on the fluorescence of the enzyme activity of a solvent control group that was not treated with the compound, where the concentration of each compound to inhibit enzyme activity inhibition by 50% was determined as an IC$_{50}$ (nM) value and obtained using Prism (Version 5.01, GraphPad) software. The results were shown in Table 2 below.

3) GST-DYRK1A

Example compounds were reacted with the purified human GST-DYRK1A (full length, Thermo scientifics) enzyme to evaluate the enzyme inhibitory ability as follows. As the reaction buffer, the composition of 40 mM Tris-HCl pH 7.4, 20 mM MgCl$_2$, 0.5 mg/mL BSA, and 50 uM DTT was used, and the reaction of all test materials was performed on the reaction buffer. During the test, the human GST-DYRK1A (full length, 10 ng) enzyme, the purified ATP (10 uM), and a specific substrate solution were reacted at 25° C. for 1 hour, and then the enzyme activity was identified using the in vitro ADP-Glo™ kinase assay (promega). Luminescence was measured by reacting the enzyme activity reaction solution, an ADP-Glo reaction solution and the enzyme potency detection solution in a ratio of 2:2:1. The degree of inhibition of enzyme activity according to the treatment concentrations of the respective compounds was calculated based on the fluorescence of the enzyme activity of a solvent control group that was not treated with the compound, where the concentration of each compound to inhibit enzyme activity inhibition by 50% was determined as an IC$_{50}$ (nM) value. The IC$_{50}$ of each compound was determined in triplicate data sets and obtained using Prism (version 7.01, GraphPad) software.

4) GST-CLK1

Example compounds were reacted with the purified human GST-CLK1 (129-end, Signalchem) enzyme to evaluate the enzyme inhibitory ability as follows. As the reaction buffer, the composition of 40 mM Tris-HCl pH 7.4, 20 mM MgCl$_2$, 0.5 mg/mL BSA, and 50 uM DTT was used, and the reaction of all test materials was performed on the reaction buffer. During the test, the human GST-CLK1 (129-end, 3 ng) enzyme, the purified ATP (10 uM), and a specific substrate solution were reacted at 25° C. for 1 hour, and then the enzyme activity was identified using the in vitro ADP-Glo™ kinase assay (promega). Luminescence was measured by reacting the enzyme activity reaction solution, an ADP-Glo reaction solution and the enzyme potency detection solution in a ratio of 2:2:1. The degree of inhibition of enzyme activity according to the treatment concentrations of the respective compounds was calculated based on the fluorescence of the enzyme activity of a solvent control group that was not treated with the compound, where the concentration of each compound to inhibit enzyme activity inhibition by 50% was determined as an IC$_{50}$ (nM) value. The IC$_{50}$ of each compound was determined in triplicate data sets and obtained using Prism (version 7.01, GraphPad) software. The results were shown in Table 2 below.

5) TTK

Example compounds were reacted with the purified human TTK (Signalchem #T20-10G) enzyme to evaluate the enzyme inhibitory ability as follows. The reaction buffer was used as the composition of 40 mM Tris-HCl pH7.4, 20 mM MgCl$_2$, 0.1 mg/ml BSA (5× kinase buffer, Signalchem #K03-09) and 50 µM DTT (Signalchem #D86-09B), and the reaction of all test materials was performed on the reaction buffer. The compound was diluted with 10 mM DMSO stock in 12 steps by a serial dilution method, and the enzyme activity was measured at the final compound concentrations of 1, 0.333333, 0.111111, 0.037037, 0.012346, 0.004115, 0.001372, 0.000457, 0.000152, 0.000051 and 0.000017 µM. In the test, the human TTK (7.5 ng) enzyme was reacted with the purified ATP (5 µM, Promega #V6930) and an MBP enzyme substrate (0.2 µg, Signalchem M42-51N) at 25° C. for 4 hours, and then the enzyme activity was identified using the in vitro ADP-Glo™ kinase assay (Promega #V6930). The enzyme activity reaction liquid, an ADP-Glo reaction liquid and an enzyme potency detection solution were reacted in a ratio of 2:2:1, and the degree of inhibition of enzyme activity was measured by luminescence. The degree of inhibition of enzyme activity according to the treatment concentrations of the respective compounds was calculated based on the luminescence degree of the enzyme activity of a solvent control group that was not treated with the compound, where the concentration of each compound to inhibit enzyme activity inhibition by 50% was determined as an IC$_{50}$ (nM) value and obtained using Prism (Version 8.2, GraphPad) software.

Meanwhile, the enzyme IC$_{50}$ measurement for some compounds was performed using Kinase HotSpot service (Reaction Biology Corporation); during the test, the ATP concentration was 10 uM, where all were conducted under the same condition; and the concentration of the compound was measured by giving a 3-fold concentration gradient with the highest concentration of 10 mM, where the values measured using Kinase HotSpot service (Reaction Biology Corporation) were marked with "*".

All experimental methods were performed as provided in Kinase HotSpot Customer Protocol (http://www.reactionbiology.com//Kinase_Assay_Protocol). The results were shown in Table 2 below.

In the table below, the following designations were used for the evaluation of enzyme inhibitory ability.

0-100 nM=A; 101-300 nM=B; 301-1000 nM=C;

TABLE 2

| Example | LRRK2 | LRRK2 (G2019S) | DYRK1 | CLK1 | TTK |
|---|---|---|---|---|---|
| 1 | | C | C | C | |
| 2 | | A | C | C | |
| 3 | | B | C | C | |
| 4 | | A | C | C | |
| 5 | | A | C | C | |
| 6 | | A | C | C | |
| 7 | | A | C | C | |
| 8 | | B | C | C | |
| 9 | | A | C | C | |
| 10 | | B | C | C | |
| 11 | | B | C | C | |
| 12 | | A | C | C | |
| 13 | | C | C | C | |
| 14 | | C | C | C | |
| 15 | | A | C | C | |
| 16 | | C | C | C | |
| 17 | | C | C | C | |
| 18 | | A | C | C | |
| 19 | | A | C | C | |
| 20 | | A | C | C | |
| 21 | | A | C | C | |
| 22 | | A | C | C | |
| 23 | | C | C | C | |
| 24 | | A | C | C | |
| 25 | B | A | C | C | |
| 26 | A | A | C | C | |
| 27 | A | A | C | C | |
| 28 | B | C | C | C | |
| 29 | A | B | C | C | |
| 30 | | C | C | C | |
| 31 | | C | C | C | |
| 32 | C | C | C | C | |
| 33 | | | C | B | |
| 34 | | | A | A | |
| 35 | | | B | B | |
| 36 | | | C | C | |
| 37 | A | A | A | A | |
| 38 | B | A | A | A | |
| 39 | B | | B | C | |
| 40 | C | | A | C | |
| 41 | A | | A | A | |
| 42 | A | B | A | B | A |
| 43 | A | | A | A | |
| 44 | A | | A | A | A |
| 45 | B | | B | C | |
| 46 | C | | C | C | |
| 47 | B | | *A | A | |
| 48 | C | C | *A | C | C |
| 49 | A | | *B | A | A |
| 50 | A | | C | A | |
| 51 | B | | C | B | |
| 52 | A | A | A | A | |
| 53 | A | A | A | A | |
| 54 | A | A | A | A | |
| 55 | A | A | A | A | B |
| 56 | | A | C | C | |
| 57 | | A | C | C | |
| 58 | | A | C | C | |
| 59 | | C | C | C | |
| 60 | | A | C | C | |
| 61 | | | C | C | |
| 62 | A | A | C | C | |
| 63 | | A | C | C | |
| 64 | C | C | C | C | |
| 65 | B | C | C | C | |
| 66 | | C | C | C | |
| 67 | | C | C | C | |
| 68 | | C | C | C | |
| 69 | C | C | C | C | |
| 70 | C | C | C | C | |
| 71 | | | C | C | |
| 72 | | C | C | C | |
| 73 | | A | C | C | |
| 74 | | B | C | C | |
| 75 | | A | C | C | |
| 76 | | A | C | C | |
| 77 | | | C | C | |

TABLE 2-continued

| Example | LRRK2 | LRRK2 (G2019S) | DYRK1 | CLK1 | TTK |
|---|---|---|---|---|---|
| 78 | | | C | C | |
| 79 | | | A | A | |
| 80 | | A | C | C | |
| 81 | | C | C | C | |
| 82 | | C | C | C | |
| 83 | | C | C | C | |
| 84 | | C | C | C | |
| 85 | C | C | B | C | |
| 86 | | | C | C | |
| 87 | | | C | C | |
| 88 | | C | C | C | |
| 89 | A | A | A | A | |
| 90 | A | A | A | A | A |
| 91 | C | C | *A | *A | C |
| 92 | A | A | A | A | A |
| 93 | A | A | *A | A | C |
| 94 | B | B | B | B | |
| 95 | B | B | A | B | |
| 96 | A | A | C | B | |
| 97 | A | A | B | A | B |
| 98 | B | A | B | C | |
| 99 | C | C | C | C | |
| 100 | C | C | A | C | |
| 101 | | | *A | C | A |
| 102 | | | *A | C | |
| 103 | B | | C | C | |
| 104 | A | | C | C | |
| 105 | A | A | A | A | A |
| 106 | A | A | C | C | |
| 107 | A | A | C | C | |
| 108 | A | A | C | C | |
| 109 | A | A | A | A | |
| 110 | A | A | C | B | |
| 111 | A | A | C | B | |
| 112 | A | A | C | C | |
| 113 | A | A | C | A | |
| 114 | A | A | A | A | |
| 115 | A | A | B | B | |
| 116 | A | A | C | B | |
| 117 | A | A | C | A | |
| 118 | A | A | C | A | |
| 119 | A | A | C | C | |
| 120 | A | B | C | C | |
| 121 | A | C | C | C | |
| 122 | A | B | C | C | |
| 123 | A | A | C | C | |
| 124 | A | B | C | C | |
| 125 | A | B | C | C | |
| 126 | A | A | C | C | |
| 127 | A | B | C | C | |
| 128 | A | C | C | C | |
| 129 | A | A | C | C | |
| 130 | A | A | B | C | |
| 131 | A | A | C | C | |
| 132 | A | B | C | C | |
| 133 | A | C | C | C | |
| 134 | A | A | C | B | |
| 135 | A | A | C | C | |
| 136 | | A | C | C | |
| 137 | A | A | C | C | |
| 138 | A | A | B | C | |
| 139 | A | A | C | C | |
| 140 | A | A | *A | A | |
| 141 | A | | A | C | |
| 142 | A | | B | C | |
| 143 | A | | C | B | |
| 144 | A | | C | B | |
| 145 | A | | B | C | |
| 146 | A | | C | C | A |
| 147 | A | | A | C | |
| 148 | A | | C | C | A |
| 149 | | | C | C | |
| 150 | | | C | C | |
| 151 | | | C | C | |
| 152 | A | A | A | A | |
| 153 | A | B | A | A | |
| 154 | C | C | C | C | |
| 155 | A | B | C | A | |
| 156 | A | C | C | C | |
| 157 | A | A | A | A | |
| 158 | A | A | A | A | |
| 159 | A | | B | A | |
| 160 | A | A | B | A | |
| 161 | A | A | B | A | |
| 162 | A | A | B | A | |
| 163 | A | A | B | A | |
| 164 | A | A | A | A | |
| 165 | A | A | A | A | |
| 166 | | | B | C | |
| 167 | | | A | A | |
| 168 | | | C | A | |
| 169 | | | C | C | |
| 170 | | | C | A | |
| 171 | A | | C | C | |
| 172 | A | | C | B | |
| 173 | A | | A | A | A |
| 174 | B | | C | C | |
| 175 | | | C | B | |
| 176 | | | A | A | |
| 177 | C | C | C | C | |
| 178 | C | C | A | C | |
| 179 | C | C | C | C | |
| 180 | C | C | C | C | |
| 181 | C | C | C | C | |
| 182 | C | C | C | C | |
| 183 | C | C | C | C | |
| 184 | *A | A | *A | *A | A |
| 185 | A | A | B | B | |
| 186 | C | C | C | C | |
| 187 | C | C | C | C | |
| 188 | A | B | C | C | |
| 189 | C | C | C | C | |
| 190 | C | C | C | C | |
| 191 | B | C | C | C | |
| 192 | B | C | A | C | |
| 193 | C | C | A | A | |
| 194 | A | A | A | A | |
| 195 | C | C | C | C | |
| 196 | A | | C | C | |
| 197 | A | A | B | A | |
| 198 | | | C | C | |
| 199 | C | C | C | C | |
| 200 | C | C | C | C | |
| 201 | B | C | C | C | |
| 202 | C | | C | C | |
| 203 | C | | C | C | |
| 204 | C | | C | C | |
| 205 | B | B | A | A | A |
| 206 | B | | C | C | |
| 207 | B | B | A | B | A |
| 208 | A | A | B | A | |
| 209 | A | A | B | C | |
| 210 | A | | A | A | |
| 211 | A | | C | C | |
| 212 | A | | A | A | |
| 213 | B | B | B | A | |
| 214 | A | A | A | A | B |
| 215 | A | A | A | A | |
| 216 | B | B | A | A | |
| 217 | A | | A | A | A |
| 218 | A | | C | C | |
| 219 | | | *A | C | |
| 220 | C | C | C | C | A |
| 221 | B | B | *A | A | A |
| 222 | C | C | *B | C | A |
| 223 | *A | *A | *A | *A | A |
| 224 | C | C | *A | C | |
| 225 | A | A | *B | C | A |
| 226 | A | A | *A | A | A |
| 227 | A | B | C | C | A |
| 228 | A | A | *A | C | A |
| 229 | B | C | C | C | |
| 230 | | | C | C | |
| 231 | A | | C | C | |

TABLE 2-continued

| Example | LRRK2 | LRRK2 (G2019S) | DYRK1 | CLK1 | TTK |
|---|---|---|---|---|---|
| 232 | B | | B | C | |
| 233 | A | A | B | A | B |
| 234 | A | A | A | A | A |
| 235 | A | | A | A | |
| 236 | A | B | A | A | |
| 237 | *B | | *A | *A | B |
| 238 | *B | | *A | *A | A |
| 239 | *A | C | *A | *A | |
| 240 | *A | C | *A | *A | |
| 241 | A | A | A | A | A |
| 242 | A | A | A | A | |
| 243 | A | A | A | A | |
| 244 | | A | A | A | A |
| 245 | | C | C | C | |
| 246 | | C | C | C | |
| 247 | | A | A | A | |
| 248 | | A | A | A | A |
| 249 | | A | A | A | |
| 250 | | B | B | A | |
| 251 | | A | B | A | |
| 252 | | A | A | A | |
| 253 | | A | A | A | |
| 254 | | A | A | A | |
| 255 | | A | A | A | |
| 256 | | C | C | B | |
| 257 | | A | A | A | |
| 258 | | C | A | B | |
| 259 | | A | A | A | |
| 260 | | A | A | A | |
| 261 | | A | B | A | |
| 262 | | A | B | A | |
| 263 | | A | A | A | |
| 264 | | A | A | A | |
| 265 | | A | B | C | |
| 266 | | B | C | C | C |
| 267 | | A | A | A | |

The values marked with * are data measured using Reaction Biology.

As shown in Table 2 above,
it can be seen that the example compounds of the present invention exhibit an effect of inhibiting LRRK2, LRRK2 (G2019S), DYRK1, CLK1 and TTK kinases.

This indicates that the example compounds of the present invention have inhibitory activity against the enzymes listed above, suggesting that they have useful effects when used in diseases related to the enzymes listed above.

Accordingly, the compound of Formula 1 of the present invention can be usefully used as a pharmaceutical composition for preventing or treating diseases related to LRRK2, LRRK2 (G2019S), DYRK1, CLK1 and TTK kinases.

<Experimental Example 2> Evaluation of MDA-MB-231, MDA-MB-468 and SHP-77 Cancer Cell Proliferation Inhibition In order to evaluate the cancer cell proliferation inhibitory activity of the compounds of the present invention, the following experiments were performed.

To evaluate the cancer cell proliferation inhibitory effect, the cell growth rate analysis was performed while culturing MDA-MB-231 cell line (Korean Cell Line Bank #30026) and MDA-MB-468 cell line as the triple-negative breast cancer cell line, and SHP-77 (ATCC #CRL-2195) as the small cell lung cancer cell line in DMEM (HyClone #SH30243) and RPMI medium (HyClone #SH3027.01), respectively. More specifically, the cell lines were each plated at 2000 cells/100 μl in each well of a 96-well flat-bottom plate (coming #3903), and then the example compounds having eleven concentrations which were diluted by ⅓ so that the final concentrations were 10.000000, 3.333333, 1.111111, 0.370370, 0.123457, 0.041152, 0.013717, 0.004572, 0.001524, 0.000508 and 0.000169 μM were treated. After 72 hours, 100 μl of Cell Titer-Glo (Promega G7573) was treated, incubated at RT for 10 minutes, and then luminescence was measured using a microplate reader. The measured luminescence degree was calculated as $GI_{50}$ using Prism (version 8.2 GraphPad) software.

In the table below, the following designations were used for the evaluation of proliferation inhibitory activity.

0-50 nM=A; 51-100 nM=B; 101-300 nM=C; 301-1000 nM=D;

TABLE 3

| Example | MDA-MB-468 $GI_{50}(nM)$ | MDA-MB-231 $GI_{50}(nM)$ | SHP-77 $GI_{50}(nM)$ |
|---|---|---|---|
| 10 | | D | D |
| 37 | | D | |
| 39 | | D | |
| 40 | | D | D |
| 41 | | D | |
| 42 | | D | D |
| 44 | | D | D |
| 47 | | D | |
| 48 | | D | |
| 49 | | D | |
| 55 | | D | |
| 90 | | D | |
| 91 | | D | |
| 92 | | D | |
| 93 | | D | |
| 94 | | D | |
| 95 | | D | |
| 96 | | D | D |
| 97 | | D | D |
| 98 | | C | D |
| 99 | | D | D |
| 100 | | D | D |
| 104 | | D | C |
| 105 | | D | |
| 112 | B | | |
| 127 | | B | A |
| 128 | | B | A |
| 129 | | C | A |
| 130 | | D | D |
| 131 | | B | A |
| 132 | | C | B |
| 133 | | C | B |
| 134 | | A | A |
| 135 | | B | A |
| 137 | | B | B |
| 138 | | A | A |
| 139 | | A | A |
| 140 | | A | B |
| 141 | | C | B |
| 146 | | D | |
| 148 | | D | |
| 149 | C | | |
| 150 | B | | |
| 151 | C | B | B |
| 152 | C | | |
| 163 | | D | |
| 173 | | D | |
| 179 | | D | D |
| 181 | | D | D |
| 184 | | D | C |
| 185 | | B | A |
| 186 | | D | D |
| 188 | | D | C |
| 189 | | D | D |
| 191 | | D | D |
| 192 | | D | D |
| 194 | | D | D |
| 195 | | D | C |

TABLE 3-continued

| Example | MDA-MB-468 GI$_{50}$(nM) | MDA-MB-231 GI$_{50}$(nM) | SHP-77 GI$_{50}$(nM) |
|---|---|---|---|
| 196 | | D | C |
| 197 | | D | C |
| 198 | | D | D |
| 199 | | D | D |
| 202 | | D | D |
| 203 | | D | D |
| 205 | | D | |
| 207 | | D | D |
| 212 | | D | |
| 214 | | D | |
| 216 | | D | |
| 217 | | D | |
| 220 | | D | |
| 221 | | D | |
| 222 | | D | D |
| 223 | | D | D |
| 225 | | D | |
| 226 | | D | |
| 227 | | D | D |
| 228 | | B | B |
| 232 | | D | D |
| 233 | | D | D |
| 234 | | D | |
| 237 | | D | |
| 238 | | D | |
| 239 | | D | D |
| 240 | | D | D |
| 241 | | D | |
| 243 | | C | B |
| 244 | | D | |
| 248 | | D | |
| 265 | | D | D |
| 266 | | D | D |

As shown in Table 3, it can be seen that the example compounds according to the present invention inhibit the proliferation of triple-negative breast cancer cells.

Therefore, the compound of Formula 1 according to the present invention can be usefully used for the treatment of triple-negative breast cancer.

<Experimental Example 3> Evaluation of Cytokine Secretion Inhibitory Activity of Human-Derived Mononuclear Cells In order to evaluate the cytokine secretion inhibitory efficacy of mononuclear cells, THP-1 cells (ATCC, #TIB-202) as a human-derived monocyte cell line were cultured in RPMI-1640 (Hyclone, SH30027.01) media in which 10% fetal bovine serum (Hyclone, SH30084.03), 1% penicillin streptomycin (Welgene, LS202-02) and 50 µM 2-Mercaptoethanol (Gibco, #21985023) were contained. In the test, 1.5-2×105 cells/250 µl per each well were dispensed in a 48-well plate (SPL, #30048) and incubated in an incubator at 37° C. and 5% $CO_2$ for 16 hours, and then the compounds were diluted in DMSO so that the final concentration was 0.5 µM. It was treated with Lipopolysaccharides (LPS) (sigma, #L6529) 1 hour before treatment. After treatment with the compound, the LPS was treated so that the final concentration was 500 ng/ml, and then the cell culture fluid was collected after culturing for 24 hours, and the degrees of the cytokines IL-6 (R&D system, #D6050) and TNF-α (R&D system, #DTA00D) contained in the culture fluid were collected using each ELISA kit. After performing the experiment according to the manufacturer's instructions, the absorbance at 450 nm was measured and analyzed using a microplate reader.

TABLE 4

| Example | THP1/IL6 (% inhib) | THP-1/TNF-a (% inhib) | THP-1 GI$_{50}$ (uM) |
|---|---|---|---|
| 37 | | 100 | 14.38 |
| 38 | 36.1 | 32.8 | |
| 42 | 48.3 | 35.7 | 16.28 |
| 44 | 47.9 | 100 | 146.5 |
| 54 | 46.9 | | |
| 90 | 12.2 | 12.4 | |
| 91 | 52.5 | 9.6 | |
| 94 | 21 | 6.6 | |
| 97 | 17 | 5.5 | |
| 105 | 33.2 | 1.7 | |
| 153 | 32.7 | 40.4 | 14.38 |
| 157 | 29.1 | 31 | |
| 173 | 9.1 | 5.9 | |
| 194 | 6.3 | 37.6 | |
| 207 | 41.7 | 39.8 | 9.39 |
| 212 | 29.1 | 2.7 | |
| 213 | 3.9 | 2.6 | |
| 214 | | 12 | |
| 233 | 4.3 | 12.5 | |
| 234 | 50.9 | 12.4 | |
| 235 | 22.9 | 36.3 | |
| 243 | 32.3 | 2.1 | |
| 244 | 40.1 | 12.7 | |
| 247 | 31.9 | 15.5 | |
| 248 | 48.4 | 9.2 | |
| 249 | 60.31 | 10.08 | |
| 253 | 49.16 | 9.83 | |
| 257 | 44.03 | 7.88 | |
| 264 | 45.52 | 11.23 | |

<Experimental Example 4> Tan Phosphorylation Inhibition Evaluation

Tau phosphorylation inhibitory efficacy was measured using the ClariCELL™ Kinase Cell-Based Assay service of Carnabio, located in the United States. The compounds are exposed to human embryonic kidney (HER 293) cells transiently expressing human DYRK1A and Tau, and then the cells are lysed to release cellular proteins. At this time, the released Tau is captured on a plate, and the degree of phosphorylation is quantified by ELISA using an antibody specific for Tau phosphorylation.

TABLE 5

| Example | % inhibition at 1 uM | % inhibition at 0.5 uM | % inhibition at 0.25 uM |
|---|---|---|---|
| 40 | 38.7 | 15.2 | 9.2 |
| 47 | 22.4 | 15.0 | 3.7 |
| 90 | 70.3 | 51.7 | 23.3 |
| 91 | 44.3 | 33.1 | 12.9 |
| 92 | 77.2 | 52.4 | 27.5 |
| 93 | 50.1 | 28.8 | 12.0 |
| 94 | 53.2 | 30.5 | 22.2 |
| 95 | 33.3 | 29.2 | 9.5 |
| 96 | 52.8 | 19.6 | 11.0 |
| 97 | 67.2 | 42.0 | 22.3 |
| 101 | 20.7 | 11.2 | 9.9 |
| 105 | 92.0 | 74.0 | 60.2 |
| 173 | 46.4 | 28.2 | 5.2 |
| 184 | 76.1 | 58.2 | 28.5 |
| 185 | 56.2 | 37.7 | 22.9 |
| 214 | 76.8 | 60.1 | 33.9 |
| 215 | 82.0 | 70.8 | 30.0 |
| 216 | 49.5 | 30.3 | 22.8 |
| 217 | 84.5 | 60.6 | 50.2 |
| 221 | 23.0 | 24.7 | 6.2 |
| 223 | 29.0 | 12.9 | 4.6 |
| 233 | 70.3 | 34.6 | 17.7 |
| 234 | 81.5 | 65.3 | 41.8 |

TABLE 5-continued

| Example | % inhibition at 1 uM | % inhibition at 0.5 uM | % inhibition at 0.25 uM |
|---|---|---|---|
| 237 | 34.5 | 20.5 | 7.7 |
| 239 | 71.2 | 50.9 | 22.0 |
| 240 | 36.3 | 16.5 | 8.9 |
| 242 | 107.9 | 77.2 | 49.8 |
| 243 | 104.5 | 85.0 | 64.4 |
| 244 | 107.1 | 86.0 | 58.0 |
| 247 | 104.5 | 76.8 | 52.3 |
| 248 | 95.1 | 76.0 | 53.5 |
| 249 | 82.9 | 76.9 | 62.4 |
| 250 | 82.8 | 59.8 | 34.0 |
| 255 | 103.9 | 89.2 | 47.7 |
| 238 | 48.3 | 26.4 | 9.8 |

<Experimental Example 5> Evaluation of Phosphorylation Inhibition of LRRK2 (Leucin-Rich Repeat Kinase-2)

In order to evaluate the effect of inhibiting phosphorylation of LRRK2 of the compound of Formula 1 according to the present invention, the following experiment was performed, and the results were shown in FIGS. 1 and 2.

Specifically, it was identified by a western blot method that NIH3T3 cell line as fibroblasts was treated with the compounds to inhibit LRRK2 phosphorylation in the cells. The NIH3T3 cell line was seeded in a 60 mm dish with $6 \times 10^5$ cells and attached for one day, and then the compound was added to have the final concentration of 100 nM, and the DMSO in the culture fluid was added to have a content of 0.1%, followed by culture in a 37° C. $CO_2$ incubator for 24 hours. After removal of the culture fluid and washing twice with PBS, the cells were lysed with 1×RIPA buffer containing a phosphatase inhibitor and a protease inhibitor and recovered. After centrifugation at 4° C. and 14000 rpm for 15 minutes, the supernatant was quantified for protein through Bradford assay and sampled with 5× sample buffer. The same amount of protein was electrophoresed on SDS PAGE gel and transferred to a nitrocellulose membrane. The membrane was blocked with 5% skim milk for 1 hour, and then anti-LRRK2 (ab133474), anti-LRRK2 (phospho S935, ab133450) and actin as primary antibodies were added thereto and refrigerated for 16 hours. After washing with 1×TBS-T buffer (0.05% tween20), a secondary antibody was added, attached for 1 hour, washed, reacted with ECL substrate, and then detected with LAS500. The results are shown in FIGS. 1 and 2.

As shown in FIGS. 1 and 2, it can be seen that the example compounds according to the present invention significantly inhibit phosphorylation of LRRK2 in the NIH3T3 cell line, which is fibroblasts. In addition, it can be seen that the amount of detected P-LRRK2 is significantly low as compared with the case where the compound according to the present invention has been not treated. This means that the compounds according to the present invention effectively inhibit phosphorylation of LRRK2.

Therefore, the compounds of Formula 1 according to the present invention effectively inhibit LRRK2 phosphorylation in cancer-causing cells, so that they can be usefully used as a pharmaceutical composition for treating or preventing LRRK2-related diseases.

<Experimental Example 6> Evaluation of Various Kinase Inhibitory Activities of the Compounds According to the Present Invention In order to evaluate the inhibitory activity of the compounds according to the present invention against more enzymes, the following experiment was performed.

Specifically, for Examples 162, 160, 105, 217, 205, 96, 207, 184, 206, 221, 238, and 237 selected among the example compounds of the present invention, it was decided to measure enzyme (kinase) selectivity by DiscoverX, and the experiment was conducted using a panel for scan-MAX™ Kinase analysis. At this time, the concentration of the drug treated with the enzyme was 1 uM in DMSO, the control percentage (% control) was determined in the same way as in Equation 1 below, and the results were shown in Table 6 below.

(example compound − positive control) [Equation 1]
/(negative control − positive control) × 100

Here, the positive control refers to a compound showing a control percentage of 0%, and the negative control is DMSO, indicating a control percentage of 100%. Also, in the enzyme selectivity of the present invention, if the control percentage for each enzyme was <35% (i.e., less than 35%), it was determined to have activity against the relevant enzyme.

TABLE 6

| Kinase | Example 162 | Example 160 | Example 105 | Example 217 | Example 205 | Example 96 | Example 207 | Example 184 | Example 206 | Example 221 | Example 238 | Example 237 |
|---|---|---|---|---|---|---|---|---|---|---|---|---|
| ALK | 0.65 | 0.65 | 0.3 | 3.8 | 1.4 | 9.5 | 5.9 | 15 | 9 | 17 | 67 | 14 |
| ALK (C1156Y) | 0.9 | 0.9 | 2 | 3.9 | 1.3 | 10 | 1.8 | 7 | 5.3 | 12 | 42 | 9.7 |
| ALK (L1196M) | 1.3 | 1.3 | 2.3 | 18 | 1.6 | 28 | 10 | 23 | 23 | 28 | 58 | 15 |
| CLK1 | 13 | 13 | 1.5 | 2.4 | 18 | 9.7 | 5.6 | 3.4 | 8.5 | 7.5 | 2.4 | 3.6 |
| CLK2 | 0.65 | 0.65 | 0.35 | 0.55 | 0.15 | 1.2 | 7.2 | 0.3 | 3.1 | 8.2 | 0.25 | 0 |
| CLK3 | 13 | 13 | 5.9 | 19 | 37 | 27 | 66 | 7.8 | 91 | 60 | 56 | 58 |
| CLK4 | 0.55 | 0.55 | 5.5 | 8.2 | 0.25 | 0.3 | 0.55 | 0.45 | 1.2 | 0.25 | 0.35 | 0.55 |
| DYRK1A | 0.35 | 0.35 | 0 | 0 | 0.25 | 1.3 | 0.4 | 0.1 | 2 | 5.1 | 1.9 | 2.2 |
| DYRK1B | 0 | 0 | 0.9 | 1.4 | 2.5 | 3 | 0 | 13 | 0 | 0.45 | 0.7 | 1.4 |
| DYRK2 | 20 | 20 | 8 | 9.7 | 28 | 21 | 18 | 14 | 45 | 18 | 89 | 62 |

TABLE 6-continued

| Kinase | Example 162 | Example 160 | Example 105 | Example 217 | Example 205 | Example 96 | Example 207 | Example 184 | Example 206 | Example 221 | Example 238 | Example 237 |
|---|---|---|---|---|---|---|---|---|---|---|---|---|
| GAK | 6.3 | 6.3 | 4.8 | 9.9 | 12 | 14 | 38 | 27 | 29 | 12 | 27 | 15 |
| LRRK2 | 2.8 | 2.8 | 0 | 1 | 18 | 4.5 | 20 | 3.8 | 23 | 14 | 48 | 36 |
| LRRK2 (G2019S) | 0.35 | 0.35 | 0 | 1 | 17 | 1.9 | 16 | 3.2 | 28 | 5.5 | 38 | 31 |
| MYLK | 0 | 0 | 1.3 | 1.8 | 0 | 37 | 5.3 | 8 | 3 | 30 | 33 | 15 |
| TTK | 3.4 | 3.4 | 2.6 | 3 | 5.5 | 2.7 | 4.8 | 0.35 | 0.65 | 4.5 | 4.1 | 3.5 |

As shown in Table 6 above, the example compounds of the present invention show a control percentage of less than 35% for ALK, ALK (C1156Y), ALK (L1196M), CLK1, CLK2, CLK3, CLK4, DYRK1A, DYRK1B, DYRK2, GAK, LRRK2, LRRK2 (G2019S), MYLK or TTK kinase, whereby it can be seen that they have inhibitory activity against the relevant enzyme.

Accordingly, the compounds of Formula 1 according to the present invention may be usefully used for the treatment of diseases related to the protein kinases.

The invention claimed is:

1. A compound of Formula 1 below, or an isomer thereof, a solvate thereof, a hydrate thereof or a pharmaceutically acceptable salt thereof:

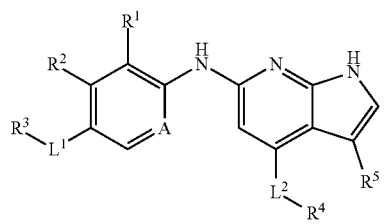

[Formula 1]

wherein, (a)

A represents a carbon atom or a nitrogen atom, $R^1$ is straight or branched C1-6 alkoxy, $R^2$ is hydrogen, or $R^1$ and $R^2$ form an 8 to 10 membered bicyclic ring containing one or more heteroatoms selected from the group consisting of N, O and S, together with the benzene ring including the carbon atoms to which they are attached, $L^1$ is sulfonyl or absent;

when $L^1$ is sulfonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen, or (b)

A represents a carbon atom or a nitrogen atom, $R^1$ and $R^2$ form an 8 to 10 membered bicyclic ring containing one or more heteroatoms selected from the group consisting of N, O and S, together with the benzene ring including the carbon atoms to which they are attached, $L^1$ is sulfonyl, carbonyl, or absent;

when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of R is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen.

2. The compound of Formula 1 according to claim 1, or an isomer thereof, a solvate thereof, a hydrate thereof or a pharmaceutically acceptable salt thereof, wherein A represents a carbon atom or a nitrogen atom, $R^1$ is straight or branched C1-6 alkoxy, $R^2$ is hydrogen, $L^1$ is sulfonyl or absent;

when $L^1$ is sulfonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen.

3. The compound of Formula 1 according to claim 1, or an isomer thereof, a solvate thereof, a hydrate thereof or a pharmaceutically acceptable salt thereof, wherein A represents a carbon atom, $R^1$ and $R^2$ form an 8 to 10 membered bicyclic ring containing one or more heteroatoms selected from the group consisting of N, O and S, together with the benzene ring including the carbon atoms to which they are attached, $L^1$ is sulfonyl, carbonyl or absent;

when $L^1$ is sulfonyl or carbonyl, $R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, when $L^1$ is absent, $R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of $R^3$ is unsubstituted or further substituted with C1-6 alkoxy or C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen.

4. The compound of Formula 1 according to claim 3, or an isomer thereof, a solvate thereof, a hydrate thereof or a pharmaceutically acceptable salt thereof, wherein $R^1$ and $R^2$ form an 8 to 10 membered bicyclic ring containing one or more heteroatoms selected from the group consisting of N, O and S, together with the benzene ring including the carbon atoms to which they are attached, where the 8 to 10 membered bicyclic ring is dihydrobenzodioxine, dihydrobenzofuran or benzodioxole.

5. The compound of Formula 1 according to claim 1, or an isomer thereof, a solvate thereof, a hydrate thereof or a pharmaceutically acceptable salt thereof, wherein A represents a carbon atom, $R^1$ is straight or branched C1-6 alkoxy, $R^2$ is hydrogen, $L^1$ is sulfonyl;

$R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl, $L^2$ is —NH—, —O— or absent;

when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl, when $L^2$ is absent, $R^4$ is C3-9 cycloalkyl or amino, where $R^4$ is unsubstituted or further substituted with one or more of C1-6 alkyl; and $R^5$ is hydrogen, cyano, C1-6 haloalkyl or halogen.

6. The compound of Formula 1 according to claim 1, or an isomer thereof, a solvate thereof, a hydrate thereof or a pharmaceutically acceptable salt thereof,
wherein A represents a carbon atom,
$R^1$ is straight or branched C1-6 alkoxy, $R^2$ is hydrogen, $L^1$ is absent;
$R^3$ is selected from phosphinic acid, azaphosphinane oxide, C1-6 alkylsulfonimidoyl and phosphine oxide, where $R^3$ is unsubstituted or substituted with one or more non-hydrogen substituents selected from the group consisting of oxetanyl, C3-9 cycloalkyl, straight or branched C1-6 alkyl, acetyl, tetrahydropyranyl and benzyl, and the non-hydrogen substituent of R is unsubstituted or further substituted with C1-6 alkoxy or C1-6 alkyl,
$L^2$ is —NH—, —O— or absent;
when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl,
when $L^2$ is absent, $R^4$ is C3-9 cycloalkyl or amino, where $R^4$ is unsubstituted or further substituted with one or more of C1-6 alkyl; and
$R^5$ is hydrogen, cyano, C1-6 haloalkyl or halogen.

7. The compound of Formula 1 according to claim 1, or an isomer thereof, a solvate thereof, a hydrate thereof or a pharmaceutically acceptable salt thereof,
wherein A represents a carbon atom,
$R^1$ and $R^2$ form an 8 to 10 membered bicyclic ring containing one or more heteroatoms selected from the group consisting of N, O and S, together with the benzene ring including the carbon atoms to which they are attached,
$L^1$ is sulfonyl or carbonyl;
$R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl,
$L^2$ is —NH—, —O— or absent;
when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl,
when $L^2$ is absent, $R^4$ is C3-9 cycloalkyl or amino, where $R^4$ is unsubstituted or further substituted with one or more of C1-6 alkyl; and
$R^5$ is hydrogen, cyano, C1-6 haloalkyl or halogen.

8. The compound of Formula 1 according to claim 1, or an isomer thereof, a solvate thereof, a hydrate thereof or a pharmaceutically acceptable salt thereof,
wherein A represents a carbon atom,
$R^1$ and $R^2$ form an 8 to 10 membered bicyclic ring containing one or more heteroatoms selected from the group consisting of N, O and S, together with the benzene ring including the carbon atoms to which they are attached, where the 8 to 10 membered bicyclic ring is dihydrobenzodioxine, dihydrobenzofuran, or benzodioxole,
$L^1$ is sulfonyl or carbonyl;
$R^3$ is selected from the group consisting of straight or branched C1-6 alkyl, morpholinyl, piperidinyl, piperazinyl, pyrrolidinyl, 2-oxa-5-azabicyclo[2.2.1]heptanyl, isoxazolidinyl and azaspirooctanyl, where $R^3$ is unsubstituted or further substituted with one or more non-hydrogen substituents selected from the group consisting of morpholinyl, oxetanyl, 2-oxa-5-azabicyclo[2.2.1]heptanyl, phenyl, amino, piperazinyl, piperidinyl, C3-9 cycloalkyl and straight or branched C1-6 alkyl, where the non-hydrogen substituent of $R^3$ is unsubstituted or further substituted with a substituent selected from the group consisting of halogen, hydroxy, C3-9 cycloalkyl and straight or branched C1-6 alkyl,
$L^2$ is —NH—, —O— or absent;
when $L^2$ is —NH— or —O—, $R^4$ is selected from the group consisting of C3-9 cycloalkyl, straight or branched C1-6 alkylamino and allyl, where $R^4$ is unsubstituted or further substituted with one or more non-hydrogen substituents selected from the group consisting of C1-6 alkylsulfonyl, C1-6 alkoxy and C1-6 alkyl,
when $L^2$ is absent, $R^4$ is C3-9 cycloalkyl or amino, where $R^4$ is unsubstituted or further substituted with one or more of C1-6 alkyl; and
$R^5$ is hydrogen, cyano, C1-6 haloalkyl or halogen.

9. The compound of Formula 1 according to claim 1, or an isomer thereof, a solvate thereof, a hydrate thereof or a pharmaceutically acceptable salt thereof,
characterized in that the compound of Formula 1 is any one selected from the following group of compounds:
<1> $N^4$-cyclopropyl-$N^6$-(2-methoxy-4-(methylsulfonyl)phenyl)-1H-pyrrolo[2,3-b]pyridine-4,6-diamine;
<2> (8-((4-(Methylamino)-1H-pyrrolo[2,3-b]pyridine-6-yl)amino)-2,3-dihydrobenzo[b][1,4]dioxin-5-yl)(morpholino)methanone;
<3> (8-((4-(ethylamino)-1H-pyrrolo[2,3-b]pyridin-6-yl)amino)-2,3-dihydrobenzo[b][1,4]dioxin-5-yl)(morpholino)methanone 2,2,2-trifluoroacetate;
<4> morpholino(8-((4-(propylamino)-1H-pyrrolo[2,3-b]pyridin-6-yl)amino)-2,3-dihydrobenzo[b][1,4]dioxin-5-yl)(morpholino)methanone 2,2,2-trifluoroacetate;
<5> (8-((4-(isopropylamino)-1H-pyrrolo[2,3-b]pyridin-6-yl)amino)-2,3-dihydrobenzo[b][1,4]dioxin-5-yl)(morpholino)methanone;
<6> (8-((4-(isobutylamino)-1H-pyrrolo[2,3-b]pyridin-6-yl)amino)-2,3-dihydrobenzo[b][1,4]dioxin-5-yl)(morpholino)methanone;
<7> (8-((4-(cyclopropylamino)-1H-pyrrolo[2,3-b]pyridin-6-yl)amino)-2,3-dihydrobenzo[b][1,4]dioxin-5-yl)(morpholino)methanone;
<8> (8-((4-(cyclohexylamino)-1H-pyrrolo[2,3-b]pyridin-6-yl)amino)-2,3-dihydrobenzo[b][1,4]dioxin-5-yl)(morpholino)methanone;
<9> (8-((4-((2-(methylsulfonyl)ethyl)amino)-1H-pyrrolo[2,3-b]pyridin-6-yl)amino)-2,3-dihydrobenzo[b][1,4]dioxin-5-yl)(morpholino)methanone;
<10> $N^6$-(2-methoxy-4-(morpholinosulfonyl)phenyl)-$N^4$-methyl-1H-pyrrolo[2,3-b]pyridine-4,6-diamine;

<11> $N^4$-ethyl-$N^6$-(2-methoxy-4-(morpholinosulfonyl)phenyl)-1H-pyrrolo[2,3-b]pyridine-4,6-diamine 2,2,2-trifluoroacetate;

<12> $N^6$-(2-methoxy-4-(morpholinosulfonyl)phenyl)-$N^4$-propyl-1H-pyrrolo[2,3-b]pyridine-4,6-diamine 2,2,2-trifluoroacetate;

<13> $N^4$-isopropyl-$N^6$-(2-methoxy-4-(morpholinosulfonyl)phenyl)-1H-pyrrolo[2,3-b]pyridine-4,6-diamine;

<14> $N^4$-isobutyl-$N^6$-(2-methoxy-4-(morpholinosulfonyl)phenyl)-1H-pyrrolo[2,3-b]pyridine-4,6-diamine;

<15> $N^4$-cyclopropyl-$N^6$-(2-methoxy-4-(morpholinosulfonyl)phenyl)-1H-pyrrolo[2,3-b]pyridine-4,6-diamine;

<16> $N^4$-cyclohexyl-$N^6$-(2-methoxy-4-(morpholinosulfonyl)phenyl)-1H-pyrrolo[2,3-b]pyridine-4,6-diamine;

<17> $N^6$-(2-methoxy-4-(morpholinosulfonyl)phenyl)-$N^4$-(2-(methylsulfonyl)ethyl)-1H-pyrrolo[2,3-b]pyridine-4,6-diamine;

<18> $N^6$-(2-methoxy-4-((4-morpholinopiperidin-1-yl)sulfonyl)phenyl)-$N^4$-methyl-1H-pyrrolo[2,3-b]pyridine-4,6-diamine;

<19> $N^4$-ethyl-$N^6$-(2-methoxy-4-((4-morpholinopiperidin-1-yl)sulfonyl)phenyl)-1H-pyrrolo[2,3-b]pyridine-4,6-diamine;

<20> $N^6$-(2-methoxy-4-((4-morpholinopiperidin-1-yl)sulfonyl)phenyl)-$N^4$-propyl-1H-pyrrolo[2,3-b]pyridine-4,6-diamine;

<21> $N^4$-isobutyl-$N^6$-(2-methoxy-4-((4-morpholinopiperidin-1-yl)sulfonyl)phenyl)-1H-pyrrolo[2,3-b]pyridine-4,6-diamine;

<22> $N^4$-cyclopropyl-$N^6$-(2-methoxy-4-((4-morpholinopiperidin-1-yl)sulfonyl)phenyl)-1H-pyrrolo[2,3-b]pyridine-4,6-diamine;

<23> $N^4$-cyclohexyl-$N^6$-(2-methoxy-4-((4-morpholinopiperidin-1-yl)sulfonyl)phenyl)-1H-pyrrolo[2,3-b]pyridine-4,6-diamine;

<24> $N^6$-(2-methoxy-4-((4-morpholinopiperidin-1-yl)sulfonyl)phenyl)-$N^4$-(2-(methylsulfonyl)ethyl)-1H-pyrrolo[2,3-b]pyridine-4,6-diamine;

<25> $N^6$-(2-methoxy-4-(methylsulfonyl)phenyl)-$N^4$-methyl-1H-pyrrolo[2,3-b]pyridine-4,6-diamine;

<26> $N^4$-ethyl-$N^6$-(2-methoxy-4-(methylsulfonyl)phenyl)-1H-pyrrolo[2,3-b]pyridine-4,6-diamine;

<27> $N^6$-(2-methoxy-4-(methylsulfonyl)phenyl)-$N^4$-propyl-1H-pyrrolo[2,3-b]pyridine-4,6-diamine;

<28> $N^4$-isopropyl-$N^6$-(2-methoxy-4-(methylsulfonyl)phenyl)-1H-pyrrolo[2,3-b]pyridine-4,6-diamine;

<29> $N^4$-isobutyl-$N^6$-(2-methoxy-4-(methylsulfonyl)phenyl)-1H-pyrrolo[2,3-b]pyridine-4,6-diamine;

<30> $N^4$-cyclohexyl-$N^6$-(2-methoxy-4-(methylsulfonyl)phenyl)-1H-pyrrolo[2,3-b]pyridine-4,6-diamine;

<31> $N^6$-(2-methoxy-4-(methylsulfonyl)phenyl)-$N^4$-(2-(methylsulfonyl)ethyl)-1H-pyrrolo[2,3-b]pyridine-4,6-diamine;

<32> (4-((4-(ethylamino)-1H-pyrrolo[2,3-b]pyridin-6-yl)amino)-3-methoxyphenyl)(methyl)phosphinic acid;

<33> 4-(ethylamino)-6-((7-(morpholine-4-carbonyl)benzo[d][1,3]dioxin-4-yl)amino)-1H-pyrrolo[2,3-b]pyridine-3-carbonitrile;

<34> 4-(ethylamino)-6-((7-(4-morpholinopiperidine-1-carbonyl)benzo[d][1,3]dioxol-4-yl)amino)-1H-pyrrolo[2,3-b]pyridine-3-carbonitrile;

<35> 4-(ethylamino)-6-((8-(4-(oxetan-3-yl)piperazine-1-carbonyl)-2,3-dihydrobenzo[b][1,4]dioxin-5-yl)amino)-1H-pyrrolo[2,3-b]pyridine-3-carbonitrile;

<36> 4-(cyclobutylamino)-6-((8-(morpholine-4-carbonyl)-2,3-dihydrobenzo[b][1,4]dioxin-5-yl)amino)-1H-pyrrolo[2,3-b]pyridine-3-carbonitrile;

<37> (7-((4-(ethylamino)-3-(trifluoromethyl)-1H-pyrrolo[2,3-b]pyridin-6-yl)amino)benzo[d][1,3]dioxol-4-yl)(4-morpholinopiperidin-1-yl)methanone;

<38> (7-((4-(methylamino)-3-(trifluoromethyl)-1H-pyrrolo[2,3-b]pyridin-6-yl)amino)benzo[d][1,3]dioxol-4-yl)(morpholino)methanone;

<39> 4-(4-((4-(ethylamino)-3-(trifluoromethyl)-1H-pyrrolo[2,3-b]pyridin-6-yl)amino)-3-methoxyphenyl)-1-(oxetan-3-yl)-1,4-azaphosphinane 4-oxide;

<40> $N^6$-(2-methoxy-4-((4-morpholinopiperidin-1-yl)sulfonyl)phenyl)-$N^4$-propyl-3-(trifluoromethyl)-1H-pyrrolo[2,3-b]pyridine-4,6-diamine;

<41> 4-(3-methoxy-4-((4-((2-methoxyethyl)amino)-3-(trifluoromethyl)-1H-pyrrolo[2,3-b]pyridin-6-yl)amino)phenyl)-1-(oxetan-3-yl)-1,4-azaphosphinane 4-oxide;

<42> 1-(4-(4-((4-(ethylamino)-3-(trifluoromethyl)-1H-pyrrolo[2,3-b]pyridin-6-yl)amino)-3-methoxyphenyl)-4-oxido-1,4-azaphosphinan-1-yl)ethan-1-one;

<43> ((1S,4S)-2-oxa-5-azabicyclo[2.2.1]heptan-5-yl)(8-((4-(methylamino)-3-(trifluoromethyl)-1H-pyrrolo[2,3-b]pyridin-6-yl)amino)-2,3-dihydrobenzo[b][1,4]dioxin-5-yl)methanone;

<44> ((1S,4S)-2-oxa-5-azabicyclo[2.2.1]heptan-5-yl)(8-((4-(ethylamino)-3-(trifluoromethyl)-1H-pyrrolo[2,3-b]pyridin-6-yl)amino)-2,3-dihydrobenzo[b][1,4]dioxin-5-yl)methanone;

<45> 1-cyclopropyl-4-(3-methoxy-4-((4-(propylamino)-3-(trifluoromethyl)-1H-pyrrolo[2,3-b]pyridin-6-yl)amino)phenyl)-1,4-azaphosphinane 4-oxide;

<46> 4-(4-((4-(cyclobutylamino)-3-(trifluoromethyl)-1H-pyrrolo[2,3-b]pyridin-6-yl)amino)-3-methoxyphenyl)-1-cyclopropyl-1,4-azaphosphinane 4-oxide;

<47> 4-(4-((4-cyclopropyl-3-(trifluoromethyl)-1H-pyrrolo[2,3-b]pyridin-6-yl)amino)-3-methoxyphenyl)-1-(oxetan-3-yl)-1,4-azaphosphinane 4-oxide;

<48> 1-(4-(4-((4-cyclopropyl-3-(trifluoromethyl)-1H-pyrrolo[2,3-b]pyridin-6-yl)amino)-3-methoxyphenyl)-4-oxido-1,4-azaphosphinan-1-yl)ethan-1-one;

<49> (7-((4-cyclopropyl-3-(trifluoromethyl)-1H-pyrrolo[2,3-b]pyridin-6-yl)amino)benzo[d][1,3]dioxol-4-yl)(4-morpholinopiperidin-1-yl)methanone;

<50> (8-((4-(dimethylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<51> (8-((4-(ethyl(methyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<52> (7-((4-(methylamino)-3-(trifluoromethyl)-1H-pyrrolo[2,3-b]pyridin-6-yl)amino)-2,3-dihydrobenzofuran-4-yl)(morpholino)methanone;

<53> (7-((4-(cyclopropylamino)-3-(trifluoromethyl)-1H-pyrrolo[2,3-b]pyridin-6-yl)amino)-2,3-dihydrobenzofuran-4-yl)(morpholino)methanone;

<54> (7-((4-((2-methoxyethyl)amino)-3-(trifluoromethyl)-1H-pyrrolo[2,3-b]pyridin-6-yl)amino)-2,3-dihydrobenzofuran-4-yl)(morpholino)methanone;

<55> (7-((4-((2-methoxyethyl)amino)-3-(trifluoromethyl)-1H-pyrrolo[2,3-b]pyridin-6-yl)amino)-2,3-dihydrobenzofuran-4-yl)(4-morpholinopiperidin-1-yl)methanone;

<56> (8-((3-chloro-4-(methylamino)-1H-pyrrolo[2,3-b]pyridin-6-yl)amino)-2,3-dihydrobenzo[b][1,4]dioxin-5-yl)(morpholino)methanone 2,2,2-trifluoroacetate;

<57> (8-((3-chloro-4-(ethylamino)-1H-pyrrolo[2,3-b]pyridin-6-yl)amino)-2,3-dihydrobenzo[b][1,4]dioxin-5-yl)(morpholino)methanone;

<58> (8-((3-chloro-4-(propylamino)-1H-pyrrolo[2,3-b]pyridin-6-yl)amino)-2,3-dihydrobenzo[b][1,4]dioxin-5-yl)(morpholino)methanone;

<59> (8-((3-chloro-4-(isopropylamino)-1H-pyrrolo[2,3-b]pyridin-6-yl)amino)-2,3-dihydrobenzo[b][1,4]dioxin-5-yl)(morpholino)methanone;

<60> (8-((3-chloro-4-(cyclopropylamino)-1H-pyrrolo[2,3-b]pyridin-6-yl)amino)-2,3-dihydrobenzo[b][1,4]dioxin-5-yl)(morpholino)methanone;

<61> (8-((3-chloro-4-(cyclohexylamino)-1H-pyrrolo[2,3-b]pyridin-6-yl)amino)-2,3-dihydrobenzo[b][1,4]dioxin-5-yl)(morpholino)methanone;

<62> (8-((3-chloro-4-((2-methoxyethyl)amino)-1H-pyrrolo[2,3-b]pyridin-6-yl)amino)-2,3-dihydrobenzo[b][1,4]dioxin-5-yl)(morpholino)methanone;

<63> (8-((3-chloro-4-((2-(methylsulfonyl)ethyl)amino)-1H-pyrrolo[2,3-b]pyridin-6-yl)amino)-2,3-dihydrobenzo[b][1,4]dioxin-5-yl)(morpholino)methanone;

<64> 3-chloro-$N^6$-(2-methoxy-4-(morpholinosulfonyl)phenyl)-$N^4$-methyl-1H-pyrrolo[2,3-b]pyridine-4,6-diamine;

<65> 3-chloro-$N^4$-ethyl-$N^6$-(2-methoxy-4-(morpholinosulfonyl)phenyl)-1H-pyrrolo[2,3-b]pyridine-4,6-diamine;

<66> 3-chloro-$N^6$-(2-methoxy-4-(morpholinosulfonyl)phenyl)-$N^4$-propyl-1H-pyrrolo[2,3-b]pyridine-4,6-diamine;

<67> 3-chloro-$N^4$-isopropyl-$N^6$-(2-methoxy-4-(morpholinosulfonyl)phenyl)-1H-pyrrolo[2,3-b]pyridine-4,6-diamine;

<68> 3-chloro-$N^4$-cyclopropyl-$N^6$-(2-methoxy-4-(morpholinosulfonyl)phenyl)-1H-pyrrolo[2,3-b]pyridine-4,6-diamine;

<69> 3-chloro-$N^4$-cyclobutyl-$N^6$-(2-methoxy-4-(morpholinosulfonyl)phenyl)-1H-pyrrolo[2,3-b]pyridine-4,6-diamine;

<70> 3-chloro-$N^4$-cyclohexyl-$N^6$-(2-methoxy-4-(morpholinosulfonyl)phenyl)-1H-pyrrolo[2,3-b]pyridine-4,6-diamine;

<71> 3-chloro-$N^6$-(2-methoxy-4-(morpholinosulfonyl)phenyl)-$N^4$-(2-methoxyethyl)-1H-pyrrolo[2,3-b]pyridine-4,6-diamine;

<72> 3-chloro-$N^6$-(2-methoxy-4-(morpholinosulfonyl)phenyl)-$N^4$-(2-(methylsulfonyl)ethyl)-1H-pyrrolo[2,3-b]pyridine-4,6-diamine;

<73> 3-chloro-$N^6$-(2-methoxy-4-((morpholinopiperidin-1-yl)sulfonyl)phenyl)-$N^4$-methyl-1H-pyrrolo[2,3-b]pyridine-4,6-diamine;

<74> 3-chloro-$N^4$-ethyl-$N^6$-(2-methoxy-4-((morpholinopiperidin-1-yl)sulfonyl)phenyl)-1H-pyrrolo[2,3-b]pyridine-4,6-diamine;

<75> 3-chloro-$N^4$-isopropyl-$N^6$-(2-methoxy-4-((morpholinopiperidin-1-yl)sulfonyl)phenyl)-1H-pyrrolo[2,3-b]pyridine-4,6-diamine;

<76> 3-chloro-$N^4$-cyclopropyl-$N^6$-(2-methoxy-4-((morpholinopiperidin-1-yl)sulfonyl)phenyl)-1H-pyrrolo[2,3-b]pyridine-4,6-diamine;

<77> 3-chloro-$N^4$-cyclohexyl-$N^6$-(2-methoxy-4-((morpholinopiperidin-1-yl)sulfonyl)phenyl)-1H-pyrrolo[2,3-b]pyridine-4,6-diamine;

<78> 3-chloro-$N^6$-(2-methoxy-4-((morpholinopiperidin-1-yl)sulfonyl)phenyl)-$N^4$-(2-methoxyethyl)-1H-pyrrolo[2,3-b]pyridine-4,6-diamine;

<79> 3-chloro-$N^6$-(2-methoxy-4-((morpholinopiperidin-1-yl)sulfonyl)phenyl)-$N^4$-(2-(methylsulfonyl)ethyl)-1H-pyrrolo[2,3-b]pyridine-4,6-diamine;

<80> 3-chloro-$N^6$-(2-methoxy-4-(methylsulfonyl)phenyl)-$N^4$-methyl-1H-pyrrolo[2,3-b]pyridine-4,6-diamine;

<81> 3-chloro-$N^4$-ethyl-$N^6$-(2-methoxy-4-(methylsulfonyl)phenyl)-1H-pyrrolo[2,3-b]pyridine-4,6-diamine;

<82> 3-chloro-$N^6$-(2-methoxy-4-(methylsulfonyl)phenyl)-$N^4$-propyl-1H-pyrrolo[2,3-b]pyridine-4,6-diamine;

<83> 3-chloro-$N^4$-isopropyl-$N^6$-(2-methoxy-4-(methylsulfonyl)phenyl)-1H-pyrrolo[2,3-b]pyridine-4,6-diamine;

<84> 3-chloro-$N^4$-cyclopropyl-$N^6$-(2-methoxy-4-(methylsulfonyl)phenyl)-1H-pyrrolo[2,3-b]pyridine-4,6-diamine;

<85> 3-chloro-$N^4$-cyclobutyl-$N^6$-(2-methoxy-4-(methylsulfonyl)phenyl)-1H-pyrrolo[2,3-b]pyridine-4,6-diamine;

<86> 3-chloro-$N^4$-cyclohexyl-$N^6$-(2-methoxy-4-(methylsulfonyl)phenyl)-1H-pyrrolo[2,3-b]pyridine-4,6-diamine;

<87> 3-chloro-$N^6$-(2-methoxy-4-(methylsulfonyl)phenyl)-$N^4$-(2-methoxyethyl)-1H-pyrrolo[2,3-b]pyridine-4,6-diamine;

<88> 3-chloro-$N^6$-(2-methoxy-4-(methylsulfonyl)phenyl)-$N^4$-(2-(methylsulfonyl)ethyl)-1H-pyrrolo[2,3-b]pyridine-4,6-diamine;

<89> (7-((4-(ethylamino)-3-(trifluoromethyl)-1H-pyrrolo[2,3-b]pyridin-6-yl)amino)-2,3-dihydrobenzofuran-4-yl)(morpholino)methanone;

<90> (7-((4-(ethylamino)-3-(trifluoromethyl)-1H-pyrrolo[2,3-b]pyridin-6-yl)amino)-2,3-dihydrobenzofurran-4-yl)(4-morpholinopiperidin-1-yl)methanone;

<91> (7-((4-cyclopropyl-3-(trifluoromethyl)-1H-pyrrolo[2,3-b]pyridin-6-yl)amino)-2,3-dihydrobenzofuran-4-yl)(morpholino)methanone;

<92> (7-((4-(cyclopropylamino)-3-(trifluoromethyl)-1H-pyrrolo[2,3-b]pyridin-6-yl)amino)-2,3-dihydrobenzofuran-4-yl)(4-morpholinopiperidin-1-yl)methanone;

<93> (7-((4-cyclopropyl-3-(trifluoromethyl)-1H-pyrrolo[2,3-b]pyridin-6-yl)amino)-2,3-dihydrobenzofuran-4-yl)(4-morpholinopiperidin-1-yl)methanone;

<94> 4-(4-((4-(ethylamino)-3-(trifluoromethyl)-1H-pyrrolo[2,3-b]pyridin-6-yl)amino)-3-methoxyphenyl)-1-(tetrahydro-2H-pyran-4-yl)-1,4-azaphosphinane 4-oxide;

<95> 4-(3-methoxy-4-((4-((2-methoxyethyl)amino)-3-(trifluoromethyl)-1H-pyrrolo[2,3-b]pyridin-6-yl)amino)phenyl)-1-(tetrahydro-2H-pyran-4-yl)-1,4-azaphosphinane 4-oxide;

<96> $N^4$-ethyl-$N^6$-(8-((4-morpholonopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine;

<97> $N^4$-(2-methoxyethyl)-$N^6$-(8-((4-morpholonopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine;

<98> $N^4$-methyl-$N^6$-(8-(morpholonosulfonyl)-2,3-dihydrobenzo[b][1,4]dioxin-5-yl)-3-(trifluoromethyl)-1H-pyrrolo[2,3-b]pyridine-4,6-diamine;

<99> N⁴-ethyl-N⁶-(8-(morpholonosulfonyl)-2,3-dihydrobenzo[b][1,4]dioxin-5-yl)-3-(trifluoromethyl)-1H-pyrrolo[2,3-b]pyridine-4,6-diamine;

<100> 4-cyclopropyl-N-(8-(morpholinosulfonyl)-2,3-dihydrobenzo[b][1,4]dioxin-5-yl)-3-(trifluoromethyl)-1H-pyrrolo[2,3-b]pyridine-6-amine;

<101> (8-((4-cyclopropyl-3-(trifluoromethyl)-1H-pyrrolo[2,3-b]pyridin-6-yl)amino)-2,3-dihydrobenzo[b][1,4]dioxin-5-yl)(4-(oxetan-3-yl)piperazin-1-yl)methanone;

<102> 4-(4-((4-cyclopropyl-3-(trifluoromethyl)-1H-pyrrolo[2,3-b]pyridin-6-yl)amino)-3-methoxyphenyl)-1-(tetrahydro-2H-pyran-4-yl)-1,4-azaphosphinane 4-oxide;

<103> N⁶-(2-methoxy-4-(s-methylsulfonylimidoyl)phenyl)-N4-methyl-3-(trifluoromethyl)-1H-pyrrolo[2,3-b]pyridine-4,6-diamine;

<104> N⁴-ethyl-N⁶-(4-((4-morpholinopiperidin-1-yl)sulfonyl)-2,3-dihydrobenzofuran-7-yl)-3-(trifluoromethyl)-1H-pyrrolo[2,3-b]pyridine-4,6-diamine;

<105> (4-((1S,4S)-2-oxa-5-azabicyclo[2.2.1]heptan-5-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<106> 4-(methylamino)-6-((8-(morpholine-4-carbonyl)-2,3-dihydrobenzo[b][1,4]dioxin-5-yl)amino)-1H-pyrrolo[2,3-b]pyridine-3-carbonitrile;

<107> 4-(ethylamino)-6-((8-(morpholine-4-carbonyl)-2,3-dihydrobenzo[b][1,4]dioxin-5-yl)amino)-1H-pyrrolo[2,3-b]pyridine-3-carbonitrile;

<108> 6-((8-(morpholine-4-carbonyl)-2,3-dihydrobenzo[b][1,4]dioxin-5-yl)amino)-4-(propylamino)-1H-pyrrolo[2,3-b]pyridine-3-carbonitrile;

<109> 4-((2-methoxyethyl)amino)-6-((8-(morpholine-4-carbonyl)-2,3-dihydrobenzo[b][1,4]dioxin-5-yl)amino)-1H-pyrrolo[2,3-b]pyridine-3-carbonitrile;

<110> 4-((2-(methylsulfonyl)ethyl)amino)-6-((8-(morpholine-4-carbonyl)-2,3-dihydrobenzo[b][1,4]dioxin-5-yl)amino)-1H-pyrrolo[2,3-b]pyridine-3-carbonitrile;

<111> 4-(cyclopropylamino)-6-((8-(morpholine-4-carbonyl)-2,3-dihydrobenzo[b][1,4]dioxin-5-yl)amino)-1H-pyrrolo[2,3-b]pyridine-3-carbonitrile;

<112> 4-(cyclopentylamino)-6-((8-(morpholine-4-carbonyl)-2,3-dihydrobenzo[b][1,4]dioxin-5-yl)amino)-1H-pyrrolo[2,3-b]pyridine-3-carbonitrile;

<113> 4-(ethylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<114> 6-((8-(4-morpholinopiperidine-1-carbonyl)-2,3-dihydrobenzo[b][1,4]dioxin-5-yl)amino)-4-(propylamino)-1H-pyrrolo[2,3-b]pyridine-3-carbonitrile;

<115> 4-(methylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<116> 4-(cyclopropylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<117> 4-(cyclobutylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<118> 4-((2-methoxyethyl)amino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<119> 6-((2-methoxy-4-(methylsulfonyl)phenyl)amino)-4-((2-(methylsulfonyl)ethyl)amino)-1H-pyrrolo[2,3-b]pyridine-3-carbonitrile;

<120> 4-(cyclobutylamino)-6-((2-methoxy-4-(methylsulfonyl)phenyl)amino)-1H-pyrrolo[2,3-b]pyridine-3-carbonitrile;

<121> 4-(cyclopentylamino)-6-((2-methoxy-4-(methylsulfonyl)phenyl)amino)-1H-pyrrolo[2,3-b]pyridine-3-carbonitrile;

<122> 4-(cyclopropylamino)-6-((2-methoxy-4-(methylsulfonyl)phenyl)amino)-1H-pyrrolo[2,3-b]pyridine-3-carbonitrile;

<123> 6-((2-methoxy-4-(morpholinosulfonyl)phenyl)amino)-4-(methylamino)-1H-pyrrolo[2,3-b]pyridine-3-carbonitrile;

<124> 4-(ethylamino)-6-((2-methoxy-4-(methylsulfonyl)phenyl)amino)-1H-pyrrolo[2,3-b]pyridine-3-carbonitrile;

<125> 6-((2-methoxy-4-(methylsulfonyl)phenyl)amino)-4-(propylamino)-1H-pyrrolo[2,3-b]pyridine-3-carbonitrile;

<126> 6-((2-methoxy-4-(methylsulfonyl)phenyl)amino)-4-((2-methoxyethyl)amino)-1H-pyrrolo[2,3-b]pyridine-3-carbonitrile;

<127> 4-cyclopropylamino)-6-((2-methoxy-4-(morpholinosulfonyl)phenyl)amino)-1H-pyrrolo[2,3-b]pyridine-3-carbonitrile;

<128> 4-cyclobutylamino)-6-((2-methoxy-4-(morpholinosulfonyl)phenyl)amino)-1H-pyrrolo[2,3-b]pyridine-3-carbonitrile;

<129> 6-((2-methoxy-4-(morpholinosulfonyl)phenyl)amino)-4-((2-methoxyethyl)amino)-1H-pyrrolo[2,3-b]pyridine-3-carbonitrile;

<130> 6-((2-methoxy-4-(morpholinosulfonyl)phenyl)amino)-4-((2-(methylsulfonyl)ethyl)amino)-1H-pyrrolo[2,3-b]pyridine-3-carbonitrile;

<131> 6-((2-methoxy-4-(morpholinosulfonyl)phenyl)amino)-4-(methylamino)-1H-pyrrolo[2,3-b]pyridine-3-carbonitrile;

<132> 4-(ethylamino)-6-((2-methoxy-4-(morpholinosulfonyl)phenyl)amino)-1H-pyrrolo[2,3-b]pyridine-3-carbonitrile;

<133> 6-((2-methoxy-4-(morpholinosulfonyl)phenyl)amino)-4-(propylamino)-1H-pyrrolo[2,3-b]pyridine-3-carbonitrile;

<134> 4-(cyclopropylamino)-6-((2-methoxy-4-((4-morpholinopiperidin-1-yl)sulfonyl)phenyl)amino)-1H-pyrrolo[2,3-b]pyridine-3-carbonitrile;

<135> 4-(cyclobutylamino)-6-((2-methoxy-4-((4-morpholinopiperidin-1-yl)sulfonyl)phenyl)amino)-1H-pyrrolo[2,3-b]pyridine-3-carbonitrile;

<136> 4-(cyclopentylamino)-6-((2-methoxy-4-((4-morpholinopiperidin-1-yl)sulfonyl)phenyl)amino)-1H-pyrrolo[2,3-b]pyridine-3-carbonitrile;

<137> 6-((2-methoxy-4-((4-morpholinopiperidin-1-yl)sulfonyl)phenyl)amino)-4-(methylamino)-1H-pyrrolo[2,3-b]pyridine-3-carbonitrile;

<138> 4-(ethylamino)-6-((2-methoxy-4-((4-morpholinopiperidin-1-yl)sulfonyl)phenyl)amino)-1H-pyrrolo[2,3-b]pyridine-3-carbonitrile;

<139> 6-((2-methoxy-4-((4-morpholinopiperidin-1-yl)sulfonyl)phenyl)amino)-4-(propylamino)-1H-pyrrolo[2,3-b]pyridine-3-carbonitrile;

<140> 6-((2-methoxy-4-((4-morpholinopiperidin-1-yl)sulfonyl)phenyl)amino)-4-((2-methoxyethyl)amino)-1H-pyrrolo[2,3-b]pyridine-3-carbonitrile;

<141> 6-((2-methoxy-4-((4-morpholinopiperidin-1-yl)sulfonyl)phenyl)amino)-4-((2-(methylsulfonyl)ethyl)amino)-1H-pyrrolo[2,3-b]pyridine-3-carbonitrile <142> 6-((2-methoxy-4-(1-(oxetan-3-yl)-4-oxido-1,4-azaphosphinan-4-yl)phenyl)amino)-4-(methylamino)-1H-pyrrolo[2,3-b]pyridine-3-carbonitrile;

<143> 4-(ethylamino)-6-((2-methoxy-4-(1-(oxetan-3-yl)-4-oxido-1,4-azaphosphinan-4-yl)phenyl)amino)-1H-pyrrolo[2,3-b]pyridine-3-carbonitrile;

<144> 6-((2-methoxy-4-(1-(oxetan-3-yl)-4-oxido-1,4-azaphosphinan-4-yl)phenyl)amino)-4-((2-methoxyethyl)amino)-1H-pyrrolo[2,3-b]pyridine-3-carbonitrile;

<145> 6-((4-(1-acetyl-4-oxido-1,4-azaphosphinan-4-yl)-2-methoxyphenyl)amino)-4-(ethylamino)-1H-pyrrolo[2,3-b]pyridine-3-carbonitrile;

<146> 6-((4-(1-cyclopropyl-4-oxido-1,4-azaphosphinan-4-yl)-2-methoxyphenyl)amino)-4-(methylamino)-1H-pyrrolo[2,3-b]pyridine-3-carbonitrile;

<147> 6-((4-(1-cyclopropyl-4-oxido-1,4-azaphosphinan-4-yl)-2-methoxyphenyl)amino)-4-(ethylamino)-1H-pyrrolo[2,3-b]pyridine-3-carbonitrile;

<148> 6-((4-(1-cyclopropyl-4-oxido-1,4-azaphosphinan-4-yl)-2-methoxyphenyl)amino)-4-((2-methoxyethyl)amino)-1H-pyrrolo[2,3-b]pyridine-3-carbonitrile;

<149> 4-(cyclohexylamino)-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<150> $N^4$-(cyclohexylamino)-$N^6$-((8-(morpholine-4-carbonyl)-2,3-dihydrobenzo[b][1,4]dioxin-5-yl)amino)-1H-pyrrolo[2,3-b]pyridine-3-carbonitrile;

<151> $N^4$-(cyclohexylamino)-$N^6$-((2-methoxy-4-((4-morpholinopiperidin-1-yl)sulfonyl)phenyl)amino)-1H-pyrrolo[2,3-b]pyridine-3-carbonitrile;

<152> (8-((4-(methylamino)-3-(trifluoromethyl)-1H-pyrrolo[2,3-b]pyridin-6-yl)amino)-2,3-dihydrobenzo[b][1,4]dioxin-5-yl)(morpholino)methanone;

<153> (8-((4-(ethylamino)-3-(trifluoromethyl)-1H-pyrrolo[2,3-b]pyridin-6-yl)amino)-2,3-dihydrobenzo[b][1,4]dioxin-5-yl)(morpholino)methanone;

<154> (8-((4-(cyclohexylamino)-3-(trifluoromethyl)-1H-pyrrolo[2,3-b]pyridin-6-yl)amino)-2,3-dihydrobenzo[b][1,4]dioxin-5-yl)(morpholino)methanone;

<155> (8-((4-(cyclopropylamino)-3-(trifluoromethyl)-1H-pyrrolo[2,3-b]pyridin-6-yl)amino)-2,3-dihydrobenzo[b][1,4]dioxin-5-yl)(morpholino)methanone 2,2,2-trifluoroacetate;

<156> (8-((4-(isobutylamino)-3-(trifluoromethyl)-1H-pyrrolo[2,3-b]pyridin-6-yl)amino)-2,3-dihydrobenzo[b][1,4]dioxin-5-yl)(morpholino)methanone;

<157> (8-((4-((2-(methylsulfonyl)ethyl)amino)-3-(trifluoromethyl)-1H-pyrrolo[2,3-b]pyridin-6-yl)amino)-2,3-dihydrobenzo[b][1,4]dioxin-5-yl)(morpholino)methanone;

<158> (8-((4-((2-methoxyethyl)amino)-3-(trifluoromethyl)-1H-pyrrolo[2,3-b]pyridin-6-yl)amino)-2,3-dihydrobenzo[b][1,4]dioxin-5-yl)(morpholino)methanone;

<159> (R)-(8-((4-((1-methoxypropan-2-yl)amino)-3-(trifluoromethyl)-1H-pyrrolo[2,3-b]pyridin-6-yl)amino)-2,3-dihydrobenzo[b][1,4]dioxin-5-yl)(morpholino)methanone;

<160> (8-((4-(methylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<161> (8-((4-(ethylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<162> (4-morpholinopiperidin-1-yl)(8-((4-(propylamino)-3-(trifluoromethyl)-1H-pyrrolo[2,3-b]pyridin-6-yl)amino)-2,3-dihydrobenzo[b][1,4]dioxin-5-yl)methanone;

<163> (8-((4-(cyclopropylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<164> (8-((4-((2-methoxyethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<165> (8-((4-((2-(methylsulfonyl)ethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<166> (8-((4-((2-ethoxyethyl)amino)-3-(trifluoromethyl)-1H-pyrrolo[2,3-b]pyridin-6-yl)amino)-2,3-dihydrobenzo[b][1,4]dioxin-5-yl)(morpholino)methanone;

<167> (8-((4-((2-ethoxyethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<168> (8-((4-(isopropylamino)-3-(trifluoromethyl)-1H-pyrrolo[2,3-b]pyridin-6-yl)amino)-2,3-dihydrobenzo[b][1,4]dioxin-5-yl)(morpholino)methanone;

<169> (8-((4-(butylamino)-3-(trifluoromethyl)-1H-pyrrolo[2,3-b]pyridin-6-yl)amino)-2,3-dihydrobenzo[b][1,4]dioxin-5-yl)(morpholino)methanone;

<170> (8-((4-(butylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<171> (8-((4-((2-(dimethylamino)ethyl)amino)-3-(trifluoromethyl)-1H-pyrrolo[2,3-b]pyridin-6-yl)amino)-2,3-dihydrobenzo[b][1,4]dioxin-5-yl)(morpholino)methanone;

<172> (8-((4-((2-(dimethylamino)ethyl)amino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<173> (8-((4-(ethylamino)-3-(trifluoromethyl)-1H-pyrrolo[2,3-b]pyridin-6-yl)amino)-2,3-dihydrobenzo[b][1,4]dioxin-5-yl)(4-(oxetan-3-yl)piperazin-1-yl)methanone;

<174> morpholino(8-((4-(propylamino)-3-(trifluoromethyl)-1H-pyrrolo[2,3-b]pyridin-6-yl)amino)-2,3-dihydrobenzo[b][1,4]dioxin-5-yl)methanone;

<175> (8-((4-(cyclobutylamino)-3-(trifluoromethyl)-1H-pyrrolo[2,3-b]pyridin-6-yl)amino)-2,3-dihydrobenzo[b][1,4]dioxin-5-yl)(morpholino)methanone 2,2,2-trifluoroacetate;

<176> (8-((4-(cyclobutylamino)-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<177> $N^6$-(2-methoxy-4-(morpholinosulfonyl)phenyl)-$N^4$-methyl-3-(trifluoromethyl)-1H-pyrrolo[2,3-b]pyridine-4,6-diamine;

<178> $N^6$-(2-methoxy-4-(methylsulfonyl)phenyl)-$N^4$-methyl-3-(trifluoromethyl)-1H-pyrrolo[2,3-b]pyridine-4,6-diamine;

<179> $N^4$-ethyl-$N^6$-(2-methoxy-4-(morpholinosulfonyl)phenyl)-3-(trifluoromethyl)-1H-pyrrolo[2,3-b]pyridine-4,6-diamine;

<180> $N^4$-ethyl-$N^6$-(2-methoxy-4-(methylsulfonyl)phenyl)-3-(trifluoromethyl)-1H-pyrrolo[2,3-b]pyridine-4,6-diamine;

<181> $N^4$-cyclohexyl-$N^6$-(2-methoxy-4-(morpholinosulfonyl)phenyl)-3-(trifluoromethyl)-1H-pyrrolo[2,3-b]pyridine-4,6-diamine;

<182> $N^4$-cyclohexyl-$N^6$-(2-methoxy-4-(methylsulfonyl)phenyl)-3-(trifluoromethyl)-1H-pyrrolo[2,3-b]pyridine-4,6-diamine;

<183> $N^4$-cyclohexyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine;

<184> $N^6$-(2-methoxy-4-((4-morpholinopiperidin-1-yl)sulfonyl)phenyl)-$N^4$-methyl-3-(trifluoromethyl)-1H-pyrrolo[2,3-b]pyridine-4,6-diamine;

<185> $N^4$-ethyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine;

<186> $N^4$-cyclopropyl-$N^6$-(2-methoxy-4-(morpholinosulfonyl)phenyl)-3-(trifluoromethyl)-1H-pyrrolo[2,3-b]pyridine-4,6-diamine;

<187> $N^4$-cyclopropyl-$N^6$-(2-methoxy-4-(methylsulfonyl)phenyl)-3-(trifluoromethyl)-1H-pyrrolo[2,3-b]pyridine-4,6-diamine;

<188> $N^4$-cyclopropyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine 2,2,2-trifluoroacetate;

<189> $N^4$-isobutyl-$N^6$-(2-methoxy-4-(morpholinosulfonyl)phenyl)-3-(trifluoromethyl)-1H-pyrrolo[2,3-b]pyridine-4,6-diamine;

<190> $N^4$-isobutyl-$N^6$-(2-methoxy-4-(methylsulfonyl)phenyl)-3-(trifluoromethyl)-1H-pyrrolo[2,3-b]pyridine-4,6-diamine;

<191> $N^4$-isobutyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine;

<192> $N^6$-(2-methoxy-4-(morpholinosulfonyl)phenyl)-$N^4$-(2-(methylsulfonyl)ethyl)-3-(trifluoromethyl)-1H-pyrrolo[2,3-b]pyridine-4,6-diamine;

<193> $N^6$-(2-methoxy-4-(methylsulfonyl)phenyl)-$N^4$-(2-(methylsulfonyl)ethyl)-3-(trifluoromethyl)-1H-pyrrolo[2,3-b]pyridine-4,6-diamine;

<194> $N^6$-(2-methoxy-4-((4-morpholinopiperidin-1-yl)sulfonyl)phenyl)-$N^4$-(2-(methylsulfonyl)ethyl)-3-(trifluoromethyl)-1H-pyrrolo[2,3-b]pyridine-4,6-diamine;

<195> $N^6$-(2-methoxy-4-(morpholinosulfonyl)phenyl)-$N^4$-(2-methoxyethyl)-3-(trifluoromethyl)-1H-pyrrolo[2,3-b]pyridine-4,6-diamine;

<196> (R)—$N^6$-(2-methoxy-4-((4-morpholinopiperidin-1-yl)sulfonyl)phenyl)-$N^4$-(1-methoxypropan-2-yl)-3-(trifluoromethyl)-1H-pyrrolo[2,3-b]pyridine-4,6-diamine;

<197> $N^6$-(2-methoxy-4-((4-morpholinopiperidin-1-yl)sulfonyl)phenyl)-$N^4$-(2-methoxyethyl)-3-(trifluoromethyl)-1H-pyrrolo[2,3-b]pyridine-4,6-diamine;

<198> $N^4$-isopropyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine;

<199> $N^6$-(2-methoxy-4-(morpholinosulfonyl)phenyl)-$N^4$-propyl-3-(trifluoromethyl)-1H-pyrrolo[2,3-b]pyridine-4,6-diamine;

<200> $N^6$-(2-methoxy-4-(methylsulfonyl)phenyl)-$N^4$-propyl-3-(trifluoromethyl)-1H-pyrrolo[2,3-b]pyridine-4,6-diamine;

<201> $N^6$-(2-methoxy-4-(methylsulfonyl)phenyl)-$N^4$-(2-methoxyethyl)-3-(trifluoromethyl)-1H-pyrrolo[2,3-b]pyridine-4,6-diamine;

<202> $N^4$-cyclobutyl-$N^6$-(2-methoxy-4-((4-morpholinopiperidin-1-yl)sulfonyl)phenyl)-3-(trifluoromethyl)-1H-pyrrolo[2,3-b]pyridine-4,6-diamine;

<203> $N^4$-cyclobutyl-$N^6$-(2-methoxy-4-(morpholinosulfonyl)phenyl)-3-(trifluoromethyl)-1H-pyrrolo[2,3-b]pyridine-4,6-diamine;

<204> $N^4$-cyclobutyl-$N^6$-(2-methoxy-4-(methylsulfonyl)phenyl)-3-(trifluoromethyl)-1H-pyrrolo[2,3-b]pyridine-4,6-diamine;

<205> 1-cyclopropyl-4-(3-methoxy-4-((4-(methylamino)-3-(trifluoromethyl)-1H-pyrrolo[2,3-b]pyridin-6-yl)amino)phenyl)-1,4-azaphosphinane 4-oxide;

<206> 1-cyclopropyl-4-(4-((4-(ethylamino)-3-(trifluoromethyl)-1H-pyrrolo[2,3-b]pyridin-6-yl)amino)-3-methoxyphenyl)-1,4-azaphosphinane 4-oxide;

<207> 1-cyclopropyl-4-(3-methoxy-4-((4-((2-methoxyethyl)amino)-3-(trifluoromethyl)-1H-pyrrolo[2,3-b]pyridin-6-yl)amino)phenyl)-1,4-azaphosphinane 4-oxide;

<208> (4-((4-(ethylamino)-3-(trifluoromethyl)-1H-pyrrolo[2,3-b]pyridin-6-yl)amino)-3-methoxyphenyl)(methyl)(4-morpholinopiperidin-1-yl)phosphine oxide;

<209> (4-((4-(ethylamino)-3-(trifluoromethyl)-1H-pyrrolo[2,3-b]pyridin-6-yl)amino)-3-methoxyphenyl)dimethylphosphine oxide;

<210> 1-ethyl-4-(4-((4-(ethylamino)-3-(trifluoromethyl)-1H-pyrrolo[2,3-b]pyridin-6-yl)amino)-3-methoxyphenyl)-1,4-azaphosphinane 4-oxide;

<211> 1-cyclopropyl-4-(4-((4-(cyclopropylamino)-3-(trifluoromethyl)-1H-pyrrolo[2,3-b]pyridin-6-yl)amino)-3-methoxyphenyl)-1,4-azaphosphinane 4-oxide;

<212> 4-(3-methoxy-4-((4-(methylamino)-3-(trifluoromethyl)-1H-pyrrolo[2,3-b]pyridin-6-yl)amino)phenyl)-1-(oxetan-3-yl)-1,4-azaphosphinane 4-oxide;

<213> (R)-(7-((4-(ethylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<214> (R)-(7-((4-(methylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<215> (S)-(7-((4-(ethylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<216> 4-(3-methoxy-4-((4-(methylamino)-3-(trifluoromethyl)-1H-pyrrolo[2,3-b]pyridin-6-yl)amino)phenyl)-1-(tetrahydro-2H-pyran-4-yl)-1,4-azaphosphinane 4-oxide;

<217> (S)-(7-((4-(methylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<218> 1-cyclopropyl-4-(4-((4-cyclopropyl-3-(trifluoromethyl)-1H-pyrrolo[2,3-b]pyridin-6-yl)amino)-3-methoxyphenyl)-1,4-azaphosphinane 4-oxide;

<219> (4-((4-cyclopropyl-3-(trifluoromethyl)-1H-pyrrolo[2,3-b]pyridin-6-yl)amino)-3-methoxyphenyl)dimethylphosphine oxide;

<220> (8-((4-cyclopropyl-3-(trifluoromethyl)-1H-pyrrolo[2,3-b]pyridin-6-yl)amino)-2,3-dihydrobenzo[b][1,4]dioxin-5-yl)(morpholino)methanone;

<221> (8-((4-cyclopropyl-3-(trifluoromethyl)-1H-pyrrolo[2,3-b]pyridin-6-yl)amino)-2,3-dihydrobenzo[b][1,4]dioxin-5-yl)(4-morpholinopiperidin-1-yl)methanone;

<222> 4-cyclopropyl-N-(2-methoxy-4-(morpholinosulfonyl)phenyl)-3-(trifluoromethyl)-1H-pyrrolo[2,3-b]pyridin-6-amine;

<223> 4-cyclopropyl-N-(2-methoxy-4-((4-morpholinopiperidin-1-yl)sulfonyl)phenyl)-3-(trifluoromethyl)-1H-pyrrolo[2,3-b]pyridin-6-amine;

<224> 4-cyclopropyl-N-(2-methoxy-4-(methylsulfonyl)phenyl)-3-(trifluoromethyl)-1H-pyrrolo[2,3-b]pyridin-6-amine;

<225> 4-cyclopropyl-6-((8-(morpholine-4-carbonyl)-2,3-dihydrobenzo[b][1,4]dioxin-5-yl)amino)-1H-pyrrolo[2,3-b]pyridine-3-carbonitrile;

<226> 4-cyclopropyl-6-((8-(4-morpholinopiperidine-1-carbonyl)-2,3-dihydrobenzo[b][1,4]dioxin-5-yl)amino)-1H-pyrrolo[2,3-b]pyridine-3-carbonitrile;

<227> 4-cyclopropyl-6-((2-methoxy-4-(morpholinosulfonyl)phenyl)amino)-1H-pyrrolo[2,3-b]pyridine-3-carbonitrile;

<228> 4-cyclopropyl-6-((2-methoxy-4-((4-morpholinopiperidin-1-yl)sulfonyl)phenyl)amino)-1H-pyrrolo[2,3-b]pyridine-3-carbonitrile;

<229> 4-cyclopropyl-6-((2-methoxy-4-(methylsulfonyl)phenyl)amino)-1H-pyrrolo[2,3-b]pyridine-3-carbonitrile;

<230> 4-cyclopropyl-6-((4-(dimethylphosphoryl)-2-methoxyphenyl)amino)-1H-pyrrolo[2,3-b]pyridine-3-carbonitrile;

<231> (8-((4-ethoxy-3-(trifluoromethyl)-1H-pyrrolo[2,3-b]pyridin-6-yl)amino)-2,3-dihydrobenzo[b][1,4]dioxin-5-yl)(morpholino)methanone;

<232> 4-ethoxy-N-(2-methoxy-4-((4-morpholinopiperidin-1-yl)sulfonyl)phenyl)-3-(trifluoromethyl)-1H-pyrrolo[2,3-b]pyridin-6-amine;

<233> $N^4$-methyl-$N^6$-(8-((4-morpholinopiperidin-1-yl)sulfonyl)-2,3-dihydrobenzo[b][1,4]dioxin-5-yl)-3-(trifluoromethyl)-1H-pyrrolo[2,3-b]pyridine-4,6-diamine;

<234> (7-((4-(methylamino)-3-(trifluoromethyl)-1H-pyrrolo[2,3-b]pyridin-6-yl)amino)-2,3-dihydrobenzofuran-4-yl)(4-morpholinopiperidin-1-yl)methanone;

<235> (7-((4-(methylamino)-3-(trifluoromethyl)-1H-pyrrolo[2,3-b]pyridin-6-yl)amino)benzo[d][1,3]dioxol-4-yl)(4-morpholinopiperidin-1-yl)methanone;

<236> (7-((4-(ethylamino)-3-(trifluoromethyl)-1H-pyrrolo[2,3-b]pyridin-6-yl)amino)benzo[d][1,3]dioxol-4-yl)(morpholino)methanone;

<237> (S)-(7-((4-cyclopropyl-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<238> (R)-(7-((4-cyclopropyl-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<239> N-(4-((4-(((1R,4R)-2-oxa-5-azabicyclo[2.2.1]heptan-5-yl)piperidin-1-yl)sulfonyl)-2-methoxyphenyl)-4-cyclopropyl-3-(trifluoromethyl)-1H-pyrrolo[2,3-b]pyridin-6-amine;

<240> N-(4-((4-(((1S,4S)-2-oxa-5-azabicyclo[2.2.1]heptan-5-yl)piperidin-1-yl)sulfonyl)-2-methoxyphenyl)-4-cyclopropyl-3-(trifluoromethyl)-1H-pyrrolo[2,3-b]pyridin-6-amine;

<241> (4-((1S,4S)-2-oxa-5-azabicyclo[2.2.1]heptan-5-yl)piperidin-1-yl)(7-((4-(methylamino)-3-(trifluoromethyl)-1H-pyrrolo[2,3-b]pyridin-6-yl)amino)-2,3-dihydrobenzofuran-4-yl)methanone;

<242> $N^6$-(4-((4-(((1S,4S)-2-oxa-5-azabicyclo[2.2.1]heptan-5-yl)piperidin-1-yl)sulfonyl)-2-methoxyphenyl)-$N^4$-methyl-3-(trifluoromethyl)-1H-pyrrolo[2,3-b]pyridine-4,6-diamine;

<243> $N^6$-(4-((4-(((1R,4R)-2-oxa-5-azabicyclo[2.2.1]heptan-5-yl)piperidin-1-yl)sulfonyl)-2-methoxyphenyl)-$N^4$-methyl-3-(trifluoromethyl)-1H-pyrrolo[2,3-b]pyridine-4,6-diamine;

<244> (4-((1R,4R)-2-oxa-5-azabicyclo[2.2.1]heptan-5-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<245> (R)-(3-(3,5-difluorophenyl)isoxazolidin-2-yl)(7-((4-(ethylamino)-3-(trifluoromethyl)-1H-pyrrolo[2,3-b]pyridin-6-yl)amino)-2,3-dihydrobenzofuran-4-yl)methanone;

<246> (S)-(3-(3,5-difluorophenyl)isoxazolidin-2-yl)(7-((4-(ethylamino)-3-(trifluoromethyl)-1H-pyrrolo[2,3-b]pyridin-6-yl)amino)-2,3-dihydrobenzofuran-4-yl)methanone;

<247> (7-((4-(ethylamino)-3-(trifluoromethyl)-1H-pyrrolo[2,3-b]pyridin-6-yl)amino)-2,3-dihydrobenzofuran-4-yl)(4-(4-methylpiperazin-1-yl)piperidin-1-yl)methanone;

<248> (7-((4-(ethylamino)-3-(trifluoromethyl)-1H-pyrrolo[2,3-b]pyridin-6-yl)amino)-2,3-dihydrobenzofuran-4-yl)(4-(oxetan-3-yl)piperazin-1-yl)methanone;

<249> (4-(dimethylamino)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<250> (4-cyclopropylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<251> (4-cyclopentylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<252> (4-allylpiperazin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<253> (7-((4-(ethylamino)-3-(trifluoromethyl)-1H-pyrrolo[2,3-b]pyridin-6-yl)amino)-2,3-dihydrobenzofuran-4-yl)(4-(2-hydroxyethyl)piperazin-1-yl)methanone;

<254> (7-((4-(ethylamino)-3-(trifluoromethyl)-1H-pyrrolo[2,3-b]pyridin-6-yl)amino)-2,3-dihydrobenzofuran-4-yl)(4-isopropylpiperazin-1-yl)methanone;

<255> (7-((4-(allylamino)-3-(trifluoromethyl)-1H-pyrrolo[2,3-b]pyridin-6-yl)amino)-2,3-dihydrobenzofuran-4-yl)(4-morpholinopiperidin-1-yl)methanone;

<256> (7-((4-(ethylamino)-3-(trifluoromethyl)-1H-pyrrolo[2,3-b]pyridin-6-yl)amino)-2,3-dihydrobenzofuran-4-yl)(6-azaspiro[2.5]octan-6-yl)methanone;

<257> (4-(cyclopropylmethyl)piperazin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<258> ((2S,6R)-2,6-dimethylmorpholino)(7-((4-(ethylamino)-3-(trifluoromethyl)-1H-pyrrolo[2,3-b]pyridin-6-yl)amino)-2,3-dihydrobenzofuran-4-yl)methanone;

<259> (S)-(7-((4-(ethylamino)-3-(trifluoromethyl)-1H-pyrrolo[2,3-b]pyridin-6-yl)amino)-2,3-dihydrobenzofuran-4-yl)(2-methylmorpholino)methanone;

<260> (R)-(7-((4-(ethylamino)-3-(trifluoromethyl)-1H-pyrrolo[2,3-b]pyridin-6-yl)amino)-2,3-dihydrobenzofuran-4-yl)(2-methylmorpholino)methanone;

<261> (R)-(7-((4-(allylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<262> (S)-(7-((4-(allylamino)-3-(trifluoromethyl)-1H-pyrrolo[2,3-b]pyridin-6-yl)amino)-2,3-dihydrobenzofuran-4-yl)(3-morpholinopyrrolidin-1-yl)methanone;

<263> (4-((2S,6R)-2,6-dimethylmorpholino)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<264> (4-(4-cyclopropylpiperazin-1-yl)piperidin-1-yl)(7-((4-(ethylamino)-3-(trifluoromethyl)-1H-pyrrolo[2,3-b]pyridin-6-yl)amino)-2,3-dihydrobenzofuran-4-yl)methanone;

<265> $N^6$-(5-fluoro-2-methoxy-4-((4-morpholinopiperidin-1-yl)sulfonyl)phenyl)-$N^4$-methyl-3-(trifluoromethyl)-1H-pyrrolo[2,3-b]pyridine-4,6-diamine;

<266> $N^4$-ethyl-$N^6$-(5-fluoro-2-methoxy-4-((4-morpholinopiperidin-1-yl)sulfonyl)phenyl)-3-(trifluoromethyl)-1H-pyrrolo[2,3-b]pyridine-4,6-diamine;

<267> 1-(2,4-dimethoxybenzyl)-4-(6-((4-(ethylamino)-3-(trifluoromethyl)-1H-pyrrolo[2,3-b]pyridin-6-yl)amino)pyridin-3-yl)-1,4-azaphosphinane 4-oxide.

10. A pharmaceutical composition for treating a disease related to a protein kinase selected from the group consisting of ALK, ALK (C1156Y), ALK (L1196M), CLK1, CLK2, CLK3, CLK4, DYRK1A, DYRK1B, DYRK2, GAK, LRRK2, LRRK2 (G2019S), MYLK, and TTK, comprising the compound of Formula 1 of claim 1, or an isomer thereof, a solvate thereof, a hydrate thereof or a pharmaceutically acceptable salt thereof as an active ingredient.

11. The pharmaceutical composition according to claim 10,
wherein the protein kinase-related disease is one or more selected from the group consisting of cancers, degenerative brain diseases, and inflammatory diseases.

12. The pharmaceutical composition according to claim 11,
wherein the degenerative brain disease is one or more selected from the group consisting of Alzheimer's disease, Parkinson's disease, Lou Gehrig's disease, dementia, Huntington's disease, multiple sclerosis, amyotrophic lateral sclerosis, stroke, apoplexia cerebri and mild cognitive impairment.

13. The pharmaceutical composition according to claim 11,
wherein the inflammatory disease is one or more selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, urethritis, cystitis, periodontitis and gingivitis.

14. The pharmaceutical composition according to claim 11,
wherein the cancer is one or more selected from the group consisting of triple-negative breast cancer, brain cancer, brain tumor, benign astrocytoma, malignant astrocytoma, pituitary adenoma, meningioma, brain lymphoma, oligodendroglioma, intracranial tumor, ependymoma, brain stem tumor, head and neck tumor, laryngeal cancer, oropharyngeal cancer, nasal/sinus cancer, nasopharyngeal cancer, salivary gland cancer, hypopharyngeal cancer, thyroid cancer, oral cancer, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cancer, female urethral cancer and skin cancer.

15. The pharmaceutical composition according to claim 10,
wherein the compound exhibits inhibitory activity against one or more protein kinases selected from the group consisting of ALK, ALK (C1156Y), ALK (L1196M), CLK1, CLK2, CLK3, CLK4, DYRK1A, DYRK1B, DYRK2, GAK, LRRK2, LRRK2 (G2019S), MYLK and TTK.

* * * * *